(12) United States Patent
Arboleda-Velasquez et al.

(10) Patent No.: US 11,229,662 B2
(45) Date of Patent: Jan. 25, 2022

(54) COMPOSITIONS AND METHODS FOR THE TREATMENT OF ABERRANT ANGIOGENESIS

(71) Applicant: The Schepens Eye Research Institute, Inc., Boston, MA (US)

(72) Inventors: Joseph F. Arboleda-Velasquez, Newton, MA (US); Leo A. Kim, Boston, MA (US); Patricia A. D'Amore, Newton, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

(21) Appl. No.: 16/348,860

(22) PCT Filed: Nov. 14, 2017

(86) PCT No.: PCT/US2017/061620
§ 371 (c)(1),
(2) Date: May 9, 2019

(87) PCT Pub. No.: WO2018/093797
PCT Pub. Date: May 24, 2018

(65) Prior Publication Data
US 2019/0350961 A1   Nov. 21, 2019

Related U.S. Application Data

(60) Provisional application No. 62/476,610, filed on Mar. 24, 2017, provisional application No. 62/422,523, filed on Nov. 15, 2016.

(51) Int. Cl.
| | | |
|---|---|---|
| *A61K 31/7088* | (2006.01) | |
| *A61P 27/02* | (2006.01) | |
| *A61P 35/04* | (2006.01) | |
| *A61K 31/5513* | (2006.01) | |
| *C12Q 1/6886* | (2018.01) | |

(52) U.S. Cl.
CPC ...... *A61K 31/7088* (2013.01); *A61K 31/5513* (2013.01); *A61P 27/02* (2018.01); *A61P 35/04* (2018.01); *C12Q 1/6886* (2013.01); *C12Q 2600/158* (2013.01)

(58) Field of Classification Search
CPC . A61K 31/7088; A61K 31/5513; A61P 27/02; A61P 35/04; C12Q 1/6886
USPC .................................................... 514/211.04
See application file for complete search history.

(56) References Cited

U.S. PATENT DOCUMENTS

| | | |
|---|---|---|
| 3,405,122 A | 10/1968 | Leo et al. |
| 4,309,404 A | 1/1982 | Deneale et al. |
| 4,309,406 A | 1/1982 | Guley et al. |
| 4,521,210 A | 6/1985 | Wong |
| 4,556,552 A | 12/1985 | Porter et al. |
| 4,704,295 A | 11/1987 | Porter et al. |
| 4,816,567 A | 3/1989 | Cabilly et al. |
| 4,853,224 A | 8/1989 | Wong |
| 4,997,652 A | 3/1991 | Wong |
| 5,036,101 A | 7/1991 | Hsu et al. |
| 5,041,438 A | 8/1991 | Hsu |
| 5,141,735 A | 8/1992 | Bellemin et al. |
| 5,164,188 A | 11/1992 | Wong |
| 5,164,376 A | 11/1992 | Hsu et al. |
| 5,443,505 A | 8/1995 | Wong et al. |
| 5,501,856 A | 3/1996 | Ohtori et al. |
| 5,545,806 A | 8/1996 | Lonberg et al. |
| 5,545,807 A | 8/1996 | Surani et al. |
| 5,569,825 A | 10/1996 | Lonberg et al. |
| 5,582,981 A | 12/1996 | Toole et al. |
| 5,625,126 A | 4/1997 | Lonberg et al. |
| 5,633,425 A | 5/1997 | Lonberg et al. |
| 5,641,673 A | 6/1997 | Haseloff et al. |
| 5,641,750 A | 6/1997 | Louis |
| 5,641,773 A | 6/1997 | Pardee et al. |
| 5,661,016 A | 8/1997 | Lonberg et al. |
| 5,731,005 A | 3/1998 | Ottoboni et al. |
| 5,766,242 A | 6/1998 | Wong et al. |
| 5,824,072 A | 10/1998 | Wong |
| 5,837,226 A | 11/1998 | Jungherr et al. |
| 5,869,079 A | 2/1999 | Wong et al. |
| 6,074,661 A | 6/2000 | Olejnik et al. |
| 6,331,313 B1 | 12/2001 | Wong et al. |
| 6,369,116 B1 | 4/2002 | Wong et al. |
| 6,699,493 B2 | 3/2004 | Wong |
| 6,719,971 B1 | 4/2004 | Carter et al. |
| 7,354,574 B2 | 4/2008 | Peyman |
| 8,053,454 B2 | 11/2011 | Kearney et al. |
| 8,293,210 B2 | 10/2012 | Huang et al. |
| 8,484,010 B2 | 7/2013 | Tuszynski et al. |

(Continued)

FOREIGN PATENT DOCUMENTS

| | | |
|---|---|---|
| WO | WO 9311161 A1 | 6/1993 |
| WO | 03078662 A1 | 9/2003 |

(Continued)

OTHER PUBLICATIONS

"Age-Related Macular Degeneration", U.S. National Library of Medicine Genetics, 8 pages.

(Continued)

Primary Examiner — Yevgeny Valenrod
(74) Attorney, Agent, or Firm — Fish & Richardson P.C.

(57) ABSTRACT

The present subject matter provides compositions, formulations, and methods for inhibiting, treating, or preventing aberrant angiogenesis in a subject.

15 Claims, 35 Drawing Sheets
Specification includes a Sequence Listing.

(56) References Cited

U.S. PATENT DOCUMENTS

| | | | |
|---|---|---|---|
| 8,697,359 B1 | 4/2014 | Zhang | |
| 9,023,649 B2 | 5/2015 | Mali et al. | |
| 9,074,199 B1 | 7/2015 | Chavez et al. | |
| 9,133,269 B2 | 9/2015 | Mcconnell et al. | |
| 9,446,048 B2* | 9/2016 | Liu | A61K 38/2013 |
| 2004/0229816 A1* | 11/2004 | Paris | A61K 38/05 |
| | | | 514/13.3 |
| 2006/0034834 A1 | 2/2006 | Marasco et al. | |
| 2006/0257452 A1 | 11/2006 | Hughes et al. | |
| 2006/0264380 A1 | 11/2006 | Hellstrom et al. | |
| 2007/0141066 A1 | 6/2007 | Phillips et al. | |
| 2008/0014180 A1 | 1/2008 | Lanza et al. | |
| 2008/0131484 A1 | 6/2008 | Robinson et al. | |
| 2009/0203011 A1 | 8/2009 | Liebenberg et al. | |
| 2009/0220488 A1 | 9/2009 | Gardner | |
| 2009/0285786 A1 | 11/2009 | Zon et al. | |
| 2010/0143380 A1 | 6/2010 | Crabb et al. | |
| 2010/0233194 A1 | 9/2010 | Combal et al. | |
| 2011/0305641 A1 | 12/2011 | Kazlauskas et al. | |
| 2013/0156795 A1 | 6/2013 | Iavarone et al. | |
| 2014/0004082 A1 | 1/2014 | Liu et al. | |
| 2014/0249135 A1 | 9/2014 | Burger et al. | |
| 2015/0174138 A1 | 6/2015 | Bernstein et al. | |
| 2020/0102384 A1 | 4/2020 | Arboleda-Velasquez et al. | |
| 2020/0103419 A1 | 4/2020 | Arboleda-Velasquez et al. | |
| 2020/0375899 A1 | 12/2020 | Kim et al. | |
| 2020/0377888 A1 | 12/2020 | Kim et al. | |

FOREIGN PATENT DOCUMENTS

| | | |
|---|---|---|
| WO | 2003078662 A1 | 9/2003 |
| WO | 2007017065 A2 | 2/2007 |
| WO | 2008130315 A1 | 10/2008 |
| WO | 2009146456 A1 | 12/2009 |
| WO | WO 2009152901 A1 | 12/2009 |
| WO | 2011163669 A2 | 12/2011 |
| WO | 2012174419 A2 | 12/2012 |
| WO | WO 2015049356 A1 | 4/2015 |
| WO | WO 2016025744 A1 | 2/2016 |
| WO | WO 2016182904 A1 | 11/2016 |
| WO | WO 2017112823 A1 | 6/2017 |
| WO | 2018183216 A1 | 10/2018 |

OTHER PUBLICATIONS

"Retinal Vein Occlusion", U.S. National Library of Medicine, 4 pages.
Yuan et al. (Dec. 1, 2015) "Notch Signaling: An Emerging Therapeutic Target for Cancer Treatment", Cancer Letters, 369(1):20-27.
Zapata et al. (Oct. 1995) "Engineering Linear F(ab')2 Fragments for Efficient Production in *Escherichia Coli* and Enhanced Anti-Proliferative Activity", Protein Engineering, 8(10):1057-1062.
Antonetti et al. (Aug. 13, 1999) "Vascular Endothelial Growth Factor Induces Rapid Phosphorylation of Tight Junction Proteins Occludin and Zonula Occluden 1", The Journal of Biological Chemistry, 274(33):23463-23467.
Yoshida et al. (Nov. 2009) "Gene Expression Profile of Fibrovascular Membranes from Patients with Proliferative Diabetic Retinopathy", The British journal of ophthalmology, 94(6):795-801.
Yadav et al. (Jun. 2015) "Tumour Angiogenesis and Angiogenic Inhibitors: A Review", Journal of Clinical and Diagnostic Research, 9(6):XE01-XE05.
Bataille et al. (May 1, 2017) "Thiazolidine Derivatives as Potent and Selective Inhibitors of the PIM Kinase Family", Bioorganic & Medicinal Chemistry, 25(9):2657-2665.
Berge et al. (Jan. 1977) "Pharmaceutical Salts", Journal of Pharmaceutical Sciences, 66(1):1-19.
Bergers et al. (Jun. 2003) "Tumorigenesis and the Angiogenic Switch", Nature Reviews Cancer, 3(6):401-410.
Verhoeyen et al. (Mar. 25, 1988) "Reshaping Human Antibodies: Grafting an Antilysozyme Activity", Science, 239 (4847):1534-1536.

Blackwell et al. (Nov. 23, 1990) "Sequence-specific DNA Binding by the c-Myc Protein", Science, 250 (4984):1149-1151.
Van Geest et al. (Jan. 2012) "A Shift in the Balance of Vascular Endothelial Growth Factor and Connective Tissue Growth Factor by Bevacizumab Causes the Angiofibrotic Switch in Proliferative Diabetic Retinopathy", British Journal of Ophthalmology, 96(4):587-590.
Shazly et al. (Mar. 2009) "Neovascular Glaucoma: Etiology, Diagnosis and Prognosis", Seminars in Ophthalmology, 24(2):113-121.
Burns et al. (Oct. 1, 2005) "Hematopoietic Stem Cell Fate Is Established by the Notch-Runx Pathway", Genes & Development, 19(19):2331-2342.
Butko et al. (Jan. 1, 2016) "Complex Regulation of HSC Emergence by the Notch Signaling Pathway", Developmental Biology, 409(1):22 Pages.
Castilla et al. (Nov. 16, 1995) "Failure of Embryonic Hematopoiesis and Lethal Hemorrhages in Mouse Embryos Heterozygous for a Knocked-In Leukemia Gene CBFB-MYH11", Cell, 87(4):687-696.
Chang et al. (Sep. 2010) "PIM Kinase Inhibitors Downregulate STAT3Tyr705 Phosphorylation", Molecular Cancer Therapeutics, 9(9):2478-2487.
Cheloufi et al. (Jun. 3, 2010) "A Dicer-Independent miRNA Biogenesis Pathway That Requires Ago Catalysis", Nature, 465(7298):584-589.
Chen et al. (1998) "Intracellular Antibodies as a New Class of Therapeutic Molecules for Gene Therapy", Human Gene Therapy, 5(5):595-601.
Chen et al. (Feb. 12, 2009) "Runx1 is Required for the Endothelial to Haematopoietic Cell Transition but Not Thereafter", Nature, 457(7231):887-891.
Chothia et al. (Aug. 20, 1987) "Canonical Structures for the Hypervariable Regions of Immunoglobulins", Journal of Molecular Biology, 196(4):901-917.
Chothia et al. (Dec. 28, 1989) "Conformations of Immunoglobulin Hypervariable Regions", Nature, 342:877-883.
Turell et al. (Jul. 2010) "Vascular Tumors of the Retina and Choroid: Diagnosis and Treatment", Middle East African Journal of Ophthalmology, 17(3):191-200.
Shao et al. (Jul. 26, 2013) "Choroid Sprouting Assay: An Ex Vivo Model of Microvascular Angiogenesis", PLoS ONE, e69552, 8(7):11 pages.
Cole et al. (Jan. 12, 1985) "Monoclonal Antibodies and Cancer Therapy", Supplement: UCLA Symposia on Molecular & Cellular Biology, 29(9A):33-74.
Connor et al. (Oct. 8, 2009) "Quantification of Oxygen-Induced Retinopathy in the Mouse: A Model of Vessel Loss, Vessel Regrowth and Pathological Angiogenesis", Nature Protocols, 4(11):18 pages.
Trapnell et al. (Apr. 2009) "TopHat: Discovering Splice Junctions with RNA-Seq", Bioinformatics, 25(9):1105-1111.
Edgar et al. (Jan. 1, 2002) "Gene Expression Omnibus: NCBI Gene Expression and Hybridization Array Data Repository", Nucleic Acids Research, 30(1):207-210.
Elbashir et al. (Dec. 3, 2001) "Functional Anatomy of siRNAs for Mediating Efficient RNAi in *Drosophila melanogaster* Embryo Lysate", The EMBO Journal, 20(23):6877-6888.
Espinoza et al. (Aug. 2013) "Notch Inhibitors for Cancer Treatment", Pharmacology & Therapeutics, 139(2):95-110.
Fire et al. (Mar. 1998) "Potent and Specific Genetic Interference by Double-Stranded RNA in Caenorhabditis Elegans", Nature, 391(6669):806-810.
Terelak-Borys et al. (Aug. 1, 2012) "Ocular Ischemic Syndrome—A Systematic Review", Medical Science Monitor, 18(8):RA138-RA144.
Gebäck et al. (Apr. 2009) "TScratch: A Novel and Simple Software Tool for Automated Analysis of Monolayer Wound Healing Assays", Biotechniques, 46(4):265-274.
Genbank (Jan. 9, 2008) "*Homo sapiens* cDNA FLJ75766 complete cds, highly similar to *Homo sapiens* pim-3 oncogene (PIM3), mRNA", Accession No. AK292005.1, 2 pages.
Genbank (Oct. 13, 2018) "*Homo sapiens* insulin like growth factor binding protein 3 (IGFBP3), transcript variant 1, mRNA", Accession No. NM_001013398.1, 4 pages.

(56) References Cited

OTHER PUBLICATIONS

Genbank (May 28, 2019) "*Homo sapiens* insulin like growth factor binding protein 3 (IGFBP3), transcript variant 2, mRNA", Accession No. NM_000598.4.
Genbank (Nov. 9, 2017) "*Homo sapiens* pim-3 mRNA for serine/threonine kinase Pim-3, Complete Cds", Accession No. AB114795.1.
Genbank (May 8, 2007) "*Homo sapiens* pim-3 oncogene, mRNA (cDNA clone MGC:167042 IMAGE:8860375), complete cds", Accession No. BC141855.1, 2 pages.
Genbank (May 8, 2020) "*Homo sapiens* Pim-3 proto-oncogene, serine/threonine kinase (PIM3), mRNA", Accession No. NM_001001852, 3 pages.
Genbank (Feb. 9, 2020) "*Homo sapiens* RUNX Family Transcription Factor 1 (RUNX1), Transcript Variant 1, mRNA", Accession No. NM_001754.4, 5 pages.
Genbank (Jun. 7, 2020) "*Homo sapiens* RUNX Family Transcription Factor 1 (RUNX1), Transcript Variant 3, mRNA", Accession No. NM_001122607.1.
Genbank (Jun. 14, 2020) "Insulin-like growth factor-binding protein 3 isoform a precursor [*Homo sapiens*]", Accession No. NP_001013416.1, 3 pages.
Genbank (Jun. 14, 2020) "Insulin-like growth factor-binding protein 3 isoform b precursor [*Homo sapiens*]", Accession No. NP_000589.2.
Genbank (May 8, 2007) "Pim-3 oncogene [*Homo sapiens*]", Accession No. AAI41856.1, 2 pages.
Sui et al. (2005) "oPOSSUM: Identification of Over-represented Transcription Factor Binding Sites in Co-Expressed Genes", Nucleic Acids Research, 33(10):3154-3164.
Genbank (May 8, 2020) "Predicted: *Homo sapiens* RUNX Family Transcription Factor 1 (RUNX1), Transcript Variant X2, mRNA", Accession No. XM_005261068.3, 3 pages.
Smith et al. (Jan. 1994) "Oxygen-Induced Retinopathy in the Mouse", Investigative Ophthalmology & Visual Science, 35(1):101-111.
Sohn et al. (Sep. 2012) "Angiofibrotic Response to Vascular Endothelial Growth Factor Inhibition in Diabetic Retinal Detachment", Archives of ophthalmology, 130(9):1127-1134.
Sang et al. (Jul. 8, 2008) "Is Blockade of Vascular Endothelial Growth Factor Beneficial for all Types of Diabetic Retinopathy?", Diabetologia, 51(9):1570-1573.
Lofqvist et al., "IGFBP3 Suppresses Retinopathy through Suppression of Oxygen-Induced Vessel Loss and Promotion of Vascular Regrowth," Proceedings of the National Academy of Sciences, 104:25, pp. 10589-10594, 2007.
Haubrich (Nov. 1995) "A Randomized Trial of the Activity and Safety of Ro 24-7429 (Tat Antagonist) Versus Nucleoside for Human Immunodeficiency Virus Infection. The AIDS Clinical Trials Group 213 Team", The Journal of Infectious Diseases, 172(5):1246-1252.
Ito et al. (Feb. 2003) "RUNX Transcription Factors as Key Targets of TGF-beta Superfamily Signaling", Current Opinion in Genetics and Development, 13(1):43-47.
Joyce (Oct. 15, 1989) "Amplification, Mutation and Selection of Catalytic RNA", Gene, 82(1):83-87.
Kim et al. (Nov. 1, 2008) "Pim-1 Kinase Phosphorylates and Stabilizes RUNX3 and Alters Its Subcellular Localization", Journal of Cellular Biochemistry, 105(4):1048-1058.
Kozlowski et al. (Aug. 7, 1975) "A Human Melanoma Line Heterogeneous With Respect to Metastatic Capacity in Athymic Nude Mice", Journal of the National Cancer Institute, 72(4):913-917.
Lichtinger, et al., "Chromatin Regulation by RUNX1", Blood Cells, Molecules and Diseases, Apr. 15, 2010, 44(4):287-290.
Marks et al. (Dec. 5, 1991) "By-Passing Immunization: Human Antibodies from V-Gene Libraries Displayed on Phage", Journal of Molecular Biology, 222(3):581-597.
Daxer (Dec. 1993) "The Fractal Geometry of Proliferative Diabetic Retinopathy: Implications for the Diagnosis and the Process of Retinal Vasculogenesis", Current Eye Research, 12(12):1103-1109.

Chung et al. (Nov. 2011) "Developmental and Pathological Angiogenesis", Annual Review of Cell and Developmental Biology, 27:563-584.
Boerner et al. (Jul. 1, 1991) "Production of Antigen-specific Human Monoclonal Antibodies from in Vitro-primed Human Splenocytes", The Journal of Immunology, 147(1):86-95.
Barberis et al. (Sep. 9, 2017) "Discovery of N-Substituted 7-Azaindoles as Pan-PIM Kinase Inhibitors—Lead Series Identification—Part II", Bioorganic & Medicinal Chemistry Letters, 27(20):4735-4740.
Arevalo et al. (Feb. 2008) "Tractional Retinal Detachment Following Intravitreal Bevacizumab (Avastin) in Patients With Severe Proliferative Diabetic Retinopathy", British Journal of Ophthalmology, 92(2):213-216.
(Aug. 1995) "The Relationship of Glycemic Exposure (HbA1c) to the Risk of Development and Progression of Retinopathy in the Diabetes Control and Complications Trial", The Diabetes Control and Complications Trial Research Group, 44(8):968-983.
"Retinopathy of Prematurity", American Association for Pediatric Ophthalmology and Strabismus.
Genbank (May 28, 2020) "Predicted: *Homo sapiens* RUNX family transcription factor 1 (RUNX1), transcript variant X6, mRNA", Accession No. XM_011529768.2.
Shaki-Loewenstein et al. (Aug. 2005) "A universal strategy for stable intracellular antibodies", Journal of Immunological Methods, 303(1-2):19-39.
McAuley et al. (May-Jun. 2014) "Vitreous Biomarkers in Diabetic Retinopathy: A Systematic Review and Meta-Analysis", Journal of Diabetic Complications, 28(3):419-425.
Genbank (May 28, 2020) "Predicted: *Homo sapiens* RUNX family transcription factor 1 (RUNX1), transcript variant X5, mRNA", Accession No. XM_005261069.4.
Cleveland Clinic (2015) "Retinal Vein Occlusion".
Boyd (2013) "Diabetic Retinopathy Diagnosis", American Academy of Ophthamology, 06 pages.
Genbank (May 28, 2020) "Predicted: *Homo sapiens* RUNX family transcription factor 1 (RUNX1), transcript variant X4, mRNA", Accession No. XM_017028487.1.
Genbank (May 28, 2020) "Predicted: *Homo sapiens* RUNX family transcription factor 1 (RUNX1), transcript variant X1, mRNA", Accession No. XM_011529766.2.
Fishwild et al. (Aug. 1996) "High-Avidity Human IgG Kappa Monoclonal Antibodies from a Novel Strain of Minilocus Transgenic Mice", Nature Biotechnology, 14(7):845-851.
Tuerk et al. (Aug. 3, 1990) "Systematic Evolution of Ligands by Exponential Enrichment: RNA Ligands to Bacteriophage T4 DNA Polymerase", Science, 249(4968):505-510.
Wang et al. (Apr. 26, 2017) "Discovery of 5-Azaindazole (GNE-955) as a Potent Pan-Pim Inhibitor With Optimized Bioavailability", 60(10):4458-4473.
Uniprot (Nov. 1, 1990) "Insulin-like growth factor-binding protein 3", Accession No. P17936.
Uniprot (Apr. 1, 1993) "Runt-related transcription factor 1", Accession No. Q01196-2.
Uniprot (Apr. 1, 1993) "Runt-related transcription factor 1", Accession No. Q01196-4.
Uniprot (Apr. 1, 1993) "Runt-related transcription factor 1", Accession No. Q01196-5.
Uniprot (Apr. 1, 1993) "Runt-related transcription factor 1", Accession No. Q01196-3.
Uniprot (Apr. 1, 1993) "Runt-related transcription factor 1", Accession No. Q01196-6.
Uniprot (Apr. 1, 1993) "Runt-related transcription factor 1", Accession No. Q01196-7.
Uniprot (Apr. 1, 1993) "Runt-related transcription factor 1", Accession No. Q01196-8.
Uniprot (Apr. 1, 1993) "Runt-related transcription factor 1", Accession No. Q01196-9.
Uniprot (Apr. 1, 1993) "Runt-related transcription factor 1", Accession No. 001196-10.
Uniprot (Apr. 1, 1993) "Runt-related transcription factor 1", Accession No. Q01196-11.
Uniprot (Nov. 21, 2003) "Serine/threonine-protein kinase pim-3", Accession No. Q86V86.

(56) References Cited

OTHER PUBLICATIONS

Rosenberg et al. (1994) "The Pharmacology of Monoclonal Antibodies", Springer-Verlag, 269-315.
Pettus et al. (Jun. 10, 2016) "Discovery and Optimization of Quinazolinone-pyrrolopyrrolones as Potent and Orally Bioavailable Pan-Pim Kinase Inhibitors", Journal of Medicinal Chemistry, 59(13):6407-6430.
Nicholls et al. (Sep. 27, 1993) "An Improved Method for Generating Single-Chain Antibodies From Hybridomas", Journal of Immunological Methods, 165(1):81-91.
Neuberger (Jul. 1996) "Generating High-Avidity Human Mabs in Mice", Nature Biotechnology, 4(7):1 page.
Nakano et al. (Dec. 15, 2015) "Design and Synthesis of an in Vivo-Efficacious PIM3 Kinase Inhibitor as a Candidate Anti-Pancreatic Cancer Agent", Bioorganic & Medicinal Chemistry Letters, 25(24):5687-5693.
Moshfeghi et al. (Oct. 29, 2013) "Retinal Capillary Angioma", American Academy of Ophthamology.
Medscape, "Ocular Ischemic Syndrome", Available at: emedicine.medscape.com/article/1201678-overview#a6.
Medscape, "Neovascular Glaucoma", Available at: https://emedicine.medscape.com/article/1205736-overview#a6.
Mayo Clinic (2015) "Diabetic Retinopathy, Tests and Diagnosis".
Saint-Geniez et al. (Nov. 3, 2008) "Endogenous VEGF is Required for Visual Function: Evidence for a Survival Role on Müller Cells and Photoreceptors", PLoS ONE, e3554, 3(11):13 pages.
Genbank (May 28, 2020) "Predicted: *Homo sapiens* RUNX family transcription factor 1 (RUNX1), transcript variant X7, misc_RNA", Accession No. XR_937576.2, 2 pages.
Genbank (May 28, 2020) "Predicted: *Homo sapiens* RUNX Family Transcription Factor 1 (RUNX1), Transcript Variant X8, mRNA", Accession No. XM_011529770.2, 2 pages.
Genbank (Nov. 9, 2017) "Serine/threonine kinase Pim-3 [*Homo sapiens*]", Accession No. BAD42438.1, 1 page.
Genbank (Jan. 9, 2008) "Unnamed protein product [*Homo sapiens*]", Accession No. BAF84694.1, 2 pages.
Giani et al. (Jun. 1, 2011) "In Vivo Evaluation of Laser-Induced Choroidal Neovascularization Using Spectral-Domain Optical Coherence Tomography", Investigative Ophthalmology & Visual Science, 52(6):3880-3887.
Riechmann et al. (Mar. 24, 1988) "Reshaping Human Antibodies for Therapy", Nature, 332:323-327.
Hakeem et al. (Jul.-Sep. 2012) "Retinopathy of Prematurity: A Study of Prevalence and Risk Factors", Middle East African Journal of Ophthalmology, 19(3):289-294.
Harris et al. (Mar. 28, 2013) "Glucose Metabolism Impacts the Spatiotemporal Onset and Magnitude of HSC Induction in Vivo", Blood, 121(13):2483-2493.
Ran et al. (Jul. 2017) "γ-Secretase Inhibitors in Cancer Clinical Trials are Pharmacologically and Functionally Distinct", EMBO Molecular Medicine, 9(7):950-966.
Hollinger et al. (Jul. 1993) ""Diabodies": Small Bivalent and Bispecific Antibody Fragments", Proceedings of the National Academy of Sciences of the United States of America, 90(14):6444-6448.
Hoogenboom et al. (Sep. 20, 1992) "By-Passing immunisation: Human Antibodies from Synthetic Repertoires of Germline VH Gene Segments Rearranged in Vitro", Journal of Molecular Biology, 227(2):381-388.
Hsu et al. (Jun. 25, 2014) "Combined Tractional and Rhegmatogenous Retinal Detachment in Proliferative Diabetic Retinopathy in the Anti-VEGF Era", Journal of Ophthalmology, Article ID 917375, 2014(7):11 pages.
Huang et al. (Jan. 2009) "Bioinformatics Enrichment Tools: Paths Toward the Comprehensive Functional Analysis of Large Gene Lists", Nucleic Acids Research, 37(1):1-13.
Iieckl et al. (Sep. 2014) "Generation of Mouse Models of Myeloid Malignancy with Combinatorial Genetic Lesions Using CRISPR-Cas9 Genome Editing", Nature Biotechnology, 32(9):14 Pages.

Illendula et al. (Nov. 1, 2017) "Small Molecule Inhibitor of CBFβ-RUNX Binding for RUNX Transcription Factor Driven Cancers", EBioMedicine, 8:117-131.
Imanirad et al. (Jan. 2014) "HIF1α is a Regulator of Hematopoietic Progenitor and Stem Cell Development in Hypoxic Sites of the Mouse Embryo", Stem Cell Research, 12(1):24-35.
Ishikawa et al. (Feb. 2015) "Microarray Analysis of Gene Expression in Fibrovascular Membranes Excised From Patients With Proliferative Diabetic Retinopathy", Investigative Ophthalmology & Visual Science, 56(2):932-946.
Rakoczy et al. (Nov. 2010) "Characterization of a Mouse Model of Hyperglycemia and Retinal Neovascularizatio", The American Journal of Pathology, 177(5):2659-2670.
Iwatsuki et al. (Feb. 1, 2005) "Runx1 Promotes Angiogenesis by Downregulation of Insulin-Like Growth Factor-Binding Protein-3", Oncogene, 24(7):1129-1137.
Jo et al. (Feb. 1, 2005) "Animal Models of Diabetic Retinopathy: Doors to Investigate Pathogenesis and Potential Therapeutics", Journal of Biomedical Science, 20(1):38.
Jones et al. (May 29, 1986) "Replacing the Complementarity-Determining Regions in a Human Antibody with those from a Mouse", Nature, 321 (6069):522-525.
Pubchem (May 28, 2019) "*Homo sapiens* RUNX Family Transcription Factor 1 (RUNX1), Transcript Variant 2, mRNA", Accession No. NM_001001890.2, 7 pages.
Kalev-Zylinska et al. (2002) "Runx1 is Required for Zebrafish Blood and Vessel Development and Expression of a Human RUNX1-CBF2T1 Transgene Advances a Model for Studies of Leukemogenesis", Development, 129 (8):2015-2030.
Kategaya (Oct. 18, 2017) "USP7 Small-Molecule Inhibitors Interfere With Ubiquitin Binding", Nature, 550 (7677):534-538.
Kim et al. (Jul. 2, 2012) "A Brief History of Anti-VEGF for the Treatment of Ocular Angiogenesis", The American Journal of Pathology, 181(2):376-379.
Kim et al. (Jun. 12, 2015) "Characterization of Cells from Patient-Derived Fibrovascular Membranes in Proliferative Diabetic Retinopathy", Molecular Vision, 21:673-687.
Presta (1992) "Antibody Engineering", Current Opinion in Structural Biology, 2(4):593-596.
Kohler et al. (Aug. 7, 1975) "Continuous Cultures of Fused Cells Secreting Antibody of Predefined Specificity", Nature, 256(5517):495-497.
Pluckthun (1994) "Antibodies from *Escherichia coli*", The Pharmacology of Monoclonal Antibodies, 113:269-315.
Kuiper et al. (Jul. 16, 2008) "The Angio-Fibrotic Switch of VEGF and CTGF in Proliferative Diabetic Retinopathy", PLoS ONE, e2675, 3(7):7 pages.
Liang et al. (Mar. 1, 2007) "In Vitro Scratch Assay: A Convenient and Inexpensive Method for Analysis of Cell Migration in Vitro", Nature Protocols, 2(2):329-333.
National Eye Institute, "Facts About Retinopathy of Prematurity (ROP)", 3 pages.
Lie-a-Ling, et al. (Sep. 11, 2014) "RUNX1 Positively Regulates a Cell Adhesion and Migration Program in Murine Hemogenic Endothelium Prior to Blood Emergence", Blood, 124(11):e11-e20.
Michaud et al. (Jul. 31, 2008) "Integrative Analysis of RUNX1 Downstream Pathways and Target Genes", BMC Genomics, 9:17 pages.
Lonberg et al. (Apr. 28, 1994) "Antigen-Specific Human Antibodies from Mice Comprising Four Distinct Genetic Modifications", Nature, 368:856-859.
Lonberg et al. (1995) "Human Antibodies from Transgenic Mice", International Reviews of Immunology, 13(1):65-93.
Ludwig (2005) "The Use of Mucoadhesive Polymers in Ocular Drug Delivery", Advanced Drug Delivery Reviews, Nov. 3, 57(11):1595-1639.
Namba et al. (Jan. 1, 2000) "Indispensable Role of the Transcription Factor PEBP2/CBF in Angiogenic Activity of a Murine Endothelial Cell MSS31", Oncogene, 19(1):106-114.
Morrison (Apr. 28, 1994) "Immunology. Success in Specification", Nature, 368:812-813.

(56) References Cited

OTHER PUBLICATIONS

Mayo Clinic (2015) "Dry Macular Degeneration", https://www.mayoclinic.org/diseasesconditions/drymaculardegeneration/diagnosis-treatment/drc-20350381, 5 pages.

Mayo Clinic (2015) "Wet Macular Degeneration", 6 pages.

McLeod et al. (Dec. 2012) "From Blood Islands to Blood Vessels: Morphologic Observations and Expression of Key Molecules during Hyaloid Vascular System Development", Investigative Ophthalmology & Visual Science, 53 (13):7912-7927.

Butko et al. (Nov. 14, 2015) "Complex regulation of HSC emergence by the Notch signaling pathway," Developmental Biology. 409:129-138.

Cunningham et al. (Sep. 4, 2012) "Identification of benzodiazepine Ro5-3335 as an inhibitor of CBF leukemia through quantitative high throughput screen against RUNX1-CBFβ interaction," Proceedings of the National Academy of Science. 109(36):14592-14597.

Heckl et al. (Mar. 1, 2015) "Generation of mouse models of myeloid malignancy with combinatorial genetic lesions using CRISPR-Cas9 genome editing," Nature Biotechnology. 32(9):941-946.

Lam et al. (Jun. 27, 2017) "Identification of RUNX1 as a Mediator of Aberrant Retinal Angiogenesis," Diabetes. 66:1950-1956.

International Search Report corresponding to International Patent Application No. PCT/US17/61620, dated Mar. 19, 2018, 24 pages.

Extended European Search Report in European Application No. 17871449.9, dated May 25, 2020, 13 pages.

PCT International Preliminary Report on Patentability in International Application No. PCT/US2017/061620, dated May 21, 2019, 17 pages.

Colyer et al., "Perforating globe injuries during operation Iraqi Freedom," Ophthalmology, 2008, 115:2087-2093.

Eliott et al., "Smoking is a risk factor for proliferative vitreoretinopathy after traumatic retinal detachment," Retina, 2017, 37(7):1229-1235.

Extended European Search Report in European Appln. No. 18878909.3, dated Jul. 22, 2021, 7 pages.

Fehniger et al., "Single-agent lenalidomide induces complete remission of acute myeloid leukemia in patients with isolated trisomy 13," Blood, 2009, 113(5):1002-1005.

Friedlander, "Fibrosis and diseases of the eye," J Clin Invest., 2007, 117(3):576-586.

Hong et al., "Runx1 stabilizes the mammary epithelial cell phenotype and prevents epithelial to mesenchymal transition," Oncotarget, Mar. 2017, 8(11):17610-17627.

Kim et al., "Inhibition of Runx1 by the Ro5-3335 benzodiazepine derivative reduces aberrant retinal angiogenesis," Abstract, Presented at Annual Meeting of the Association for Research in Vision and Ophthalmology (ARVO), Baltimore, MD, USA; May 7-11, 2017; IOVS, Jun. 2017, 58(8):4029, 3 pages.

Martinez-Hoyer et al., "RUNX1 Loss of Function Drives Resistance to Lenalidomide in Del(5Q) Myelodysplastic Syndrome Patients," Leukemia Research, 2017, 1(55):S43-S44.

Masoumpour et al., "Current and Future Techniques in Wound Healing Modulation after Glaucoma Filtering Surgeries," Open Ophthalmol J., 2016, 10:68-85.

PCT International Preliminary Report on Patentability in International Appln. No. PCT/US2018/061110, dated May 28, 2020, 12 pages.

PCT International Search Report and the Written Opinion in International Appln. No. PCT/US2018/061110, dated Mar. 25, 2019, 17 pages.

Zhou et al., "RUNX proteins desensitize multiple myeloma to lenalidomide via protecting IKZFs from degradation," Leukemia, 2019, 33:2006-2021.

* cited by examiner

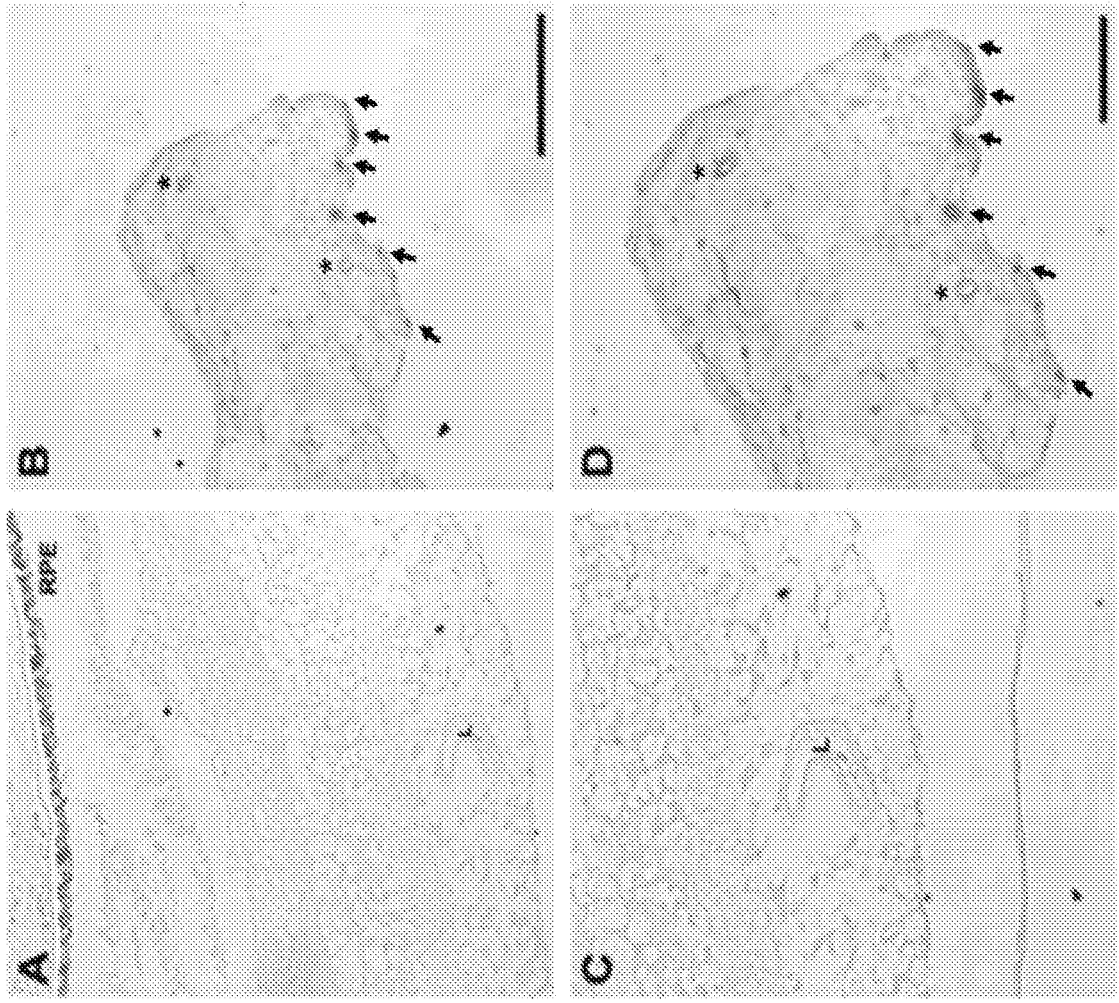
FIGS. 5A-D

FIG. 6B-D

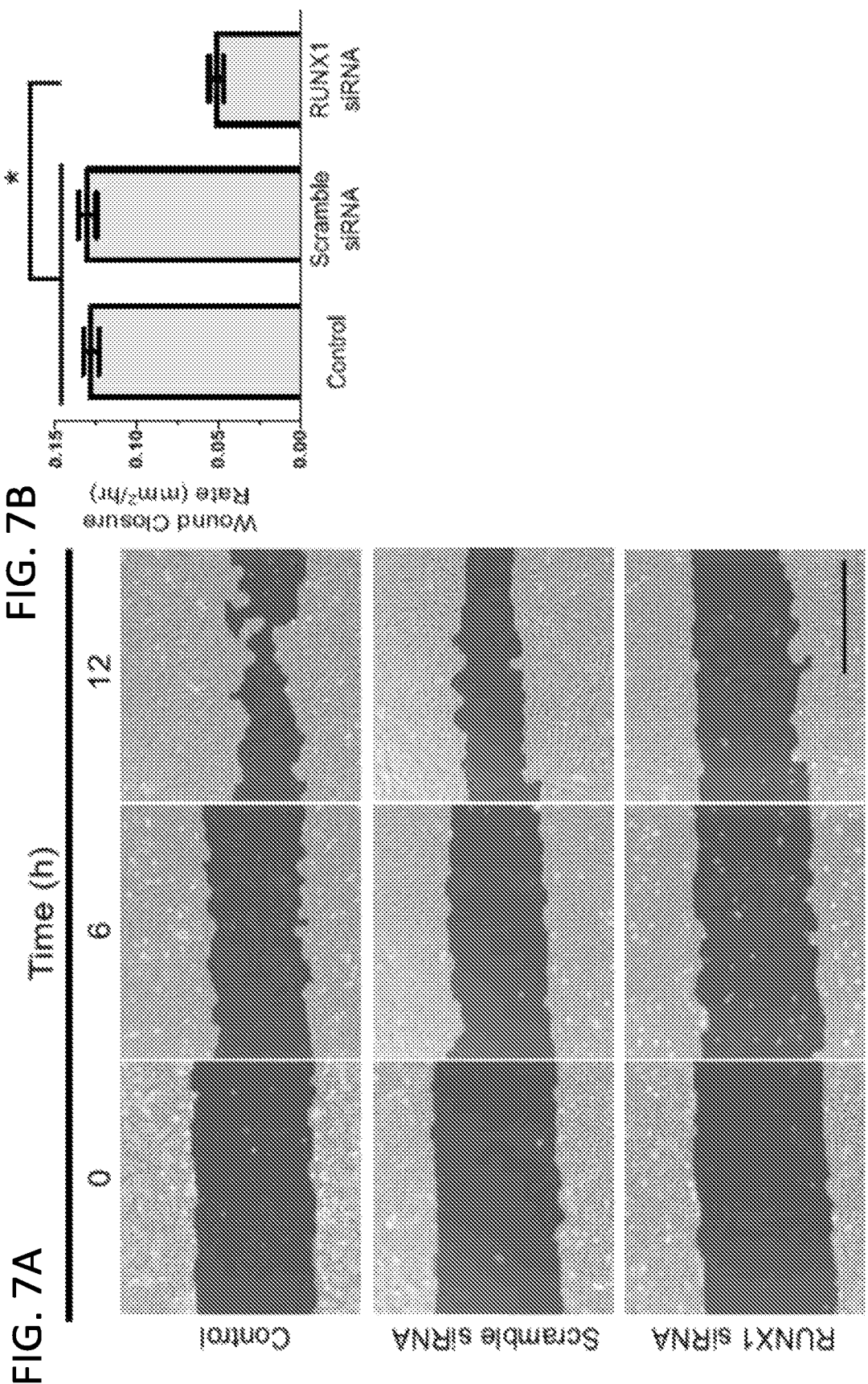

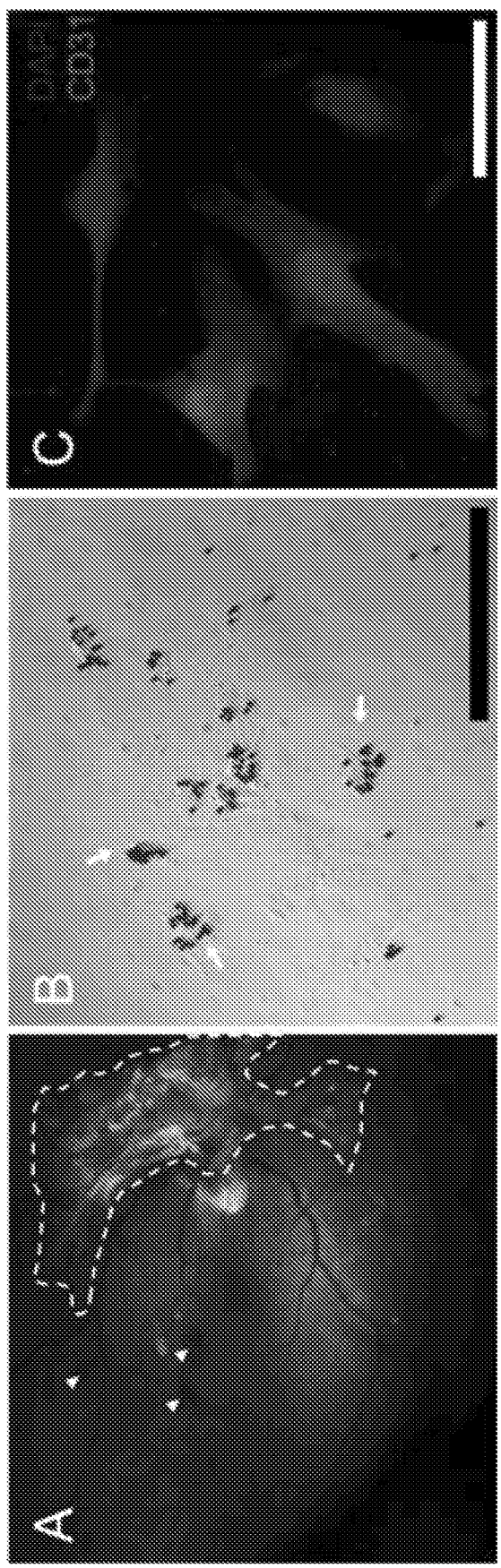
FIG. 9A-C

SEQUENCE LISTING

```
<160> NUMBER OF SEQ ID NOS: 257

<210> SEQ ID NO 1
<211> LENGTH: 453
<212> TYPE: PRT
<213> ORGANISM: Homo sapiens

<400> SEQUENCE: 1

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
        35                  40                  45

Arg Ser Met Val Glu Val Leu Ala Asp His Pro Gly Glu Leu Val Arg
    50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110
```

```
Tyr Ser Ala Glu Leu Arg Asn Ala Thr Ala Ala Met Lys Asn Gln Val
        115                 120                 125

Ala Arg Phe Asn Asp Leu Arg Phe Val Gly Arg Ser Gly Arg Gly Lys
130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Arg His Arg Gln Lys Leu Asp Asp Gln Thr Lys Pro Gly Ser Leu
            180                 185                 190

Ser Phe Ser Glu Arg Leu Ser Glu Leu Glu Gln Leu Arg Arg Thr Ala
        195                 200                 205

Met Arg Val Ser Pro His His Pro Ala Pro Thr Pro Asn Pro Arg Ala
210                 215                 220

Ser Leu Asn His Ser Thr Ala Phe Asn Pro Gln Pro Gln Ser Gln Met
225                 230                 235                 240

Gln Asp Thr Arg Gln Ile Gln Pro Ser Pro Pro Trp Ser Tyr Asp Gln
                245                 250                 255

Ser Tyr Gln Tyr Leu Gly Ser Ile Ala Ser Pro Ser Val His Pro Ala
            260                 265                 270

Thr Pro Ile Ser Pro Gly Arg Ala Ser Gly Met Thr Thr Leu Ser Ala
        275                 280                 285

Glu Leu Ser Ser Arg Leu Ser Thr Ala Pro Asp Leu Thr Ala Phe Ser
    290                 295                 300

Asp Pro Arg Gln Phe Pro Ala Leu Pro Ser Ile Ser Asp Pro Arg Met
305                 310                 315                 320

His Tyr Pro Gly Ala Phe Thr Tyr Ser Pro Thr Pro Val Thr Ser Gly
                325                 330                 335

Ile Gly Ile Gly Met Ser Ala Met Gly Ser Ala Thr Arg Tyr His Thr
            340                 345                 350

Tyr Leu Pro Pro Pro Tyr Pro Gly Ser Ser Gln Ala Gln Gly Gly Pro
        355                 360                 365

Phe Gln Ala Ser Ser Pro Ser Tyr His Leu Tyr Tyr Gly Ala Ser Ala
    370                 375                 380

Gly Ser Tyr Gln Phe Ser Met Val Gly Gly Glu Arg Ser Pro Pro Arg
385                 390                 395                 400

Ile Leu Pro Pro Cys Thr Asn Ala Ser Thr Gly Ser Ala Leu Leu Asn
                405                 410                 415

Pro Ser Leu Pro Asn Gln Ser Asp Val Val Glu Ala Glu Gly Ser His
            420                 425                 430

Ser Asn Ser Pro Thr Asn Met Ala Pro Ser Ala Arg Leu Glu Glu Ala
        435                 440                 445

Val Trp Arg Pro Tyr
    450

<210> SEQ ID NO 2
<211> LENGTH: 472
<212> TYPE: PRT
<213> ORGANISM: Homo sapiens

<400> SEQUENCE: 2

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
```

-continued

```
                    20                  25                  30
Ala Pro Asp Ala Gly Ala Ala Leu Ala Gly Lys Leu Arg Ser Gly Asp
            35                  40                  45

Arg Ser Met Val Glu Val Leu Ala Asp His Pro Gly Glu Leu Val Arg
50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
            85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
            115                 120                 125

Ala Arg Phe Asn Asp Leu Arg Phe Val Gly Arg Ser Gly Arg Gly Lys
            130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
            165                 170                 175

Arg Arg His Arg Gln Lys Leu Asp Asp Gln Thr Lys Pro Gly Ser Leu
            180                 185                 190

Ser Phe Ser Glu Arg Leu Ser Glu Leu Glu Gln Leu Arg Arg Thr Ala
            195                 200                 205

Met Arg Val Ser Pro His His Pro Ala Pro Thr Pro Asn Pro Arg Ala
            210                 215                 220

Ser Leu Asn His Ser Thr Ala Phe Asn Pro Gln Pro Gln Ser Gln Met
225                 230                 235                 240

Gln Asp Thr Arg Gln Ile Gln Pro Ser Pro Pro Trp Ser Tyr Asp Gln
            245                 250                 255

Ser Tyr Gln Tyr Leu Gly Ser Ile Ala Ser Pro Ser Val His Pro Ala
            260                 265                 270

Thr Pro Ile Ser Pro Gly Arg Ala Ser Gly Met Thr Thr Leu Ser Ala
            275                 280                 285

Glu Leu Ser Ser Arg Leu Ser Thr Ala Pro Asp Leu Thr Ala Phe Ser
            290                 295                 300

Asp Pro Arg Gln Phe Pro Ala Leu Pro Ser Ile Ser Asp Pro Arg Met
305                 310                 315                 320

His Tyr Pro Gly Ala Phe Thr Tyr Ser Pro Thr Pro Val Thr Ser Gly
            325                 330                 335

Ile Gly Ile Gly Met Ser Ala Met Gly Ser Ala Thr Arg Tyr His Thr
            340                 345                 350

Tyr Leu Pro Pro Pro Tyr Pro Gly Ser Ser Gln Ala Gln Gly Gly Pro
            355                 360                 365

Phe Gln Ala Ser Ser Pro Ser Tyr His Leu Tyr Tyr Gly Ala Ser Ala
            370                 375                 380

Gly Ser Tyr Gln Phe Ser Met Val Gly Gly Glu Arg Ser Pro Pro Arg
385                 390                 395                 400

Ile Leu Pro Pro Cys Thr Asn Ala Ser Thr Gly Ser Ala Leu Leu Asn
            405                 410                 415

Pro Ser Leu Pro Asn Gln Ser Asp Val Val Glu Ala Glu Gly Ser His
            420                 425                 430

Ser Asn Ser Pro Thr Asn Met Gly Gly Ala Ser Cys Ser Arg Gln Ala
            435                 440                 445
```

Arg Arg Asp Pro Gly Pro Trp Ala Arg Thr Pro Ser Trp Gly Arg Gly
            450                 455                 460

Arg Pro Thr Asp Arg Ile Ser Leu
465                 470

<210> SEQ ID NO 3
<211> LENGTH: 250
<212> TYPE: PRT
<213> ORGANISM: Homo sapiens

<400> SEQUENCE: 3

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
        35                  40                  45

Arg Ser Met Val Glu Val Leu Ala Asp His Pro Gly Glu Leu Val Arg
    50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
        115                 120                 125

Ala Arg Phe Asn Asp Leu Arg Phe Val Gly Arg Ser Gly Arg Gly Lys
    130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Arg His Arg Gln Lys Leu Asp Asp Gln Thr Lys Pro Gly Ser Leu
            180                 185                 190

Ser Phe Ser Glu Arg Leu Ser Glu Leu Glu Gln Leu Arg Arg Thr Ala
        195                 200                 205

Met Arg Val Ser Pro His His Pro Ala Pro Thr Pro Asn Pro Arg Ala
    210                 215                 220

Ser Leu Asn His Ser Thr Ala Phe Asn Pro Gln Pro Gln Ser Gln Met
225                 230                 235                 240

Gln Glu Glu Asp Thr Ala Pro Trp Arg Cys
                245                 250

<210> SEQ ID NO 4
<211> LENGTH: 257
<212> TYPE: PRT
<213> ORGANISM: Homo sapiens

<400> SEQUENCE: 4

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
        35                  40                  45

```
Arg Ser Met Val Glu Val Leu Ala Asp His Pro Gly Glu Leu Val Arg
    50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
                100                 105                 110

Tyr Ser Ala Glu Leu Arg Asn Ala Thr Ala Ala Met Lys Asn Gln Val
                115                 120                 125

Ala Arg Phe Asn Asp Leu Arg Phe Val Gly Arg Ser Gly Arg Gly Lys
            130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Arg His Arg Gln Lys Leu Asp Asp Gln Thr Lys Pro Gly Ser Leu
                180                 185                 190

Ser Phe Ser Glu Arg Leu Ser Glu Leu Glu Gln Leu Arg Arg Thr Ala
            195                 200                 205

Met Arg Val Ser Pro His His Pro Ala Pro Thr Pro Asn Pro Arg Ala
    210                 215                 220

Ser Leu Asn His Ser Thr Ala Phe Asn Pro Gln Pro Gln Ser Gln Met
225                 230                 235                 240

Gln Asp Thr Arg Gln Ile Gln Pro Ser Pro Pro Trp Ser Tyr Asp Gln
                245                 250                 255

Ser

<210> SEQ ID NO 5
<211> LENGTH: 224
<212> TYPE: PRT
<213> ORGANISM: Homo sapiens

<400> SEQUENCE: 5

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
                20                  25                  30

Ala Pro Asp Ala Gly Ala Ala Leu Ala Gly Lys Leu Arg Ser Gly Asp
            35                  40                  45

Arg Ser Met Val Glu Val Leu Ala Asp His Pro Gly Glu Leu Val Arg
    50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
                100                 105                 110

Tyr Ser Ala Glu Leu Arg Asn Ala Thr Ala Ala Met Lys Asn Gln Val
                115                 120                 125

Ala Arg Phe Asn Asp Leu Arg Phe Val Gly Arg Ser Gly Arg Gly Lys
            130                 135                 140

Ser Phe Thr Leu Thr Ile Thr Val Phe Thr Asn Pro Pro Gln Val Ala
145                 150                 155                 160
```

Thr Tyr His Arg Ala Ile Lys Ile Thr Val Asp Gly Pro Arg Glu Pro
                165                 170                 175

Arg Ser Lys Cys Ile His Leu Gly Leu Val His Pro Pro Gly Trp Tyr
            180                 185                 190

Thr Leu Gln Ala Gly Ile Leu Arg Asp His Val Ser Asp Ser Leu Gly
        195                 200                 205

Ser Thr Phe Pro Pro Gly Gly Trp Gln Ala Pro Val Lys Pro Lys Ser
    210                 215                 220

<210> SEQ ID NO 6
<211> LENGTH: 188
<212> TYPE: PRT
<213> ORGANISM: Homo sapiens

<400> SEQUENCE: 6

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
        35                  40                  45

Arg Ser Met Val Glu Val Leu Ala Asp His Pro Gly Glu Leu Val Arg
    50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
        115                 120                 125

Ala Arg Phe Asn Asp Leu Arg Phe Val Gly Arg Ser Gly Arg Gly Lys
    130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Asn Ser Leu Thr Trp Pro Arg Tyr Pro His Ile
            180                 185

<210> SEQ ID NO 7
<211> LENGTH: 242
<212> TYPE: PRT
<213> ORGANISM: Homo sapiens

<400> SEQUENCE: 7

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
        35                  40                  45

Arg Ser Met Val Glu Val Leu Ala Asp His Pro Gly Glu Leu Val Arg
    50                  55                  60

Thr Asp Ser Pro Asn Phe Leu Cys Ser Val Leu Pro Thr His Trp Arg
65                  70                  75                  80

```
Cys Asn Lys Thr Leu Pro Ile Ala Phe Lys Val Val Ala Leu Gly Asp
                85                  90                  95
Val Pro Asp Gly Thr Leu Val Thr Val Met Ala Gly Asn Asp Glu Asn
            100                 105                 110
Tyr Ser Ala Glu Leu Arg Asn Ala Thr Ala Ala Met Lys Asn Gln Val
        115                 120                 125
Ala Arg Phe Asn Asp Leu Arg Phe Val Asp Gly Pro Arg Glu Pro Arg
    130                 135                 140
Arg His Arg Gln Lys Leu Asp Asp Gln Thr Lys Pro Gly Ser Leu Ser
145                 150                 155                 160
Phe Ser Glu Arg Leu Ser Glu Leu Glu Gln Leu Arg Arg Thr Ala Met
                165                 170                 175
Arg Val Ser Pro His Pro Ala Pro Thr Pro Asn Pro Arg Ala Ser
            180                 185                 190
Leu Asn His Ser Thr Ala Phe Asn Pro Gln Pro Gln Ser Gln Met Gln
        195                 200                 205
Asp Thr Arg Gln Ile Gln Pro Ser Pro Pro Trp Ser Tyr Asp Gln Ser
    210                 215                 220
Tyr Gln Tyr Leu Gly Ser Ile Ala Ser Pro Ser Val His Pro Ala Thr
225                 230                 235                 240
Pro Ile

<210> SEQ ID NO 8
<211> LENGTH: 480
<212> TYPE: PRT
<213> ORGANISM: Homo sapiens

<400> SEQUENCE: 8

Met Ala Ser Asp Ser Ile Phe Glu Ser Phe Pro Ser Tyr Pro Gln Cys
1               5                   10                  15
Phe Met Arg Glu Cys Ile Leu Gly Met Asn Pro Ser Arg Asp Val His
                20                  25                  30
Asp Ala Ser Thr Ser Arg Arg Phe Thr Pro Pro Ser Thr Ala Leu Ser
            35                  40                  45
Pro Gly Lys Met Ser Glu Ala Leu Pro Leu Gly Ala Pro Asp Ala Gly
        50                  55                  60
Ala Ala Leu Ala Gly Lys Leu Arg Ser Gly Asp Arg Ser Met Val Glu
65                  70                  75                  80
Val Leu Ala Asp His Pro Gly Glu Leu Val Arg Thr Asp Ser Pro Asn
                85                  90                  95
Phe Leu Cys Ser Val Leu Pro Thr His Trp Arg Cys Asn Lys Thr Leu
            100                 105                 110
Pro Ile Ala Phe Lys Val Val Ala Leu Gly Asp Val Pro Asp Gly Thr
        115                 120                 125
Leu Val Thr Val Met Ala Gly Asn Asp Glu Asn Tyr Ser Ala Glu Leu
    130                 135                 140
Arg Asn Ala Thr Ala Ala Met Lys Asn Gln Val Ala Arg Phe Asn Asp
145                 150                 155                 160
Leu Arg Phe Val Gly Arg Ser Gly Arg Gly Lys Ser Phe Thr Leu Thr
                165                 170                 175
Ile Thr Val Phe Thr Asn Pro Pro Gln Val Ala Thr Tyr His Arg Ala
            180                 185                 190
Ile Lys Ile Thr Val Asp Gly Pro Arg Glu Pro Arg Arg His Arg Gln
        195                 200                 205
```

-continued

Lys Leu Asp Asp Gln Thr Lys Pro Gly Ser Leu Ser Phe Ser Glu Arg
            210                 215                 220

Leu Ser Glu Leu Glu Gln Leu Arg Arg Thr Ala Met Arg Val Ser Pro
225                 230                 235                 240

His His Pro Ala Pro Thr Pro Asn Pro Arg Ala Ser Leu Asn His Ser
                245                 250                 255

Thr Ala Phe Asn Pro Gln Pro Gln Ser Gln Met Gln Asp Thr Arg Gln
            260                 265                 270

Ile Gln Pro Ser Pro Pro Trp Ser Tyr Asp Gln Ser Tyr Gln Tyr Leu
            275                 280                 285

Gly Ser Ile Ala Ser Pro Ser Val His Pro Ala Thr Pro Ile Ser Pro
        290                 295                 300

Gly Arg Ala Ser Gly Met Thr Thr Leu Ser Ala Glu Leu Ser Ser Arg
305                 310                 315                 320

Leu Ser Thr Ala Pro Asp Leu Thr Ala Phe Ser Asp Pro Arg Gln Phe
                325                 330                 335

Pro Ala Leu Pro Ser Ile Ser Asp Pro Arg Met His Tyr Pro Gly Ala
            340                 345                 350

Phe Thr Tyr Ser Pro Thr Pro Val Thr Ser Gly Ile Gly Ile Gly Met
            355                 360                 365

Ser Ala Met Gly Ser Ala Thr Arg Tyr His Thr Tyr Leu Pro Pro Pro
370                 375                 380

Tyr Pro Gly Ser Ser Gln Ala Gln Gly Gly Pro Phe Gln Ala Ser Ser
385                 390                 395                 400

Pro Ser Tyr His Leu Tyr Gly Ala Ser Ala Gly Ser Tyr Gln Phe
                405                 410                 415

Ser Met Val Gly Gly Glu Arg Ser Pro Pro Arg Ile Leu Pro Pro Cys
            420                 425                 430

Thr Asn Ala Ser Thr Gly Ser Ala Leu Leu Asn Pro Ser Leu Pro Asn
            435                 440                 445

Gln Ser Asp Val Val Glu Ala Glu Gly Ser His Ser Asn Ser Pro Thr
        450                 455                 460

Asn Met Ala Pro Ser Ala Arg Leu Glu Glu Ala Val Trp Arg Pro Tyr
465                 470                 475                 480

<210> SEQ ID NO 9
<211> LENGTH: 456
<212> TYPE: PRT
<213> ORGANISM: Homo sapiens

<400> SEQUENCE: 9

Met Asn Pro Ser Arg Asp Val His Asp Ala Ser Thr Ser Arg Arg Phe
1               5                   10                  15

Thr Pro Pro Ser Thr Ala Leu Ser Pro Gly Lys Met Ser Glu Ala Leu
            20                  25                  30

Pro Leu Gly Ala Pro Asp Ala Gly Ala Ala Leu Ala Gly Lys Leu Arg
        35                  40                  45

Ser Gly Asp Arg Ser Met Val Glu Val Leu Ala Asp His Pro Gly Glu
    50                  55                  60

Leu Val Arg Thr Asp Ser Pro Asn Phe Leu Cys Ser Val Leu Pro Thr
65                  70                  75                  80

His Trp Arg Cys Asn Lys Thr Leu Pro Ile Ala Phe Lys Val Val Ala
                85                  90                  95

Leu Gly Asp Val Pro Asp Gly Thr Leu Val Thr Val Met Ala Gly Asn

```
            100                 105                 110
Asp Glu Asn Tyr Ser Ala Glu Leu Arg Asn Ala Thr Ala Ala Met Lys
        115                 120                 125

Asn Gln Val Ala Arg Phe Asn Asp Leu Arg Phe Val Gly Arg Ser Gly
    130                 135                 140

Arg Gly Lys Ser Phe Thr Leu Thr Ile Thr Val Phe Thr Asn Pro Pro
145                 150                 155                 160

Gln Val Ala Thr Tyr His Arg Ala Ile Lys Ile Thr Val Asp Gly Pro
                165                 170                 175

Arg Glu Pro Arg Arg His Arg Gln Lys Leu Asp Asp Gln Thr Lys Pro
            180                 185                 190

Gly Ser Leu Ser Phe Ser Glu Arg Leu Ser Glu Leu Glu Gln Leu Arg
        195                 200                 205

Arg Thr Ala Met Arg Val Ser Pro His Pro Ala Pro Thr Pro Asn
    210                 215                 220

Pro Arg Ala Ser Leu Asn His Ser Thr Ala Phe Asn Pro Gln Pro Gln
225                 230                 235                 240

Ser Gln Met Gln Asp Thr Arg Gln Ile Gln Pro Ser Pro Pro Trp Ser
                245                 250                 255

Tyr Asp Gln Ser Tyr Gln Tyr Leu Gly Ser Ile Ala Ser Pro Ser Val
            260                 265                 270

His Pro Ala Thr Pro Ile Ser Pro Gly Arg Ala Ser Gly Met Thr Thr
        275                 280                 285

Leu Ser Ala Glu Leu Ser Ser Arg Leu Ser Thr Ala Pro Asp Leu Thr
    290                 295                 300

Ala Phe Ser Asp Pro Arg Gln Phe Pro Ala Leu Pro Ser Ile Ser Asp
305                 310                 315                 320

Pro Arg Met His Tyr Pro Gly Ala Phe Thr Tyr Ser Pro Thr Pro Val
                325                 330                 335

Thr Ser Gly Ile Gly Ile Gly Met Ser Ala Met Gly Ser Ala Thr Arg
            340                 345                 350

Tyr His Thr Tyr Leu Pro Pro Pro Tyr Pro Gly Ser Ser Gln Ala Gln
        355                 360                 365

Gly Gly Pro Phe Gln Ala Ser Ser Pro Ser Tyr His Leu Tyr Tyr Gly
    370                 375                 380

Ala Ser Ala Gly Ser Tyr Gln Phe Ser Met Val Gly Gly Glu Arg Ser
385                 390                 395                 400

Pro Pro Arg Ile Leu Pro Pro Cys Thr Asn Ala Ser Thr Gly Ser Ala
                405                 410                 415

Leu Leu Asn Pro Ser Leu Pro Asn Gln Ser Asp Val Val Glu Ala Glu
            420                 425                 430

Gly Ser His Ser Asn Ser Pro Thr Asn Met Ala Pro Ser Ala Arg Leu
        435                 440                 445

Glu Glu Ala Val Trp Arg Pro Tyr
    450                 455

<210> SEQ ID NO 10
<211> LENGTH: 468
<212> TYPE: PRT
<213> ORGANISM: Homo sapiens

<400> SEQUENCE: 10

Met Pro Ala Ala Pro Arg Gly Pro Ala Gln Gly Glu Ala Ala Ala Arg
1               5                   10                  15
```

Thr Arg Ser Arg Asp Ala Ser Thr Ser Arg Arg Phe Thr Pro Pro Ser
            20                  25                  30

Thr Ala Leu Ser Pro Gly Lys Met Ser Glu Ala Leu Pro Leu Gly Ala
        35                  40                  45

Pro Asp Ala Gly Ala Ala Leu Ala Gly Lys Leu Arg Ser Gly Asp Arg
    50                  55                  60

Ser Met Val Glu Val Leu Ala Asp His Pro Gly Glu Leu Val Arg Thr
65                  70                  75                  80

Asp Ser Pro Asn Phe Leu Cys Ser Val Leu Pro Thr His Trp Arg Cys
                85                  90                  95

Asn Lys Thr Leu Pro Ile Ala Phe Lys Val Val Ala Leu Gly Asp Val
            100                 105                 110

Pro Asp Gly Thr Leu Val Thr Val Met Ala Gly Asn Asp Glu Asn Tyr
        115                 120                 125

Ser Ala Glu Leu Arg Asn Ala Thr Ala Met Lys Asn Gln Val Ala
    130                 135                 140

Arg Phe Asn Asp Leu Arg Phe Val Gly Arg Ser Gly Arg Gly Lys Ser
145                 150                 155                 160

Phe Thr Leu Thr Ile Thr Val Phe Thr Asn Pro Pro Gln Val Ala Thr
                165                 170                 175

Tyr His Arg Ala Ile Lys Ile Thr Val Asp Gly Pro Arg Glu Pro Arg
            180                 185                 190

Arg His Arg Gln Lys Leu Asp Asp Gln Thr Lys Pro Gly Ser Leu Ser
        195                 200                 205

Phe Ser Glu Arg Leu Ser Glu Leu Glu Gln Leu Arg Arg Thr Ala Met
210                 215                 220

Arg Val Ser Pro His His Pro Ala Pro Thr Pro Asn Pro Arg Ala Ser
225                 230                 235                 240

Leu Asn His Ser Thr Ala Phe Asn Pro Gln Pro Gln Ser Gln Met Gln
                245                 250                 255

Asp Thr Arg Gln Ile Gln Pro Ser Pro Pro Trp Ser Tyr Asp Gln Ser
            260                 265                 270

Tyr Gln Tyr Leu Gly Ser Ile Ala Ser Pro Ser Val His Pro Ala Thr
        275                 280                 285

Pro Ile Ser Pro Gly Arg Ala Ser Gly Met Thr Thr Leu Ser Ala Glu
290                 295                 300

Leu Ser Ser Arg Leu Ser Thr Ala Pro Asp Leu Thr Ala Phe Ser Asp
305                 310                 315                 320

Pro Arg Gln Phe Pro Ala Leu Pro Ser Ile Ser Asp Pro Arg Met His
                325                 330                 335

Tyr Pro Gly Ala Phe Thr Tyr Ser Pro Thr Pro Val Thr Ser Gly Ile
            340                 345                 350

Gly Ile Gly Met Ser Ala Met Gly Ser Ala Thr Arg Tyr His Thr Tyr
        355                 360                 365

Leu Pro Pro Pro Tyr Pro Gly Ser Ser Gln Ala Gln Gly Gly Pro Phe
370                 375                 380

Gln Ala Ser Ser Pro Ser Tyr His Leu Tyr Tyr Gly Ala Ser Ala Gly
385                 390                 395                 400

Ser Tyr Gln Phe Ser Met Val Gly Gly Glu Arg Ser Pro Pro Arg Ile
                405                 410                 415

Leu Pro Pro Cys Thr Asn Ala Ser Thr Gly Ser Ala Leu Leu Asn Pro
            420                 425                 430

Ser Leu Pro Asn Gln Ser Asp Val Val Glu Ala Glu Gly Ser His Ser

```
                435                 440                 445
Asn Ser Pro Thr Asn Met Ala Pro Ser Ala Arg Leu Glu Glu Ala Val
    450                 455                 460
Trp Arg Pro Tyr
465

<210> SEQ ID NO 11
<211> LENGTH: 348
<212> TYPE: PRT
<213> ORGANISM: Homo sapiens

<400> SEQUENCE: 11

Met Ala Gly Asn Asp Glu Asn Tyr Ser Ala Glu Leu Arg Asn Ala Thr
1               5                   10                  15

Ala Ala Met Lys Asn Gln Val Ala Arg Phe Asn Asp Leu Arg Phe Val
            20                  25                  30

Gly Arg Ser Gly Arg Gly Lys Ser Phe Thr Leu Thr Ile Thr Val Phe
        35                  40                  45

Thr Asn Pro Pro Gln Val Ala Thr Tyr His Arg Ala Ile Lys Ile Thr
    50                  55                  60

Val Asp Gly Pro Arg Glu Pro Arg Arg His Arg Gln Lys Leu Asp Asp
65                  70                  75                  80

Gln Thr Lys Pro Gly Ser Leu Ser Phe Ser Glu Arg Leu Ser Glu Leu
                85                  90                  95

Glu Gln Leu Arg Arg Thr Ala Met Arg Val Ser Pro His His Pro Ala
            100                 105                 110

Pro Thr Pro Asn Pro Arg Ala Ser Leu Asn His Ser Thr Ala Phe Asn
        115                 120                 125

Pro Gln Pro Gln Ser Gln Met Gln Asp Thr Arg Gln Ile Gln Pro Ser
    130                 135                 140

Pro Pro Trp Ser Tyr Asp Gln Ser Tyr Gln Tyr Leu Gly Ser Ile Ala
145                 150                 155                 160

Ser Pro Ser Val His Pro Ala Thr Pro Ile Ser Pro Gly Arg Ala Ser
                165                 170                 175

Gly Met Thr Thr Leu Ser Ala Glu Leu Ser Ser Arg Leu Ser Thr Ala
            180                 185                 190

Pro Asp Leu Thr Ala Phe Ser Asp Pro Arg Gln Phe Pro Ala Leu Pro
        195                 200                 205

Ser Ile Ser Asp Pro Arg Met His Tyr Pro Gly Ala Phe Thr Tyr Ser
    210                 215                 220

Pro Thr Pro Val Thr Ser Gly Ile Gly Ile Gly Met Ser Ala Met Gly
225                 230                 235                 240

Ser Ala Thr Arg Tyr His Thr Tyr Leu Pro Pro Tyr Pro Gly Ser
                245                 250                 255

Ser Gln Ala Gln Gly Gly Pro Phe Gln Ala Ser Ser Pro Ser Tyr His
            260                 265                 270

Leu Tyr Tyr Gly Ala Ser Ala Gly Ser Tyr Gln Phe Ser Met Val Gly
        275                 280                 285

Gly Glu Arg Ser Pro Pro Arg Ile Leu Pro Pro Cys Thr Asn Ala Ser
    290                 295                 300

Thr Gly Ser Ala Leu Leu Asn Pro Ser Leu Pro Asn Gln Ser Asp Val
305                 310                 315                 320

Val Glu Ala Glu Gly Ser His Ser Asn Ser Pro Thr Asn Met Ala Pro
                325                 330                 335
```

Ser Ala Arg Leu Glu Glu Ala Val Trp Arg Pro Tyr
        340                 345

<210> SEQ ID NO 12
<211> LENGTH: 7274
<212> TYPE: DNA
<213> ORGANISM: Artificial Sequence
<220> FEATURE:
<223> OTHER INFORMATION: RUNX1 cDNA Sequence

<400> SEQUENCE: 12

| | | | | | |
|---|---|---|---|---|---|
| catagagcca | gcgggcgcgg | gcgggacggg | cgccccgcgg | ccggacccag | ccagggcacc | 60 |
| acgctgcccg | gccctgcgcc | gccaggcact | tctttccggg | gctcctaggg | acgccagaag | 120 |
| gaagtcaacc | tctgctgctt | ctccttggcc | tgcgttggac | cttcctttt | ttgttgtttt | 180 |
| ttttgtttt | tccccttct | tccttttgaa | ttaactggct | tcttggctgg | atgttttcaa | 240 |
| cttctttcct | ggctgcgaac | ttttccccaa | ttgttttcct | tttacaacag | ggggagaaag | 300 |
| tgctctgtgg | tccgaggcga | gccgtgaagt | tgcgtgtgcg | tggcagtgtg | cgtggcagga | 360 |
| tgtgcgtgcg | tgtgtaaccc | gagccgcccg | atctgtttcg | atctgcgccg | cggagccctc | 420 |
| cctcaaggcc | cgctccacct | gctgcggtta | cgcggcgctc | gtgggtgttc | gtgcctcgga | 480 |
| gcagctaacc | ggcgggtgct | gggcgacggt | ggaggagtat | cgtctcgctg | ctgcccgagt | 540 |
| cagggctgag | tcacccagct | gatgtagaca | gtggctgcct | tccgaagagt | gcgtgtttgc | 600 |
| atgtgtgtga | ctctgcggct | gctcaactcc | caacaaacca | gaggaccagc | acaaacttaa | 660 |
| accaacatcc | ccaaacccga | gttcacagat | gtgggagagc | tgtagaaccc | tgagtgtcat | 720 |
| cgactgggcc | ttcttatgat | tgttgtttta | agattagctg | aagatctctg | aaacgctgaa | 780 |
| ttttctgcac | tgagcgtttt | gacagaattc | attgagagaa | cagagaacat | gacaagtact | 840 |
| tctagctcag | cactgctcca | actactgaag | ctgattttca | aggctactta | aaaaaatctg | 900 |
| cagcgtacat | taatggattt | ctgttgtgtt | taaattctcc | acagattgta | ttgtaaatat | 960 |
| tttatgaagt | agagcatatg | tatatattta | tatatacgtg | cacatacatt | agtagcacta | 1020 |
| cctttggaag | tctcagctct | tgcttttcgg | gactgaagcc | agttttgcat | gataaaagtg | 1080 |
| gccttgttac | gggagataat | tgtgttctgt | tgggacttta | gacaaaactc | acctgcaaaa | 1140 |
| aactgacagg | cattaactac | tggaacttcc | aaataatgtg | tttgctgatc | gttttactct | 1200 |
| tcgcataaat | attttaggaa | gtgtatgaga | attttgcctt | caggaacttt | tctaacagcc | 1260 |
| aaagacagaa | cttaacctct | gcaagcaaga | ttcgtggaag | atagtctcca | cttttaatg | 1320 |
| cactaagcaa | tcggttgcta | ggagcccatc | ctgggtcaga | ggccgatccg | cagaaccaga | 1380 |
| acgttttccc | ctcctggact | gttagtaact | tagtctccct | cctcccctaa | ccaccccgc | 1440 |
| ccccccccac | ccccccgcagt | aataaaggcc | cctgaacgtg | tatgttggtc | tcccgggagc | 1500 |
| tgcttgctga | agatccgcgc | ccctgtcgcc | gtctggtagg | agctgtttgc | agggtcctaa | 1560 |
| ctcaatcggc | ttgttgtgat | gcgtatcccc | gtagatgcca | gcacgagccg | ccgcttcacg | 1620 |
| ccgccttcca | ccgcgctgag | cccaggcaag | atgagcgagg | cgttgccgct | gggcgccccg | 1680 |
| gacgccggcg | ctgccctggc | cggcaagctg | aggagcggcg | accgcagcat | ggtggaggtg | 1740 |
| ctggccgacc | acccgggcga | gctggtgcgc | accgacagcc | ccaacttcct | ctgctccgtg | 1800 |
| ctgcctacgc | actggcgctg | caacaagacc | ctgcccatcg | ctttcaaggt | ggtggcccta | 1860 |
| ggggatgttc | cagatggcac | tctggtcact | gtgatggctg | gcaatgatga | aaactactcg | 1920 |
| gctgagctga | gaaatgctac | cgcagccatg | aagaaccagg | ttgcaagatt | taatgacctc | 1980 |

```
aggtttgtcg gtcgaagtgg aagagggaaa agcttcactc tgaccatcac tgtcttcaca    2040
aacccaccgc aagtcgccac ctaccacaga gccatcaaaa tcacagtgga tgggccccga    2100
gaacctcgaa gacatcggca gaaactagat gatcagacca agcccgggag cttgtccttt    2160
tccgagcggt tcagtgaact ggagcagctg cggcgcacag ccatgagggt cagcccacac    2220
cacccagccc ccacgcccaa ccctcgtgcc tccctgaacc actccactgc ctttaaccct    2280
cagcctcaga gtcagatgca ggatacaagg cagatccaac catccccacc gtggtcctac    2340
gatcagtcct accaatacct gggatccatt gcctctcctt ctgtgcaccc agcaacgccc    2400
atttcacctg gacgtgccag cggcatgaca accctctctg cagaactttc cagtcgactc    2460
tcaacggcac ccgacctgac agcgttcagc gacccgcgcc agttcccccgc gctgccctcc   2520 atctccgacc cccgcatgca ctatccaggc gccttcacct actccccgac gccggtcacc    2580
tcgggcatcg gcatcggcat gtcggccatg ggctcggcca cgcgctacca cacctacctg    2640
ccgccgccct accccggctc gtcgcaagcg cagggaggcc cgttccaagc cagctcgccc    2700
tcctaccacc tgtactacgg cgcctcggcc ggctcctacc agttctccat ggtgggcggc    2760
gagcgctcgc cgccgcgcat cctgccgccc tgcaccaacg cctccaccgg ctccgcgctg    2820 ctcaaccccca gcctccgaa ccagagcgac gtggtggagg ccgagggcag ccacagcaac    2880 tccccccacca acatggcgcc ctccgcgcgc ctggaggagg ccgtgtggag gccctactga   2940
ggcgccaggc ctggcccggc tgggccccgc gggccgccgc cttcgcctcc gggcgcgcgg    3000
gcctcctgtt cgcgacaagc ccgccgggat cccgggccct gggcccggcc accgtcctgg    3060
ggccgagggc gcccgacggc caggatctcg ctgtaggtca ggcccgcgca gcctcctgcg    3120
cccagaagcc cacgccgccg ccgtctgctg gcgccccggc cctcgcggag gtgtccgagg    3180
cgacgcacct cgagggtgtc cgccggcccc agcacccagg ggacgcgctg gaaagcaaac    3240
aggaagattc ccggagggaa actgtgaatg cttctgattt agcaatgctg tgaataaaaa    3300
gaaagatttt atacccttga cttaactttt taaccaagtt gtttattcca aagagtgtgg    3360 aatttttggtt ggggtggggg gagaggaggg atgcaactcg ccctgtttgg catctaattc    3420 ttattttaa tttttccgca ccttatcaat tgcaaaatgc gtatttgcat ttgggtggtt     3480 tttatttta tatacgttta tataaatata tataaattga gcttgcttct ttcttgcttt     3540
gaccatggaa agaaatatga ttccttttc tttaagtttt atttaacttt tcttttggac    3600
ttttgggtag ttgttttttt tgttttgtt ttgtttttt gagaaacagc tacagctttg      3660
ggtcattttt aactactgta ttcccacaag gaatccccag atatttatgt atcttgatgt    3720
tcagacattt atgtgttgat aattttttaa ttatttaaat gtacttatat taagaaaaat    3780
atcaagtact acattttctt ttgttcttga tagtagccaa agttaaatgt atcacattga    3840
agaaggctag aaaaaagaa tgagtaatgt gatcgcttgg ttatccagaa gtattgttta    3900
cattaaactc cctttcatgt taatcaaaca agtgagtagc tcacgcagca acgttttaa     3960 taggattttt agacactgag ggtcactcca aggatcagaa gtatggaatt ttctgccagg    4020
ctcaacaagg gtctcatatc taacttcctc cttaaaacag agaaggtcaa tctagttcca    4080
gagggttgag gcaggtgcca ataattacat ctttggagag gatttgattt ctgcccaggg    4140
atttgctcac cccaaggtca tctgataatt tcacagatgc tgtgtaacag aacacagcca    4200
aagtaaactg tgtaggggag ccacatttac ataggaacca aatcaatgaa tttaggggtt    4260
acgattatag caatttaagg gcccaccaga agcaggcctc gaggagtcaa tttgcctctg    4320
tgtgcctcag tggagacaag tgggaaaaca tggtcccacc tgtgcgagac cccctgtcct    4380
```

```
gtgctgctca ctcaacaaca tctttgtgtt gctttcacca ggctgagacc ctaccctatg    4440
gggtatatgg gcttttacct gtgcaccagt gtgacaggaa agattcatgt cactactgtc    4500
cgtggctaca attcaaaggt atccaatgtc gctgtaaatt ttatggcact attttttattg   4560 gaggatttgg tcagaatgca gttgttgtac aactcataaa tactaactgc tgattttgac    4620
acatgtgtgc tccaaatgat ctggtggtta tttaacgtac ctcttaaaat tcgttgaaac    4680
gatttcaggt caactctgaa gagtatttga aagcaggact tcagaacagt gtttgatttt    4740
tattttataa atttaagcat tcaaattagg caaatctttg gctgcaggca gcaaaaacag    4800
ctggacttat ttaaaacaac ttgttttttga gttttcttat atatatattg attatttgtt    4860
ttacacacat gcagtagcac tttggtaaga gttaaagagt aaagcagctt atgttgtcag    4920
gtcgttctta tctagagaag agctatagca gatctcggac aaactcagaa tatattcact    4980 ttcattttg acaggattcc ctccacaact cagtttcata tattattccg tattacattt      5040
ttgcagctaa attaccataa aatgtcagca aatgtaaaaa tttaatttct gaaaagcacc    5100
attagcccat ttcccccaaa ttaaacgtaa atgtttttt tcagcacatg ttaccatgtc      5160
tgacctgcaa aaatgctgga gaaaatgaa ggaaaaaatt atgttttca gtttaattct       5220 gttaactgaa gatattccaa ctcaaaacca gcctcatgct ctgattagat aatcttttac    5280
attgaacctt tactctcaaa gccatgtgtg gagggggctt gtcactattg taggctcact    5340
ggattggtca tttagagttt cacagactct taccagcata tatagtattt aattgtttca    5400
aaaaaaatca aactgtagtt gttttggcga taggtctcac gcaacacatt tttgtatgtg    5460
tgtgtgtgtg cgtgtgtgtg tgtgtgtgtg aaaaattgca ttcattgact tcaggtagat    5520
taaggtatct ttttattcat tgccctcagg aaagttaagg tatcaatgag acccttaagc    5580
caatcatgta ataactgcat gtgtctggtc caggagaagt attgaataag ccatttctac    5640
tgcttactca tgtccctatt tatgatttca acatggatac atatttcagt tctttctttt    5700
tctcactatc tgaaaataca tttccctccc tctcttcccc ccaatatctc ccttttttc     5760 tctcttcctc tatcttccaa accccacttt ctccctcctc cttttcctgt gttctcttaa    5820
gcagatagca catacccca cccagtacca aatttcagaa cacaagaagg tccagttctt     5880
cccccttcac ataaaggaac atggtttgtc agcctttctc ctgtttatgg gtttcttcca    5940
gcagaacaga gacattgcca accatattgg atctgcttgc tgtccaaacc agcaaacttt    6000
cctgggcaaa tcacaatcag tgagtaaata gacagccttt ctgctgcctt gggtttctgt    6060
gcagataaac agaaatgctc tgattagaaa ggaaatgaat ggttccactc aaatgtcctg    6120
caatttagga ttgcagattt ctgccttgaa atacctgttt ctttgggaca ttccgtcctg    6180
atgattttta ttttgttgg ttttatttt tggggggaat gacatgtttg ggtcttttat      6240
acatgaaaat ttgtttgaca ataatctcac aaaacatatt ttacatctga acaaaatgcc    6300
tttttgttta ccgtagcgta tacatttgtt ttgggatttt tgtgtgtttg ttgggaatttt   6360 tgttttagc caggtcagta ttgatgaggc tgatcatttg gctcttttt tccttccaga      6420 agagttgcat caacaaagtt aattgtattt atgtatgtaa atagatttta agcttcatta    6480
taaaatattg ttaatgccta aactttttt tcaattttt tgtgtgtgtt tctaaggact      6540
ttttcttagg tttgctaaat actgtaggga aaaaaatgct tctttctact tgtttatttt    6600
tagactttaa aatgagctac ttcttattca cttttgtaaa cagctaatag catggttcca    6660
atttttttta agttcacttt tttgttcta ggggaaatga atgtgcaaaa aagaaaaag      6720
```

```
aactgttggt tatttgtgtt attctggatg tataaaaatc aatggaaaaa aataaacttt    6780
caaattgaaa tgacggtata acacatctac tgaaaaagca acgggaaatg tggtcctatt    6840
taagccagcc cccacctagg gtctatttgt gtggcagtta ttgggtttgg tcacaaaaca    6900
tcctgaaaat tcgtgcgtgg gcttctttct ccctggtaca aacgtatgga atgcttctta    6960
aaggggaact gtcaagctgg tgtcttcagc cagatgacat gagagaatat cccagaaccc    7020
tctctccaag gtgtttctag atagcacagg agagcaggca ctgcactgtc acagtccac     7080 ggtacacagt cgggtgggcc gcctcccctc tcctgggagc attcgtcgtg cccagcctga    7140
gcagggcagc tggactgctg ctgttcagga gccaccagag ccttcctctc tttgtaccac    7200
agtttcttct gtaaatccag tgttacaatc agtgtgaatg gcaaataaac agtttgacaa    7260
gtacatacac cata                                                      7274

<210> SEQ ID NO 13
<211> LENGTH: 5967
<212> TYPE: DNA
<213> ORGANISM: Artificial Sequence
<220> FEATURE:
<223> OTHER INFORMATION: RUNX1 cDNA sequence

<400> SEQUENCE: 13
ctttgggcct cataaacaac cacagaacca caagttgggt agcctggcag tgtcagaagt      60
ctgaacccag catagtggtc agcaggcagg acgaatcaca ctgaatgcaa accacagggt     120
ttcgcagcgt ggtaaaagaa atcattgagt cccccgcctt cagaagaggg tgcattttca     180
ggaggaagcg atggcttcag acagcatatt tgagtcattt ccttcgtacc cacagtgctt     240
catgagagaa tgcatacttg aatgaatcc ttctagagac gtccacgatg ccagcacgag      300
ccgccgcttc acgccgcctt ccaccgcgct gagcccaggc aagatgagcg aggcgttgcc     360
gctgggcgcc ccggacgccg cgctgccct ggccggcaag ctgaggagcg cgaccgcag       420 catggtggag gtgctggccg accacccggg cgagctggtg cgcaccgaca gcccaactt      480 cctctgctcc gtgctgccta cgcactggcg ctgcaacaag accctgccca tcgctttcaa     540
ggtggtggcc ctaggggatg ttccagatgg cactctggtc actgtgatgg ctggcaatga     600
tgaaaactac tcggctgagc tgagaaatgc taccgcagcc atgaagaacc aggttgcaag     660
atttaatgac ctcaggtttg tcggtcgaag tggaagaggg aaaagcttca ctctgaccat     720
cactgtcttc acaaacccac cgcaagtcgc cacctaccac agagccatca aaatcacagt     780
ggatgggccc cgagaacctc gaagacatcg gcagaaacta gatgatcaga ccaagcccgg     840
gagcttgtcc ttttccgagc ggctcagtga actggagcag ctgcggcgca cagccatgag     900
ggtcagccca caccacccag cccccacgcc caacccctcgt gcctccctga ccactccac     960 tgcctttaac cctcagcctc agagtcagat gcaggataca aggcagatcc aaccatcccc    1020
accgtggtcc tacgatcagt cctaccaata cctgggatcc attgcctctc cttctgtgca    1080
cccagcaacg cccattttcac ctggacgtgc cagcggcatg acaaccctct ctgcagaact    1140
ttccagtcga ctctcaacgg cacccgacct gacagcgttc agcgaccgc gccagttccc    1200 cgcgctgccc tccatctccg accccgcat gcactatcca ggcgccttca ctactcccc    1260 gacgccggtc acctcgggca tcggcatcgg catgtcggcc atgggctcgg ccacgcgcta    1320
ccacacctac ctgcccgccg cctacccccg ctcgtcgcaa gcgcagggag gccgttcca     1380 agccagctcg ccctcctacc acctgtacta cggcgcctcg gccggctcct accagttctc    1440
catggtgggc ggcgagcgct cgccgccgcg catcctgccg ccctgcacca acgcctccac    1500
```

-continued

```
cggctccgcg ctgctcaacc ccagcctccc gaaccagagc gacgtggtgg aggccgaggg    1560
cagccacagc aactccccca ccaacatggc gccctccgcg cgcctggagg aggccgtgtg    1620
gaggccctac tgaggcgcca ggcctggccc ggctgggccc cgcgggccgc cgccttcgcc    1680
tccgggcgcg cgggcctcct gttcgcgaca agcccgccgg gatcccgggc cctgggcccg    1740
gccaccgtcc tggggccgag ggcgcccgac ggccaggatc tcgctgtagg tcaggcccgc    1800
gcagcctcct gcgcccagaa gcccacgccg ccgccgtctg ctggcgcccc ggccctcgcg    1860
gaggtgtccg aggcgacgca cctcgagggt gtccgccggc cccagcaccc aggggacgcg    1920
ctggaaagca acaggaaga ttcccggagg gaaactgtga atgcttctga tttagcaatg     1980
ctgtgaataa aagaaagat tttatacct tgacttaact ttttaaccaa gttgtttatt      2040
ccaaagagtg tggaattttg gttggggtgg gggagaggga gggatgcaac tcgccctgtt    2100
tggcatctaa ttcttatttt taattttcc gccccttatc aattgcaaaa tgcgtatttg     2160
catttgggtg gttttatttt ttatatacgt ttatataaat atatataaat tgagcttgct    2220
tctttcttgc tttgaccatg gaaagaaata tgattccctt ttctttaagt tttatttaac    2280
ttttcttttg gacttttggg tagttgtttt tttttgtttt gttttgtttt tttgagaaac    2340
agctacagct ttgggtcatt tttaactact gtattcccac aaggaatccc cagatattta    2400
tgtatcttga tgttcagaca tttatgtgtt gataatttt taattattta aatgtactta    2460
tattaagaaa aatatcaagt actacatttt cttttgttct tgatagtagc caaagttaaa    2520
tgtatcacat tgaagaaggc tagaaaaaaa gaatgagtaa tgtgatcgct tggttatcca    2580
gaagtattgt ttacattaaa ctcccttca tgttaatcaa acaagtgagt agctcacgca     2640
gcaacgtttt taataggatt tttagacact gagggtcact ccaaggatca gaagtatgga    2700
attttctgcc aggctcaaca agggtctcat atctaacttc ctccttaaaa cagagaaggt    2760
caatctagtt ccagagggtt gaggcaggtg ccaataatta catctttgga gaggatttga    2820
tttctgccca gggatttgct caccccaagg tcatctgata atttcacaga tgctgtgtaa    2880
cagaacacag ccaaagtaaa ctgtgtaggg gagccacatt tacataggaa ccaaatcaat    2940
gaatttaggg gttacgatta tagcaattta agggcccacc agaagcaggc ctcgaggagt    3000
caatttgcct ctgtgtgcct cagtggagac aagtgggaaa acatggtccc acctgtgcga    3060
gaccccctgt cctgtgctgc tcactcaaca acatctttgt gttgctttca ccaggctgag    3120
accctaccct atggggtata tgggctttta cctgtgcacc agtgtgacag gaaagattca    3180
tgtcactact gtccgtggct acaattcaaa ggtatccaat gtcgctgtaa attttatggc    3240
actattttta ttggaggatt tggtcagaat gcagttgttg tacaactcat aaatactaac    3300
tgctgatttt gacacatgtg tgctccaaat gatctggtgg ttatttaacg tacctcttaa    3360
aattcgttga aacgatttca ggtcaactct gaagagtatt tgaaagcagg acttcagaac    3420
agtgtttgat ttttatttta taaatttaag cattcaaatt aggcaaatct ttggctgcag    3480
gcagcaaaaa cagctggact tatttaaaac aacttgtttt tgagttttct tatatatata    3540
ttgattattt gttttacaca catgcagtag cactttggta agagttaaag agtaaagcag    3600
cttatgttgt caggtcgttc ttatctagag aagagctata gcagatctcg gacaaactca    3660
gaatatattc actttcattt ttgacaggat tccctccaca actcagtttc atatattatt    3720
ccgtattaca tttttgcagc taaattacca taaaatgtca gcaaatgtaa aaatttaatt    3780
tctgaaaagc accattagcc catttccccc aaattaaacg taaatgtttt ttttcagcac    3840
```

```
atgttaccat gtctgacctg caaaaatgct ggagaaaaat gaaggaaaaa attatgtttt    3900
tcagtttaat tctgttaact gaagatattc caactcaaaa ccagcctcat gctctgatta    3960
gataatcttt tacattgaac ctttactctc aaagccatgt gtggagggg cttgtcacta     4020 ttgtaggctc actggattgg tcatttagag tttcacagac tcttaccagc atatatagta    4080
tttaattgtt tcaaaaaaaa tcaaactgta gttgttttgg cgataggtct cacgcaacac    4140 attttttgtat gtgtgtgtgt gtgcgtgtgt gtgtgtgtgt gtgaaaaatt gcattcattg   4200
acttcaggta gattaaggta tcttttatt cattgccctc aggaaagtta aggtatcaat     4260 gagacccta agccaatcat gtaataactg catgtgtctg gtccaggaga agtattgaat     4320
aagccatttc tactgcttac tcatgtccct atttatgatt tcaacatgga tacatatttc    4380
agttctttct ttttctcact atctgaaaat acatttccct ccctctcttc cccccaatat    4440 ctccctttt ttctctcttc ctctatcttc caaaccccac tttctccctc ctccttttcc     4500
tgtgttctct taagcagata gcacataccc ccacccagta ccaaatttca gaacacaaga    4560
aggtccagtt cttccccctt cacataaagg aacatggttt gtcagccttt ctcctgttta    4620
tgggtttctt ccagcagaac agagacattg ccaaccatat tggatctgct tgctgtccaa    4680
accagcaaac tttcctgggc aaatcacaat cagtgagtaa atagacagcc tttctgctgc    4740
cttgggtttc tgtgcagata aacagaaatg ctctgattag aaaggaaatg aatggttcca    4800
ctcaaatgtc ctgcaattta ggattgcaga tttctgcctt gaaatacctg tttctttggg    4860
acattccgtc ctgatgattt ttatttttgt tggtttttat ttttgggggg aatgacatgt    4920
ttgggtcttt tatacatgaa aatttgtttg acaataatct cacaaaacat attttacatc    4980
tgaacaaaat gccttttgt ttaccgtagc gtatacattt gttttgggat ttttgtgtgt     5040
ttgttgggaa ttttgttttt agccaggtca gtattgatga ggctgatcat ttggctcttt    5100
ttttccttcc agaagagttg catcaacaaa gttaattgta tttatgtatg taaatagatt    5160
ttaagcttca ttataaaata ttgttaatgc ctataacttt ttttcaattt ttttgtgtgt    5220
gtttctaagg acttttttctt aggtttgcta aatactgtag ggaaaaaat gcttctttct    5280 actttgttta tttttagactt taaaatgagc tacttcttat tcacttttgt aaacagctaa   5340
tagcatggtt ccaatttttt ttaagttcac ttttttttgtt ctaggggaaa tgaatgtgca   5400
aaaaaagaaa aagaactgtt ggttatttgt gttattctgg atgtataaaa atcaatggaa    5460
aaaaataaac tttcaaattg aaatgacggt ataacacatc tactgaaaaa gcaacgggaa    5520
atgtggtcct attaagcca gccccccacct agggtctatt tgtgtggcag ttattggtt     5580 tggtcacaaa acatcctgaa aattcgtgcg tgggcttctt tctccctggt acaaacgtat    5640
ggaatgcttc ttaaagggga actgtcaagc tggtgtcttc agccagatga catgagagaa    5700
tatcccagaa ccctctctcc aaggtgtttc tagatagcac aggagagcag gcactgcact    5760
gtccacagtc cacggtacac agtcgggtgg gccgcctccc ctctcctggg agcattcgtc    5820
gtgcccagcc tgagcagggc agctggactg ctgctgttca ggagccacca gagccttcct   5880
ctctttgtac cacagtttct tctgtaaatc cagtgttaca atcagtgtga atggcaaata    5940
aacagtttga caagtacata caccata                                       5967
```

<210> SEQ ID NO 14
<211> LENGTH: 2722
<212> TYPE: DNA
<213> ORGANISM: Artificial Sequence
<220> FEATURE:
<223> OTHER INFORMATION: RUNX1 cDNA sequence

<400> SEQUENCE: 14

```
catagagcca gcgggcgcgg gcgggacggg cgccccgcgg ccggacccag ccagggcacc      60
acgctgcccg gccctgcgcc gccaggcact tctttccggg gctcctaggg acgccagaag     120
gaagtcaacc tctgctgctt ctccttggcc tgcgttggac cttccttttt ttgttgtttt     180
tttttgtttt tccccttttct tcctttttgaa ttaactggct tcttggctgg atgttttcaa   240
cttctttcct ggctgcgaac ttttccccaa ttgttttcct tttacaacag ggggagaaag     300
tgctctgtgg tccgaggcga gccgtgaagt tgcgtgtgcg tggcagtgtg cgtggcagga     360
tgtgcgtgcg tgtgtaaccc gagccgcccg atctgtttcg atctgcgccg cggagccctc     420
cctcaaggcc cgctccacct gctgcggtta cgcggcgctc gtgggtgttc gtgcctcgga     480
gcagctaacc ggcgggtgct gggcgacggt ggaggagtat cgtctcgctg ctgcccgagt     540
cagggctgag tcacccagct gatgtagaca gtggctgcct tccgaagagt gcgtgtttgc     600
atgtgtgtga ctctgcggct gctcaactcc caacaaacca gaggaccagc cacaaactta     660
accaacatcc ccaaacccga gttcacagat gtgggagagc tgtagaaccc tgagtgtcat     720
cgactgggcc ttcttatgat tgttgtttta agattagctg aagatctctg aaacgctgaa     780
ttttctgcac tgagcgtttt gacagaattc attgagagaa cagagaacat gacaagtact     840
tctagctcag cactgctcca actactgaag ctgattttca aggctactta aaaaaatctg     900
cagcgtacat taatggattt ctgttgtgtt taaattctcc acagattgta ttgtaaatat     960
tttatgaagt agagcatatg tatatattta tatacgtg cacatacatt agtagcacta    1020
cctttggaag tctcagctct tgcttttcgg gactgaagcc agttttgcat gataaaagtg    1080
gccttgttac gggagataat tgtgttctgt tgggactta gacaaaactc acctgcaaaa     1140
aactgacagg cattaactac tggaacttcc aaataatgtg tttgctgatc gttttactct    1200
tcgcataaat attttaggaa gtgtatgaga attttgcctt caggaacttt tctaacagcc    1260
aaagacagaa cttaacctct gcaagcaaga ttcgtggaag atagtctcca ctttttaatg    1320
cactaagcaa tcggttgcta ggagcccatc ctgggtcaga ggccgatccg cagaaccaga    1380
acgttttccc ctcctggact gttagtaact tagtctccct cctccctaa ccaccccgc      1440
ccccccccac cccccgcagt aataaaggcc cctgaacgtg tatgttggtc tcccgggagc    1500
tgcttgctga agatccgcgc ccctgtcgcc gtctggtagg agctgtttgc agggtcctaa    1560
ctcaatcggc ttgttgtgat gcgtatcccc gtagatgcca gcacgagccg ccgcttcacg    1620
ccgccttcca ccgcgctgag cccaggcaag atgagcgagg cgttgccgct gggcgccccg    1680
gacgccggcg ctgccctggc cggcaagctg aggagcggcg accgcagcat ggtggaggtg    1740
ctggccgacc acccgggcga gctggtgcgc accgacagcc caacttcct ctgctccgtg     1800
ctgcctacgc actggcgctg caacaagacc ctgcccatcg ctttcaaggt ggtggcccta    1860
ggggatgttc cagatggcac tctggtcact gtgatggctg gcaatgatga aaactactcg    1920
gctgagctga gaaatgctac cgcagccatg aagaaccagg ttgcaagatt taatgacctc    1980
aggtttgtcg gtcgaagtgg aagagggaaa agcttcactc tgaccatcac tgtcttcaca    2040
aacccaccgc aagtcgccac ctaccacaga gccatcaaaa tcacagtgga tgggcccga    2100
gaacctcgaa gacatcggca gaaactagat gatcagacca agcccgggag cttgtccttt    2160
tccgagcggc tcagtgaact ggagcagctg cggcgcacag ccatgagggt cagcccacac    2220
cacccagccc ccacgcccaa ccctcgtgcc tccctgaacc actccactgc ctttaaccct    2280
```

| | |
|---|---:|
| cagcctcaga gtcagatgca ggaggaagac acagcaccct ggagatgtta aggcagaagt | 2340 |
| cagttcttct gtccatccct ctccccagcc aggatagagc tatcttttcc atctcatcct | 2400 |
| cagaagagac tcagaagaaa gatgacagcc ctcagaatgc acgttatgag gaaggcagaa | 2460 |
| tgtgggtctg taattcctcc gtgtcccttc tccccctctg caaaccgtcg taacaataat | 2520 |
| agttcctaac acatgggaca attgtgagga ttaaatgagt tagcctgcag aaatcacttg | 2580 |
| atgcacagca catgggaagc attgtgtgta tttattaatc cttcacaaag tctttgagat | 2640 |
| atatttttat caaatattta gcatggatcc cggtacactt tcaatactta ataaatggtc | 2700 |
| aatgttattc tttttcacta tt | 2722 |

<210> SEQ ID NO 15
<211> LENGTH: 6230
<212> TYPE: DNA
<213> ORGANISM: Artificial Sequence
<220> FEATURE:
<223> OTHER INFORMATION: RUNX1 cDNA sequence

<400> SEQUENCE: 15

| | |
|---|---:|
| agggcggctg ctgcccsctg gcgtccgcca gagcccgcgg cgcgtcccga cagctccgcg | 60 |
| cagtccgggc ccgcccggga aaggcctcca cgccagtcaa ccccggcccc ctcctgcgtc | 120 |
| cgggcccgcg gcaacgcccg gggacagtcc ctgcgcggca gcggccacag caccctagcc | 180 |
| ctggggagg gaggagcggg cgtcagggc cccgtgaggt cggcgaggga ccccgcgcc | 240 |
| ggggagctta attgagggc tccgcgggga ccacaaagca gcccgcggtg aacggggcc | 300 |
| gggatccggg gactgggttg cagccccggg gtggatgaga ggccccggga ggtgcagggc | 360 |
| ccggcaggga gggcgtggag ggactcatgg tgacgggagc agcctccgct gggagggagc | 420 |
| cccgccgggc ggggtcggag ttggcagcgc acgccggacc gggggcgggg ccctccgagc | 480 |
| tccgcgaaaa tgcccgcagc accgcgggga ccggcgcagg gggaagcggc cgcccgcacg | 540 |
| cgaagccggg atgccagcac gagccgccgc ttcacgccgc cttccaccgc gctgagccca | 600 |
| ggcaagatga gcgaggcgtt gccgctgggc gccccggacg ccggcgctgc cctggccggc | 660 |
| aagctgagga cggcgaccg cagcatggtg gaggtgctgg ccgaccaccc gggcgagctg | 720 |
| gtgcgcaccg acagccccaa cttcctctgc tccgtgctgc ctacgcactg gcgctgcaac | 780 |
| aagaccctgc ccatcgcttt caaggtggtg gccctagggg atgttccaga tggcactctg | 840 |
| gtcactgtga tggctggcaa tgatgaaaac tactcggctg agctgagaaa tgctaccgca | 900 |
| gccatgaaga accaggttgc aagatttaat gaccctcagg ttgtcggtcg aagtggaaga | 960 |
| gggaaaagct tcactctgac catcactgtc ttcacaaacc caccgcaagt cgccacctac | 1020 |
| cacagagcca tcaaaatcac agtggatggg ccccgagaac ctcgaagaca tcggcagaaa | 1080 |
| ctagatgatc agaccaagcc cgggagcttg tccttttccg agcggctcag tgaactggag | 1140 |
| cagctgcggc gcacagccat gagggtcagc ccacaccacc cagcccccac gcccaaccct | 1200 |
| cgtgcctccc tgaaccactc cactgccttt aaccctcagc ctcagagtca gatgcaggat | 1260 |
| acaaggcaga tccaaccatc cccaccgtgg tcctacgatc agtcctacca atacctggga | 1320 |
| tccattgcct ctccttctgt gcacccagca acgcccattt cacctggacg tgccagcggc | 1380 |
| atgacaaccc tctctgcaga actttccagt cgactctcaa cggcacccga cctgacagcg | 1440 |
| ttcagcgacc cgcgccagtt cccgcgcgct gcctccatct ccgaccccgg catgcactat | 1500 |
| ccaggcgcct tcacctactc cccgacgccg gtcacctcgg gcatcggcat cggcatgtcg | 1560 |
| gccatgggct cggccacgcg ctaccacacc tacctgcgc cgccctaccc cggctcgtcg | 1620 |

-continued

```
caagcgcagg gaggcccgtt ccaagccagc tcgccctcct accacctgta ctacggcgcc    1680
tcggccggct cctaccagtt ctccatggtg ggcggcgagc gctcgccgcc gcgcatcctg    1740
ccgccctgca ccaacgcctc caccggctcc gcgctgctca accccagcct cccgaaccag    1800
agcgacgtgg tggaggccga gggcagccac agcaactccc ccaccaacat ggcgccctcc    1860
gcgcgcctgg aggaggccgt gtggaggccc tactgaggcg ccaggcctgg cccggctggg    1920
ccccgcgggc cgccgccttc gcctccgggc gcgcgggcct cctgttcgcg acaagcccgc    1980
cgggatcccg ggccctgggc ccggccaccg tcctggggcc gagggcgccc gacggccagg    2040
atctcgctgt aggtcaggcc cgcgcagcct cctgcgccca gaagcccacg ccgccgccgt    2100
ctgctggcgc cccggccctc gcggaggtgt ccgaggcgac gcacctcgag ggtgtccgcc    2160
ggccccagca cccaggggac gcgctggaaa gcaaacagga agattcccgg agggaaactg    2220
tgaatgcttc tgatttagca atgctgtgaa taaaagaaa gattttatac ccttgactta     2280 acttttaac caagttgttt attccaaaga gtgtggaatt ttggttgggg tggggggaga     2340
ggagggatgc aactcgccct gtttggcatc taattcttat ttttaatttt tccgcacctt    2400
atcaattgca aaatgcgtat ttgcatttgg gtggttttta tttttatata cgtttatata    2460
aatatatata aattgagctt gcttctttct tgctttgacc atggaaagaa atatgattcc    2520
cttttcttta gtttttatttt aacttttctt tggacttttt gggtagttgt tttttttgt    2580 tttgttttgt ttttttgaga aacagctaca gctttgggtc attttttaact actgtattcc   2640 cacaaggaat ccccagatat ttatgtatct tgatgttcag acatttatgt gttgataatt    2700
ttttaattat ttaaatgtac ttatattaag aaaaatatca agtactacat tttcttttgt    2760
tcttgatagt agccaaagtt aaatgtatca cattgaagaa ggctagaaaa aaagaatgag    2820
taatgtgatc gcttggttat ccagaagtat tgtttacatt aaactccctt tcatgttaat    2880
caaacaagtg agtagctcac gcagcaacgt ttttaatagg attttagac actgagggtc     2940 actccaagga tcagaagtat ggaattttct gccaggctca acaagggtct catatctaac    3000
ttcctcctta aaacagagaa ggtcaatcta gttccagagg gttgaggcag gtgccaataa    3060
ttacatcttt ggagaggatt tgatttctgc ccagggattt gctcacccca aggtcatctg    3120
ataatttcac agatgctgtg taacagaaca cagccaaagt aaactgtgta ggggagccac    3180
atttacatag gaaccaaatc aatgaattta ggggttacga ttatagcaat ttaagggccc    3240
accagaagca ggcctcgagg agtcaatttg cctctgtgtg cctcagtgga gacaagtggg    3300
aaaacatggt cccacctgtg cgagacccc tgtcctgtgc tgctcactca acaacatctt     3360
tgtgttgctt tcaccaggct gagaccctac cctatggggt atatgggctt ttacctgtgc    3420
accagtgtga caggaaagat tcatgtcact actgtccgtg gctacaattc aaaggtatcc    3480
aatgtcgctg taaattttat ggcactattt ttattggagg atttggtcag aatgcagttg    3540
ttgtacaact cataaatact aactgctgat tttgacacat gtgtgctcca aatgatctgg    3600
tggttattta acgtacctct taaaattcgt tgaaacgatt tcaggtcaac tctgaagagt    3660
atttgaaagc aggacttcag aacagtgttt gatttttatt ttataaattt aagcattcaa    3720
attaggcaaa tctttggctg caggcagcaa aaacagctgg acttatttaa acaacttgt     3780 ttttgagttt tcttatatat atattgatta tttgttttac acacatgcag tagcactttg    3840
gtaagagtta aagagtaaag cagcttatgt tgtcaggtcg ttcttatcta gagaagagct    3900
atagcagatc tcggacaaac tcagaatata ttcactttca ttttgacag gattccctcc     3960
```

-continued

```
acaactcagt tcatatatt attccgtatt acattttgc agctaaatta ccataaaatg       4020
tcagcaaatg taaaaattta atttctgaaa agcaccatta gcccatttcc cccaaattaa       4080
acgtaaatgt tttttttcag cacatgttac catgtctgac ctgcaaaaat gctggagaaa       4140
aatgaaggaa aaaattatgt ttttcagttt aattctgtta actgaagata ttccaactca       4200
aaaccagcct catgctctga ttagataatc ttttacattg aacctttact ctcaaagcca       4260
tgtgtggagg gggcttgtca ctattgtagg ctcactggat tggtcattta gagtttcaca       4320
gactcttacc agcatatata gtatttaatt gtttcaaaaa aaatcaaact gtagttgttt       4380
tggcgatagg tctcacgcaa cacattttg tatgtgtgtg tgtgtgcgtg tgtgtgtgtg        4440
tgtgtgaaaa attgcattca ttgacttcag gtagattaag gtatcttttt attcattgcc       4500
ctcaggaaag ttaaggtatc aatgagaccc ttaagccaat catgtaataa ctgcatgtgt       4560
ctggtccagg agaagtattg aataagccat ttctactgct tactcatgtc cctatttatg       4620
atttcaacat ggatacatat ttcagttctt ctttttctc actatctgaa aatacatttc        4680
cctccctctc ttccccccaa tatctccctt tttttctctc ttcctctatc ttccaaaccc       4740
cactttctcc ctcctccttt tcctgtgttc tcttaagcag atagcacata cccccaccca       4800
gtaccaaatt tcagaacaca agaaggtcca gttcttcccc cttcacataa aggaacatgg       4860
tttgtcagcc tttctcctgt ttatgggttt cttccagcag aacagagaca ttgccaacca       4920
tattggatct gcttgctgtc caaaccagca aactttcctg gcaaatcac aatcagtgag        4980 taaatagaca gcctttctgc tgccttgggt ttctgtgcag ataaacagaa atgctctgat       5040
tagaaaggaa atgaatggtt ccactcaaat gtcctgcaat ttaggattgc agatttctgc       5100
cttgaaatac ctgtttcttt gggacattcc gtcctgatga ttttattttt gttggtttt       5160 tatttttggg gggaatgaca tgtttgggtc ttttatacat gaaaatttgt ttgacaataa       5220
tctcacaaaa catattttac atctgaacaa aatgccttt tgtttaccgt agcgtataca        5280
tttgttttgg gattttgtgt gtttgttgg gaatttgtt tttagccagg tcagtattga        5340
tgaggctgat catttggctc ttttttttcct tccagaagag ttgcatcaac aaagttaatt     5400
gtatttatgt atgtaaatag attttaagct tcattataaa atattgttaa tgcctataac      5460
tttttttcaa tttttttgtg tgtgtttcta aggactttt cttaggtttg ctaaatactg       5520
tagggaaaaa aatgcttctt tctactttgt ttattttaga ctttaaaatg agctacttct      5580
tattcacttt tgtaaacagc taatagcatg gttccaattt tttttaagtt cacttttttt      5640
gttctagggg aaatgaatgt gcaaaaaaag aaaaagaact gttggttatt tgtgttattc      5700
tggatgtata aaaatcaatg gaaaaaaata aactttcaaa ttgaaatgac ggtataacac      5760
atctactgaa aaagcaacgg gaaatgtggt cctatttaag ccagccccca cctagggtct      5820
atttgtgtgg cagttattgg gtttggtcac aaaacatcct gaaaattcgt gcgtgggctt      5880
cttctcccct ggtacaaacg tatggaatgc ttcttaaagg ggaactgtca agctggtgtc      5940
ttcagccaga tgacatgaga gaatatccca gaaccctctc tccaaggtgt ttctagatag      6000
cacaggagag caggcactgc actgtccaca gtccacggta cacagtcggg tgggccgcct      6060
cccctctcct gggagcattc gtcgtgccca gcctgagcag ggcagctgga ctgctgctgt      6120
tcaggagcca ccagagcctt cctctctttg taccacagtt tcttctgtaa atccagtgtt      6180
acaatcagtg tgaatggcaa ataaacagtt tgacaagtac atacaccata               6230
```

<210> SEQ ID NO 16
<211> LENGTH: 1452

```
<212> TYPE: DNA
<213> ORGANISM: Artificial Sequence
<220> FEATURE:
<223> OTHER INFORMATION: RUNX1 cDNA sequence

<400> SEQUENCE: 16
acagttaaat tgtaatttg ggttgtgtga aacttctttt gggcctcata acaaccaca      60
gaaccacaag ttgggtagcc tggcagtgtc agaagtctga acccagcata gtggtcagca    120
ggcaggacga atcacactga atgcaaacca cagggtttcg cagcgtggta aagaaatca    180
ttgagtcccc cgccttcaga agagggtgca ttttcaggag gaagcgatgg cttcagacag    240
catatttgag tcatttcctt cgtacccaca gtgcttcatg agagaatgca tacttggaat    300
gaatccttct agagacgtcc acgatgccag cacgagccgc cgcttcacgc cgccttccac    360
cgcgctgagc ccaggcaaga tgagcgaggc gttgccgctg ggcgcccgg acgccggcgc    420
tgccctggcc ggcaagctga ggagcggcga ccgcagcatg gtggaggtgc tggccgacca    480
cccgggcgag ctggtgcgca ccgacagccc caacttcctc tgctccgtgc tgcctacgca    540
ctggcgctgc aacaagaccc tgcccatcgc tttcaaggtg gtggccctag ggatgttcc    600
agatggcact ctggtcactg tgatggctgg caatgatgaa aactactcgg ctgagctgag    660
aaatgctacc gcagccatga agaaccaggt tgcaagattt aatgacctca ggtttgtcgg    720
tcgaagtgga agagggaaaa gcttcactct gaccatcact gtcttcacaa acccaccgca    780
agtcgccacc taccacagag ccatcaaaat cacagtggat gggccccgag aacctcgaag    840
acatcggcag aaactagatg atcagaccaa gcccgggagc ttgtccttt ccgagcggct    900
cagtgaactg gagcagctgc ggcgcacagc catgagggtc agcccacacc cccagcccc    960
cacgcccaac cctcgtgcct ccctgaacca ctccactgcc tttaaccctc agcctcagag   1020
tcagatgcag gaggaagaca cagcaccctg gatgttaa ggcagaagtc agttcttctg    1080
tccatccctc tccccagcca ggatagagct atcttttcca tctcatcctc agaagagact   1140
cagaagaaag atgacagccc tcagaatgca cgttatgagg aaggcagaat gtgggtctgt   1200
aattcctccg tgtccttct ccccctctgc aaaccgtcgt aacaataata gttcctaaca   1260
catgggacaa ttgtgaggat taaatgagtt agcctgcaga aatcacttga tgcacagcac   1320
atgggaagca ttgtgtgtat ttattaatcc ttcacaaagt ctttgagata tattttatc   1380
aaatatttag catggatccc ggtacacttt caatacttaa taaatggtca atgttattct   1440
ttttcactat ta                                                      1452

<210> SEQ ID NO 17
<211> LENGTH: 4693
<212> TYPE: DNA
<213> ORGANISM: Artificial Sequence
<220> FEATURE:
<223> OTHER INFORMATION: RUNX1 cDNA sequence

<400> SEQUENCE: 17
acagttaaat ttgtaatttg ggttgtgtga aacttctttt gggcctcata acaaccaca      60
gaaccacaag ttgggtagcc tggcagtgtc agaagtctga acccagcata gtggtcagca    120
ggcaggacga atcacactga atgcaaacca cagggtttcg cagcgtggta aagaaatca    180
ttgagtcccc cgccttcaga agagggtgca ttttcaggag gaagcgatgg cttcagacag    240
catatttgag tcatttcctt cgtacccaca gtgcttcatg agagaatgca tacttggaat    300
gaatccttct agagacgtcc acgatgccag cacgagccgc cgcttcacgc cgccttccac    360
```

-continued

```
cgcgctgagc ccaggcaaga tgagcgaggc gttgccgctg ggcgccccgg acgccggcgc    420
tgccctggcc ggcaagctga ggagcggcga ccgcagcatg gtggaggtgc tggccgacca    480
cccgggcgag ctggtgcgca ccgacagccc caacttcctc tgctccgtgc tgcctacgca    540
ctggcgctgc aacaagaccc tgcccatcgc tttcaaggtg gtggccctag ggatgttcc     600 agatggcact ctggtcactg tgatggctgg caatgatgaa aactactcgg ctgagctgag    660
aaatgctacc gcagccatga agaaccaggt tgcaagattt aatgacctca ggtttgtcgg    720
tcgaagtgga agagggaaaa gcttcactct gaccatcact gtcttcacaa acccaccgca    780
agtcgccacc taccacagag ccatcaaaat cacagtggat gggccccgag aacctcgaag    840
acatcggcag aaactagatg atcagaccaa gcccgggagc ttgtcctttt ccgagcggct    900
cagtgaactg gagcagctgc ggcgcacagc catgagggtc agcccacacc cccagcccc    960 cacgcccaac cctcgtgcct ccctgaacca ctccactgcc tttaaccctc agcctcagag   1020
tcagatgcag gatacaaggc agatccaacc atccccaccg tggtcctacg atcagtccta   1080
ccaatacctg ggatccattg cctctccttc tgtgcaccca gcaacgccca tttcacctgg   1140
acgtgccagc ggcatgacaa ccctctctgc agaactttcc agtcgactct caaacagttg   1200
tgattacttc aggtttcacc agatgcctta gctgctgttc agagcttcac agaatgcctt   1260
ctaagagctt cacaacggca gtactattga catttggggc caaataattc tttgttgggg   1320
ggggtctgtc ctgagcatcg gagaatattt agcagcatcc ttggcctcta gatgccaata   1380
gcatccccct caccccagtt aggacaataa aaaatgtttc cagacattgc caaatttccc   1440
aaggggcaaa actgtcccca ggtgagaacc actgccttcc agtgttcttg ggtggtacag   1500
taaaatagga aaccaactt aagtgcttgg ttttcacatt acttttggcc attaatgcca    1560
atattttcat ggtacattct gctccaaggc attgagagta gcacaggtat cttggcatct   1620
tgtttagctt gtggtttcta gaagcttatc cctcaagaac aaaggcactt gtcagctttt   1680
actgattgtt ctcagggcac ccctctgcac accggctacg gtcttcacct gaaataatgc   1740
ctgttctcct tcaaatgttc ctgctatggg tctatccttt ggaatttatt acataagtct   1800
tttgacttgg tcatcaccca agatcagcac cttatagtcc aagaacccta ggggccaact   1860
cctccagctg actggtgttc agatggtagg gtgactttt aaataaaagg aatgagtaac    1920
atgtgcactc caaagtccca tatcacagtt acatttgtga atatcctgga cttcaatcac   1980
ccaaggagta agagagaaca ttttatggca tgggagtgtg aagtagataa aaaccatgcc   2040
tcatttcaga acccaagaat gattcttttc tttttggagg gaggacagaa ttccagatga   2100
gctttcacag tggcatagaa cagtatggga gactgctctt caatttggca gaactccctc   2160
tgagaaatca agcctggagc acaggcctga aaagtgttgt cataaacctg gaggcaggag   2220
gggggtggaa tacataaaag gaaagtggct gcctggccga cagctttgag aacctgacac   2280
tgctctgtgg ctgcttttgcc ttttaatcca gcccgacagc tttgtgctct gcccctcttc   2340
ccggccccag cccacctgg gcttccttct gcgctgggga cttggactct gtctgtctct     2400
ctctctctat cctttgcaga cagactccac accttgtctg aaaagagttg tcatctagag   2460
gtttactttt ttttttcttt ttcaaaaaaa attaatgttt agctgccaac ctgggcgaca   2520
gacagcatgc attaatctga gtcatgcaaa agctccttt aaggcagcca ttacctgctc    2580
aggttgttta atcctctggg ggcagtagga ggggccctgt agcgaggctg ctttcatcca   2640
tgtcaagctg gagagcgaag acttgagctg tcatggcaaa tatttagccc catcaatggg   2700
aaaacacttc caaccaaaat acctggacct cctaagcccc agatttccta ctcttaaaaa   2760
```

```
ctctctgtga atatcagggg atcccaactc cccccacact tctgctgaat caggggacac    2820
caggccagcc aaaaggacag aagagctaca gctggatggg tgaactgcgc agactgatgg    2880
gtttgaataa gggatctgag acaagacaca aagatgaaaa ccaacatttg aatatagcat    2940
ttgaatctga gcatatctag aaggcctaag atattgtatt atcaaaatgt gtgtaaaaaa    3000
gatagtttga ccaaatggat ggtcttttgt agtatgacgt tgctcatgtg tacatagaag    3060
aaggatcaca ggcagcattg cagctctttc ttttggatgt tctcctcaca agtgaaagaa    3120
ctattttccc ccaacagctg agaccataac atcattccag tacttatgtc catgacaaat    3180
cacggactca ctctggattc cagtaacttg gtaccatcac cacattacca tgtagtagtt    3240
ggaacctact ggcagagcat gtccagacat tgctgtaaaa cagggtgacc tttcgttcat    3300
tttccagtgg attcacccttt ttgtctcagg gcaaatgaag caagaggaat aatgggcaga    3360
gtcatttatt tgtgtccaga gtattgcatc agatgacaac aaactgactg tatttgccta    3420
atgcttttcc tcctgtccca gcttctccgt agactctata aatctaaatg gaaaaatgga    3480
gtaaagcttc ctgttaactc tcaaacatgt cacagctctc catgtcagca aaaacaagtg    3540
acacagggct tgctcacaga tggccccaaa gagcgggcag ggatgaaccc tgtggaatga    3600
ggtgtggcct ggctcgagaa tgactagagt gtggccaagg aagggcagcc tcagaaccac    3660
tgtccgttta caacgttttc cctgcccaca tgtctgcctg gctttgaaaa gattaacagg    3720
agtgtttgtt tgaaagtcag actcctggtt tcctcattag tgaagggatc tgctacagac    3780
ttgggctgtt tctataaact ttaattacct ctgatgagga gtgtatcccc tcatcacatt    3840
caccccaaag gtacagagga gttcattttt aaaaatgtgt tagagcaata aaaggccatt    3900
agagggaggg aggatggggt gtggaagaga cgagagagcg agcgagagag agagaaaaca    3960
cactagctct ccctgctgga ataataggct tgaaatatga ggaagttgat caactgccgc    4020
tgccttccaa aaacagatta atccaccttg gtagctttcc tttcagagca agcttttggc    4080
tctgtcgact ttctctatca gcctgaactc aaaaggacac aggccacatg ccatctgagc    4140
ttaagagtta ttttgtgtgt tgatctgaga acttcacatt ttaaaacaat gaattcatgt    4200
ttctactgtt tgttgctgtc tgtggatttg ctgatataaa gaggagagtc ctagcctggt    4260
catttaatga ataattctaa ggaacctgaa cttctccagg gtgcccttct acatctgcag    4320
tggtggttct cagctggggt gactttgctt ccgtcacccc acccgcagga tatctggcaa    4380
tgtctggaga cattctgagt tgtcacaaga ggggcgggcg atgctactaa cacctaatgg    4440
gtaaagcaga gatgctgcca cacatcctac gatgaacgag acagcccct ccaccccagc     4500 aaatcatgat ctggcccaaa atgtcaacag tgtcaacagt tgagaaactc tgatctacag    4560
atatagggaa ccctgcctaa tacacaaatc ctccgtagtt cccaagggcg gcctgtagcg    4620
gcacccgacc tgacagcgtt cagcgacccg cgccagttcc ccgcgctgcc ctccatctcc    4680 gaccccgca tgc                                                        4693
```

<210> SEQ ID NO 18
<211> LENGTH: 5772
<212> TYPE: DNA
<213> ORGANISM: Artificial Sequence
<220> FEATURE:
<223> OTHER INFORMATION: RUNX1 cDNA sequence

<400> SEQUENCE: 18

```
acagttaaat ttgtaatttg ggttgtgtga aaacttcttt gggcctcata aacaaccaca     60
```

```
gaaccacaag ttgggtagcc tggcagtgtc agaagtctga acccagcata gtggtcagca    120
ggcaggacga atcacactga atgcaaacca cagggtttcg cagcgtggta aaagaaatca    180
ttgagtcccc cgccttcaga agagggtgca ttttcaggag gaagcgatgg cttcagacag    240
catatttgag tcatttcctt cgtacccaca gtgcttcatg agagatgcca gcacgagccg    300
ccgcttcacg ccgccttcca ccgcgctgag cccaggcaag atgagcgagg cgttgccgct    360
gggcgccccg gacgccggcg ctgccctggc cggcaagctg aggagcggcg accgcagcat    420
ggtggaggtg ctggccgacc acccgggcga gctggtgcgc accgacagcc caacttcct    480
ctgctccgtg ctgcctacgc actggcgctg caacaagacc ctgcccatcg ctttcaaggt    540
ggtggcccta ggggatgttc cagatggcac tctggtcact gtgatggctg caatgatga    600
aaactactcg gctgagctga gaaatgctac cgcagccatg aagaaccagg ttgcaagatt    660
taatgacctc aggtttgtcg gtcgaagtgg aagagggaaa agcttcactc tgaccatcac    720
tgtcttcaca aacccaccgc aagtcgccac ctaccacaga gccatcaaaa tcacagtgga    780
tgggccccga gaacctcgaa atacaaggca gatccaacca tccccaccgt ggtcctacga    840
tcagtcctac caatacctgg gatccattgc ctctccttct gtgcacccag caacgcccat    900
ttcacctgga cgtgccagcg gcatgacaac cctctctgca gaactttcca gtcgactctc    960
aacggcaccc gacctgacag cgttcagcga cccgcgccag ttccccgcgc tgccctccat   1020
ctccgacccc gcatgcact atccaggcgc cttcacctac tccccgacgc cggtcacctc   1080
gggcatcggc atcggcatgt cggccatggg ctcggccacg cgctaccaca cctacctgcc   1140
gccgccctac cccggctcgt cgcaagcgca gggaggcccg ttccaagcca gctcgccctc   1200
ctaccacctg tactacggcg cctcggccgg ctcctaccag ttctccatgg tgggcggcga   1260
gcgctcgccg ccgcgcatcc tgccgcctg caccaacgcc tccaccggct ccgcgctgct   1320
caaccccagc ctcccgaacc agagcgacgt ggtggaggcc gagggcagcc acagcaactc   1380
ccccaccaac atggcgccct ccgcgcgcct ggaggaggcc gtgtggaggc cctactgagg   1440
cgccaggcct ggcccggctg gccccgcgg gccgccgcct tcgctccgg gcgcgcgggc   1500
ctcctgttcg cgacaagccc gccgggatcc cgggccctgg gccggccac cgtcctgggg   1560
ccgagggcgc ccgacggcca ggatctcgct gtaggtcagg cccgcgcagc ctcctgcgcc   1620
cagaagccca cgccgccgcc gtctgctggc gccccggccc tcgcggaggt gtccgaggcg   1680
acgcacctcg agggtgtccg ccggccccag cacccagggg acgcgctgga aagcaaacag   1740
gaagattccc ggagggaaac tgtgaatgct tctgatttag caatgctgtg aataaaaga    1800
aagattttat acccttgact taacttttta accaagttgt ttattccaaa gagtgtggaa    1860
ttttggttgg ggtgggggga gaggaggat gcaactcgcc ctgtttggca tctaattctt   1920
atttttaatt tttccgcacc ttatcaattg caaaatgcgt atttgcattt gggtggtttt   1980
tattttata tacgtttata taaatatata taaattgagc ttgcttcttt cttgctttga   2040
ccatggaaag aaatatgatt cccttttctt taagttttat ttaacttttc ttttggactt   2100
ttgggtagtt gttttttttt gttttgtttt gtttttttga gaaacagcta cagctttggg   2160
tcatttttaa ctactgtatt cccacaagga atccccagat atttatgtat cttgatgttc   2220
agacatttat gtgttgataa tttttttaatt atttaaatgt acttatatta agaaaaatat   2280
caagtactac attttctttt gttcttgata gtagccaaag ttaaatgtat cacattgaag   2340
aaggctagaa aaaagaatg agtaatgtga tcgcttggtt atccagaagt attgtttaca   2400
ttaaactccc tttcatgtta atcaaacaag tgagtagctc acgcagcaac gttttaata   2460
```

```
ggattttttag acactgaggg tcactccaag gatcagaagt atggaattt  ctgccaggct   2520 caacaagggt ctcatatcta acttcctcct taaaacagaa aaggtcaatc tagttccaga   2580
gggttgaggc aggtgccaat aattacatct ttggagagga tttgatttct gcccagggat   2640
ttgctcaccc caaggtcatc tgataatttc acagatgctg tgtaacagaa cacagccaaa   2700
gtaaactgtg tagggagcc  acatttacat aggaaccaaa tcaatgaatt taggggttac   2760
gattatagca atttaagggc ccaccagaag caggcctcga ggagtcaatt tgcctctgtg   2820
tgcctcagtg gagacaagtg ggaaaacatg gtcccacctg tgcgagaccc cctgtcctgt   2880
gctgctcact caacaacatc tttgtgttgc tttcaccagg ctgagaccct accctatggg   2940
gtatatgggc ttttacctgt gcaccagtgt gacaggaaag attcatgtca ctactgtccg   3000
tggctacaat tcaaaggtat ccaatgtcgc tgtaaatttt atggcactat ttttattgga   3060
ggatttggtc agaatgcagt tgttgtacaa ctcataaata ctaactgctg attttgacac   3120
atgtgtgctc caaatgatct ggtggttatt taacgtacct cttaaaattc gttgaaacga   3180
tttcaggtca actctgaaga gtatttgaaa gcaggacttc agaacagtgt ttgatttta   3240 ttttataaat ttaagcattc aaattaggca aatctttggc tgcaggcagc aaaaacagct   3300
ggacttattt aaaacaactt gttttgagt tttcttatat atatattgat tatttgtttt   3360
acacacatgc agtagcactt tggtaagagt taaagagtaa agcagcttat gttgtcaggt   3420
cgttcttatc tagagaagag ctatagcaga tctcggacaa actcagaata tattcacttt   3480 cattttgac  aggattccct ccacaactca gtttcatata ttattccgta ttacatttt    3540 gcagctaaat taccataaaa tgtcagcaaa tgtaaaaatt taatttctga aaagcaccat   3600
tagcccattt cccccaaatt aaacgtaaat gtttttttc agcacatgtt accatgtctg    3660
acctgcaaaa atgctggaga aaaatgaagg aaaaaattat gtttttcagt ttaattctgt   3720
taactgaaga tattccaact caaaaccagc ctcatgctct gattagataa tcttttacat   3780 tgaacccttta ctctcaaagc catgtgtgga gggggcttgt cactattgta ggctcactgg  3840
attggtcatt tagagtttca cagactctta ccagcatata tagtatttaa ttgtttcaaa   3900
aaaaatcaaa ctgtagttgt tttggcgata ggtctcacgc aacacatttt tgtatgtgtg   3960
tgtgtgtgcg tgtgtgtgtg tgtgtgtgaa aaattgcatt cattgacttc aggtagatta   4020
aggtatcttt ttattcattg ccctcaggaa agttaaggta tcaatgagac ccttaagcca   4080
atcatgtaat aactgcatgt gtctggtcca ggagaagtat tgaataagcc atttctactg   4140
cttactcatg tccctatttta tgatttcaac atggatacat atttcagttc tttctttttc   4200
tcactatctg aaaatacatt tccctccctc tcttccccc  aatatctccc ttttttctc    4260 tcttcctcta tcttccaaac cccactttct ccctcctcct tttcctgtgt tctcttaagc   4320
agatagcaca taccccaccc cagtaccaaa tttcagaaca caagaaggtc cagttcttcc   4380
cccttcacat aaaggaacat ggtttgtcag ccttttctcct gtttatgggt ttcttccagc   4440
agaacagaga cattgccaac catattggat ctgcttgctg tccaaaccag caaactttcc   4500
tgggcaaatc acaatcagtg agtaaataga cagcctttct gctgccttgg gtttctgtgc   4560
agataaacag aaatgctctg attagaaagg aaatgaatgg ttccactcaa atgtcctgca   4620
atttaggatt gcagatttct gccttgaaat acctgtttct ttgggacatt ccgtcctgat   4680
gatttttatt tttgttggtt tttatttttg gggaatga  catgtttggg tcttttatac    4740
atgaaaattt gtttgacaat aatctcacaa aacatatttt acatctgaac aaaatgcctt   4800
```

```
tttgtttacc gtagcgtata catttgtttt gggattttg tgtgtttgtt gggaattttg     4860
tttttagcca ggtcagtatt gatgaggctg atcatttggc tcttttttc cttccagaag     4920
agttgcatca acaaagttaa ttgtatttat gtatgtaaat agattttaag cttcattata   4980
aaatattgtt aatgcctata acttttttc aatttttttg tgtgtgtttc taaggacttt   5040
ttcttaggtt tgctaaatac tgtagggaaa aaatgcttc tttctacttt gtttatttta   5100
gactttaaaa tgagctactt cttattcact tttgtaaaca gctaatagca tggttccaat   5160
ttttttaag ttcactttt ttgttctagg ggaaatgaat gtgcaaaaaa agaaaaagaa     5220
ctgttggtta tttgtgttat tctggatgta taaaaatcaa tggaaaaaa taaactttca    5280
aattgaaatg acggtataac acatctactg aaaaagcaac gggaaatgtg gtcctattta   5340
agccagcccc cacctagggt ctatttgtgt ggcagttatt gggtttggtc acaaaacatc   5400
ctgaaaattc gtgcgtgggc ttcttctcc ctggtacaaa cgtatggaat gcttcttaaa    5460
ggggaactgt caagctggtg tcttcagcca gatgacatga gagaatatcc cagaaccctc   5520
tctccaaggt gtttctagat agcacaggag agcaggcact gcactgtcca cagtccacgg   5580
tacacagtcg ggtgggccgc ctcccctctc ctgggagcat tcgtcgtgcc cagcctgagc   5640
agggcagctg gactgctgct gttcaggagc caccagagcc ttcctctctt tgtaccacag   5700
tttcttctgt aaatccagtg ttacaatcag tgtgaatggc aaataaacag tttgacaagt   5760
acatacacca ta                                                       5772

<210> SEQ ID NO 19
<211> LENGTH: 5811
<212> TYPE: DNA
<213> ORGANISM: Artificial Sequence
<220> FEATURE:
<223> OTHER INFORMATION: RUNX1 cDNA sequence

<400> SEQUENCE: 19
acagttaaat tgtaatttg ggttgtgtga aaacttcttt gggcctcata acaaccaca       60
gaaccacaag ttgggtagcc tggcagtgtc agaagtctga acccagcata gtggtcagca    120
ggcaggacga atcacactga atgcaaacca cagggtttcg cagcgtggta aagaaaatca    180
ttgagtcccc cgccttcaga agagggtgca ttttcaggag gaagcgatgg cttcagacag    240
catatttgag tcatttcctt cgtacccaca gtgcttcatg agagaatgca tacttggaat   300
gaatccttct agagacgtcc acgatgccag cacgagccgc cgcttcacgc cgccttccac   360
cgcgctgagc ccaggcaaga tgagcgaggc gttgccgctg ggcgcccgg acgcggcgc     420
tgccctggcc ggcaagctga ggagcggcga ccgcagcatg gtggaggtgc tggccgacca   480
cccgggcgag ctggtgcgca ccgacagccc caacttcctc tgctccgtgc tgcctacgca   540
ctggcgctgc aacaagaccc tgcccatcgc tttcaaggtg gtggccctag ggatgttcc    600
agatggcact ctggtcactg tgatggctgg caatgatgaa aactactcgg ctgagctgag   660
aaatgctacc gcagccatga agaaccaggt tgcaagattt aatgacctca ggtttgtcgg   720
tcgaagtgga agagggaaaa gcttcactct gaccatcact gtcttcacaa acccaccgca   780
agtcgccacc taccacagag ccatcaaaat cacagtggat gggccccgag aacctcgaaa   840
tacaaggcag atccaaccat ccccaccgtg gtcctacgat cagtcctacc aatacctggg   900
atccattgcc tctccttctg tgcacccagc aacgcccatt tcacctggac gtgccagcgg   960
catgacaacc ctctctgcag aacttttccag tcgactctca acggcacccg acctgacagc   1020
gttcagcgac ccgcgccagt tccccgcgct gccctccatc tccgaccccc gcatgcacta   1080
```

```
tccaggcgcc ttcacctact ccccgacgcc ggtcacctcg ggcatcggca tcggcatgtc   1140
ggccatgggc tcggccacgc gctaccacac ctacctgccg ccgccctacc ccggctcgtc   1200
gcaagcgcag ggaggcccgt tccaagccag ctcgccctcc taccacctgt actacggcgc   1260
ctcggccggc tcctaccagt tctccatggt gggcggcgag cgctcgccgc cgcgcatcct   1320
gccgccctgc accaacgcct ccaccggctc cgcgctgctc aaccccagcc tcccgaacca   1380
gagcgacgtg gtggaggccg agggcagcca cagcaactcc cccaccaaca tggcgccctc   1440
cgcgcgcctg gaggaggccg tgtggaggcc ctactgaggc gccaggcctg gcccggctgg   1500
gccccgcggg ccgccgcctt cgcctccggg cgcgcgggcc tcctgttcgc gacaagcccg   1560
ccgggatccc gggccctggg cccggccacc gtcctggggc cgagggcgcc cgacggccag   1620
gatctcgctg taggtcaggc ccgcgcagcc tcctgcgccc agaagcccac gccgccgccg   1680
tctgctggcg ccccggccct cgcggaggtg tccgaggcga cgcacctcga gggtgtccgc   1740
cggccccagc acccagggga cgcgctggaa agcaaacagg aagattcccg gagggaaact   1800
gtgaatgctt ctgatttagc aatgctgtga ataaaaagaa agattttata cccttgactt   1860 aacttttaa ccaagttgtt tattccaaag agtgtggaat tttggttggg gtgggggggag   1920 aggagggatg caactcgccc tgtttggcat ctaattctta tttttaattt ttccgcacct   1980
tatcaattgc aaaatgcgta tttgcatttg ggtggttttt attttatat acgtttatat   2040 aaatatatat aaattgagct tgcttctttc ttgctttgac catggaaaga aatatgattc   2100
ccttttcttt aagtttttatt taactttct tttggactttt tgggtagttg ttttttttttg  2160 ttttgttttg tttttttgag aaacagctac agctttgggt catttttaac tactgtattc   2220
ccacaaggaa tccccagata tttatgtatc ttgatgttca dacatttatg tgttgataat   2280
tttttaatta tttaaatgta cttatattaa gaaaatatc aagtactaca ttttcttttg    2340
ttcttgatag tagccaaagt taaatgtatc acattgaaga aggctagaaa aaaagaatga   2400
gtaatgtgat cgcttggtta ccagaagta ttgtttacat taaactccct ttcatgttaa    2460
tcaaacaagt gagtagctca cgcagcaacg ttttttaatag gattttttaga cactgagggt   2520 cactccaagg atcagaagta tggaattttc tgccaggctc aacaagggtc tcatatctaa   2580
cttcctcctt aaaacagaga aggtcaatct agttccagag ggttgaggca ggtgccaata   2640
attacatctt tggagaggat ttgatttctg cccaggatt tgctcacccc aaggtcatct    2700
gataatttca cagatgctgt gtaacagaac acagccaaag taaactgtgt aggggagcca   2760
catttacata ggaaccaaat caatgaattt aggggttacg attatagcaa tttaagggcc   2820
caccagaagc aggcctcgag gagtcaattt gcctctgtgt gcctcagtgg agacaagtgg   2880
gaaaacatgg tcccacctgt gcgagacccc ctgtcctgtg ctgctcactc aacaacatct   2940
ttgtgttgct ttcaccaggc tgagacccta ccctatgggg tatatgggct tttacctgtg   3000
caccagtgtg acaggaaaga ttcatgtcac tactgtccgt ggctacaatt caaaggtatc   3060
caatgtcgct gtaaatttta tggcactatt tttattggag atttggtca gaatgcagtt    3120 gttgtacaac tcataaatac taactgctga ttttgacaca tgtgtgctcc aaatgatctg   3180
gtggttattt aacgtacctc ttaaaattcg ttgaaacgat ttcaggtcaa ctctgaagag   3240
tatttgaaag caggacttca gaacagtgtt tgattttttat tttataaatt taagcattca  3300
aattaggcaa atcttggct gcaggcagca aaaacagctg gacttattta aaacaacttg    3360
tttttgagtt ttcttatata tatattgatt atttgtttta cacacatgca gtagcacttt   3420
```

```
ggtaagagtt aaagagtaaa gcagcttatg ttgtcaggtc gttcttatct agagaagagc    3480
tatagcagat ctcggacaaa ctcagaatat attcactttc attttttgaca ggattccctc   3540 cacaactcag tttcatatat tattccgtat tacatttttg cagctaaatt accataaaat   3600
gtcagcaaat gtaaaaattt aatttctgaa aagcaccatt agcccatttc ccccaaatta   3660
aacgtaaatg ttttttttca gcacatgtta ccatgtctga cctgcaaaaa tgctggagaa   3720
aaatgaagga aaaaattatg tttttcagtt taattctgtt aactgaagat attccaactc   3780
aaaaccagcc tcatgctctg attagataat cttttacatt gaacctttac tctcaaagcc   3840
atgtgtggag ggggcttgtc actattgtag gctcactgga ttggtcattt agagtttcac   3900
agactcttac cagcatatat agtatttaat tgtttcaaaa aaaatcaaac tgtagttgtt   3960
ttggcgatag gtctcacgca acacattttt gtatgtgtgt gtgtgtgcgt gtgtgtgtgt   4020
gtgtgtgaaa aattgcattc attgacttca ggtagattaa ggtatctttt tattcattgc   4080
cctcaggaaa gttaaggtat caatgagacc cttaagccaa tcatgtaata actgcatgtg   4140
tctggtccag gagaagtatt gaataagcca tttctactgc ttactcatgt ccctatttat   4200
gatttcaaca tggatacata tttcagttct ttcttttttct cactatctga aaatacattt   4260
ccctccctct cttcccccca atatctccct tttttttctct cttcctctat cttccaaacc   4320
ccactttctc cctcctcctt ttcctgtgtt ctcttaagca gatagcacat accccccaccc   4380 agtaccaaat ttcagaacac aagaaggtcc agttcttccc ccttcacata aaggaacatg   4440
gtttgtcagc cttctctcctg tttatgggtt tcttccagca gaacagagac attgccaacc   4500
atattggatc tgcttgctgt ccaaaccagc aaactttcct gggcaaatca caatcagtga   4560
gtaaatagac agcctttctg ctgccttggg tttctgtgca gataaacaga aatgctctga   4620
ttagaaagga aatgaatggt tccactcaaa tgtcctgcaa tttaggattg cagatttctg   4680
ccttgaaata cctgtttctt tgggacattc cgtcctgatg atttttattt ttgttggttt   4740 ttattttttgg ggggaatgac atgtttgggt cttttataca tgaaaatttg tttgacaata   4800
atctcacaaa acatatttta catctgaaca aaatgccttt ttgtttaccg tagcgtatac   4860
atttgttttg ggattttttgt gtgtttgttg ggaattttgt ttttagccag gtcagtattg   4920
atgaggctga tcatttggct cttttttttcc ttccagaaga gttgcatcaa caaagttaat   4980
tgtatttatg tatgtaaata gattttaagc ttcattataa aatattgtta atgcctataa   5040 cttttttttca atttttttgt gtgtgttttct aaggactttt tcttaggttt gctaaatact   5100
gtagggaaaa aaatgcttct ttctactttg tttattttag actttaaaat gagctacttc   5160
ttattcactt ttgtaaacag ctaatagcat ggttccaatt tttttttaagt tcactttttt   5220 tgttctaggg gaaatgaatg tgcaaaaaaa gaaaagaac tgttggttat ttgtgttatt   5280
ctggatgtat aaaaatcaat ggaaaaaaat aaactttcaa attgaaatga cggtataaca   5340
catctactga aaaagcaacg ggaaatgtgg tcctatttaa gccagccccc acctagggtc   5400
tatttgtgtg gcagttattg ggtttggtca caaaacatcc tgaaaattcg tgcgtgggct   5460
tctttctccc tggtacaaac gtatggaatg cttcttaaag gggaactgtc aagctggtgt   5520
cttcagccag atgacatgag agaatatccc agaaccctct ctccaaggtg tttctagata   5580
gcacaggaga gcaggcactg cactgtccac agtccacggt acacagtcgg gtgggccgcc   5640
tcccctctcc tgggagcatt cgtcgtgccc agcctgagca gggcagctgg actgctgctg   5700
ttcaggagcc accagagcct tcctctcttt gtaccacagt ttcttctgta aatccagtgt   5760
tacaatcagt gtgaatggca aataaacagt ttgacaagta catacaccat a            5811
```

<210> SEQ ID NO 20
<211> LENGTH: 5772
<212> TYPE: DNA
<213> ORGANISM: Artificial Sequence
<220> FEATURE:
<223> OTHER INFORMATION: RUNX1 cDNA sequence

<400> SEQUENCE: 20

```
cacttttaa tgcactaagc aatcggttgc taggagccca tcctgggtca gaggccgatc      60
cgcagaacca gaacgttttc cctcctgga ctatgccagc acgagccgcc gcttcacgcc     120
gccttccacc gcgctgagcc caggcaagat gagcgaggcg ttgccgctgg cgcccggga    180
cgccggcgct gccctggccg gcaagctgag gagcggcgac cgcagcatgg tggaggtgct    240
ggccgaccac ccgggcgagc tggtgcgcac cgacagcccc aacttcctct gctccgtgct    300
gcctacgcac tggcgctgca caagaccct gcccatcgct ttcaaggtgg tggccctagg    360
ggatgttcca gatggcactc tggtcactgt gatggctggc aatgatgaaa actactcggc    420
tgagctgaga aatgctaccg cagccatgaa gaaccaggtt gcaagattta atgacctcag    480
gtttgtcggt cgaagtggaa gagggaaaag cttcactctg accatcactg tcttcacaaa    540
cccaccgcaa gtcgccacct accacagagc catcaaaatc acagtggatg gccccgaga    600
acctcgaaga catcggcaga aactagatga tcagaccaag cccgggagct tgtccttttc    660
cgagcggctc agtgaactgg agcagctgcg gcgcacagcc atgagggtca gcccacacca    720
cccagccccc acgcccaacc ctcgtgcctc cctgaaccac tccactgcct ttaaccctca    780
gcctcagagt cagatgcagg atacaaggca gatccaacca tccccaccgt ggtcctacga    840
tcagtcctac caatacctgg gatccattgc ctctcctct gtgcacccag caacgcccat    900
ttcacctgga cgtgccagcg gcatgacaac cctctctgca gaactttcca gtcgactctc    960
aacggcaccc gacctgacag cgttcagcga cccgcgccag ttccccgcgc tgccctccat   1020
ctccgacccc cgcatgcact atccaggcgc cttcacctac tccccgacgc cggtcacctc   1080
gggcatcggc atcggcatgt cggccatggg ctcggccacg cgctaccaca cctacctgcc   1140
gccgcctac cccggctcgt cgcaagcgca gggaggcccg ttccaagcca gctcgccctc   1200
ctaccacctg tactacggcg cctcggccgg ctcctaccag ttctccatgg tgggcggcga   1260
gcgctcgccg ccgcgcatcc tgccgccctg caccaacgcc tccaccggct ccgcgctgct   1320
caaccccagc ctcccgaacc agagcgacgt ggtggaggcc gagggcagcc acagcaactc   1380
ccccaccaac atggcgccct ccgcgcgcct ggaggaggcc gtgtggaggc ctactgagg   1440
cgccaggcct ggcccggctg ggccccgcgg gccgccgcct tcgcctccgg gcgcgcgggc   1500
ctcctgttcg cgacaagccc gccgggatcc cgggccctgg gccggccac cgtcctgggg   1560
ccgagggcgc ccgacggcca ggatctcgct gtaggtcagg cccgcgcagc ctcctgcgcc   1620
cagaagccca cgccgccgcc gtctgctggc gccccgccc tcgcggaggt gtccgaggcg   1680
acgcacctcg agggtgtccg ccggccccag cacccagggg acgcgctgga aagcaaacag   1740
gaagattccc ggagggaaac tgtgaatgct tctgatttag caatgctgtg aataaaaaga   1800
aagattttat acccttgact taactttta accaagttgt ttattccaaa gagtgtggaa   1860
ttttggttgg ggtgggggga gaggagggat gcaactcgcc ctgtttggca tctaattctt   1920
attttaatt tttccgcacc ttatcaattg caaaatgcgt atttgcattt gggtggtttt   1980
tattttata tacgttatata taaatatata taaattgagc ttgcttcttt cttgctttga   2040
```

```
ccatggaaag aaatatgatt cccttttctt taagttttat ttaacttttc ttttggactt    2100
ttgggtagtt gttttttttt gttttgtttt gttttttttga gaaacagcta cagctttggg    2160 tcattttaa ctactgtatt cccacaagga atccccagat atttatgtat cttgatgttc     2220
agacatttat gtgttgataa tttttaatt atttaaatgt acttatatta agaaaaatat     2280
caagtactac attttctttt gttcttgata gtagccaaag ttaaatgtat cacattgaag    2340
aaggctagaa aaaagaatg agtaatgtga tcgcttggtt atccagaagt attgtttaca     2400
ttaaactccc tttcatgtta atcaaacaag tgagtagctc acgcagcaac gttttaata    2460 ggattttag acactgaggg tcactccaag gatcagaagt atggaatttt ctgccaggct    2520 caacaaggt ctcatatcta acttcctcct taaaacagag aaggtcaatc tagttccaga    2580
gggttgaggc aggtgccaat aattacatct tggagagga tttgatttct gcccagggat    2640
ttgctcaccc caaggtcatc tgataatttc acagatgctg tgtaacagaa cacagccaaa   2700
gtaaactgtg taggggagcc acatttacat aggaaccaaa tcaatgaatt tagggtttac   2760
gattatagca atttaagggc ccaccagaag caggcctcga ggagtcaatt tgcctctgtg    2820
tgcctcagtg gagacaagtg ggaaaacatg gtcccacctg tgcgagaccc cctgtcctgt   2880
gctgctcact caacaacatc tttgtgttgc tttcaccagg ctgagaccct accctatggg    2940
gtatatgggc ttttacctgt gcaccagtgt gacaggaaag attcatgtca ctactgtccg    3000
tggctacaat tcaaaggtat ccaatgtcgc tgtaaatttt atggcactat ttttattgga    3060
ggatttggtc agaatgcagt tgttgtacaa ctcataaata ctaactgctg attttgacac    3120
atgtgtgctc caaatgatct ggtggttatt taacgtacct cttaaaattc gttgaaacga   3180
tttcaggtca actctgaaga gtatttgaaa gcaggacttc agaacagtgt tgatttta     3240 ttttataaat ttaagcattc aaattaggca aatctttggc tgcaggcagc aaaaacagct   3300
ggacttattt aaaacaactt gttttgagt tttcttatat atatattgat tatttgtttt    3360
acacacatgc agtagcactt tggtaagagt taaagagtaa agcagcttat gttgtcaggt    3420
cgttcttatc tagagaagag ctatagcaga tctcggacaa actcagaata tattcacttt    3480 cattttgac aggattccct ccacaactca gtttcatata ttattccgta ttacatttt    3540 gcagctaaat taccataaaa tgtcagcaaa tgtaaaaatt taatttctga aaagcaccat    3600
tagcccattt cccccaaatt aaacgtaaat gttttttttc agcacatgtt accatgtctg    3660
acctgcaaaa atgctggaga aaaatgaagg aaaaaattat gttttcagt ttaattctgt    3720 taactgaaga tattccaact caaaaccagc ctcatgctct gattagataa tctttacat   3780 tgaacctta ctctcaaagc catgtgtgga gggggcttgt cactattgta ggctcactgg    3840
attggtcatt tagagtttca cagactctta ccagcatata tagtatttaa ttgtttcaaa    3900
aaaaatcaaa ctgtagttgt tttggcgata ggtctcacgc aacacatttt tgtatgtgtg    3960
tgtgtgtgcg tgtgtgtgtg tgtgtgtgaa aaattgcatt cattgacttc aggtagatta    4020
aggtatcttt ttattcattg ccctcaggaa agttaaggta tcaatgagac ccttaagcca    4080
atcatgtaat aactgcatgt gtctggtcca ggagaagtat tgaataagcc atttctactg    4140
cttactcatg tccctattta tgatttcaac atggatacat atttcagttc tttcttttc     4200 tcactatctg aaaatacatt tccctccctc tcttcccccc aatatctccc ttttttctc    4260 tcttcctcta tcttccaaac cccactttct ccctcctcct tttcctgtgt tctcttaagc    4320
agatagcaca taccccacc cagtaccaaa tttcagaaca caagaggtc cagttcttcc    4380 cccttcacat aaaggaacat ggtttgtcag ccttctcct gtttatgggt ttcttccagc    4440
```

-continued

```
agaacagaga cattgccaac catattggat ctgcttgctg tccaaaccag caaactttcc    4500
tgggcaaatc acaatcagtg agtaaataga cagcctttct gctgccttgg gtttctgtgc    4560
agataaacag aaatgctctg attagaaagg aaatgaatgg ttccactcaa atgtcctgca    4620
atttaggatt gcagatttct gccttgaaat acctgtttct tgggacatt ccgtcctgat     4680 gatttttatt tttgttggtt tttattttg ggggaatga catgtttggg tcttttatac      4740
atgaaaattt gtttgacaat aatctcacaa aacatatttt acatctgaac aaaatgcctt    4800
tttgtttacc gtagcgtata catttgtttt gggattttg tgtgtttgtt gggaattttg     4860
tttttagcca ggtcagtatt gatgaggctg atcatttggc tctttttttc cttccagaag    4920
agttgcatca acaaagttaa ttgtatttat gtatgtaaat agattttaag cttcattata    4980
aaatattgtt aatgcctata acttttttc aattttttg tgtgtgttc taaggacttt       5040 ttcttaggtt tgctaaatac tgtagggaaa aaaatgcttc tttctacttt gtttatttta    5100
gactttaaaa tgagctactt cttattcact tttgtaaaca gctaatagca tggttccaat    5160 ttttttaag ttcacttttt ttgttctagg ggaaatgaat gtgcaaaaaa agaaaaagaa     5220
ctgttggtta tttgtgttat tctggatgta taaaaatcaa tggaaaaaaa taaactttca    5280
aattgaaatg acgtataac acatctactg aaaaagcaac gggaaatgtg gtcctattta    5340
agccagcccc cacctagggt ctatttgtgt ggcagttatt gggtttggtc acaaaacatc    5400
ctgaaaattc gtgcgtgggc ttcttcctcc ctggtacaaa cgtatggaat gcttcttaaa   5460
ggggaactgt caagctggtg tcttcagcca gatgacatga gagaatatcc cagaaccctc    5520
tctccaaggt gtttctagat agcacaggag agcaggcact gcactgtcca cagtccacgg    5580
tacacagtcg ggtgggccgc ctcccctctc ctgggagcat tcgtcgtgcc cagcctgagc    5640
agggcagctg gactgctgct gttcaggagc caccagagcc ttcctctctt tgtaccacag    5700
tttcttctgt aaatccagtg ttacaatcag tgtgaatggc aaataaacag tttgacaagt    5760
acatacacca ta                                                        5772
```

<210> SEQ ID NO 21
<211> LENGTH: 5964
<212> TYPE: DNA
<213> ORGANISM: Artificial Sequence
<220> FEATURE:
<223> OTHER INFORMATION: RUNX1 cDNA sequence

<400> SEQUENCE: 21

```
acagttaaat ttgtaatttg ggttgtgtga aacttctttt gggcctcata acaaccaca      60 gaaccacaag ttgggtagcc tggcagtgtc agaagtctga acccagcata gtggtcagca    120
ggcaggacga atcacactga atgcaaacca cagggtttcg cagcgtggta aaagaaatca    180
ttgagtcccc cgccttcaga agagggtgca ttttcaggag gaagcgatgg cttcagacag    240
catatttgag tcatttcctt cgtacccaca gtgcttcatg agatgccag cacgagccg      300 ccgcttcacg ccgccttcca ccgcgctgag cccaggcaag atgagcgagg cgttgccgct    360
gggcgccccg gacgccggcg ctgccctggc cggcaagctg aggagcggcg accgcagcat    420
ggtggaggtg ctggccgacc acccgggcga gctggtgcgc accgacagcc ccaacttcct    480
ctgctccgtg ctgcctacgc actggcgctg caacaagacc ctgcccatcg ctttcaaggt    540
ggtggcccta ggggatgttc cagatggcac tctggtcact gtgatggctg caatgatga    600 aaactactcg gctgagctga gaaatgctac cgcagccatg aagaaccagg ttgcaagatt   660
```

```
taatgacctc aggtttgtcg gtcgaagtgg aagagggaaa agcttcactc tgaccatcac    720
tgtcttcaca acccaccgc aagtcgccac ctaccacaga gccatcaaaa tcacagtgga    780
tgggccccga gaacctcgaa gacatcggca gaaactagat gatcagacca agcccgggag    840
cttgtccttt tccgagcggc tcagtgaact ggagcagctg cggcgcacag ccatgagggt    900
cagcccacac cacccagccc ccacgcccaa ccctcgtgcc tccctgaacc actccactgc    960
ctttaaccct cagcctcaga gtcagatgca ggatacaagg cagatccaac catccccacc   1020
gtggtcctac gatcagtcct accaatacct gggatccatt gcctctcctt ctgtgcaccc   1080
agcaacgccc atttcacctg gacgtgccag cggcatgaca accctctctg cagaactttc   1140
cagtcgactc tcaacggcac ccgacctgac agcgttcagc gacccgcgcc agttccccgc   1200
gctgccctcc atctccgacc cccgcatgca ctatccaggc gccttcacct actcccgac   1260
gccggtcacc tcgggcatcg gcatcggcat gtcggccatg ggctcggcca cgcgctacca   1320
cacctacctg ccgccgccct accccggctc gtcgcaagcg cagggaggcc cgttccaagc   1380
cagctcgccc tcctaccacc tgtactacgg cgcctcggcc ggctcctacc agttctccat   1440
ggtgggcggc gagcgctcgc cgccgcgcat cctgccgccc tgcaccaacg cctccaccgg   1500
ctccgcgctg ctcaacccca gcctcccgaa ccagagcgac gtggtggagg ccgagggcag   1560
ccacagcaac tcccccacca acatggcgcc ctccgcgcgc ctggaggagg ccgtgtggag   1620
gccctactga ggcgccaggc ctggcccggc tgggccccgc gggccgccgc cttcgcctcc   1680
gggcgcgcgg gcctcctgtt cgcgacaagc ccgccgggat cccgggccct gggcccggcc   1740
accgtcctgg ggccgagggc gcccgacggc caggatctcg ctgtaggtca ggcccgcgca   1800
gcctcctgcg cccagaagcc cacgccgccg ccgtctgctg gcgcccccggc cctcgcggag   1860
gtgtccgagc cgacgcacct cgagggtgtc cgccggcccc agcacccagg ggacgcgctg   1920
gaaagcaaac aggaagattc ccggagggaa actgtgaatg cttctgattt agcaatgctg   1980
tgaataaaaa gaaagatttt ataccccttga cttaactttt taaccaagtt gtttattcca   2040
aagagtgtgg aatttttggtt ggggtggggg gagaggaggg atgcaactcg ccctgtttgg   2100
catctaattc ttatttttaa ttttttccgca ccttatcaat tgcaaaatgc gtatttgcat   2160
ttgggtggtt tttatttta tatacgttta tataaatata tataaattga gcttgcttct   2220
ttcttgcttt gaccatggaa agaaatatga ttcccttttc tttaagtttt atttaacttt   2280
tcttttggac ttttgggtag ttgttttttt ttgttttgtt ttgttttttt gagaaacagc   2340
tacagctttg ggtcatttttt aactactgta ttcccacaag gaatcccag atatttatgt   2400
atcttgatgt tcagacattt atgtgttgat aattttttaa ttatttaaat gtacttatat   2460
taagaaaaat atcaagtact acattttctt ttgttcttga tagtagccaa agttaaatgt   2520
atcacattga agaaggctag aaaaaaagaa tgagtaatgt gatcgcttgg ttatccagaa   2580
gtattgttta cattaaactc cctttcatgt taatcaaaca agtgagtagc tcacgcagca   2640
acgttttttaa taggattttt agacactgag ggtcactcca aggatcagaa gtatggaatt   2700
ttctgccagg ctcaacaagg gtctcatatc taacttcctc cttaaaacag agaaggtcaa   2760
tctagttcca gagggttgag gcaggtgcca ataattacat ctttggagag gatttgatttt  2820
ctgcccaggg atttgctcac cccaaggtca tctgataatt tcacagatgc tgtgtaacag   2880
aacacagcca agtaaactg tgtaggggag ccacatttac ataggaacca aatcaatgaa   2940
tttaggggtt acgattatag caatttaagg gcccaccaga agcaggcctc gaggagtcaa   3000
tttgcctctg tgtgcctcag tggagacaag tgggaaaaca tggtcccacc tgtgcgagac   3060
```

```
cccctgtcct gtgctgctca ctcaacaaca tctttgtgtt gctttcacca ggctgagacc    3120
ctaccctatg gggtatatgg gcttttacct gtgcaccagt gtgacaggaa agattcatgt    3180
cactactgtc cgtggctaca attcaaaggt atccaatgtc gctgtaaatt ttatggcact    3240 attttttattg gaggatttgg tcagaatgca gttgttgtac aactcataaa tactaactgc   3300
tgattttgac acatgtgtgc tccaaatgat ctggtggtta tttaacgtac ctcttaaaat    3360
tcgttgaaac gatttcaggt caactctgaa gagtatttga aagcaggact tcagaacagt    3420
gtttgatttt tattttataa atttaagcat tcaaattagg caaatctttg gctgcaggca    3480
gcaaaaacag ctggacttat ttaaaacaac ttgttttttga gttttcttat atatatattg   3540
attatttgtt ttacacacat gcagtagcac tttggtaaga gttaaagagt aaagcagctt    3600
atgttgtcag gtcgttctta tctagagaag agctatagca gatctcggac aaactcagaa    3660
tatattcact ttcattttttg acaggattcc ctccacaact cagtttcata tattattccg   3720
tattacattt ttgcagctaa attaccataa aatgtcagca aatgtaaaaa tttaatttct    3780
gaaaagcacc attagcccat ttcccccaaa ttaaacgtaa atgtttttttt tcagcacatg   3840 ttaccatgtc tgacctgcaa aaatgctgga gaaaaatgaa ggaaaaaatt atgttttttca   3900 gtttaattct gttaactgaa gatattccaa ctcaaaacca gcctcatgct ctgattagat    3960
aatcttttac attgaacctt tactctcaaa gccatgtgtg gagggggctt gtcactattg    4020
taggctcact ggattggtca tttagagttt cacagactct taccagcata tatagtatttt   4080 aattgtttca aaaaaaatca aactgtagtt gttttggcga taggtctcac gcaacacatt    4140
tttgtatgtg tgtgtgtgtg cgtgtgtgtg tgtgtgtgtg aaaaattgca ttcattgact    4200
tcaggtagat taaggtatct ttttattcat tgccctcagg aaagttaagg tatcaatgag    4260
acccttaagc caatcatgta ataactgcat gtgtctggtc caggagaagt attgaataag    4320
ccatttctac tgcttactca tgtccctatt tatgatttca acatggatac atatttcagt    4380 tctttcttttt tctcactatc tgaaaataca tttccctccc tctcttcccc ccaatatctc    4440
cctttttttc tctcttcctc tatcttccaa accccacttt ctccctcctc cttttcctgt     4500
gttctcttaa gcagatagca catacccca cccagtacca aatttcagaa cacaagaagg      4560
tccagttctt ccccctccac ataaaggaac atggtttgtc agcctttctc ctgtttatgg     4620
gtttcttcca gcagaacaga gacattgcca accatattgg atctgcttgc tgtccaaacc    4680
agcaaacttt cctgggcaaa tcacaatcag tgagtaaata gacagccttt ctgctgcctt    4740
gggtttctgt gcagataaac agaaatgctc tgattagaaa ggaaatgaat ggttccactc    4800
aaatgtcctg caatttagga ttgcagattt ctgccttgaa atacctgttt ctttgggaca    4860
ttccgtcctg atgattttta ttttttgttgg ttttttatttt tggggggaat gacatgtttg    4920
ggtcttttat acatgaaaat ttgtttgaca ataatctcac aaaacatatt ttacatctga    4980
acaaaatgcc ttttttgttta ccgtagcgta tacatttgtt ttgggatttt tgtgtgtttg   5040
ttgggaattt tgttttttagc caggtcagta ttgatgaggc tgatcatttg gctctttttt    5100
tccttccaga agagttgcat caacaaagtt aattgtatttt atgtatgtaa atagattttta   5160 agcttcatta taaaatattg ttaatgccta taactttttt tcaattttttt tgtgtgtgtt     5220 tctaaggact ttttcttagg tttgctaaat actgtaggga aaaaaatgct tctttctact    5280 ttgtttatttt tagactttaa aatgagctac ttccttattca cttttgtaaa cagctaatag    5340
catggttcca attttttttta agttcacttt ttttgttcta ggggaaatga atgtgcaaaa    5400
```

```
aaagaaaaag aactgttggt tatttgtgtt attctggatg tataaaaatc aatggaaaaa      5460 ataaacttt caaattgaaa tgacggtata acacatctac tgaaaaagca acgggaaatg       5520
tggtcctatt taagccagcc cccacctagg gtctatttgt gtggcagtta ttgggtttgg      5580
tcacaaaaca tcctgaaaat tcgtgcgtgg gcttctttct ccctggtaca aacgtatgga     5640
atgcttctta aggggaact gtcaagctgg tgtcttcagc cagatgacat gagagaatat      5700
cccagaaccc tctctccaag gtgtttctag atagcacagg agagcaggca ctgcactgtc     5760
cacagtccac ggtacacagt cgggtgggcc gcctcccctc tcctgggagc attcgtcgtg     5820
cccagcctga gcagggcagc tggactgctg ctgttcagga gccaccgag ccttcctctc      5880 tttgtaccac agtttcttct gtaaatccag tgttacaatc agtgtgaatg caaataaac      5940 agtttgacaa gtacatacac cata                                            5964

<210> SEQ ID NO 22
<211> LENGTH: 6078
<212> TYPE: DNA
<213> ORGANISM: Artificial Sequence
<220> FEATURE:
<223> OTHER INFORMATION: RUNX1 cDNA sequence

<400> SEQUENCE: 22
gtaatttggg ttgtgtgaaa acttctttgg gcctcataaa caaccacaga accacaagtt     60
gggtagcctg gcagtgtcag aagtctgaac ccagcatagt ggtcagcagg caggacgaat     120
cacactgaat gcaaaccaca gggtttcgca gcgtggtgag catcaccaac ccacagccaa     180
ggcggcgctg gcttttttttt tttttttaat ctttaacaat ttgaatattt gtttttacaa    240
aggtaaaaga aatcattgag tccccgcct tcagaagagg gtgcattttc aggaggaagc      300
gatggcttca gacagcatat ttgagtcatt tccttcgtac ccacagtgct tcatgagaga    360
atgcatactt ggaatgaatc cttctagaga cgtccacgat gccagcacga gccgccgctt    420
cacgccgcct tccaccgcgc tgagcccagg caagatgagc gaggcgttgc cgctgggcgc    480
cccggacgcc ggcgctgccc tggccggcaa gctgaggagc ggcgaccgca gcatggtgga    540
ggtgctggcc gaccacccgg gcgagctggt gcgcaccgac agcccaact tcctctgctc     600 cgtgctgcct acgcactggc gctgcaacaa gaccctgccc atcgctttca aggtggtggc    660
cctaggggat gttccagatg gcactctggt cactgtgatg gctggcaatg atgaaaacta    720
ctcggctgag ctgagaaatg ctaccgcagc catgaagaac caggttgcaa gatttaatga    780
cctcaggttt gtcggtcgaa gtggaagagg gaaaagcttc actctgacca tcactgtctt    840
cacaaaccca ccgcaagtcg ccacctacca cagagccatc aaaatcacag tggatgggcc    900
ccgagaacct cgaagacatc ggcagaaact agatgatcag accaagcccg ggagcttgtc    960
cttttccgag cggctcagtg aactggagca gctgcggcgc acagccatga gggtcagccc   1020
acaccaccca gccccacgc ccaacccctcg tgcctccctg aaccactcca ctgccttaa    1080 ccctcagcct cagagtcaga tgcaggatac aaggcagatc caaccatccc accgtggtc    1140 ctacgatcag tcctaccaat acctgggatc cattgcctct ccttctgtgc acccagcaac   1200
gcccatttca cctggacgtg ccagcggcat gacaacctc tctgcagaac tttccagtcg    1260
actctcaacg gcacccgacc tgacagcgtt cagcgacccg cgccagttcc ccgcgctgcc   1320
ctccatctcc gaccccgca tgcactatcc aggcgccttc acctactccc cgacgccggt    1380
cacctcgggc atcggcatcg gcatgtcggc catgggctcg gccacgcgct accacaccta   1440
cctgccgccg ccctaccccg gctcgtcgca agcgcaggga ggccccgttcc aagccagctc   1500
```

```
gccctcctac cacctgtact acggcgcctc ggccggctcc taccagttct ccatggtggg    1560
cggcgagcgc tcgccgccgc gcatcctgcc gccctgcacc aacgcctcca ccggctccgc    1620
gctgctcaac cccagcctcc cgaaccagag cgacgtggtg gaggccgagg cagccacag    1680 caactccccc accaacatgg cgcctccgc gcgcctggag gaggccgtgt ggaggcccta    1740
ctgaggcgcc aggcctggcc cggctgggcc ccgcgggccg ccgccttcgc ctccgggcgc    1800
gcgggcctcc tgttcgcgac aagcccgccg ggatcccggg ccctgggccc ggccaccgtc    1860
ctggggccga gggcgcccga cggccaggat ctcgctgtag gtcaggcccg cgcagcctcc    1920
tgcgcccaga gcccacgcc gccgccgtct gctggcgccc cggccctcgc ggaggtgtcc    1980
gaggcgacgc acctcgaggg tgtccgccgg ccccagcacc caggggacgc gctggaaagc    2040
aaacaggaag attcccggag ggaaactgtg aatgcttctg atttagcaat gctgtgaata    2100
aaaagaaaga ttttataccc ttgacttaac ttttttaacca agttgtttat ccaaagagt    2160 gtggaatttt ggttggggtg gggggagagg agggatgcaa ctcgccctgt ttggcatcta    2220
attcttattt ttaattttc cgcaccttat caattgcaaa atgcgtattt gcatttgggt    2280
ggtttttatt tttatatacg tttatataaa tatatataaa ttgagcttgc ttctttcttg    2340
ctttgaccat ggaaagaaat atgattccct tttctttaag ttttatttaa cttttctttt    2400
ggacttttgg gtagttgttt tttttttgttt tgttttgttt tttgagaaa cagctacagc    2460 tttgggtcat ttttaactac tgtattccca caaggaatcc ccagatattt atgtatcttg    2520
atgttcagac atttatgtgt tgataattt ttaattattt aaatgtactt atattaagaa    2580
aaatatcaag tactacattt tcttttgttc ttgatagtag ccaaagttaa atgtatcaca    2640
ttgaagaagg ctagaaaaaa agaatgagta atgtgatcgc ttggttatcc agaagtattg    2700
tttacattaa actccctttc atgttaatca acaagtgag tagctcacgc agcaacgttt    2760
ttaataggat ttttagacac tgagggtcac tccaaggatc agaagtatgg aattttctgc    2820
caggctcaac aagggtctca tatctaactt cctccttaaa acagagaagg tcaatctagt    2880
tccagagggt tgaggcaggt gccaataatt acatctttgg agaggatttg atttctgccc    2940
agggatttgc tcaccccaag gtcatctgat aatttcacag atgctgtgta acagaacaca    3000
gccaaagtaa actgtgtagg ggagccacat ttacatagga accaaatcaa tgaatttagg    3060
ggttacgatt atagcaattt aagggcccac cagaagcagg cctcgaggag tcaatttgcc    3120
tctgtgtgcc tcagtggaga caagtgggaa acatggtcc cacctgtgcg agacccctg    3180 tcctgtgctg ctcactcaac aacatctttg tgttgctttc accaggctga gaccctaccc    3240
tatggggtat atgggctttt acctgtgcac cagtgtgaca ggaaagattc atgtcactac    3300
tgtccgtggc tacaattcaa aggtatccaa tgtcgctgta aattttatgg cactattttt    3360
attggaggat ttggtcagaa tgcagttgtt gtacaactca taaatactaa ctgctgattt    3420
tgacacatgt gtgctccaaa tgatctggtg gttatttaac gtacctctta aaattcgttg    3480
aaacgatttc aggtcaactc tgaagagtat ttgaaagcag acttcagaa cagtgtttga    3540 tttttatttt ataaatttaa gcattcaaat taggcaaatc tttggctgca ggcagcaaaa    3600
acagctggac ttatttaaaa caacttgttt ttgagttttc ttatatatat attgattatt    3660
tgttttacac acatgcagta gcactttggt aagagttaaa gagtaaagca gcttatgttg    3720
tcaggtcgtt cttatctaga gaagagctat agcagatctc ggacaaactc agaatatatt    3780
cactttcatt tttgacagga ttccctccac aactcagttt catatattat tccgtattac    3840
```

| | |
|---|---|
| atttttgcag ctaaattacc ataaaatgtc agcaaatgta aaaatttaat ttctgaaaag | 3900 |
| caccattagc ccatttcccc caaattaaac gtaaatgttt tttttcagca catgttacca | 3960 |
| tgtctgacct gcaaaaatgc tggagaaaaa tgaaggaaaa aattatgttt ttcagtttaa | 4020 |
| ttctgttaac tgaagatatt ccaactcaaa accagcctca tgctctgatt agataatctt | 4080 |
| ttacattgaa cctttactct caaagccatg tgtggagggg gcttgtcact attgtaggct | 4140 |
| cactggattg gtcatttaga gtttcacaga ctcttaccag catatatagt atttaattgt | 4200 |
| ttcaaaaaaa atcaaactgt agttgttttg gcgataggtc tcacgcaaca cattttttgta | 4260 |
| tgtgtgtgtg tgtgcgtgtg tgtgtgtgtg tgtgaaaaat tgcattcatt gacttcaggt | 4320 |
| agattaaggt atctttttat tcattgccct caggaaagtt aaggtatcaa tgagacccatt | 4380 |
| aagccaatca tgtaataact gcatgtgtct ggtccaggag aagtattgaa taagccatttt | 4440 |
| ctactgctta ctcatgtccc tatttatgat ttcaacatgg atacatattt cagttctttc | 4500 |
| tttttctcac tatctgaaaa tacatttccc tccctctctt cccccaata tctccctttt | 4560 |
| tttctctctt cctctatctt ccaaaccccca ctttctccct cctcctttttc ctgtgttctc | 4620 |
| ttaagcagat agcacatacc cccacccagt accaaatttc agaacacaag aaggtccagt | 4680 |
| tcttccccct tcacataaag gaacatggtt tgtcagcctt tctcctgttt atgggtttct | 4740 |
| tccagcagaa cagagacatt gccaaccata ttggatctgc ttgctgtcca aaccagcaaa | 4800 |
| cttttcctggg caaatcacaa tcagtgagta aatagacagc ctttctgctg ccttgggttt | 4860 |
| ctgtgcagat aaacagaaat gctctgatta gaaggaaat gaatggttcc actcaaatgt | 4920 |
| cctgcaattt aggattgcag atttctgcct tgaaatacct gtttctttgg gacattccgt | 4980 |
| cctgatgatt tttattttttg ttggtttta tttttggggg gaatgacatg tttgggtctt | 5040 |
| ttatacatga aaatttgttt gacaataatc tcacaaaaca tatttacat ctgaacaaaa | 5100 |
| tgcctttttg tttaccgtag cgtatacatt tgtttttggga ttttttgtgtg tttgttggga | 5160 |
| attttgttttt tagccaggtc agtattgatg aggctgatca tttggctctt ttttttccttc | 5220 |
| cagaagagtt gcatcaacaa agttaattgt atttatgtat gtaaatagat tttaagcttc | 5280 |
| attataaaat attgttaatg cctataactt tttttcaatt ttttttgtgtg tgtttctaag | 5340 |
| gacttttttct taggtttgct aaatactgta gggaaaaaaa tgcttctttc tactttgttt | 5400 |
| attttagact ttaaaatgag ctacttctta ttcacttttg taaacagcta atagcatggt | 5460 |
| tccaatttttt tttaagttca ctttttttgt tctagggaa atgaatgtgc aaaaaaagaa | 5520 |
| aaagaactgc tggttatttg tgttattctg gatgtataaa aatcaatgga aaaaaataaa | 5580 |
| cttttcaaatt gaaatgacgg tataacacat ctactgaaaa agcaacggga aatgtggtcc | 5640 |
| tatttaagcc agcccccacc tagggtctat ttgtgtggca gttattgggt ttggtcacaa | 5700 |
| aacatcctga aaattcgtgc gtgggcttct ttctccctgg tacaaacgta tggaatgctt | 5760 |
| cttaaagggg aactgtcaag ctggtgtctt cagccagatg acatgagaga atatcccaga | 5820 |
| accctctctc caaggtgttt ctagatagca caggagagca ggcactgcac tgtccacagt | 5880 |
| ccacggtaca cagtcgggtg ggccgcctcc cctctcctgg gagcattcgt cgtgcccagc | 5940 |
| ctgagcaggg cagctggact gctgctgttc aggagccacc agagccttcc tctctttgta | 6000 |
| ccacagtttc ttctgtaaat ccagtgttac aatcagtgtg aatggcaaat aaacagtttg | 6060 |
| acaagtacat acaccata | 6078 |

<210> SEQ ID NO 23
<211> LENGTH: 326

<212> TYPE: PRT
<213> ORGANISM: Homo sapiens

<400> SEQUENCE: 23

Met Leu Leu Ser Lys Phe Gly Ser Leu Ala His Leu Cys Gly Pro Gly
1               5                   10                  15

Gly Val Asp His Leu Pro Val Lys Ile Leu Gln Pro Ala Lys Ala Asp
            20                  25                  30

Lys Glu Ser Phe Glu Lys Ala Tyr Gln Val Gly Ala Val Leu Gly Ser
        35                  40                  45

Gly Gly Phe Gly Thr Val Tyr Ala Gly Ser Arg Ile Ala Asp Gly Leu
    50                  55                  60

Pro Val Ala Val Lys His Val Val Lys Glu Arg Val Thr Glu Trp Gly
65                  70                  75                  80

Ser Leu Gly Gly Ala Thr Val Pro Leu Glu Val Val Leu Leu Arg Lys
                85                  90                  95

Val Gly Ala Ala Gly Gly Ala Arg Gly Val Ile Arg Leu Leu Asp Trp
            100                 105                 110

Phe Glu Arg Pro Asp Gly Phe Leu Leu Val Leu Glu Arg Pro Glu Pro
        115                 120                 125

Ala Gln Asp Leu Phe Asp Phe Ile Thr Glu Arg Gly Ala Leu Asp Glu
    130                 135                 140

Pro Leu Ala Arg Arg Phe Phe Ala Gln Val Leu Ala Ala Val Arg His
145                 150                 155                 160

Cys His Ser Cys Gly Val Val His Arg Asp Ile Lys Asp Glu Asn Leu
                165                 170                 175

Leu Val Asp Leu Arg Ser Gly Glu Leu Lys Leu Ile Asp Phe Gly Ser
            180                 185                 190

Gly Ala Leu Leu Lys Asp Thr Val Tyr Thr Asp Phe Asp Gly Thr Arg
        195                 200                 205

Val Tyr Ser Pro Pro Glu Trp Ile Arg Tyr His Arg Tyr His Gly Arg
    210                 215                 220

Ser Ala Thr Val Trp Ser Leu Gly Val Leu Leu Tyr Asp Met Val Cys
225                 230                 235                 240

Gly Asp Ile Pro Phe Glu Gln Asp Glu Glu Ile Leu Arg Gly Arg Leu
                245                 250                 255

Leu Phe Arg Arg Arg Val Ser Pro Glu Cys Gln Gln Leu Ile Arg Trp
            260                 265                 270

Cys Leu Ser Leu Arg Pro Ser Glu Arg Pro Ser Leu Asp Gln Ile Ala
        275                 280                 285

Ala His Pro Trp Met Leu Gly Ala Asp Gly Gly Val Pro Glu Ser Cys
    290                 295                 300

Asp Leu Arg Leu Cys Thr Leu Asp Pro Asp Asp Val Ala Ser Thr Thr
305                 310                 315                 320

Ser Ser Ser Glu Ser Leu
                325

<210> SEQ ID NO 24
<211> LENGTH: 326
<212> TYPE: PRT
<213> ORGANISM: Homo sapiens

<400> SEQUENCE: 24

Met Leu Leu Ser Lys Phe Gly Ser Leu Ala His Leu Cys Gly Pro Gly
1               5                   10                  15

Gly Val Asp His Leu Pro Val Lys Ile Leu Gln Pro Ala Lys Ala Asp
            20                  25                  30

Lys Glu Ser Phe Glu Lys Ala Tyr Gln Val Gly Ala Val Leu Gly Ser
            35                  40                  45

Gly Gly Phe Gly Thr Val Tyr Ala Gly Ser Arg Ile Ala Asp Gly Leu
 50                  55                  60

Pro Val Ala Val Lys His Val Lys Glu Arg Val Thr Glu Trp Gly
 65                  70                  75                  80

Ser Leu Gly Gly Ala Thr Val Pro Leu Glu Val Val Leu Leu Arg Lys
            85                  90                  95

Val Gly Ala Ala Gly Ala Arg Gly Val Ile Arg Leu Leu Asp Trp
            100                 105                 110

Phe Glu Arg Pro Asp Gly Phe Leu Leu Val Leu Glu Arg Pro Glu Pro
            115                 120                 125

Ala Gln Asp Leu Phe Asp Phe Ile Thr Glu Arg Gly Ala Leu Asp Glu
            130                 135                 140

Pro Leu Ala Arg Arg Phe Phe Ala Gln Val Leu Ala Ala Val Arg His
145                 150                 155                 160

Cys His Ser Cys Gly Val Val His Arg Asp Ile Lys Asp Glu Asn Leu
            165                 170                 175

Leu Val Asp Leu Arg Ser Gly Glu Leu Lys Leu Ile Asp Phe Gly Ser
            180                 185                 190

Gly Ala Leu Leu Lys Asp Thr Val Tyr Thr Asp Phe Asp Gly Thr Arg
            195                 200                 205

Val Tyr Ser Pro Pro Glu Trp Ile Arg Tyr His Arg Tyr His Gly Arg
            210                 215                 220

Ser Ala Thr Val Trp Ser Leu Gly Val Leu Leu Tyr Asp Met Val Cys
225                 230                 235                 240

Gly Asp Ile Pro Phe Glu Gln Asp Glu Glu Ile Leu Arg Gly Arg Leu
            245                 250                 255

Leu Phe Arg Arg Arg Val Ser Pro Glu Cys Gln Gln Leu Ile Arg Trp
            260                 265                 270

Cys Leu Ser Leu Arg Pro Ser Glu Arg Pro Ser Leu Asp Gln Ile Ala
            275                 280                 285

Ala His Pro Trp Met Leu Gly Ala Asp Gly Gly Ala Pro Glu Ser Cys
            290                 295                 300

Asp Leu Arg Leu Cys Thr Leu Asp Pro Asp Asp Val Ala Ser Thr Thr
305                 310                 315                 320

Ser Ser Ser Glu Ser Leu
            325

<210> SEQ ID NO 25
<211> LENGTH: 326
<212> TYPE: PRT
<213> ORGANISM: Homo sapiens

<400> SEQUENCE: 25

Met Leu Leu Ser Lys Phe Gly Ser Leu Ala His Leu Cys Gly Pro Gly
1               5                   10                  15

Gly Val Asp His Leu Pro Val Lys Ile Leu Gln Pro Ala Lys Ala Asp
            20                  25                  30

Lys Glu Ser Phe Glu Lys Ala Tyr Gln Val Gly Ala Val Leu Gly Ser
            35                  40                  45

Gly Gly Phe Gly Thr Val Tyr Ala Gly Ser Arg Ile Ala Asp Gly Leu
 50                  55                  60

Pro Val Ala Val Lys His Val Val Lys Glu Arg Val Thr Glu Trp Gly
65                  70                  75                  80

Ser Leu Gly Gly Ala Thr Val Pro Leu Glu Val Val Leu Leu Arg Lys
                85                  90                  95

Val Gly Ala Ala Gly Gly Ala Arg Gly Val Ile Arg Leu Leu Asp Trp
            100                 105                 110

Phe Glu Arg Pro Asp Gly Phe Leu Leu Val Leu Glu Arg Pro Glu Pro
        115                 120                 125

Ala Gln Asp Leu Phe Asp Phe Ile Thr Glu Arg Gly Ala Leu Asp Glu
130                 135                 140

Pro Leu Ala Arg Arg Phe Phe Ala Gln Val Leu Ala Val Arg His
145                 150                 155                 160

Cys His Ser Cys Gly Val Val His Arg Asp Ile Lys Asp Glu Asn Leu
                165                 170                 175

Leu Val Asp Leu Arg Ser Gly Glu Leu Lys Leu Ile Asp Phe Gly Ser
            180                 185                 190

Gly Ala Leu Leu Lys Asp Thr Val Tyr Thr Asp Phe Asp Gly Thr Arg
        195                 200                 205

Val Tyr Ser Pro Pro Glu Trp Ile Arg Tyr His Arg Tyr His Gly Arg
    210                 215                 220

Ser Ala Thr Val Trp Ser Leu Gly Val Leu Leu Tyr Asp Met Val Cys
225                 230                 235                 240

Gly Asp Ile Pro Phe Glu Gln Asp Glu Glu Ile Leu Arg Gly Arg Leu
                245                 250                 255

Leu Phe Arg Arg Arg Val Ser Pro Glu Cys Gln Gln Leu Ile Arg Trp
            260                 265                 270

Cys Leu Ser Leu Arg Pro Ser Glu Arg Pro Ser Leu Asp Gln Ile Ala
        275                 280                 285

Ala His Pro Trp Met Leu Gly Ala Asp Gly Gly Ala Pro Glu Ser Cys
    290                 295                 300

Asp Leu Arg Leu Cys Thr Leu Asp Pro Asp Asp Val Ala Ser Thr Thr
305                 310                 315                 320

Ser Ser Ser Glu Ser Leu
                325

<210> SEQ ID NO 26
<211> LENGTH: 326
<212> TYPE: PRT
<213> ORGANISM: Homo sapiens

<400> SEQUENCE: 26

Met Leu Leu Ser Lys Phe Gly Ser Leu Ala His Leu Cys Gly Pro Gly
1               5                   10                  15

Gly Val Asp His Leu Pro Val Lys Ile Leu Gln Pro Ala Lys Ala Asp
            20                  25                  30

Lys Glu Ser Phe Lys Lys Ala Tyr Gln Val Gly Ala Val Leu Gly Ser
        35                  40                  45

Gly Gly Phe Gly Thr Val Tyr Ala Gly Ser Arg Ile Ala Asp Gly Leu
    50                  55                  60

Pro Val Ala Val Lys His Val Val Lys Glu Arg Val Thr Glu Trp Gly
65                  70                  75                  80

Ser Leu Gly Gly Ala Thr Val Pro Leu Glu Val Val Leu Leu Arg Lys
                85                  90                  95

Val Gly Ala Ala Gly Gly Ala Arg Gly Val Ile Arg Leu Leu Asp Trp

|     |     |     |     |     | 100 |     |     |     | 105 |     |     |     | 110 |     |
| --- | --- | --- | --- | --- | --- | --- | --- | --- | --- | --- | --- | --- | --- | --- |
| Phe | Glu | Arg | Pro | Asp | Gly | Phe | Leu | Leu | Val | Leu | Glu | Arg | Pro | Glu | Pro |
|     |     |     | 115 |     |     |     |     | 120 |     |     |     |     | 125 |     |     |

Phe Glu Arg Pro Asp Gly Phe Leu Leu Val Leu Glu Arg Pro Glu Pro
                115                    120                    125

Ala Gln Asp Leu Phe Asp Phe Ile Thr Glu Arg Gly Ala Leu Asp Glu
    130                    135                    140

Pro Leu Ala Arg Arg Phe Ala Gln Val Leu Ala Ala Val Arg His
145                 150                    155                    160

Cys His Ser Cys Gly Val Val His Arg Asp Ile Lys Asp Glu Asn Leu
                    165                    170                    175

Leu Val Asp Leu Arg Ser Gly Glu Leu Lys Leu Ile Asp Phe Gly Ser
                180                    185                    190

Gly Ala Leu Leu Lys Asp Thr Val Tyr Thr Asp Phe Asp Gly Thr Arg
                195                    200                    205

Val Tyr Ser Pro Pro Glu Trp Ile Arg Tyr His Arg Tyr His Gly Arg
    210                    215                    220

Ser Ala Thr Val Trp Ser Leu Gly Val Leu Leu Tyr Asp Met Val Cys
225                    230                    235                    240

Gly Asp Ile Pro Phe Glu Gln Asp Glu Glu Ile Leu Arg Gly Arg Leu
                245                    250                    255

Leu Phe Arg Arg Arg Val Ser Pro Glu Cys Gln Gln Leu Ile Arg Trp
                260                    265                    270

Cys Leu Ser Leu Arg Pro Ser Glu Arg Pro Ser Leu Asp Gln Ile Ala
                275                    280                    285

Ala His Pro Trp Met Leu Gly Ala Asp Gly Gly Ala Pro Glu Ser Cys
                290                    295                    300

Asp Leu Arg Leu Cys Thr Leu Asp Pro Asp Asp Val Ala Ser Thr Thr
305                    310                    315                    320

Ser Ser Ser Glu Ser Leu
                325

<210> SEQ ID NO 27
<211> LENGTH: 2410
<212> TYPE: DNA
<213> ORGANISM: Artificial Sequence
<220> FEATURE:
<223> OTHER INFORMATION: PIM3 cDNA sequence

<400> SEQUENCE: 27

```
gagagcgtga gcgcggagag cggaccgacg cgacacgccg tgcgcctccg cggctgcgct      60
acgaaaacga gtcccggagc ggccccgcgc ccgccgcacc cggccctcgc ccgcccgaag     120
acaggcgcca agctgccccg ccgtctcccc agctagcgcc cggccgccgc cgcctcgcgg     180
gccccgggcg gaaggggcg gggtcccgat tcgccccgcc ccgcggagg gatacgcggc       240
gccgcggccc aaaaccccg gcgaggcgg ccggggcggg tgaggcgctc cgcctgctgc       300
gcgtctacgc ggtccccgcg ggccttccgg gcccactgcg ccgcgcggac cgcctcgggc    360
tcggacggcc ggtgtcccccg gcgcgccgct cgcccggatc ggccgcgggct tcggcgcctg   420
gggctcgggg ctccggggag gccgtcgccc gcgatgctgc tctccaagtt cggctccctg   480
gcgcacctct gcgggcccgg cggcgtggac cacctcccgg tgaagatcct gcagccagcc   540
aaggcggaca aggagagctt cgagaaggcg taccaggtgg cgccgtgct gggtagcggc    600
ggcttcggca cggtctacgc gggtagccgc atcgccgacg ggctcccggt ggctgtgaag   660
cacgtggtga aggagcgggt gaccgagtgg ggcagcctgg gcggcgcgac cgtgcccctg   720
gaggtggtgc tgctgcgcaa ggtgggcgcg gcggcggcg cgcgcggcgt catccgcctg    780
```

| | |
|---|---|
| ctggactggt tcgagcggcc cgacggcttc ctgctggtgc tggagcggcc cgagccggcg | 840 |
| caggacctct tcgactttat cacggagcgc ggcgccctgg acgagccgct ggcgcgccgc | 900 |
| ttcttcgcgc aggtgctggc cgccgtgcgc cactgccaca gctgcggggt cgtgcaccgc | 960 |
| gacattaagg acgaaaatct gcttgtggac ctgcgctccg agagctcaa gctcatcgac | 1020 |
| ttcggttcgg gtgcgctgct caaggacacg gtctacaccg acttcgacgg caccccgagtg | 1080 |
| tacagccccc cggagtggat ccgctaccac cgctaccacg ggcgctcggc caccgtgtgg | 1140 |
| tcgctgggcg tgcttctcta cgatatggtg tgtggggaca tcccccttcga gcaggacgag | 1200 |
| gagatcctcc gaggccgcct gctcttccgg aggagggtct ctccagagtg ccagcagctg | 1260 |
| atccggtggt gcctgtccct gcggccctca gagcggccgt cgctggatca gattgcggcc | 1320 |
| catccctgga tgctggggc tgacggggc gtccccgaga gctgtgacct gcggctgtgc | 1380 |
| accctcgacc ctgatgacgt ggccagcacc acgtccagca gcgagagctt gtgaggagct | 1440 |
| gcacctgact gggagctagg ggaccacctg ccttggccag acctgggacg ccccagacc | 1500 |
| ctgactttct cctgcgtggg ccgtctcctc ctgcggaagc agtgacctct gaccctggt | 1560 |
| gaccttcgct ttgagtgcct tttgaacgct ggtcccgcgg gacttggttt tctcaagctc | 1620 |
| tgtctgtcca agacgctcc ggtcgaggtc ccgcctgccc tgggtggata cttgaacccc | 1680 |
| agacgccct ctgtgctgct gtgtccggag gcggccttcc catctgcctg cccacccgga | 1740 |
| gctctttccg ccggcgcagg gtcccaagcc cacctcccgc cctcagtcct gcggtgtgcg | 1800 |
| tctgggcacg tcctgcacac acaatgcaag tcctggcctc cgcgcccgcc cgcccacgcg | 1860 |
| agccgtaccc gccgccaact ctgttattta tggtgtgacc cctggaggt gccctcggcc | 1920 |
| caccgggct atttattgtt taatttattt gttgaggtta tttcctctga gcagtctgcc | 1980 |
| tctcccaagc cccaggggac agtggggagg caggggaggg ggtggctgtg gtccagggac | 2040 |
| cccaggccct gattcctgtg cctggcgtct gtcccggccc cgcctgtcag aagatgaaca | 2100 |
| tgtatagtgg ctaacttaag gggagtgggt gaccctgaca cttccaggca ctgtgcccag | 2160 |
| ggtttgggtt ttaaattatt gactttgtac agtctgcttg tgggctctga agctggggt | 2220 |
| ggggccagag cctgagcgtt taattttattc agtacctgtg tttgtgtgaa tgcggtgtgt | 2280 |
| gcaggcatcg cagatggggg ttcttttcagt tcaaaagtga gatgtctgga gatcatattt | 2340 |
| ttttatacag gtatttcaat taaaatgttt ttgtacataa aaaaaaaaa aaaaaaaaa | 2400 |
| aaaaaaaaa | 2410 |

<210> SEQ ID NO 28
<211> LENGTH: 2004
<212> TYPE: DNA
<213> ORGANISM: Artificial Sequence
<220> FEATURE:
<223> OTHER INFORMATION: PIM3 cDNA sequence

<400> SEQUENCE: 28

| | |
|---|---|
| gctcgcccgg atcggccgcg gcttcggcgc ctggggctcg gggctccggg gaggccgtcg | 60 |
| cccgcgatgc tgctctccaa gttcggctcc ctggcgcacc tctgcgggcc cggcggcgtg | 120 |
| gaccacctcc cggtgaagat cctgcagcca gccaaggcgg acaaggagag cttcaagaag | 180 |
| gcgtaccagg tgggcgccgt gctgggtagc ggcggcttcg gcacggtcta cgcgggtagc | 240 |
| cgcatcgccg acgggctccc ggtggctgtg aagcacgtgg tgaaggagcg ggtgaccgag | 300 |
| tggggcagcc tgggcggcgc gaccgtgccc ctggaggtgg tgctgctgcg caaggtgggc | 360 |

-continued

```
gcggcgggcg gcgcgcgcgg cgtcatccgc ctgctggact ggttcgagcg gcccgacggc    420
ttcctgctgg tgctggagcg gcccgagccg gcgcaggacc tcttcgactt tatcacggag    480
cgcggcgccc tggacgagcc gctggcgcgc cgcttcttcg cgcaggtgct ggccgccgtg    540
cgccactgcc acagctgcgg ggtcgtgcac cgcgacatta aggacgaaaa tctgcttgtg    600
gacctgcgct ccggagagct caagctcatc gacttcggtt cgggtgcgct gctcaaggac    660
acggtctaca ccgacttcga cggcacccga gtgtacagcc cccggagtg atccgctac     720 caccgctacc acgggcgctc ggccaccgtg tggtcgctgg gcgtgcttct ctacgatatg    780
gtgtgtgggg acatcccctt cgagcaggac gaggagatcc tccgaggccg cctgctcttc    840
cggaggaggg tctctccaga gtgccagcag ctgatccggt ggtgcctgtc cctgcggccc    900
tcagagcggc cgtcgctgga tcagattgcg gcccatccct ggatgctggg ggctgacggg    960
ggcgccccgg agagctgtga cctgcggctg tgcaccctcg accctgatga cgtggccagc   1020
accacgtcca gcagcgagag cttgtgagga gctgcacctg actgggagct aggggaccac   1080
ctgccttggc cagacctggg acgccccag accctgactt tttcctgcgt gggccgtctc   1140
ctcctgcgga agcagtgacc tctgaccccct ggtgaccttc gctttgagtg ccttttgaac   1200
gctggtcccg cgggacttgg ttttctcaag ctctgtctgt ccaaagaggc tccagtcgag   1260
gtcccgcctg ccctgggtgg atacttgaac cccagacgcc cctctgtgct gctgtgtccg   1320
gaggcggcct tccatctgc ctgcccaccc ggagctcttt ccgccggcgc agggtcccaa    1380
gcccacctcc cgcccctcagt cctgcggtgt gcgtctgggc acgtcctgca cacacaatgc   1440
aagtcctggc ctccgcgccc gcccgcccac gcgagccgta cccgccgcca actctgttat   1500
ttatggtgtg accccctgga ggtgccctcg gccaccgggg ctatttatt gtttaattta    1560 tttgttgagg ttatttcctc tgagcagtct gcctctccca gccccaggg gacagtgggg    1620 ggcaggggag ggggtggctt tggtccaggg accccaggcc ctgattcctg tgcctggcgt    1680
ctgtcctggc cccgcctgtc agaagatgaa catgtgtagt ggctaactta aggggagtgg    1740
gtgaccctga cacttccagg cactgtgccc agggtttggg ttttaaatta ttgactttgt    1800
acagtctgct tgtgggctct gaaagctggg gtggggccag agcctgagcg tttaattat    1860 tcagtacctg tgtttgtgtg aatgcggtgt gtgcaggcat cgcagatggg ggttctttca   1920
gttcaaaagt gagatgtctg gagatcatat tttttatac aggtatttca attaaaatgt   1980
ttttgtacaa aaaaaaaaa aaaa                                            2004
```

<210> SEQ ID NO 29
<211> LENGTH: 2392
<212> TYPE: DNA
<213> ORGANISM: Artificial Sequence
<220> FEATURE:
<223> OTHER INFORMATION: PIM3 cDNA sequence

<400> SEQUENCE: 29

```
agcggaccga cgcgacacgc cgtgcgcctc cgcggctgcg ctacgaaaac gagtcccgga     60
gcggccccgc gcccgccgca cccggccctc gcccacccga agacaggcgc ccagctgccc    120
cgccgtctcc ccagctagcg cccggccgcc ccgcctcgc gggcccccggg cggaaggggg    180 cggggtcccg attcgccccg ccccccgcgga gggatacgcg gcgccgcggc ccaaaacccc    240
cgggcgaggc ggccggggcg ggtgaggcgc tccgcctgct gctcgtctac gcggtccccg    300
cgggccttcc gggcccactg cgccgcgcgg accgcctcgg gctcggacgg ccggtgtccc    360
cggcgcgccg ctcgcccgga tcggccgcgg cttcggcgcc tggggctcgg ggctccgggg    420
```

```
aggccgtcgc ccgcgatgct gctctccaag ttcggctccc tggcgcacct ctgcgggccc      480
ggcggcgtgg accacctccc ggtgaagatc ctgcagccag ccaaggcgga caaggagagc      540
ttcgagaagg cgtaccaggt gggcgccgtg ctgggtagcg gcggcttcgg cacggtctac      600
gcgggtagcc gcatcgccga cgggctcccg gtggctgtga agcacgtggt gaaggagcgg      660
gtgaccgagt ggggcagcct gggcggcgcg accgtgcccc tggaggtggt gctgctgcgc      720
aaggtgggcg cggcgggcgg cgcgcgcggc gtcatccgcc tgctggactg gttcgagcgg      780
cccgacggct cctgctggt gctggagcgg cccgagccgg cgcaggacct cttcgacttt      840
atcacggagc gcggcgccct ggacgagccg ctggcgcgcc gcttcttcgc gcaggtgctg      900
gccgccgtgc gccactgcca cagctgcggg gtcgtgcacc gcgacattaa ggacgaaaat      960
ctgcttgtgg acctgcgctc cggagagctc aagctcatcg acttcggttc gggtgcgctg     1020
ctcaaggaca cggtctacac cgacttcgac ggcacccgag tgtacagccc cccggagtgg     1080
atccgctacc accgctacca cgggcgctcg gccaccgtgt ggtcgctggg cgtgcttctc     1140
tacgatatgg tgtgtgggga catccccttc gagcaggacg aggagatcct ccgaggccgc     1200
ctgctcttcc ggaggagggt ctctccagag tgccagcagc tgatccggtg gtgcctgtcc     1260
ctgcggccct cagagcggcc gtcgctggat cagattgcgg cccatccctg gatgctgggg     1320
gctgacgggg gcgccccgga gagctgtgac ctgcggctgt gcaccctcga ccctgatgac     1380
gtggccagca ccacgtccag cagcgagagc ttgtgaggag ctgcacctga ctgggagcta     1440
ggggaccacc tgccttggcc agacctggga cgcccccaga ccctgacttt ttcctgcgtg     1500
ggccgtctcc tcctgcggaa gcagtgacct ctgacccctg gtgaccttcg cttttgagtgc    1560 cttttgaacg ctggtcccgc gggacttggt tttctcaagc tctgtctgtc caaagacgct     1620
ccggtcgagg tcccgcctgc cctgggtgga tacttgaacc cagacgccc ctctgtgctg     1680 ctgtgtccgg aggcggcctt cccatctgcc tgcccacccg gagctctttc cgccggcgca     1740
gggtcccaag cccacctccc gccctcagtc ctgcggtgtg cgtctgggca cgtcctgcac     1800
acacaatgca agtcctggcc tccgcgcccc cccgcccacg cgagccgtac ccgccgccaa     1860
ctctgttatt tatggtgtga cccctggag gtgccctcgg cccaccgggg ctatttattg      1920
tttaatttat ttgttgaggt tatttcctct gagcagtctg cctctcccaa gccccagggg     1980
acagtgggga ggcaggggag ggggtggctg tggtccaggg accccaggcc ctgattcctg     2040
tgcctggcgt ctgtcctggc cccgcctgtc agaagatgaa catgtatagt ggctaactta     2100
aggggagtgg gtgaccctga cacttccagg cactgtgccc agggtttggg ttttaaatta     2160
ttgactttgt acagtctgct tgtgggctct gaaagctggg gtggggccag agcctgagcg     2220 tttaattat tcagtacctg tgtttgtgtg aatgcggtgt gtgcaggcat cgcagatggg     2280
ggttctttca gttcaaaagt gagatgtctg gagatcatat tttttttatac aggtatttca    2340 attaaaatgt ttttgtacat aaaaaaaaaa aaaaaaaaa aaaaaaaaaa aa               2392
```

<210> SEQ ID NO 30
<211> LENGTH: 1524
<212> TYPE: DNA
<213> ORGANISM: Artificial Sequence
<220> FEATURE:
<223> OTHER INFORMATION: PIM3 cDNA sequence

<400> SEQUENCE: 30

```
tctcgggctc ggacggccgg tgtccccggc gcgccgctcg cccggatcgg ccgcggcttc       60
```

-continued

```
ggcgcctggg gctcggggct ccggggaggc cgtcgcccgc gatgctgctc tccaagttcg    120
gctccctggc gcacctctgc gggcccggcg gcgtggacca cctcccggtg aagatcctgc    180
agccagccaa ggcggacaag gagagcttcg agaaggcgta ccaggtgggc gccgtgctgg    240
gtagcggcgg cttcggcacg gtctacgcgg gtagccgcat cgccgacggg ctcccggtgg    300
ctgtgaagca cgtggtgaag gagcgggtga ccgagtgggg cagcctgggc ggcgcgaccg    360 tgccctgga ggtggtgctg ctgcgcaagg tgggcgcggc gggcggcgcg cgcggcgtca    420
tccgcctgct ggactggttc gagcggcccg acggcttcct gctggtgctg gagcggcccg    480
agccggcgca ggacctcttc gactttatca cggagcgcgg cgccctggac gagccgctgg    540
cgcgccgctt cttcgcgcag gtgctggccg ccgtgcgcca ctgccacagc tgcggggtcg    600
tgcaccgcga cattaaggac gaaaatctgc ttgtggacct cgctccgga gagctcaagc    660 tcatcgactt cggttcgggt gcgctgctca aggacacggt ctacaccgac ttcgacggca    720
cccgagtgta cagccccccg gagtggatcc gctaccaccg ctaccacggg cgctcggcca    780
ccgtgtggtc gctgggcgtg cttctctacg atatggtgtg tgggacatc cccttcgagc    840 aggacgagga gatcctccga ggccgcctgc tcttccggag gagggtctct ccagagtgcc    900
agcagctgat ccggtggtgc ctgtccctgc ggccctcaga gcggccgtcg ctggatcaga    960
ttgcggccca tccctggatg ctgggggctg acggggcgc cccggagagc tgtgacctgc   1020
ggctgtgcac cctcgaccct gatgacgtgg ccagcaccac gtccagcagc gagagcttgt   1080
gaggagctgc acctgactgg gagctagggg accacctgcc ttggccagac ctgggacgcc   1140
cccagaccct gaccttttcc tgcgtgggcc gtctcctcct gcggaagcag tgacctctga   1200
cccctggtga ccttcgctttt gagtgccttt tgaacgctgg tcccgcggga cttggttttc   1260
tcaagctctg tctgtccaaa gacgctccgg tcgaggtccc gcctgccctg ggtggatact   1320
tgaaccccag acgcccctct gtgctgctgt gtccggaggc ggccttccca tctgcctgcc   1380
cacccggagc tctttccgcc ggcgcagggt cccaagccca cctcccgccc tcagtcctgc   1440
ggtgtgcgtc tgggcacgtc ctgcacacac aatgcaagtc ctggcctccg cgcccgcccg   1500
cccacgcgag ccgtacccgc cgcc                                         1524
```

<210> SEQ ID NO 31
<211> LENGTH: 291
<212> TYPE: PRT
<213> ORGANISM: Homo sapiens

<400> SEQUENCE: 31

```
Met Gln Arg Ala Arg Pro Thr Leu Trp Ala Ala Leu Thr Leu Leu
1               5                   10                  15

Val Leu Leu Arg Gly Pro Pro Val Ala Arg Ala Gly Ala Ser Ser Ala
            20                  25                  30

Gly Leu Gly Pro Val Val Arg Cys Glu Pro Cys Asp Ala Arg Ala Leu
        35                  40                  45

Ala Gln Cys Ala Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
                85                  90                  95

Ser Pro Asp Glu Ala Arg Pro Leu Gln Ala Leu Leu Asp Gly Arg Gly
            100                 105                 110
```

```
Leu Cys Val Asn Ala Ser Ala Val Ser Arg Leu Arg Ala Tyr Leu Leu
            115                 120                 125

Pro Ala Pro Pro Ala Pro Gly Asn Ala Ser Glu Ser Glu Glu Asp Arg
130                 135                 140

Ser Ala Gly Ser Val Glu Ser Pro Ser Val Ser Ser Thr His Arg Val
145                 150                 155                 160

Ser Asp Pro Lys Phe His Pro Leu His Ser Lys Ile Ile Ile Ile Lys
                165                 170                 175

Lys Gly His Ala Lys Asp Ser Gln Arg Tyr Lys Val Asp Tyr Glu Ser
            180                 185                 190

Gln Ser Thr Asp Thr Gln Asn Phe Ser Ser Glu Ser Lys Arg Glu Thr
        195                 200                 205

Glu Tyr Gly Pro Cys Arg Arg Glu Met Glu Asp Thr Leu Asn His Leu
    210                 215                 220

Lys Phe Leu Asn Val Leu Ser Pro Arg Gly Val His Ile Pro Asn Cys
225                 230                 235                 240

Asp Lys Lys Gly Phe Tyr Lys Lys Lys Gln Cys Arg Pro Ser Lys Gly
                245                 250                 255

Arg Lys Arg Gly Phe Cys Trp Cys Val Asp Lys Tyr Gly Gln Pro Leu
            260                 265                 270

Pro Gly Tyr Thr Thr Lys Gly Lys Glu Asp Val His Cys Tyr Ser Met
        275                 280                 285

Gln Ser Lys
    290

<210> SEQ ID NO 32
<211> LENGTH: 297
<212> TYPE: PRT
<213> ORGANISM: Homo sapiens

<400> SEQUENCE: 32

Met Gln Arg Ala Arg Pro Thr Leu Trp Ala Ala Ala Leu Thr Leu Leu
1               5                   10                  15

Val Leu Leu Arg Gly Pro Pro Val Ala Arg Ala Gly Ala Ser Ser Ala
            20                  25                  30

Gly Leu Gly Pro Val Val Arg Cys Glu Pro Cys Asp Ala Arg Ala Leu
        35                  40                  45

Ala Gln Cys Ala Pro Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
                85                  90                  95

Ser Pro Asp Glu Ala Arg Pro Leu Gln Ala Leu Leu Asp Gly Arg Gly
            100                 105                 110

Leu Cys Val Asn Ala Ser Ala Val Ser Arg Leu Arg Ala Tyr Leu Leu
        115                 120                 125

Pro Ala Pro Pro Ala Pro Gly Glu Pro Pro Ala Pro Gly Asn Ala Ser
    130                 135                 140

Glu Ser Glu Glu Asp Arg Ser Ala Gly Ser Val Glu Ser Pro Ser Val
145                 150                 155                 160

Ser Ser Thr His Arg Val Ser Asp Pro Lys Phe His Pro Leu His Ser
                165                 170                 175

Lys Ile Ile Ile Ile Lys Lys Gly His Ala Lys Asp Ser Gln Arg Tyr
            180                 185                 190
```

```
Lys Val Asp Tyr Glu Ser Gln Ser Thr Asp Thr Gln Asn Phe Ser Ser
            195                 200                 205

Glu Ser Lys Arg Glu Thr Glu Tyr Gly Pro Cys Arg Arg Glu Met Glu
210                 215                 220

Asp Thr Leu Asn His Leu Lys Phe Leu Asn Val Leu Ser Pro Arg Gly
225                 230                 235                 240

Val His Ile Pro Asn Cys Asp Lys Lys Gly Phe Tyr Lys Lys Lys Gln
            245                 250                 255

Cys Arg Pro Ser Lys Gly Arg Lys Arg Gly Phe Cys Trp Cys Val Asp
                260                 265                 270

Lys Tyr Gly Gln Pro Leu Pro Gly Tyr Thr Thr Lys Gly Lys Glu Asp
            275                 280                 285

Val His Cys Tyr Ser Met Gln Ser Lys
            290                 295

<210> SEQ ID NO 33
<211> LENGTH: 291
<212> TYPE: PRT
<213> ORGANISM: homo sapiens

<400> SEQUENCE: 33

Met Gln Arg Ala Arg Pro Thr Leu Trp Ala Ala Ala Leu Thr Leu Leu
1               5                   10                  15

Val Leu Leu Arg Gly Pro Pro Val Ala Arg Ala Gly Ala Ser Ser Ala
                20                  25                  30

Gly Leu Gly Pro Val Val Arg Cys Glu Pro Cys Asp Ala Arg Ala Leu
            35                  40                  45

Ala Gln Cys Ala Pro Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
                85                  90                  95

Ser Pro Asp Glu Ala Arg Pro Leu Gln Ala Leu Leu Asp Gly Arg Gly
            100                 105                 110

Leu Cys Val Asn Ala Ser Ala Val Ser Arg Leu Arg Ala Tyr Leu Leu
        115                 120                 125

Pro Ala Pro Pro Ala Pro Gly Asn Ala Ser Glu Ser Glu Glu Asp Arg
    130                 135                 140

Ser Ala Gly Ser Val Glu Ser Pro Ser Val Ser Ser Thr His Arg Val
145                 150                 155                 160

Ser Asp Pro Lys Phe His Pro Leu His Ser Lys Ile Ile Ile Lys
                165                 170                 175

Lys Gly His Ala Lys Asp Ser Gln Arg Tyr Lys Val Asp Tyr Glu Ser
            180                 185                 190

Gln Ser Thr Asp Thr Gln Asn Phe Ser Ser Glu Ser Lys Arg Glu Thr
        195                 200                 205

Glu Tyr Gly Pro Cys Arg Arg Glu Met Glu Asp Thr Leu Asn His Leu
    210                 215                 220

Lys Phe Leu Asn Val Leu Ser Pro Arg Gly Val His Ile Pro Asn Cys
225                 230                 235                 240

Asp Lys Lys Gly Phe Tyr Lys Lys Lys Gln Cys Arg Pro Ser Lys Gly
                245                 250                 255

Arg Lys Arg Gly Phe Cys Trp Cys Val Asp Lys Tyr Gly Gln Pro Leu
```

```
            260                 265                 270
Pro Gly Tyr Thr Thr Lys Gly Lys Glu Asp Val His Cys Tyr Ser Met
            275                 280                 285

Gln Ser Lys
        290
```

<210> SEQ ID NO 34
<211> LENGTH: 297
<212> TYPE: PRT
<213> ORGANISM: homo sapiens

<400> SEQUENCE: 34

```
Met Gln Arg Ala Arg Pro Thr Leu Trp Ala Ala Leu Thr Leu Leu
 1               5                  10                  15

Val Leu Leu Arg Gly Pro Pro Val Ala Arg Ala Gly Ala Ser Ser Ala
            20                  25                  30

Gly Leu Gly Pro Val Val Arg Cys Glu Pro Cys Asp Ala Arg Ala Leu
        35                  40                  45

Ala Gln Cys Ala Pro Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
                85                  90                  95

Ser Pro Asp Glu Ala Arg Pro Leu Gln Ala Leu Leu Asp Gly Arg Gly
            100                 105                 110

Leu Cys Val Asn Ala Ser Ala Val Ser Arg Leu Arg Ala Tyr Leu Leu
        115                 120                 125

Pro Ala Pro Pro Ala Pro Gly Glu Pro Pro Ala Pro Gly Asn Ala Ser
    130                 135                 140

Glu Ser Glu Glu Asp Arg Ser Ala Gly Ser Val Glu Ser Pro Ser Val
145                 150                 155                 160

Ser Ser Thr His Arg Val Ser Asp Pro Lys Phe His Pro Leu His Ser
                165                 170                 175

Lys Ile Ile Ile Ile Lys Lys Gly His Ala Lys Asp Ser Gln Arg Tyr
            180                 185                 190

Lys Val Asp Tyr Glu Ser Gln Ser Thr Asp Thr Gln Asn Phe Ser Ser
        195                 200                 205

Glu Ser Lys Arg Glu Thr Glu Tyr Gly Pro Cys Arg Arg Glu Met Glu
    210                 215                 220

Asp Thr Leu Asn His Leu Lys Phe Leu Asn Val Leu Ser Pro Arg Gly
225                 230                 235                 240

Val His Ile Pro Asn Cys Asp Lys Lys Gly Phe Tyr Lys Lys Lys Gln
                245                 250                 255

Cys Arg Pro Ser Lys Gly Arg Lys Arg Gly Phe Cys Trp Cys Val Asp
            260                 265                 270

Lys Tyr Gly Gln Pro Leu Pro Gly Tyr Thr Thr Lys Gly Lys Glu Asp
        275                 280                 285

Val His Cys Tyr Ser Met Gln Ser Lys
    290                 295
```

<210> SEQ ID NO 35
<211> LENGTH: 2638
<212> TYPE: DNA
<213> ORGANISM: Artificial Sequence
<220> FEATURE:

<223> OTHER INFORMATION: IGFBP3 cDNA sequence

<400> SEQUENCE: 35

```
agatgcgagc actgcggctg ggcgctgagg atcagccgct tcctgcctgg attccacagc      60
ttcgcgccgt gtactgtcgc cccatccctg cgcgcccagc ctgccaagca gcgtgccccg     120
gttgcaggcg tcatgcagcg ggcgcgaccc acgctctggg ccgctgcgct gactctgctg     180
gtgctgctcc gcgggccgcc ggtggcgcgg gctggcgcga gctcggcggg cttgggtccc     240
gtggtgcgct gcgagccgtg cgacgcgcgt gcactggccc agtgcgcgcc tccgcccgcc     300
gtgtgcgcgg agctggtgcg cgagccgggc tgcggctgct gcctgacgtg cgcactgagc     360
gagggccagc cgtgcggcat ctacaccgag cgctgtggct ccggccttcg ctgccagccg     420
tcgcccgacg aggcgcgacc gctgcaggcg ctgctggacg gccgcgggct ctgcgtcaac     480
gctagtgccg tcagccgcct gcgcgcctac ctgctgccag cgccgccagc tccaggtgag     540
ccgcccgcgc caggaaatgc tagtgagtcg gaggaagacc gcagcgccgg cagtgtggag     600
agcccgtccg tctccagcac gcaccgggtg tctgatccca gttccacccc cctccattca     660
aagataatca tcatcaagaa agggcatgct aaagacagcc agcgctacaa agttgactac     720
gagtctcaga gcacagatac ccagaacttc tcctccgagt ccaagcggga gacagaatat     780
ggtccctgcc gtagagaaat ggaagacaca ctgaatcacc tgaagttcct caatgtgctg     840
agtcccaggg gtgtacacat tcccaactgt gacaagaagg gatttataa gaaaagcag     900
tgtcgccctt ccaaaggcag gaagcggggc ttctgctggt gtgtggataa gtatgggcag     960
cctctcccag gctacaccac caaggggaag gaggacgtgc actgctacag catgcagagc    1020
aagtagacgc ctgccgcaag gttaatgtgg agctcaaata tgccttattt tgcacaaaag    1080
actgccaagg acatgaccag cagctggcta cagcctcgat ttatatttct gtttgtggtg    1140
aactgatttt ttttaaacca aagtttagaa agaggttttt gaaatgccta tggtttcttt    1200
gaatggtaaa cttgagcatc ttttcacttt ccagtagtca gcaaagagca gtttgaattt    1260
tcttgtcgct tcctatcaaa atattcagag actcgagcac agcacccaga cttcatgcgc    1320
ccgtggaatg ctcaccacat gttggtcgaa gcggccgacc actgactttg tgacttaggc    1380
ggctgtgttg cctatgtaga aacacgctt cacccccact ccccgtacag tgcgcacagg    1440
ctttatcgag aataggaaaa cctttaaacc ccggtcatcc ggacatccca acgcatgctc    1500
ctggagctca cagccttctg tggtgtcatt tctgaaacaa gggcgtggat ccctcaacca    1560
agaagaatgt ttatgtcttc aagtgacctg tactgcttgg ggactattgg agaaaataag    1620
gtggagtcct acttgtttaa aaaatatgta tctaagaatg ttctagggca ctctgggaac    1680
ctataaaggc aggtatttcg ggccctcctc ttcaggaatc ttcctgaaga catgcccag     1740
tcgaaggccc aggatggctt tgctgcggc cccgtggggt aggagggaca gagagacagg    1800
gagagtcagc ctccacattc agaggcatca caagtaatgg cacaattctt cggatgactg    1860
cagaaaatag tgttttgtag ttcaacaact caagacgaag cttatttctg aggataagct    1920
ctttaaaggc aaagctttat tttcatctct catctttgt cctccttagc acaatgtaaa     1980
aaagaatagt aatatcagaa caggaaggag gaatggcttg ctggggagcc catccaggac    2040
actgggagca catagagatt cacccatgtt tgttgaactt agagtcattc tcatgctttt    2100
ctttataatt cacacatata tgcagagaag atatgttctt gttaacattg tatacaacat    2160
agccccaaat atagtaagat ctatactaga taatcctaga tgaaatgtta gagatgctat    2220
atgatacaac tgtggccatg actgaggaaa ggagctcacg cccagagact gggctgctct    2280
```

| | | |
|---|---|---|
| cccggaggcc aaacccaaga aggtctggca aagtcaggct cagggagact ctgccctgct | 2340 |
| gcagacctcg gtgtggacac acgctgcata gagctctcct tgaaaacaga ggggtctcaa | 2400 |
| gacattctgc ctaccatta gcttttcttt atttttttaa cttttgggg ggaaaagtat | 2460 |
| ttttgagaag tttgtcttgc aatgtattta taaatagtaa ataaagtttt taccattaaa | 2520 |
| aaaatatctt tcccttgtt attgaccatc tctgggcttt gtatcactaa ttattttatt | 2580 |
| ttattatata ataattattt tattataata aaatcctgaa agggaaaat aaaaaaaa | 2638 |

<210> SEQ ID NO 36
<211> LENGTH: 2620
<212> TYPE: DNA
<213> ORGANISM: Artificial Sequence
<220> FEATURE:
<223> OTHER INFORMATION: IGFBP3 cDNA sequence

<400> SEQUENCE: 36

| | | |
|---|---|---|
| agatgcgagc actgcggctg ggcgctgagg atcagccgct tcctgcctgg attccacagc | 60 |
| ttcgcgccgt gtactgtcgc cccatccctg cgcgcccagc ctgccaagca gcgtgccccg | 120 |
| gttgcaggcg tcatgcagcg ggcgcgaccc acgctctggg ccgctgcgct gactctgctg | 180 |
| gtgctgctcc gcgggccgcc ggtggcgcgg gctggcgcga gctcggcggg cttgggtccc | 240 |
| gtggtgcgct gcgagccgtg cgacgcgcgt gcactggccc agtgcgcgcc tccgccgcc | 300 |
| gtgtgcgcgg agctggtgcg cgagccgggc tgcggctgct gcctgacgtg cgcactgagc | 360 |
| gagggccagc cgtgcggcat ctacaccgag cgctgtggct ccggccttcg ctgccagccg | 420 |
| tcgcccgacg aggcgcgacc gctgcaggcg ctgctggacg gccgcgggct ctgcgtcaac | 480 |
| gctagtgccg tcagccgcct gcgcgcctac ctgctgccag cgccgccagc tccaggaaat | 540 |
| gctagtgagt cggaggaaga ccgcagcgcc ggcagtgtgg agagcccgtc cgtctccagc | 600 |
| acgcaccggg tgtctgatcc caagttccac ccctccatt caaagataat catcatcaag | 660 |
| aaagggcatg ctaaagacag ccagcgctac aaagttgact acgagtctca gagcacagat | 720 |
| acccagaact tctcctccga gtccaagcgg gagacagaat atggtccctg ccgtagagaa | 780 |
| atggaagaca cactgaatca cctgaagttc ctcaatgtgc tgagtcccag gggtgtacac | 840 |
| attcccaact gtgacaagaa gggatttat aagaaaaagc agtgtcgccc ttccaaaggc | 900 |
| aggaagcggg gcttctgctg gtgtgtggat aagtatgggc agcctctccc aggctacacc | 960 |
| accaagggga aggaggacgt gcactgctac agcatgcaga gcaagtagac gcctgccgca | 1020 |
| aggttaatgt ggagctcaaa tatgccttat tttgcacaaa agactgccaa ggacatgacc | 1080 |
| agcagctggc tacagcctcg atttatattt ctgtttgtgg tgaactgatt tttttaaac | 1140 |
| caaagtttag aaagaggttt ttgaaatgcc tatggtttct ttgaatggta aacttgagca | 1200 |
| tcttttcact ttccagtagt cagcaaagag cagtttgaat tttcttgtcg cttcctatca | 1260 |
| aaatattcag agactcgagc acagcaccca gacttcatgc gcccgtggaa tgctcaccac | 1320 |
| atgttggtcg aagcggccga ccactgactt tgtgacttag gcggctgtgt tgcctatgta | 1380 |
| gagaacacgc ttcaccccca ctccccgtac agtgcgcaca ggctttatcg agaataggaa | 1440 |
| aacctttaaa ccccggtcat ccggacatcc aacgcatgc tcctggagct cacagccttc | 1500 |
| tgtggtgtca tttctgaaac aagggcgtgg atccctcaac caagaagaat gtttatgtct | 1560 |
| tcaagtgacc tgtactgctt ggggactatt ggagaaaata aggtgagtc ctacttgttt | 1620 |
| aaaaaatatg tatctaagaa tgttctaggg cactctggga acctataaag gcaggtattt | 1680 |

```
cgggccctcc tcttcaggaa tcttcctgaa gacatggccc agtcgaaggc ccaggatggc    1740
ttttgctgcg gccccgtggg gtaggaggga cagagagaca gggagagtca gcctccacat    1800
tcagaggcat cacaagtaat ggcacaattc ttcggatgac tgcagaaaat agtgttttgt    1860
agttcaacaa ctcaagacga agcttatttc tgaggataag ctctttaaag gcaaagcttt    1920
attttcatct ctcatctttt gtcctcctta gcacaatgta aaaagaata gtaatatcag     1980 aacaggaagg aggaatggct tgctggggag cccatccagg acactgggag cacatagaga    2040
ttcacccatg tttgttgaac ttagagtcat tctcatgctt ttctttataa ttcacacata    2100
tatgcagaga agatatgttc ttgttaacat tgtatacaac atagcoccaa atatagtaag    2160 atctatacta gataatccta gatgaaatgt tagagatgct atatgataca actgtggcca    2220
tgactgagga aaggagctca cgcccagaga ctgggctgct ctcccggagg ccaaacccaa    2280
gaaggtctgg caaagtcagg ctcagggaga ctctgccctg ctgcagacct cggtgtggac    2340
acacgctgca tagagctctc cttgaaaaca gaggggtctc aagacattct gcctacctat    2400 tagctttct ttattttttt aacttttgg ggggaaaagt attttttgaga agtttgtctt     2460 gcaatgtatt tataaatagt aaataaagtt tttaccatta aaaaaatatc tttcccttg     2520 ttattgacca tctctgggct ttgtatcact aattatttta ttttattata taataattat    2580
tttattataa taaaatcctg aaaggggaaa ataaaaaaaa                          2620

<210> SEQ ID NO 37
<211> LENGTH: 20
<212> TYPE: DNA
<213> ORGANISM: Artificial Sequence
<220> FEATURE:
<223> OTHER INFORMATION: AIF1 Forward Primer Sequence

<400> SEQUENCE: 37
gatgatgctg ggcaagagat                                                  20

<210> SEQ ID NO 38
<211> LENGTH: 20
<212> TYPE: DNA
<213> ORGANISM: Artificial Sequence
<220> FEATURE:
<223> OTHER INFORMATION: AIF1 Reverse primer Sequence

<400> SEQUENCE: 38
ccttcaaatc agggcaactc                                                  20

<210> SEQ ID NO 39
<211> LENGTH: 20
<212> TYPE: DNA
<213> ORGANISM: Artificial Sequence
<220> FEATURE:
<223> OTHER INFORMATION: AMPD3 Forward Primer Sequence

<400> SEQUENCE: 39
aaaaggaagc caaggagagg                                                  20

<210> SEQ ID NO 40
<211> LENGTH: 20
<212> TYPE: DNA
<213> ORGANISM: Artificial Sequence
<220> FEATURE:
<223> OTHER INFORMATION: AMPD3 Reverse primer Sequence

<400> SEQUENCE: 40
gggaccgaat catcttgaaa                                                  20
```

```
<210> SEQ ID NO 41
<211> LENGTH: 20
<212> TYPE: DNA
<213> ORGANISM: Artificial Sequence
<220> FEATURE:
<223> OTHER INFORMATION: APOE Forward Primer Sequence

<400> SEQUENCE: 41
ttctgtgggc tgcgttgctg                                          20

<210> SEQ ID NO 42
<211> LENGTH: 20
<212> TYPE: DNA
<213> ORGANISM: Artificial Sequence
<220> FEATURE:
<223> OTHER INFORMATION: APOE Reverse primer Sequence

<400> SEQUENCE: 42
tacactgcca ggcgcttctg                                          20

<210> SEQ ID NO 43
<211> LENGTH: 21
<212> TYPE: DNA
<213> ORGANISM: Artificial Sequence
<220> FEATURE:
<223> OTHER INFORMATION: ARL4C Forward Primer Sequence

<400> SEQUENCE: 43
ccagtccctg catatcgtca t                                        21

<210> SEQ ID NO 44
<211> LENGTH: 22
<212> TYPE: DNA
<213> ORGANISM: Artificial Sequence
<220> FEATURE:
<223> OTHER INFORMATION: ARL4C Reverse primer Sequence

<400> SEQUENCE: 44
ttcacgaact cgttgaactt ga                                       22

<210> SEQ ID NO 45
<211> LENGTH: 23
<212> TYPE: DNA
<213> ORGANISM: Artificial Sequence
<220> FEATURE:
<223> OTHER INFORMATION: ATP6AP2 Forward Primer Sequence

<400> SEQUENCE: 45
agggagtgaa caaactggct cta                                      23

<210> SEQ ID NO 46
<211> LENGTH: 30
<212> TYPE: DNA
<213> ORGANISM: Artificial Sequence
<220> FEATURE:
<223> OTHER INFORMATION: ATP6AP2 Reverse primer Sequence

<400> SEQUENCE: 46
taccatatac actctattct ccaaagggta                               30

<210> SEQ ID NO 47
<211> LENGTH: 19
<212> TYPE: DNA
<213> ORGANISM: Artificial Sequence
<220> FEATURE:
```

<223> OTHER INFORMATION: AXL Forward Primer Sequence

<400> SEQUENCE: 47
ccgtggacct actctggct                                           19

<210> SEQ ID NO 48
<211> LENGTH: 19
<212> TYPE: DNA
<213> ORGANISM: Artificial Sequence
<220> FEATURE:
<223> OTHER INFORMATION: AXL Reverse primer Sequence

<400> SEQUENCE: 48
ccttggcgtt atgggcttc                                           19

<210> SEQ ID NO 49
<211> LENGTH: 20
<212> TYPE: DNA
<213> ORGANISM: Artificial Sequence
<220> FEATURE:
<223> OTHER INFORMATION: B2M Forward Primer Sequence

<400> SEQUENCE: 49
actgaattca cccccactga                                          20

<210> SEQ ID NO 50
<211> LENGTH: 20
<212> TYPE: DNA
<213> ORGANISM: Artificial Sequence
<220> FEATURE:
<223> OTHER INFORMATION: B2M Reverse primer Sequence

<400> SEQUENCE: 50
cctccatgat gctgcttaca                                          20

<210> SEQ ID NO 51
<211> LENGTH: 20
<212> TYPE: DNA
<213> ORGANISM: Artificial Sequence
<220> FEATURE:
<223> OTHER INFORMATION: BASP1 Forward Primer Sequence

<400> SEQUENCE: 51
cggagcccac ttagcttgtc                                          20

<210> SEQ ID NO 52
<211> LENGTH: 24
<212> TYPE: DNA
<213> ORGANISM: Artificial Sequence
<220> FEATURE:
<223> OTHER INFORMATION: BASP1 Reverse primer Sequence

<400> SEQUENCE: 52
gagagaatgt ttgtcactcc caaa                                     24

<210> SEQ ID NO 53
<211> LENGTH: 20
<212> TYPE: DNA
<213> ORGANISM: Artificial Sequence
<220> FEATURE:
<223> OTHER INFORMATION: BGN Forward Primer Sequence

<400> SEQUENCE: 53
ctggcatccc caaagacctc                                          20

```
<210> SEQ ID NO 54
<211> LENGTH: 20
<212> TYPE: DNA
<213> ORGANISM: Artificial Sequence
<220> FEATURE:
<223> OTHER INFORMATION: BGN Reverse primer Sequence

<400> SEQUENCE: 54
gctcccgttc tcgatcatcc                                               20

<210> SEQ ID NO 55
<211> LENGTH: 20
<212> TYPE: DNA
<213> ORGANISM: Artificial Sequence
<220> FEATURE:
<223> OTHER INFORMATION: BMF Forward Primer Sequence

<400> SEQUENCE: 55
gacccaaccc gggagcttgc                                               20

<210> SEQ ID NO 56
<211> LENGTH: 20
<212> TYPE: DNA
<213> ORGANISM: Artificial Sequence
<220> FEATURE:
<223> OTHER INFORMATION: BMF Reverse primer Sequence

<400> SEQUENCE: 56
gaaggccagg gccacagcag                                               20

<210> SEQ ID NO 57
<211> LENGTH: 19
<212> TYPE: DNA
<213> ORGANISM: Artificial Sequence
<220> FEATURE:
<223> OTHER INFORMATION: C10orf10 Forward Primer Sequence

<400> SEQUENCE: 57
tgcccacaat tcgggagac                                                19

<210> SEQ ID NO 58
<211> LENGTH: 21
<212> TYPE: DNA
<213> ORGANISM: Artificial Sequence
<220> FEATURE:
<223> OTHER INFORMATION: C10orf10 Reverse primer Sequence

<400> SEQUENCE: 58
agacctcacg tagtcatcca g                                             21

<210> SEQ ID NO 59
<211> LENGTH: 20
<212> TYPE: DNA
<213> ORGANISM: Artificial Sequence
<220> FEATURE:
<223> OTHER INFORMATION: CCL2 Forward Primer Sequence

<400> SEQUENCE: 59
gcctccagca tgaaagtctc                                               20

<210> SEQ ID NO 60
<211> LENGTH: 19
<212> TYPE: DNA
<213> ORGANISM: Artificial Sequence
<220> FEATURE:
<223> OTHER INFORMATION: CCL2 Reverse primer Sequence
```

```
<400> SEQUENCE: 60
aggtgactgg ggcattgat                                                      19

<210> SEQ ID NO 61
<211> LENGTH: 20
<212> TYPE: DNA
<213> ORGANISM: Artificial Sequence
<220> FEATURE:
<223> OTHER INFORMATION: CCL20 Forward Primer Sequence

<400> SEQUENCE: 61
gtgctgctac tccacctctg                                                     20

<210> SEQ ID NO 62
<211> LENGTH: 20
<212> TYPE: DNA
<213> ORGANISM: Artificial Sequence
<220> FEATURE:
<223> OTHER INFORMATION: CCL20 Reverse primer Sequence

<400> SEQUENCE: 62
cgtgtgaagc ccacaataaa                                                     20

<210> SEQ ID NO 63
<211> LENGTH: 20
<212> TYPE: DNA
<213> ORGANISM: Artificial Sequence
<220> FEATURE:
<223> OTHER INFORMATION: CCND1 Forward Primer Sequence

<400> SEQUENCE: 63
gctgcgaagt ggaaaccatc                                                     20

<210> SEQ ID NO 64
<211> LENGTH: 22
<212> TYPE: DNA
<213> ORGANISM: Artificial Sequence
<220> FEATURE:
<223> OTHER INFORMATION: CCND1 Reverse primer Sequence

<400> SEQUENCE: 64
cctccttctg cacacatttg aa                                                  22

<210> SEQ ID NO 65
<211> LENGTH: 19
<212> TYPE: DNA
<213> ORGANISM: Artificial Sequence
<220> FEATURE:
<223> OTHER INFORMATION: CD14 Forward Primer Sequence

<400> SEQUENCE: 65
acgccagaac cttgtgagc                                                      19

<210> SEQ ID NO 66
<211> LENGTH: 22
<212> TYPE: DNA
<213> ORGANISM: Artificial Sequence
<220> FEATURE:
<223> OTHER INFORMATION: CD14 Reverse primer Sequence

<400> SEQUENCE: 66
gcatggatct ccacctctac tg                                                  22

<210> SEQ ID NO 67
<211> LENGTH: 21
```

```
<212> TYPE: DNA
<213> ORGANISM: Artificial Sequence
<220> FEATURE:
<223> OTHER INFORMATION: CD300LF Forward Primer Sequence

<400> SEQUENCE: 67
ggaaccgacc tactgcaaca t                                          21

<210> SEQ ID NO 68
<211> LENGTH: 21
<212> TYPE: DNA
<213> ORGANISM: Artificial Sequence
<220> FEATURE:
<223> OTHER INFORMATION: CD300LF Reverse primer Sequence

<400> SEQUENCE: 68
ctgatggtgc tgtattccgt g                                          21

<210> SEQ ID NO 69
<211> LENGTH: 20
<212> TYPE: DNA
<213> ORGANISM: Artificial Sequence
<220> FEATURE:
<223> OTHER INFORMATION: CD44 Forward Primer Sequence

<400> SEQUENCE: 69
cggacaccat ggacaagttt                                            20

<210> SEQ ID NO 70
<211> LENGTH: 20
<212> TYPE: DNA
<213> ORGANISM: Artificial Sequence
<220> FEATURE:
<223> OTHER INFORMATION: CD44 Reverse primer Sequence

<400> SEQUENCE: 70
gaaagccttg cagaggtcag                                            20

<210> SEQ ID NO 71
<211> LENGTH: 20
<212> TYPE: DNA
<213> ORGANISM: Artificial Sequence
<220> FEATURE:
<223> OTHER INFORMATION: CD83 Forward Primer Sequence

<400> SEQUENCE: 71
ctccgaagat gtggacttgc                                            20

<210> SEQ ID NO 72
<211> LENGTH: 20
<212> TYPE: DNA
<213> ORGANISM: Artificial Sequence
<220> FEATURE:
<223> OTHER INFORMATION: CD83 Reverse primer Sequence

<400> SEQUENCE: 72
tccatcctct cttcaccacc                                            20

<210> SEQ ID NO 73
<211> LENGTH: 20
<212> TYPE: DNA
<213> ORGANISM: Artificial Sequence
<220> FEATURE:
<223> OTHER INFORMATION: CDCP1 Forward Primer Sequence

<400> SEQUENCE: 73
```
ctgaactgcg gggtctctat                                              20

<210> SEQ ID NO 74
<211> LENGTH: 20
<212> TYPE: DNA
<213> ORGANISM: Artificial Sequence
<220> FEATURE:
<223> OTHER INFORMATION: CDCP1 Reverse primer Sequence

<400> SEQUENCE: 74
ggcagagcaa tctcaaaagc                                              20

<210> SEQ ID NO 75
<211> LENGTH: 23
<212> TYPE: DNA
<213> ORGANISM: Artificial Sequence
<220> FEATURE:
<223> OTHER INFORMATION: CDH13 Forward Primer Sequence

<400> SEQUENCE: 75
agtgttccat atcaatcagc cag                                          23

<210> SEQ ID NO 76
<211> LENGTH: 21
<212> TYPE: DNA
<213> ORGANISM: Artificial Sequence
<220> FEATURE:
<223> OTHER INFORMATION: CDH13 Reverse primer Sequence

<400> SEQUENCE: 76
cgagacctca tagcgtagct t                                            21

<210> SEQ ID NO 77
<211> LENGTH: 20
<212> TYPE: DNA
<213> ORGANISM: Artificial Sequence
<220> FEATURE:
<223> OTHER INFORMATION: CECR1 Forward Primer Sequence

<400> SEQUENCE: 77
cagagagcat ctggcttcaa                                              20

<210> SEQ ID NO 78
<211> LENGTH: 20
<212> TYPE: DNA
<213> ORGANISM: Artificial Sequence
<220> FEATURE:
<223> OTHER INFORMATION: CECR1 Reverse primer Sequence

<400> SEQUENCE: 78
tcatggtgct ctccactgag                                              20

<210> SEQ ID NO 79
<211> LENGTH: 22
<212> TYPE: DNA
<213> ORGANISM: Artificial Sequence
<220> FEATURE:
<223> OTHER INFORMATION: CHMP1B Forward Primer Sequence

<400> SEQUENCE: 79
aaagaactga gtaggagtgc ca                                           22

<210> SEQ ID NO 80
<211> LENGTH: 22
<212> TYPE: DNA
<213> ORGANISM: Artificial Sequence

```
<220> FEATURE:
<223> OTHER INFORMATION: CHMP1B Reverse primer Sequence

<400> SEQUENCE: 80
tgtatcctcg caacttccat gt                                              22

<210> SEQ ID NO 81
<211> LENGTH: 20
<212> TYPE: DNA
<213> ORGANISM: Artificial Sequence
<220> FEATURE:
<223> OTHER INFORMATION: CHST11 Forward Primer Sequence

<400> SEQUENCE: 81
tccctttggt gtggacatct                                                 20

<210> SEQ ID NO 82
<211> LENGTH: 20
<212> TYPE: DNA
<213> ORGANISM: Artificial Sequence
<220> FEATURE:
<223> OTHER INFORMATION: CHST11 Reverse primer Sequence

<400> SEQUENCE: 82
gcaggacagc agtgtttgag                                                 20

<210> SEQ ID NO 83
<211> LENGTH: 20
<212> TYPE: DNA
<213> ORGANISM: Artificial Sequence
<220> FEATURE:
<223> OTHER INFORMATION: COLEC12 Forward Primer Sequence

<400> SEQUENCE: 83
agaggaggag gaggtgcaat                                                 20

<210> SEQ ID NO 84
<211> LENGTH: 22
<212> TYPE: DNA
<213> ORGANISM: Artificial Sequence
<220> FEATURE:
<223> OTHER INFORMATION: COLEC12 Reverse primer Sequence

<400> SEQUENCE: 84
tgatagaaaa cttcagtgcc ca                                              22

<210> SEQ ID NO 85
<211> LENGTH: 21
<212> TYPE: DNA
<213> ORGANISM: Artificial Sequence
<220> FEATURE:
<223> OTHER INFORMATION: CREG1 Forward Primer Sequence

<400> SEQUENCE: 85
ggcgtgccct atttctacct g                                               21

<210> SEQ ID NO 86
<211> LENGTH: 23
<212> TYPE: DNA
<213> ORGANISM: Artificial Sequence
<220> FEATURE:
<223> OTHER INFORMATION: CREG1 Reverse primer Sequence

<400> SEQUENCE: 86
caaagtcatg gtcagtgtag cat                                             23
```

```
<210> SEQ ID NO 87
<211> LENGTH: 20
<212> TYPE: DNA
<213> ORGANISM: Artificial Sequence
<220> FEATURE:
<223> OTHER INFORMATION: CST3 Forward Primer Sequence

<400> SEQUENCE: 87
ccagcaacga catgtaccac                                                    20

<210> SEQ ID NO 88
<211> LENGTH: 20
<212> TYPE: DNA
<213> ORGANISM: Artificial Sequence
<220> FEATURE:
<223> OTHER INFORMATION: CST3 Reverse primer Sequence

<400> SEQUENCE: 88
cagctccacg tccaagaagt                                                    20

<210> SEQ ID NO 89
<211> LENGTH: 21
<212> TYPE: DNA
<213> ORGANISM: Artificial Sequence
<220> FEATURE:
<223> OTHER INFORMATION: CTSB Forward Primer Sequence

<400> SEQUENCE: 89
acaacgtgga catgagctac t                                                  21

<210> SEQ ID NO 90
<211> LENGTH: 23
<212> TYPE: DNA
<213> ORGANISM: Artificial Sequence
<220> FEATURE:
<223> OTHER INFORMATION: CTSB Reverse primer Sequence

<400> SEQUENCE: 90
tcggtaaaca taactctctg ggg                                                23

<210> SEQ ID NO 91
<211> LENGTH: 17
<212> TYPE: DNA
<213> ORGANISM: Artificial Sequence
<220> FEATURE:
<223> OTHER INFORMATION: CTSD Forward Primer Sequence

<400> SEQUENCE: 91
agccctccag ccttctg                                                       17

<210> SEQ ID NO 92
<211> LENGTH: 19
<212> TYPE: DNA
<213> ORGANISM: Artificial Sequence
<220> FEATURE:
<223> OTHER INFORMATION: CTSD Reverse primer Sequence

<400> SEQUENCE: 92
cggatggacg tgaacttgt                                                     19

<210> SEQ ID NO 93
<211> LENGTH: 17
<212> TYPE: DNA
<213> ORGANISM: Artificial Sequence
<220> FEATURE:
<223> OTHER INFORMATION: CTSL Forward Primer Sequence
```

<400> SEQUENCE: 93
gcgcgtgact ggttgag                                          17

<210> SEQ ID NO 94
<211> LENGTH: 20
<212> TYPE: DNA
<213> ORGANISM: Artificial Sequence
<220> FEATURE:
<223> OTHER INFORMATION: CTSL Reverse primer Sequence

<400> SEQUENCE: 94
aaaggcagca aggatgagtg                                       20

<210> SEQ ID NO 95
<211> LENGTH: 21
<212> TYPE: DNA
<213> ORGANISM: Artificial Sequence
<220> FEATURE:
<223> OTHER INFORMATION: CTSS Forward Primer Sequence

<400> SEQUENCE: 95
cttgtggttg gctatggtga t                                     21

<210> SEQ ID NO 96
<211> LENGTH: 20
<212> TYPE: DNA
<213> ORGANISM: Artificial Sequence
<220> FEATURE:
<223> OTHER INFORMATION: CTSS Reverse primer Sequence

<400> SEQUENCE: 96
cctttatttc ttgccatccg                                       20

<210> SEQ ID NO 97
<211> LENGTH: 19
<212> TYPE: DNA
<213> ORGANISM: Artificial Sequence
<220> FEATURE:
<223> OTHER INFORMATION: CXCL16 Forward Primer Sequence

<400> SEQUENCE: 97
gtgtgtggag gcaacaagg                                        19

<210> SEQ ID NO 98
<211> LENGTH: 20
<212> TYPE: DNA
<213> ORGANISM: Artificial Sequence
<220> FEATURE:
<223> OTHER INFORMATION: CXCL16 Reverse primer Sequence

<400> SEQUENCE: 98
cacaatcccc gagtaagcat                                       20

<210> SEQ ID NO 99
<211> LENGTH: 20
<212> TYPE: DNA
<213> ORGANISM: Artificial Sequence
<220> FEATURE:
<223> OTHER INFORMATION: CXCL2 Forward Primer Sequence

<400> SEQUENCE: 99
gggcagaaag cttgtctcaa                                       20

<210> SEQ ID NO 100

```
<211> LENGTH: 20
<212> TYPE: DNA
<213> ORGANISM: Artificial Sequence
<220> FEATURE:
<223> OTHER INFORMATION: CXCL2 Reverse primer Sequence

<400> SEQUENCE: 100
gcttcctcct tccttctggt                                             20

<210> SEQ ID NO 101
<211> LENGTH: 18
<212> TYPE: DNA
<213> ORGANISM: Artificial Sequence
<220> FEATURE:
<223> OTHER INFORMATION: CXCR4 Forward Primer Sequence

<400> SEQUENCE: 101
ccagtagcca ccgcatct                                               18

<210> SEQ ID NO 102
<211> LENGTH: 20
<212> TYPE: DNA
<213> ORGANISM: Artificial Sequence
<220> FEATURE:
<223> OTHER INFORMATION: CXCR4 Reverse primer Sequence

<400> SEQUENCE: 102
atagtcccct gagcccattt                                             20

<210> SEQ ID NO 103
<211> LENGTH: 20
<212> TYPE: DNA
<213> ORGANISM: Artificial Sequence
<220> FEATURE:
<223> OTHER INFORMATION: DBI Forward Primer Sequence

<400> SEQUENCE: 103
tggccactac aaacaagcaa                                             20

<210> SEQ ID NO 104
<211> LENGTH: 20
<212> TYPE: DNA
<213> ORGANISM: Artificial Sequence
<220> FEATURE:
<223> OTHER INFORMATION: DBI Reverse primer Sequence

<400> SEQUENCE: 104
tccctttcag ctcattccag                                             20

<210> SEQ ID NO 105
<211> LENGTH: 19
<212> TYPE: DNA
<213> ORGANISM: Artificial Sequence
<220> FEATURE:
<223> OTHER INFORMATION: DHRS3 Forward Primer Sequence

<400> SEQUENCE: 105
ttcctgccac gtatgctgg                                              19

<210> SEQ ID NO 106
<211> LENGTH: 22
<212> TYPE: DNA
<213> ORGANISM: Artificial Sequence
<220> FEATURE:
<223> OTHER INFORMATION: DHRS3 Reverse primer Sequence

<400> SEQUENCE: 106
```

```
tttggatgtg cagtagtcga tg                                              22

<210> SEQ ID NO 107
<211> LENGTH: 20
<212> TYPE: DNA
<213> ORGANISM: Artificial Sequence
<220> FEATURE:
<223> OTHER INFORMATION: EGR2 Forward Primer Sequence

<400> SEQUENCE: 107
ttgaccagat gaacggagtg                                                 20

<210> SEQ ID NO 108
<211> LENGTH: 20
<212> TYPE: DNA
<213> ORGANISM: Artificial Sequence
<220> FEATURE:
<223> OTHER INFORMATION: EGR2 Reverse primer Sequence

<400> SEQUENCE: 108
agcaaagctg ctgggatatg                                                 20

<210> SEQ ID NO 109
<211> LENGTH: 17
<212> TYPE: DNA
<213> ORGANISM: Artificial Sequence
<220> FEATURE:
<223> OTHER INFORMATION: EPB41L3 Forward Primer Sequence

<400> SEQUENCE: 109
gagcctagtc cccacgc                                                    17

<210> SEQ ID NO 110
<211> LENGTH: 20
<212> TYPE: DNA
<213> ORGANISM: Artificial Sequence
<220> FEATURE:
<223> OTHER INFORMATION: EPB41L3 Reverse primer Sequence

<400> SEQUENCE: 110
gcttggattc cgagtctgat                                                 20

<210> SEQ ID NO 111
<211> LENGTH: 22
<212> TYPE: DNA
<213> ORGANISM: Artificial Sequence
<220> FEATURE:
<223> OTHER INFORMATION: EZR Forward Primer Sequence

<400> SEQUENCE: 111
accaatcaat gtccgagtta cc                                              22

<210> SEQ ID NO 112
<211> LENGTH: 22
<212> TYPE: DNA
<213> ORGANISM: Artificial Sequence
<220> FEATURE:
<223> OTHER INFORMATION: EZR Reverse primer Sequence

<400> SEQUENCE: 112
gccgatagtc tttaccacct ga                                              22

<210> SEQ ID NO 113
<211> LENGTH: 20
<212> TYPE: DNA
```

```
<213> ORGANISM: Artificial Sequence
<220> FEATURE:
<223> OTHER INFORMATION: FAM49A Forward Primer Sequence

<400> SEQUENCE: 113
agctaagctg gttcatccca                                               20

<210> SEQ ID NO 114
<211> LENGTH: 20
<212> TYPE: DNA
<213> ORGANISM: Artificial Sequence
<220> FEATURE:
<223> OTHER INFORMATION: FAM49A Reverse primer Sequence

<400> SEQUENCE: 114
gactttgagc aggtttccca                                               20

<210> SEQ ID NO 115
<211> LENGTH: 22
<212> TYPE: DNA
<213> ORGANISM: Artificial Sequence
<220> FEATURE:
<223> OTHER INFORMATION: FAT1 Forward Primer Sequence

<400> SEQUENCE: 115
catcctgtca agatgggtgt tt                                            22

<210> SEQ ID NO 116
<211> LENGTH: 23
<212> TYPE: DNA
<213> ORGANISM: Artificial Sequence
<220> FEATURE:
<223> OTHER INFORMATION: FAT1 Reverse primer Sequence

<400> SEQUENCE: 116
tccgagaatg tactcttcag ctt                                           23

<210> SEQ ID NO 117
<211> LENGTH: 20
<212> TYPE: DNA
<213> ORGANISM: Artificial Sequence
<220> FEATURE:
<223> OTHER INFORMATION: FSCN1 Forward Primer Sequence

<400> SEQUENCE: 117
caaggacgag ctctttgctc                                               20

<210> SEQ ID NO 118
<211> LENGTH: 20
<212> TYPE: DNA
<213> ORGANISM: Artificial Sequence
<220> FEATURE:
<223> OTHER INFORMATION: FSCN1 Reverse primer Sequence

<400> SEQUENCE: 118
tgattggcag acaggtccat                                               20

<210> SEQ ID NO 119
<211> LENGTH: 17
<212> TYPE: DNA
<213> ORGANISM: Artificial Sequence
<220> FEATURE:
<223> OTHER INFORMATION: G0S2 Forward Primer Sequence

<400> SEQUENCE: 119
ctgaccgctg ccaactg                                                  17
```

```
<210> SEQ ID NO 120
<211> LENGTH: 20
<212> TYPE: DNA
<213> ORGANISM: Artificial Sequence
<220> FEATURE:
<223> OTHER INFORMATION: G0S2 Reverse primer Sequence

<400> SEQUENCE: 120
ctcctggacc gtttccatct                                                    20

<210> SEQ ID NO 121
<211> LENGTH: 20
<212> TYPE: DNA
<213> ORGANISM: Artificial Sequence
<220> FEATURE:
<223> OTHER INFORMATION: GAL3ST4 Forward Primer Sequence

<400> SEQUENCE: 121
tccacatcct ctgtcaccac                                                    20

<210> SEQ ID NO 122
<211> LENGTH: 20
<212> TYPE: DNA
<213> ORGANISM: Artificial Sequence
<220> FEATURE:
<223> OTHER INFORMATION: GAL3ST4 Reverse primer Sequence

<400> SEQUENCE: 122
ggtctcggac aatggaaaaa                                                    20

<210> SEQ ID NO 123
<211> LENGTH: 21
<212> TYPE: DNA
<213> ORGANISM: Artificial Sequence
<220> FEATURE:
<223> OTHER INFORMATION: GPR183 Forward Primer Sequence

<400> SEQUENCE: 123
actggagaat cggagatgcc t                                                  21

<210> SEQ ID NO 124
<211> LENGTH: 22
<212> TYPE: DNA
<213> ORGANISM: Artificial Sequence
<220> FEATURE:
<223> OTHER INFORMATION: GPR183 Reverse primer Sequence

<400> SEQUENCE: 124
aatgaagcgg tcaatactca gg                                                 22

<210> SEQ ID NO 125
<211> LENGTH: 20
<212> TYPE: DNA
<213> ORGANISM: Artificial Sequence
<220> FEATURE:
<223> OTHER INFORMATION: GPX1 Forward Primer Sequence

<400> SEQUENCE: 125
caaccagttt gggcatcagr                                                    20

<210> SEQ ID NO 126
<211> LENGTH: 19
<212> TYPE: DNA
<213> ORGANISM: Artificial Sequence
<220> FEATURE:
```

<223> OTHER INFORMATION: GPX1 Reverse primer Sequence

<400> SEQUENCE: 126
gttcacctcg cacttctcg                                        19

<210> SEQ ID NO 127
<211> LENGTH: 19
<212> TYPE: DNA
<213> ORGANISM: Artificial Sequence
<220> FEATURE:
<223> OTHER INFORMATION: GRN Forward Primer Sequence

<400> SEQUENCE: 127
aggagaacgc taccacgga                                        19

<210> SEQ ID NO 128
<211> LENGTH: 21
<212> TYPE: DNA
<213> ORGANISM: Artificial Sequence
<220> FEATURE:
<223> OTHER INFORMATION: GRN Reverse primer Sequence

<400> SEQUENCE: 128
ggcagcaggt atagccatct g                                     21

<210> SEQ ID NO 129
<211> LENGTH: 20
<212> TYPE: DNA
<213> ORGANISM: Artificial Sequence
<220> FEATURE:
<223> OTHER INFORMATION: GTF2B Forward Primer Sequence

<400> SEQUENCE: 129
gccggtgata tgatctgtcc                                       20

<210> SEQ ID NO 130
<211> LENGTH: 20
<212> TYPE: DNA
<213> ORGANISM: Artificial Sequence
<220> FEATURE:
<223> OTHER INFORMATION: GTF2B Reverse primer Sequence

<400> SEQUENCE: 130
gtcattgctg aaagttcgcc                                       20

<210> SEQ ID NO 131
<211> LENGTH: 20
<212> TYPE: DNA
<213> ORGANISM: Artificial Sequence
<220> FEATURE:
<223> OTHER INFORMATION: HES1 Forward Primer Sequence

<400> SEQUENCE: 131
acgtgcgagg gcgttaatac                                       20

<210> SEQ ID NO 132
<211> LENGTH: 20
<212> TYPE: DNA
<213> ORGANISM: Artificial Sequence
<220> FEATURE:
<223> OTHER INFORMATION: HES1 Reverse primer Sequence

<400> SEQUENCE: 132
ggggtaggtc atggcattga                                       20

```
<210> SEQ ID NO 133
<211> LENGTH: 20
<212> TYPE: DNA
<213> ORGANISM: Artificial Sequence
<220> FEATURE:
<223> OTHER INFORMATION: HIF3A Forward Primer Sequence

<400> SEQUENCE: 133
cccagtcgga gagtatcgtc                                          20

<210> SEQ ID NO 134
<211> LENGTH: 20
<212> TYPE: DNA
<213> ORGANISM: Artificial Sequence
<220> FEATURE:
<223> OTHER INFORMATION: HIF3A Reverse primer Sequence

<400> SEQUENCE: 134
gaatgggtct gcgagagtgt                                          20

<210> SEQ ID NO 135
<211> LENGTH: 21
<212> TYPE: DNA
<213> ORGANISM: Artificial Sequence
<220> FEATURE:
<223> OTHER INFORMATION: HPRT1 Forward Primer Sequence

<400> SEQUENCE: 135
cctggcgtcg tgattagtga t                                        21

<210> SEQ ID NO 136
<211> LENGTH: 22
<212> TYPE: DNA
<213> ORGANISM: Artificial Sequence
<220> FEATURE:
<223> OTHER INFORMATION: HPRT1 Reverse primer Sequence

<400> SEQUENCE: 136
agacgttcag tcctgtccat aa                                       22

<210> SEQ ID NO 137
<211> LENGTH: 20
<212> TYPE: DNA
<213> ORGANISM: Artificial Sequence
<220> FEATURE:
<223> OTHER INFORMATION: HTRA1 Forward Primer Sequence

<400> SEQUENCE: 137
tggaatctcc tttgcaatcc                                          20

<210> SEQ ID NO 138
<211> LENGTH: 20
<212> TYPE: DNA
<213> ORGANISM: Artificial Sequence
<220> FEATURE:
<223> OTHER INFORMATION: HTRA1 Reverse primer Sequence

<400> SEQUENCE: 138
ttcttggtga tggctttcc                                           20

<210> SEQ ID NO 139
<211> LENGTH: 20
<212> TYPE: DNA
<213> ORGANISM: Artificial Sequence
<220> FEATURE:
<223> OTHER INFORMATION: IDH1 Forward Primer Sequence
```

```
<400> SEQUENCE: 139
gtcgtcatgc ttatggggat                                               20

<210> SEQ ID NO 140
<211> LENGTH: 20
<212> TYPE: DNA
<213> ORGANISM: Artificial Sequence
<220> FEATURE:
<223> OTHER INFORMATION: IDH1 Reverse primer Sequence

<400> SEQUENCE: 140
cttttgggtt ccgtcacttg                                               20

<210> SEQ ID NO 141
<211> LENGTH: 20
<212> TYPE: DNA
<213> ORGANISM: Artificial Sequence
<220> FEATURE:
<223> OTHER INFORMATION: IFI30 Forward Primer Sequence

<400> SEQUENCE: 141
gctagccttc ctgaccattg                                               20

<210> SEQ ID NO 142
<211> LENGTH: 20
<212> TYPE: DNA
<213> ORGANISM: Artificial Sequence
<220> FEATURE:
<223> OTHER INFORMATION: IFI30 Reverse primer Sequence

<400> SEQUENCE: 142
ccatgatagt gtctggcgac                                               20

<210> SEQ ID NO 143
<211> LENGTH: 20
<212> TYPE: DNA
<213> ORGANISM: Artificial Sequence
<220> FEATURE:
<223> OTHER INFORMATION: IGFBP3 Forward Primer Sequence

<400> SEQUENCE: 143
ctctgcgtca acgctagtgc                                               20

<210> SEQ ID NO 144
<211> LENGTH: 20
<212> TYPE: DNA
<213> ORGANISM: Artificial Sequence
<220> FEATURE:
<223> OTHER INFORMATION: IGFBP3 Reverse primer Sequence

<400> SEQUENCE: 144
cggtcttcct ccgactcact                                               20

<210> SEQ ID NO 145
<211> LENGTH: 21
<212> TYPE: DNA
<213> ORGANISM: Artificial Sequence
<220> FEATURE:
<223> OTHER INFORMATION: IRAK2 Forward Primer Sequence

<400> SEQUENCE: 145
ctgccacccc aatgtcttac c                                             21

<210> SEQ ID NO 146
<211> LENGTH: 21
```

```
<212> TYPE: DNA
<213> ORGANISM: Artificial Sequence
<220> FEATURE:
<223> OTHER INFORMATION: IRAK2 Reverse primer Sequence

<400> SEQUENCE: 146
agggaaccat tgccatgta g                                            21

<210> SEQ ID NO 147
<211> LENGTH: 20
<212> TYPE: DNA
<213> ORGANISM: Artificial Sequence
<220> FEATURE:
<223> OTHER INFORMATION: IRS2 Forward Primer Sequence

<400> SEQUENCE: 147
acctacgcca gcattgactt                                             20

<210> SEQ ID NO 148
<211> LENGTH: 21
<212> TYPE: DNA
<213> ORGANISM: Artificial Sequence
<220> FEATURE:
<223> OTHER INFORMATION: IRS2 Reverse primer Sequence

<400> SEQUENCE: 148
catcctggtg ataaagccag a                                           21

<210> SEQ ID NO 149
<211> LENGTH: 20
<212> TYPE: DNA
<213> ORGANISM: Artificial Sequence
<220> FEATURE:
<223> OTHER INFORMATION: LAPTM5 Forward Primer Sequence

<400> SEQUENCE: 149
agacctgctg ctgcttcaat                                             20

<210> SEQ ID NO 150
<211> LENGTH: 20
<212> TYPE: DNA
<213> ORGANISM: Artificial Sequence
<220> FEATURE:
<223> OTHER INFORMATION: LAPTM5 Reverse primer Sequence

<400> SEQUENCE: 150
catgggccac ctctactgag                                             20

<210> SEQ ID NO 151
<211> LENGTH: 20
<212> TYPE: DNA
<213> ORGANISM: Artificial Sequence
<220> FEATURE:
<223> OTHER INFORMATION: LGALS1 Forward Primer Sequence

<400> SEQUENCE: 151
tcgccagcaa cctgaatctc                                             20

<210> SEQ ID NO 152
<211> LENGTH: 20
<212> TYPE: DNA
<213> ORGANISM: Artificial Sequence
<220> FEATURE:
<223> OTHER INFORMATION: LGALS1 Reverse primer Sequence

<400> SEQUENCE: 152
```
gcacgaagct cttagcgtca                                               20

<210> SEQ ID NO 153
<211> LENGTH: 17
<212> TYPE: DNA
<213> ORGANISM: Artificial Sequence
<220> FEATURE:
<223> OTHER INFORMATION: LGALS3BP Forward Primer Sequence

<400> SEQUENCE: 153
gaggaggctc cacacgg                                                  17

<210> SEQ ID NO 154
<211> LENGTH: 18
<212> TYPE: DNA
<213> ORGANISM: Artificial Sequence
<220> FEATURE:
<223> OTHER INFORMATION: LGALS3BP Reverse primer Sequence

<400> SEQUENCE: 154
agcagccaca cccagaag                                                 18

<210> SEQ ID NO 155
<211> LENGTH: 20
<212> TYPE: DNA
<213> ORGANISM: Artificial Sequence
<220> FEATURE:
<223> OTHER INFORMATION: LGMN Forward Primer Sequence

<400> SEQUENCE: 155
ctgaagatgg aggcaagcac                                               20

<210> SEQ ID NO 156
<211> LENGTH: 20
<212> TYPE: DNA
<213> ORGANISM: Artificial Sequence
<220> FEATURE:
<223> OTHER INFORMATION: LGMN Reverse primer Sequence

<400> SEQUENCE: 156
ttgcggtgaa tgatctggta                                               20

<210> SEQ ID NO 157
<211> LENGTH: 20
<212> TYPE: DNA
<213> ORGANISM: Artificial Sequence
<220> FEATURE:
<223> OTHER INFORMATION: LHFPL2 Forward Primer Sequence

<400> SEQUENCE: 157
tcttcaatgt ctgtgggctg                                               20

<210> SEQ ID NO 158
<211> LENGTH: 20
<212> TYPE: DNA
<213> ORGANISM: Artificial Sequence
<220> FEATURE:
<223> OTHER INFORMATION: LHFPL2 Reverse primer Sequence

<400> SEQUENCE: 158
gtctatggcc ttctggcaac                                               20

<210> SEQ ID NO 159
<211> LENGTH: 20
<212> TYPE: DNA
<213> ORGANISM: Artificial Sequence

```
<220> FEATURE:
<223> OTHER INFORMATION: LST1 Forward Primer Sequence

<400> SEQUENCE: 159
ctggccagtt tggagtctgt                                              20

<210> SEQ ID NO 160
<211> LENGTH: 20
<212> TYPE: DNA
<213> ORGANISM: Artificial Sequence
<220> FEATURE:
<223> OTHER INFORMATION: LST1 Reverse primer Sequence

<400> SEQUENCE: 160
tccttgctct tttaggcgaa                                              20

<210> SEQ ID NO 161
<211> LENGTH: 18
<212> TYPE: DNA
<213> ORGANISM: Artificial Sequence
<220> FEATURE:
<223> OTHER INFORMATION: LTBP2 Forward Primer Sequence

<400> SEQUENCE: 161
accttggcca gagcacag                                                18

<210> SEQ ID NO 162
<211> LENGTH: 17
<212> TYPE: DNA
<213> ORGANISM: Artificial Sequence
<220> FEATURE:
<223> OTHER INFORMATION: LTBP2 Reverse primer Sequence

<400> SEQUENCE: 162
tgggaagggt gggtctg                                                 17

<210> SEQ ID NO 163
<211> LENGTH: 20
<212> TYPE: DNA
<213> ORGANISM: Artificial Sequence
<220> FEATURE:
<223> OTHER INFORMATION: LYN Forward Primer Sequence

<400> SEQUENCE: 163
ctgaactcaa gtcaccgtgg                                              20

<210> SEQ ID NO 164
<211> LENGTH: 20
<212> TYPE: DNA
<213> ORGANISM: Artificial Sequence
<220> FEATURE:
<223> OTHER INFORMATION: LYN Reverse primer Sequence

<400> SEQUENCE: 164
tccatcgtca ctcaagctgt                                              20

<210> SEQ ID NO 165
<211> LENGTH: 20
<212> TYPE: DNA
<213> ORGANISM: Artificial Sequence
<220> FEATURE:
<223> OTHER INFORMATION: MAFB Forward Primer Sequence

<400> SEQUENCE: 165
catagagaac gtggcagcaa                                              20
```

```
<210> SEQ ID NO 166
<211> LENGTH: 20
<212> TYPE: DNA
<213> ORGANISM: Artificial Sequence
<220> FEATURE:
<223> OTHER INFORMATION: MAFB Reverse primer Sequence

<400> SEQUENCE: 166
atgcccggaa cttttctttt                                                 20

<210> SEQ ID NO 167
<211> LENGTH: 19
<212> TYPE: DNA
<213> ORGANISM: Artificial Sequence
<220> FEATURE:
<223> OTHER INFORMATION: MMP19 Forward Primer Sequence

<400> SEQUENCE: 167
gcctcgttgt ggcctagag                                                  19

<210> SEQ ID NO 168
<211> LENGTH: 21
<212> TYPE: DNA
<213> ORGANISM: Artificial Sequence
<220> FEATURE:
<223> OTHER INFORMATION: MMP19 Reverse primer Sequence

<400> SEQUENCE: 168
atgcggaaag tcaggtgctt c                                               21

<210> SEQ ID NO 169
<211> LENGTH: 20
<212> TYPE: DNA
<213> ORGANISM: Artificial Sequence
<220> FEATURE:
<223> OTHER INFORMATION: MMP2 Forward Primer Sequence

<400> SEQUENCE: 169
cagatgcctg gaatgccatc                                                 20

<210> SEQ ID NO 170
<211> LENGTH: 20
<212> TYPE: DNA
<213> ORGANISM: Artificial Sequence
<220> FEATURE:
<223> OTHER INFORMATION: MMP2 Reverse primer Sequence

<400> SEQUENCE: 170
gcagcctagc cagtcggatt                                                 20

<210> SEQ ID NO 171
<211> LENGTH: 22
<212> TYPE: DNA
<213> ORGANISM: Artificial Sequence
<220> FEATURE:
<223> OTHER INFORMATION: NEK6 Forward Primer Sequence

<400> SEQUENCE: 171
caggactgtg tcaaggagat cg                                              22

<210> SEQ ID NO 172
<211> LENGTH: 21
<212> TYPE: DNA
<213> ORGANISM: Artificial Sequence
<220> FEATURE:
<223> OTHER INFORMATION: NEK6 Reverse primer Sequence
```

```
<400> SEQUENCE: 172
atgttcagct cgttgtcttc g                                         21

<210> SEQ ID NO 173
<211> LENGTH: 21
<212> TYPE: DNA
<213> ORGANISM: Artificial Sequence
<220> FEATURE:
<223> OTHER INFORMATION: NFKBIZ Forward Primer Sequence

<400> SEQUENCE: 173
acacccacaa accaactctg g                                         21

<210> SEQ ID NO 174
<211> LENGTH: 22
<212> TYPE: DNA
<213> ORGANISM: Artificial Sequence
<220> FEATURE:
<223> OTHER INFORMATION: NFKBIZ Reverse primer Sequence

<400> SEQUENCE: 174
ggcaaaactg tgattctgga cc                                        22

<210> SEQ ID NO 175
<211> LENGTH: 20
<212> TYPE: DNA
<213> ORGANISM: Artificial Sequence
<220> FEATURE:
<223> OTHER INFORMATION: NINJ1 Forward Primer Sequence

<400> SEQUENCE: 175
accgaggagt acgagctcaa                                           20

<210> SEQ ID NO 176
<211> LENGTH: 20
<212> TYPE: DNA
<213> ORGANISM: Artificial Sequence
<220> FEATURE:
<223> OTHER INFORMATION: NINJ1 Reverse primer Sequence

<400> SEQUENCE: 176
gctcttcttg ctggcgtaat                                           20

<210> SEQ ID NO 177
<211> LENGTH: 20
<212> TYPE: DNA
<213> ORGANISM: Artificial Sequence
<220> FEATURE:
<223> OTHER INFORMATION: NPC2 Forward Primer Sequence

<400> SEQUENCE: 177
agctacattc ctgctcctgg                                           20

<210> SEQ ID NO 178
<211> LENGTH: 20
<212> TYPE: DNA
<213> ORGANISM: Artificial Sequence
<220> FEATURE:
<223> OTHER INFORMATION: NPC2 Reverse primer Sequence

<400> SEQUENCE: 178
tgggctcaca ttcacttcct                                           20

<210> SEQ ID NO 179
```

```
<211> LENGTH: 19
<212> TYPE: DNA
<213> ORGANISM: Artificial Sequence
<220> FEATURE:
<223> OTHER INFORMATION: NR4A2 Forward Primer Sequence

<400> SEQUENCE: 179
cgacatttct gccttctcc                                                   19

<210> SEQ ID NO 180
<211> LENGTH: 20
<212> TYPE: DNA
<213> ORGANISM: Artificial Sequence
<220> FEATURE:
<223> OTHER INFORMATION: NR4A2 Reverse primer Sequence

<400> SEQUENCE: 180
ggtaaagtgt ccaggaaaag                                                  20

<210> SEQ ID NO 181
<211> LENGTH: 17
<212> TYPE: DNA
<213> ORGANISM: Artificial Sequence
<220> FEATURE:
<223> OTHER INFORMATION: ODC1 Forward Primer Sequence

<400> SEQUENCE: 181
ggctgcgact caggctc                                                     17

<210> SEQ ID NO 182
<211> LENGTH: 19
<212> TYPE: DNA
<213> ORGANISM: Artificial Sequence
<220> FEATURE:
<223> OTHER INFORMATION: ODC1 Reverse primer Sequence

<400> SEQUENCE: 182
cccttggaac agcagtgac                                                   19

<210> SEQ ID NO 183
<211> LENGTH: 20
<212> TYPE: DNA
<213> ORGANISM: Artificial Sequence
<220> FEATURE:
<223> OTHER INFORMATION: OLFML2B Forward Primer Sequence

<400> SEQUENCE: 183
ccccgaagaa gaagatgaca                                                  20

<210> SEQ ID NO 184
<211> LENGTH: 21
<212> TYPE: DNA
<213> ORGANISM: Artificial Sequence
<220> FEATURE:
<223> OTHER INFORMATION: OLFML2B Reverse primer Sequence

<400> SEQUENCE: 184
ccatatgtgt tctgggtggt c                                                21

<210> SEQ ID NO 185
<211> LENGTH: 20
<212> TYPE: DNA
<213> ORGANISM: Artificial Sequence
<220> FEATURE:
<223> OTHER INFORMATION: PDGFA Forward Primer Sequence

<400> SEQUENCE: 185
```

```
tccacgccac taagcatgtg                                                    20

<210> SEQ ID NO 186
<211> LENGTH: 22
<212> TYPE: DNA
<213> ORGANISM: Artificial Sequence
<220> FEATURE:
<223> OTHER INFORMATION: PDGFA Reverse primer Sequence

<400> SEQUENCE: 186
cgtaaatgac cgtcctggtc tt                                                 22

<210> SEQ ID NO 187
<211> LENGTH: 20
<212> TYPE: DNA
<213> ORGANISM: Artificial Sequence
<220> FEATURE:
<223> OTHER INFORMATION: PHLDA1 Forward Primer Sequence

<400> SEQUENCE: 187
ctccaactct gcctgaaagg                                                    20

<210> SEQ ID NO 188
<211> LENGTH: 22
<212> TYPE: DNA
<213> ORGANISM: Artificial Sequence
<220> FEATURE:
<223> OTHER INFORMATION: PHLDA1 Reverse primer Sequence

<400> SEQUENCE: 188
tgttttgctt ttgatccaag tg                                                 22

<210> SEQ ID NO 189
<211> LENGTH: 22
<212> TYPE: DNA
<213> ORGANISM: Artificial Sequence
<220> FEATURE:
<223> OTHER INFORMATION: PIM3 Forward Primer Sequence

<400> SEQUENCE: 189
aaggacgaaa atctgcttgt gg                                                 22

<210> SEQ ID NO 190
<211> LENGTH: 20
<212> TYPE: DNA
<213> ORGANISM: Artificial Sequence
<220> FEATURE:
<223> OTHER INFORMATION: PIM3 Reverse primer Sequence

<400> SEQUENCE: 190
cgaagtcggt gtagaccgtg                                                    20

<210> SEQ ID NO 191
<211> LENGTH: 22
<212> TYPE: DNA
<213> ORGANISM: Artificial Sequence
<220> FEATURE:
<223> OTHER INFORMATION: PLAU Forward Primer Sequence

<400> SEQUENCE: 191
gggaatggtc acttttaccg ag                                                 22

<210> SEQ ID NO 192
<211> LENGTH: 19
<212> TYPE: DNA
```

```
<213> ORGANISM: Artificial Sequence
<220> FEATURE:
<223> OTHER INFORMATION: PLAU Reverse primer Sequence

<400> SEQUENCE: 192
gggcatggta cgtttgctg                                             19

<210> SEQ ID NO 193
<211> LENGTH: 20
<212> TYPE: DNA
<213> ORGANISM: Artificial Sequence
<220> FEATURE:
<223> OTHER INFORMATION: PLAUR Forward Primer Sequence

<400> SEQUENCE: 193
agccttaccg aggttgtgtg                                            20

<210> SEQ ID NO 194
<211> LENGTH: 20
<212> TYPE: DNA
<213> ORGANISM: Artificial Sequence
<220> FEATURE:
<223> OTHER INFORMATION: PLAUR Reverse primer Sequence

<400> SEQUENCE: 194
aaatgcattc gaggtaacgg                                            20

<210> SEQ ID NO 195
<211> LENGTH: 20
<212> TYPE: DNA
<213> ORGANISM: Artificial Sequence
<220> FEATURE:
<223> OTHER INFORMATION: PLD3 Forward Primer Sequence

<400> SEQUENCE: 195
ggagatctgc ctcaatggaa                                            20

<210> SEQ ID NO 196
<211> LENGTH: 21
<212> TYPE: DNA
<213> ORGANISM: Artificial Sequence
<220> FEATURE:
<223> OTHER INFORMATION: PLD3 Reverse primer Sequence

<400> SEQUENCE: 196
ccacgttgag tagagccttc a                                          21

<210> SEQ ID NO 197
<211> LENGTH: 20
<212> TYPE: DNA
<213> ORGANISM: Artificial Sequence
<220> FEATURE:
<223> OTHER INFORMATION: PMP22 Forward Primer Sequence

<400> SEQUENCE: 197
tcaggaaatg tccaccactg                                            20

<210> SEQ ID NO 198
<211> LENGTH: 20
<212> TYPE: DNA
<213> ORGANISM: Artificial Sequence
<220> FEATURE:
<223> OTHER INFORMATION: PMP22 Reverse primer Sequence

<400> SEQUENCE: 198
gctgaagatg atcgacagga                                            20
```

```
<210> SEQ ID NO 199
<211> LENGTH: 20
<212> TYPE: DNA
<213> ORGANISM: Artificial Sequence
<220> FEATURE:
<223> OTHER INFORMATION: PPIB Forward Primer Sequence

<400> SEQUENCE: 199
aaggacttca tgatccaggg                                          20

<210> SEQ ID NO 200
<211> LENGTH: 20
<212> TYPE: DNA
<213> ORGANISM: Artificial Sequence
<220> FEATURE:
<223> OTHER INFORMATION: PPIB Reverse primer Sequence

<400> SEQUENCE: 200
tgaagttctc atcggggaag                                          20

<210> SEQ ID NO 201
<211> LENGTH: 20
<212> TYPE: DNA
<213> ORGANISM: Artificial Sequence
<220> FEATURE:
<223> OTHER INFORMATION: PPIF Forward Primer Sequence

<400> SEQUENCE: 201
acagggtgat cccttccttc                                          20

<210> SEQ ID NO 202
<211> LENGTH: 20
<212> TYPE: DNA
<213> ORGANISM: Artificial Sequence
<220> FEATURE:
<223> OTHER INFORMATION: PPIF Reverse primer Sequence

<400> SEQUENCE: 202
aagttctcgt caggaaagcg                                          20

<210> SEQ ID NO 203
<211> LENGTH: 21
<212> TYPE: DNA
<213> ORGANISM: Artificial Sequence
<220> FEATURE:
<223> OTHER INFORMATION: PRNP Forward Primer Sequence

<400> SEQUENCE: 203
cacgactgcg tcaatatcac a                                        21

<210> SEQ ID NO 204
<211> LENGTH: 22
<212> TYPE: DNA
<213> ORGANISM: Artificial Sequence
<220> FEATURE:
<223> OTHER INFORMATION: PRNP Reverse primer Sequence

<400> SEQUENCE: 204
ctccatcatc ttaacgtcgg tc                                       22

<210> SEQ ID NO 205
<211> LENGTH: 21
<212> TYPE: DNA
<213> ORGANISM: Artificial Sequence
<220> FEATURE:
```

<223> OTHER INFORMATION: RCC2 Forward Primer Sequence

<400> SEQUENCE: 205
aaggagcgcg tcaaacttga a        21

<210> SEQ ID NO 206
<211> LENGTH: 22
<212> TYPE: DNA
<213> ORGANISM: Artificial Sequence
<220> FEATURE:
<223> OTHER INFORMATION: RCC2 Reverse primer Sequence

<400> SEQUENCE: 206
gcttgctgtt taggcacttc tt        22

<210> SEQ ID NO 207
<211> LENGTH: 21
<212> TYPE: DNA
<213> ORGANISM: Artificial Sequence
<220> FEATURE:
<223> OTHER INFORMATION: REL Forward Primer Sequence

<400> SEQUENCE: 207
gcagagggga atgcgtttta g        21

<210> SEQ ID NO 208
<211> LENGTH: 22
<212> TYPE: DNA
<213> ORGANISM: Artificial Sequence
<220> FEATURE:
<223> OTHER INFORMATION: REL Reverse primer Sequence

<400> SEQUENCE: 208
agaagggtat gttcggttgt tg        22

<210> SEQ ID NO 209
<211> LENGTH: 20
<212> TYPE: DNA
<213> ORGANISM: Artificial Sequence
<220> FEATURE:
<223> OTHER INFORMATION: RGS1 Forward Primer Sequence

<400> SEQUENCE: 209
ggaaaaactt cttgccaacc        20

<210> SEQ ID NO 210
<211> LENGTH: 20
<212> TYPE: DNA
<213> ORGANISM: Artificial Sequence
<220> FEATURE:
<223> OTHER INFORMATION: RGS1 Reverse Primer Sequence

<400> SEQUENCE: 210
tagtcttcac aagccagcca        20

<210> SEQ ID NO 211
<211> LENGTH: 20
<212> TYPE: DNA
<213> ORGANISM: Artificial Sequence
<220> FEATURE:
<223> OTHER INFORMATION: RHOG Forward Primer Sequence

<400> SEQUENCE: 211
acgatgcaga gcatcaagtg        20

```
<210> SEQ ID NO 212
<211> LENGTH: 20
<212> TYPE: DNA
<213> ORGANISM: Artificial Sequence
<220> FEATURE:
<223> OTHER INFORMATION: RHOG Reverse primer Sequence

<400> SEQUENCE: 212
tttggggaaa gcgttagttg                                               20

<210> SEQ ID NO 213
<211> LENGTH: 23
<212> TYPE: DNA
<213> ORGANISM: Artificial Sequence
<220> FEATURE:
<223> OTHER INFORMATION: RILPL2 Forward Primer Sequence

<400> SEQUENCE: 213
acgtgtatga catctcctac ctg                                           23

<210> SEQ ID NO 214
<211> LENGTH: 20
<212> TYPE: DNA
<213> ORGANISM: Artificial Sequence
<220> FEATURE:
<223> OTHER INFORMATION: RILPL2 Reverse primer Sequence

<400> SEQUENCE: 214
acgcggacga ctttgaactg                                               20

<210> SEQ ID NO 215
<211> LENGTH: 20
<212> TYPE: DNA
<213> ORGANISM: Artificial Sequence
<220> FEATURE:
<223> OTHER INFORMATION: RUNX1 Forward Primer Sequence

<400> SEQUENCE: 215
tccacaaacc caccgcaagt                                               20

<210> SEQ ID NO 216
<211> LENGTH: 19
<212> TYPE: DNA
<213> ORGANISM: Artificial Sequence
<220> FEATURE:
<223> OTHER INFORMATION: RUNX1 Reverse primer Sequence

<400> SEQUENCE: 216
cgctcggaaa aggacaagc                                                19

<210> SEQ ID NO 217
<211> LENGTH: 22
<212> TYPE: DNA
<213> ORGANISM: Artificial Sequence
<220> FEATURE:
<223> OTHER INFORMATION: RUNX2 Forward Primer Sequence

<400> SEQUENCE: 217
accatggtgg agatcatcgc cg                                            22

<210> SEQ ID NO 218
<211> LENGTH: 24
<212> TYPE: DNA
<213> ORGANISM: Artificial Sequence
<220> FEATURE:
<223> OTHER INFORMATION: RUNX2 Reverse primer Sequence
```

```
<400> SEQUENCE: 218
tcccatctgg tacctctccg aggg                                    24

<210> SEQ ID NO 219
<211> LENGTH: 22
<212> TYPE: DNA
<213> ORGANISM: Artificial Sequence
<220> FEATURE:
<223> OTHER INFORMATION: Runx3 Forward Primer Sequence

<400> SEQUENCE: 219
aggcaatgac gagaactact cc                                      22

<210> SEQ ID NO 220
<211> LENGTH: 20
<212> TYPE: DNA
<213> ORGANISM: Artificial Sequence
<220> FEATURE:
<223> OTHER INFORMATION: Runx3 Reverse primer Sequence

<400> SEQUENCE: 220
gtggggttgg tgaacacagt                                         20

<210> SEQ ID NO 221
<211> LENGTH: 20
<212> TYPE: DNA
<213> ORGANISM: Artificial Sequence
<220> FEATURE:
<223> OTHER INFORMATION: SAMSN1 Forward Primer Sequence

<400> SEQUENCE: 221
tgctcaagag aaagccatcc                                         20

<210> SEQ ID NO 222
<211> LENGTH: 21
<212> TYPE: DNA
<213> ORGANISM: Artificial Sequence
<220> FEATURE:
<223> OTHER INFORMATION: SAMSN1 Reverse primer Sequence

<400> SEQUENCE: 222
ttattccgaa aacgatcgaa a                                       21

<210> SEQ ID NO 223
<211> LENGTH: 23
<212> TYPE: DNA
<213> ORGANISM: Artificial Sequence
<220> FEATURE:
<223> OTHER INFORMATION: SCD Forward Primer Sequence

<400> SEQUENCE: 223
ttcctacctg caagttctac acc                                     23

<210> SEQ ID NO 224
<211> LENGTH: 20
<212> TYPE: DNA
<213> ORGANISM: Artificial Sequence
<220> FEATURE:
<223> OTHER INFORMATION: SCD Reverse primer Sequence

<400> SEQUENCE: 224
ccgagctttg taagagcggt                                         20

<210> SEQ ID NO 225
<211> LENGTH: 19
```

```
<212> TYPE: DNA
<213> ORGANISM: Artificial Sequence
<220> FEATURE:
<223> OTHER INFORMATION: SDC4 Forward Primer Sequence

<400> SEQUENCE: 225
tccccaccga acccaagaa                                                19

<210> SEQ ID NO 226
<211> LENGTH: 21
<212> TYPE: DNA
<213> ORGANISM: Artificial Sequence
<220> FEATURE:
<223> OTHER INFORMATION: SDC4 Reverse primer Sequence

<400> SEQUENCE: 226
ccttgttgga cacatcctca c                                             21

<210> SEQ ID NO 227
<211> LENGTH: 18
<212> TYPE: DNA
<213> ORGANISM: Artificial Sequence
<220> FEATURE:
<223> OTHER INFORMATION: SH2B3 Forward Primer Sequence

<400> SEQUENCE: 227
ctggagctct tcgaccca                                                 18

<210> SEQ ID NO 228
<211> LENGTH: 20
<212> TYPE: DNA
<213> ORGANISM: Artificial Sequence
<220> FEATURE:
<223> OTHER INFORMATION: SH2B3 Reverse primer Sequence

<400> SEQUENCE: 228
gttgtcaggc atctcaagcc                                               20

<210> SEQ ID NO 229
<211> LENGTH: 20
<212> TYPE: DNA
<213> ORGANISM: Artificial Sequence
<220> FEATURE:
<223> OTHER INFORMATION: SMS Forward Primer Sequence

<400> SEQUENCE: 229
cctcactatg gcagcagcac                                               20

<210> SEQ ID NO 230
<211> LENGTH: 20
<212> TYPE: DNA
<213> ORGANISM: Artificial Sequence
<220> FEATURE:
<223> OTHER INFORMATION: SMS Reverse primer Sequence

<400> SEQUENCE: 230
tcctggaaaa tggactggag                                               20

<210> SEQ ID NO 231
<211> LENGTH: 20
<212> TYPE: DNA
<213> ORGANISM: Artificial Sequence
<220> FEATURE:
<223> OTHER INFORMATION: THBS1 Forward Primer Sequence

<400> SEQUENCE: 231
```
caatgccaca gttcctgatg                                              20

<210> SEQ ID NO 232
<211> LENGTH: 21
<212> TYPE: DNA
<213> ORGANISM: Artificial Sequence
<220> FEATURE:
<223> OTHER INFORMATION: THBS1 Reverse primer Sequence

<400> SEQUENCE: 232
cacagctcgt agaacaggag g                                            21

<210> SEQ ID NO 233
<211> LENGTH: 20
<212> TYPE: DNA
<213> ORGANISM: Artificial Sequence
<220> FEATURE:
<223> OTHER INFORMATION: THY1 Forward Primer Sequence

<400> SEQUENCE: 233
tcaggaaatg cttttccca                                               20

<210> SEQ ID NO 234
<211> LENGTH: 23
<212> TYPE: DNA
<213> ORGANISM: Artificial Sequence
<220> FEATURE:
<223> OTHER INFORMATION: THY1 Reverse primer Sequence

<400> SEQUENCE: 234
tcctcaatga gatgccataa gct                                          23

<210> SEQ ID NO 235
<211> LENGTH: 20
<212> TYPE: DNA
<213> ORGANISM: Artificial Sequence
<220> FEATURE:
<223> OTHER INFORMATION: TNFAIP2 Forward Primer Sequence

<400> SEQUENCE: 235
cacctacatg ctgctgctct                                              20

<210> SEQ ID NO 236
<211> LENGTH: 19
<212> TYPE: DNA
<213> ORGANISM: Artificial Sequence
<220> FEATURE:
<223> OTHER INFORMATION: TNFAIP2 Reverse primer Sequence

<400> SEQUENCE: 236
cccataccct gcagctcac                                               19

<210> SEQ ID NO 237
<211> LENGTH: 21
<212> TYPE: DNA
<213> ORGANISM: Artificial Sequence
<220> FEATURE:
<223> OTHER INFORMATION: TNFAIP3 Forward Primer Sequence

<400> SEQUENCE: 237
ttgtcctcag tttcgggaga t                                            21

<210> SEQ ID NO 238
<211> LENGTH: 22
<212> TYPE: DNA
<213> ORGANISM: Artificial Sequence

```
<220> FEATURE:
<223> OTHER INFORMATION: TNFAIP3 Reverse primer Sequence

<400> SEQUENCE: 238
acttctcgac accagttgag tt                                              22

<210> SEQ ID NO 239
<211> LENGTH: 21
<212> TYPE: DNA
<213> ORGANISM: Artificial Sequence
<220> FEATURE:
<223> OTHER INFORMATION: TTYH2 Forward Primer Sequence

<400> SEQUENCE: 239
cccctgtctc cgagtacatg a                                               21

<210> SEQ ID NO 240
<211> LENGTH: 21
<212> TYPE: DNA
<213> ORGANISM: Artificial Sequence
<220> FEATURE:
<223> OTHER INFORMATION: TTYH2 Reverse primer Sequence

<400> SEQUENCE: 240
ctcccgatta gtggcacgtt c                                               21

<210> SEQ ID NO 241
<211> LENGTH: 23
<212> TYPE: DNA
<213> ORGANISM: Artificial Sequence
<220> FEATURE:
<223> OTHER INFORMATION: UNC93B1 Forward Primer Sequence

<400> SEQUENCE: 241
ttttggaacg aagtggatga tgt                                             23

<210> SEQ ID NO 242
<211> LENGTH: 19
<212> TYPE: DNA
<213> ORGANISM: Artificial Sequence
<220> FEATURE:
<223> OTHER INFORMATION: UNC93B1 Reverse primer Sequence

<400> SEQUENCE: 242
ggcacaagcg tgtagtagc                                                  19

<210> SEQ ID NO 243
<211> LENGTH: 20
<212> TYPE: DNA
<213> ORGANISM: Artificial Sequence
<220> FEATURE:
<223> OTHER INFORMATION: VAMP8 Forward Primer Sequence

<400> SEQUENCE: 243
acttggaaca tctccgcaac                                                 20

<210> SEQ ID NO 244
<211> LENGTH: 20
<212> TYPE: DNA
<213> ORGANISM: Artificial Sequence
<220> FEATURE:
<223> OTHER INFORMATION: VAMP8 Reverse primer Sequence

<400> SEQUENCE: 244
cttccaccag aatttccgag                                                 20
```

<210> SEQ ID NO 245
<211> LENGTH: 19
<212> TYPE: DNA
<213> ORGANISM: Artificial Sequence
<220> FEATURE:
<223> OTHER INFORMATION: ZSWIM6 Forward Primer Sequence

<400> SEQUENCE: 245
aagcggctgc gtagacaac                                            19

<210> SEQ ID NO 246
<211> LENGTH: 21
<212> TYPE: DNA
<213> ORGANISM: Artificial Sequence
<220> FEATURE:
<223> OTHER INFORMATION: ZSWIM6 Reverse primer Sequence

<400> SEQUENCE: 246
ggctccgatt gtattgcagg t                                         21

<210> SEQ ID NO 247
<211> LENGTH: 25
<212> TYPE: RNA
<213> ORGANISM: Artificial Sequence
<220> FEATURE:
<223> OTHER INFORMATION: RUNX1 siRNA sequence

<400> SEQUENCE: 247 ccuucaugu uaaucaaaca aguga                                      25

<210> SEQ ID NO 248
<211> LENGTH: 27
<212> TYPE: RNA
<213> ORGANISM: Artificial Sequence
<220> FEATURE:
<223> OTHER INFORMATION: RUNX1 siRNA sequence

<400> SEQUENCE: 248
ucacuuguuu gauuaacaug aaaggga                                   27

<210> SEQ ID NO 249
<211> LENGTH: 25
<212> TYPE: RNA
<213> ORGANISM: Artificial Sequence
<220> FEATURE:
<223> OTHER INFORMATION: RUNX1 siRNA sequence

<400> SEQUENCE: 249
acuagaugau cagaccaagc ccggg                                     25

<210> SEQ ID NO 250
<211> LENGTH: 27
<212> TYPE: RNA
<213> ORGANISM: Artificial Sequence
<220> FEATURE:
<223> OTHER INFORMATION: RUNX1 siRNA sequence

<400> SEQUENCE: 250
cccgggcuug gucugaucau cuaguuu                                   27

<210> SEQ ID NO 251
<211> LENGTH: 24
<212> TYPE: DNA
<213> ORGANISM: Artificial Sequence
<220> FEATURE:
<223> OTHER INFORMATION: PIM3 siRNA sequence

```
<400> SEQUENCE: 251
ccugagcguu uaauuuauuc agta                                          24

<210> SEQ ID NO 252
<211> LENGTH: 27
<212> TYPE: RNA
<213> ORGANISM: Artificial Sequence
<220> FEATURE:
<223> OTHER INFORMATION: PIM3 siRNA sequence

<400> SEQUENCE: 252
uacugaauaa auuaaacgcu caggcuc                                       27

<210> SEQ ID NO 253
<211> LENGTH: 25
<212> TYPE: DNA
<213> ORGANISM: Artificial Sequence
<220> FEATURE:
<223> OTHER INFORMATION: PIM3 siRNA sequence

<400> SEQUENCE: 253
ggcgugcuuc ucuacgauau ggugt                                         25

<210> SEQ ID NO 254
<211> LENGTH: 27
<212> TYPE: RNA
<213> ORGANISM: Artificial Sequence
<220> FEATURE:
<223> OTHER INFORMATION: PIM3 siRNA sequence

<400> SEQUENCE: 254
acaccauauc guagagaagc acgccca                                       27

<210> SEQ ID NO 255
<211> LENGTH: 23
<212> TYPE: DNA
<213> ORGANISM: Artificial Sequence
<220> FEATURE:
<223> OTHER INFORMATION: RUNX1 guide RNA

<400> SEQUENCE: 255
gatgagcgag gcgttgccgc tgg                                           23

<210> SEQ ID NO 256
<211> LENGTH: 23
<212> TYPE: DNA
<213> ORGANISM: Artificial Sequence
<220> FEATURE:
<223> OTHER INFORMATION: RUNX1 guide RNA

<400> SEQUENCE: 256
tagatgatca gaccaagccc ggg                                           23

<210> SEQ ID NO 257
<211> LENGTH: 23
<212> TYPE: DNA
<213> ORGANISM: Artificial Sequence
<220> FEATURE:
<223> OTHER INFORMATION: RUNX1 guide RNA

<400> SEQUENCE: 257
tggcaatgat gaaaactact cgg                                           23
```

COMPOSITIONS AND METHODS FOR THE TREATMENT OF ABERRANT ANGIOGENESIS

RELATED APPLICATIONS

This application is the U.S. national stage application, filed under 35 U.S.C. § 371, of PCT International Patent Application No. PCT/US17/61620, filed Nov. 14, 2017, which claims the benefit of U.S. Provisional Application 62/476,610 filed on Mar. 24, 2017, which claims the benefit of and priority under 35 U.S.C. § 119(3) of U.S. Provisional Application 62/422,523 filed on Nov. 15, 2016. The entire contents of these applications are incorporated herein by reference in their entirety.

STATEMENT AS TO FEDERALLY SPONSORED RESEARCH

This invention was made with government support under R01EY005318, R00EY021624, K12EY16335, UH2NS100121-01, R21EY027061, and P30EY003790 awarded by the National Institutes of Health. The government has certain rights in the invention.

FIELD OF THE INVENTION

The present invention relates to aberrant angiogenesis.

SEQUENCE LISTING

The entire content of the text file named 36770-554001WO_SEQLISTING.txt, which was created on Nov. 14, 2017, and is 195,667 bytes in size, is hereby incorporated by reference.

BACKGROUND

Neovascularization is a pathological feature of proliferative diabetic retinopathy (PDR), age-related macular degeneration (AMD), retinopathy of prematurity (ROP), cancer, and other conditions [Chung A S & Ferrara N (2011) Annu Rev Cell Dev Biol 27:563-584]. Abnormal vessel growth is thought to develop when there is an imbalance between pro- and anti-angiogenic signals, a process known as the angiogenic switch [Bergers G & Benjamin L E (2003) Nat Rev Cancer 3(6):401-410]. The resulting new vessels can be located in physiologically avascular regions such as the surface of the retina or within the vitreous of the eye. The new vessels generally display irregular branching patterns and increased permeability, leaving them prone to hemorrhage [Daxer A (1993) Curr Eye Res 12(12):1103-1109; Antonetti et al. (1999) J Biol Chem 274(33):23463-23467]. Anti-angiogenic therapies typically target vascular endothelial growth factor (VEGF) and are effective treatments for a number of neovascular ocular diseases and some solid tumors [Yadav et al. J Clin Diagn Res 9(6):XE01-XE05; Kim L A & D'Amore P A (2012) Am J Pathol 181(2):376-379].

Despite the success of anti-VEGF therapies, there is a need for new therapeutic approaches to treat aberrant angiogenesis, as current therapies are not universally effective and prolonged inhibition of VEGF may lead to tissue atrophy and other side effects [Saint-Geniez M, et al. (2008) PLoS One 3(11):e3554; Sang D N & D'Amore P A (2008) Diabetologia 51(9):1570-1573]. For example, anti-VEGF therapies are sometimes avoided in the treatment of PDR because they may precipitate the angio-fibrotic switch, enhancing the conversion of neovascular membranes into fibrovascular membranes (FVMs), which may contract and cause hemorrhages and tractional retinal detachments in patients with PDR while extended therapy may lead to tissue atropy, ischemia, and reperfusion injury [Arevalo J F, et al. (2008) Br J Ophthalmol 92(2):213-216; Hsu et al. (2014) Era. Journal of ophthalmology 2014:917375; Kuiper E J, et al. (2008) PLoS One 3(7):e2675]. Complex surgical procedures are required to remove intraocular hemorrhage, excise FVMs, and relieve associated traction in order to restore vision. The molecular mechanisms underlying the transition from a proliferative to a fibrotic state in PDR are largely unknown, though some reports implicate the balance between VEGF and connective tissue growth factor (CTGF) as critical to this process [Kuiper E J, et al. (2008) PLoS One 3(7):e2675; Van Geest R J, et al. (2012) Br J Ophthalmol 96(4):587-590; Sohn E H, et al. (2012) Arch Ophthalmol 130(9):1127-1134].

ROP, diabetic retinopathy (DR), and AMD, are leading causes of blindness in infants, working-age adults, and the elderly, respectively. ROP is believed to account for 6-18% of childhood blindness in developed countries [Hakeem et al., Middle East Afr J Ophthalmol. 2012 July-September; 19(3): 289-294]; the number of Americans with DR is expected to nearly double between 2010-2050, from 7.7 million to 14.6 million (nei.nih.gov/eyedata/diabetic); and AMD accounts for 8-7% of all blindness worldwide and is the most common cause of blindness in developed countries (www.who.int/blindness/causes/priority/en/).

Currently, there are no medical treatments for PDR, which is the most severe manifestation of DR. Current standard of care for PDR includes panretinal photocoagulation, or vitreo-retinal surgery to surgically remove fibrovascular membranes. Compositions and methods for the treatment of aberrant angiogenesis in diseases such as PDR are needed.

SUMMARY OF THE INVENTION

Provided herein are, inter alia, solutions to the clinical needs and problems described above. The present subject matter provides compositions, formulations, and methods for inhibiting, treating, or preventing aberrant angiogenesis, e.g., aberrant angiogenesis in the eye such as ocular neovascularization, in a subject. Aspects of the present subject matter provide a method for inhibiting, treating, or preventing aberrant angiogenesis in a subject, comprising administering to the subject an effective amount of a Runt-Related Transcription Factor 1 (RUNX1) or PIM3 Proto-Oncogene, Serine/Threonine Kinase (PIM3) inhibitor or modulator.

In some embodiments, the PIM3 inhibitor is co-administered with an ubiquitin-specific protease-7 (USP7) inhibitor.

In various embodiments, the aberrant angiogenesis comprises aberrant ocular angiogenesis (aberrant angiogenesis in the eye). In some embodiments, the subject comprises proliferative diabetic retinopathy (PDR), macular edema, non-proliferative diabetic retinopathy, age-related macular degeneration (AMD), or ocular neovascularization. In certain embodiments, the AMD comprises dry AMD. In various embodiments, the AMD comprises wet AMD.

In some embodiments, the subject comprises a cancer. In certain embodiments, the cancer is other than leukemia. In various embodiments, the cancer comprises melanoma. In some embodiments, the cancer comprises a solid tumor. For example, the aberrant angiogenesis may include blood vessel growth toward, into, and/or within the solid tumor. In certain embodiments, the solid tumor comprises a dimension that is greater than at least about 1, 2, 3, 4, 5, 6, 7, 8, 9, 10 mm or more and/or a volume of at least about 1, 1.5, 2, 3, 4, 5, 6, 7, 8, 9, 10 mm$^3$ or more.

In various embodiments, the RUNX1 inhibitor or the PIM3 inhibitor is administered as part of a treatment regimen that does not comprise an additional antiangiogenic inhibitor. In a non-limiting example, the treatment regimen does not comprise a vascular endothelial growth factor (VEGF) pathway inhibitor. In some embodiments, the RUNX1 or PIM3 inhibitor is administered as a monotherapy. In various embodiments, a PIM3 inhibitor is co-administered with an USP7 inhibitor.

In certain embodiments, the subject is an animal other than a pregnant animal, an infant, a fetus, or an embryo.

In some embodiments, the subject comprises diabetes. For example, the diabetes may be type 1 diabetes or type 2 diabetes.

In various embodiments, the subject comprises retinopathy of prematurity (ROP), diabetic retinopathy (DR), age-related macular degeneration (AMD), a retinal vein occlusion, a vascular malformation, a cerebral cavernous malformation, macular edema, non-proliferative diabetic retinopathy, ocular ischemic syndrome, neovascular glaucoma, a hemangioma, a retinal hemangioma, Coats' Disease, Norrie Disease, or Von Hippel-Lindau disease, or any condition that includes pathological angiogenesis as part of its pathobiology.

In certain embodiments, the subject is at least about 10, 20, 30, 40, 50, 60, 70, 80, or 90 years old.

In various embodiments, the RUNX1 inhibitor is a gamma-secretase inhibitor or modulator. In some embodiments, the gamma-secretase inhibitor reduces the expression of RUNX1. In certain embodiments, the gamma-secretase inhibitor is Compound E.

In some embodiments, the RUNX1 inhibitor or the PIM3 inhibitor comprises an aptamer, an oligonucleotide, a peptide, an antibody or a fragment thereof, or a small molecule. In a non-limiting example, the RUNX1 inhibitor binds to RUNX1 and/or CBFβ. In various embodiments, the RUNX1 inhibitor binds to RUNX1. In some embodiments the PIM3 inhibitor binds to PIM3. In certain embodiments, the RUNX1 inhibitor comprises Ro5-3335. In some embodiments, the RUX1 inhibitor comprises Ro24-7429. In various embodiments, the RUNX1 inhibitor or the PIM3 inhibitor comprises an oligonucleotide. For example, the oligonucleotide may comprise at least about 10, 15, 20, 25, 30, or more nucleotides in a sequence that is complementary to a nucleotide sequence within a gene or mRNA molecule that encodes RUNX1 or PIM3.

Aspects of the present subject matter also provide a composition comprising an effective amount of a RUNX1 inhibitor or a PIM3 inhibitor and an ophthalmically acceptable vehicle.

Aspects of the present subject matter relate to targeting RUNX1 or PIM3 for the treatment of a wide variety of retinal neovascular disorders including but not limited to: retinal vein occlusions, ocular ischemic syndrome, neovascular glaucoma, retinal hemangiomas, Coats' Disease, Norrie Disease, and retinopathy of prematurity, as well as other conditions that include aberrant angiogenesis.

The present subject matter also provides a method for inhibiting, treating, or preventing aberrant angiogenesis in a subject, comprising altering a RUNX1 or PIM3 gene in said subject. In various embodiments, altering a gene comprises altering a promoter, enhancer or other regulatory element of the gene, or an exon, an intron, or an intron-exon splice site of the gene. In some embodiments, altering the RUNX1 or PIM3 gene comprises the administration of (i) a Cas protein, a zinc finger nuclease (ZFN), or a transcription activator-like effector-based nuclease (TALEN), or (ii) an expression vector encoding a Cas protein, a ZFN, or a TALEN, to said subject. For example, in certain embodiments the gene is altered with via a CRISPR-Cas9 system.

The present subject matter further includes a method for inhibiting, treating, or preventing aberrant angiogenesis in a subject, comprising administering to said subject a NOTCH inhibitor in an amount that is effective to reduce RUNX1 expression or activity.

Included herein are compositions, formulations, and methods for inhibiting, treating, or preventing small vessel diseases (SVDs). Aspects of the present subject matter relate to the use of RUNX1 or PIM3 inhibitors or modulators for the treatment of a wide variety of SVDs including but not limited to cerebral small vessel disease, cerebral autosomal recessive arteriopathy with subcortical infarcts and leukoencephalopathy (CARASIL), age-related macular degeneration (AMD), cerebral autosomal-dominant arteriopathy with subcortical infarcts and leukoencephalopathy (CADASIL), NOTCH3 loss-of-function-associated SVD (e.g., a SVD associated with a mutation that reduces the expression and/or activity of NOTCH3), nephropathy, microangiopathy, heart failure, Alagille syndrome, familial tetralogy of Fallot, patent ductus arteriosus, cerebral cavernous malformation, diabetic retinopathy, and familial exudative vitreoretinopathy (FEVR). In various embodiments, during development there is less development of vessels in the retinal periphery but blindness occurs when subjects (e.g., child subjects such as subjects less than 18, 17, 16, 15, 14, 13, 12, 11, 10, 9, 8, 7, 6, 5, 4, 3, or 2 years of age) grow and have compensatory aberrant ocular angiogenesis. In some embodiments, RUNX1 or PIM3 inhibition is useful to treating such aberrant ocular angiogenesis.

In various embodiments, an SVD comprises aberrant angiogenesis such as aberrant ocular angiogenesis.

Aspects of the present subject matter provide a method for inhibiting, treating, or preventing aberrant angiogenesis or an SVD in a subject, comprising administering to the subject an effective amount of insulin growth factor binding protein 3 (IGFBP3) (e.g., recombinant IGFBP3 such as recombinantly produced human IGFBP3). Alternatively or in addition, aberrant angiogenesis or an SVD may be treated by, e.g., increasing the expression of IGFBP3. In some embodiments, the expression of IGFBP3 is increased by a method comprising genetically modifying a subject's IGFBP3 gene to increase the expression thereof (e.g., by altering or replacing the promoter or another regulatory sequence of the IGFBP3 gene, or by inserting an additional copy of the IGFBP3 gene into a subject, or by targeting enhancers of transcription to the promoter using CRISPR or TALEN). In certain embodiments, increasing the expression of IGFBP3 comprises administering a vector that encodes IGFBP3 to the subject. In various embodiments, the vector comprises a viral vector or a plasmid.

In various embodiments, a subject who is treated by any method disclosed herein has been identified as at risk of aberrant antiogenesis, or as having aberrant angiogenesis, by a diagnostic or prognostic method provided herein, or with a battery of testing comprising a diagnostic or prognostic method provided herein.

Various implementations relate to a method for detecting or diagnosing aberrant angiogenesis in a subject comprising (a) providing a test sample from the subject; (b) assaying the level of RUNX1, PIM3, or IGFBP3 protein or mRNA in the test sample; and (c) diagnosing the subject as having aberrant angiogenesis if the level of RUNX1 or PIM3 protein or mRNA is elevated in the test sample compared to a normal control, or diagnosing the subject as having aberrant angiogenesis if the level of IGFBP3 protein or mRNA is lower in the test sample compared to a normal control. In some embodiments, the subject is diagnosed with the aberrant angiogenesis if the level of RUNX1 or PIM3 protein or mRNA is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control. In certain embodiments, the subject is diagnosed with the aberrant angiogenesis if the level of IGFBP3 protein or mRNA in said test sample is less than about 5%, 10%, 15%, 20%, 25%, 30%, 40%, 45%, 50%, 55%, 60%, 65%, 70%, 75%, 80%, or 90% of the level than a normal control. In some embodiments, the level of RUNX1 protein is the level of phosphorylated RUNX1 protein (pRUNX1). In certain embodiments, the level of pRUNX1 comprises pRUNX1 that is prosphorylated at 5249.

In various embodiments, IGFBP3 is a biomarker for RUNX1 activity, and a decrease in IGFBP3 protein or mRNA indicates an increase in RUNX1 activity. In some embodiments, lower level of IGFBP3 protein or mRNA in a sample compared to a normal control sample (e.g., a level that is less than about 5%, 10%, 15%, 20%, 25%, 30%, 40%, 45%, 50%, 55%, 60%, 65%, 70%, 75%, 80%, or 90% of the level than a normal control) indicates an abnormally high level of RUNX1 activity, such as a level of RUNX1 activity that is indicative of aberrant angiogenesis. In some embodiments, the level of RUNX1 protein is the level of pRUNX1. In certain embodiments, the level of pRUNX1 comprises pRUNX1 that is prosphorylated at 5249. In certain embodiments, the level of IGFBP3 is measured in affected tissue, the vitreous, or blood (e.g., whole blood, plasma, or serum).

Aspects of the present subject matter provide a method for identifying whether a subject is at risk of developing a disease comprising aberrant angiogenesis comprising (a) providing a test sample from said subject; (b) assaying the level of RUNX1, PIM3, or IGFBP3 protein or mRNA in the test sample; and (c) identifying the subject as at risk of developing the disease if the level of RUNX1 or PIM3 protein or mRNA is elevated in the test sample compared to a normal control, or identifying the subject as at risk of developing the disease if the level of IGFBP3 protein or mRNA is lower in the test sample compared to a normal control. In some embodiments, the subject is identified as at risk of developing the disease if the level of RUNX1 or PIM3 protein or mRNA is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control. In certain embodiments, the subject is identified as at risk of developing the disease if the level of IGFBP3 protein or mRNA in said test sample is less than about 5%, 10%, 15%, 20%, 25%, 30%, 40%, 45%, 50%, 55%, 60%, 65%, 70%, 75%, 80%, or 90% of the level than a normal control. In some embodiments, the level of RUNX1 protein is the level of pRUNX1. In certain embodiments, the level of pRUNX1 comprises pRUNX1 that is prosphorylated at S249.

In some embodiments, the method further comprises directing the subject to obtain (i) additional screening or an additional diagnostic test for the disease if the subject is identified as at risk of developing the disease; or (ii) treatment to reduce, delay, or prevent the onset or progression of the disease.

The present subject matter also includes a method for monitoring whether a disease that comprises aberrant angiogenesis is progressing in a subject who has been diagnosed with the disease, comprising periodically determining the level of RUNX1, PIM3, or IGFBP3 protein or mRNA in the subject, and (1) identifying the disease as worsening if the level of RUNX1 or PIM3 protein or mRNA increases over time, or if the level of IGFBP3 protein or mRNA decreases over time; (2) identifying the disease as improving if the level of RUNX1 or PIM3 protein or mRNA decreases over time, or if the level of IGFBP3 protein or mRNA increases over time; or (3) identifying the disease as neither worsening nor improving if the level of RUNX1, PIM3, or IGFBP3 protein or mRNA remains the same or about the same over time, wherein determining the level of RUNX1, PIM3, or IGFBP3 protein or mRNA comprises (a) providing a test sample from the subject; and (b) assaying the level of RUNX1, PIM3, or IGFBP3 protein or mRNA in the test sample. In some embodiments, the level of RUNX1, PIM3, or IGFBP3 protein or mRNA is determined at least about 1, 2, 3, 4, 5, 6, 7, 8, 9, 10 or more times and/or at least once every 1, 2, 3, or 4 weeks; at least once every 1, 2, 3, 4, 5, or 6 weeks; or at least once every 1, 2, 3, 4, or 5 years. In some embodiments, the level of RUNX1 protein is the level of pRUNX1. In certain embodiments, the level of pRUNX1 comprises pRUNX1 that is prosphorylated at 5249.

Aspects of the present subject matter also provide a method of prophylaxis for a disease comprising aberrant angiogenesis, comprising identifying whether a subject is at risk of suffering from the disease, and administering to the subject a treatment for the disease if the subject is identified as at risk of suffering from the disease.

Also included is a method for adjusting the dose of a compound that is administered to a subject during a treatment regimen for a disease that comprises aberrant angiogenesis, comprising periodically determining the level of RUNX1, PIM3, or IGFBP3 protein or mRNA in the subject, and (1) increasing the dose of the compound if the level of RUNX1 or PIM3 protein or mRNA increases over time, or if the level of IGFBP3 protein or mRNA decreases over time; (2) maintaining or decreasing the dose of the compound if the level of RUNX1 or PIM3 protein or mRNA decreases over time, or if the level of IGFBP3 protein or mRNA increases over time; or (3) maintaining or increasing the dose of the compound if the level of RUNX1, PIM3, or IGFBP3 protein or mRNA remains the same or about the same over time, wherein determining the level of RUNX1, PIM3, or IGFBP3 protein or mRNA comprises (a) providing a test sample from the subject; and (b) assaying the level of RUNX1, PIM3, or IGFBP3 protein or mRNA in the test sample. In some embodiments, the level of RUNX1 protein is the level of pRUNX1. In certain embodiments, the level of pRUNX1 comprises pRUNX1 that is prosphorylated at 5249.

The present subject matter further includes a method for identifying whether a therapy has reduced or ameliorated a disease that comprises aberrant angiogenesis in a subject comprising (a) providing a pre-therapy test sample from the subject; (b) assaying the pre-therapy level of RUNX1, PIM3, or IGFBP3 protein or mRNA in the pre-therapy test sample; (c) administering the therapy to the subject; (d) providing a post-therapy test sample from the subject; (e) assaying the post-therapy level of RUNX1, PIM3, or IGFBP3 protein or mRNA in the post-therapy test sample; and (f) identifying the therapy as having reduced or ameliorated said disease if the level of RUNX1 or PIM3 protein or mRNA in the post-therapy test sample is lower than the level of RUNX1 or PIM3 protein or mRNA in the pre-therapy test sample, or if the level of IGFBP3 protein or mRNA in the post-therapy test sample is higher than the level of IGFBP3 protein or mRNA in the pre-therapy test sample. In some embodiments, the level of RUNX1 protein is the level of pRUNX1. In certain embodiments, the level of pRUNX1 comprises pRUNX1 that is prosphorylated at S249.

Various implementations relate to a method for detecting or diagnosing aberrant angiogenesis in a subject comprising (a) providing a test sample from the subject; (b) assaying the level of PPIF or CD44 protein or mRNA in the test sample; and (c) diagnosing the subject as having aberrant angiogenesis if the level of PPIF (Peptidylprolyl Isomerase F) or CD44 protein or mRNA is elevated in the test sample compared to a normal control. In some embodiments, the subject is diagnosed with the aberrant angiogenesis if the level of PPIF or CD44 protein or mRNA is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control.

Aspects of the present subject matter provide a method for identifying whether a subject is at risk of developing a disease comprising aberrant angiogenesis comprising (a) providing a test sample from said subject; (b) assaying the level of PPIF or CD44 protein or mRNA in the test sample; and (c) identifying the subject as at risk of developing the disease if the level of PPIF or CD44 protein or mRNA is elevated in the test sample compared to a normal control. In some embodiments, the subject is identified as at risk of developing the disease if the level of PPIF or CD44 protein or mRNA is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control.

In some embodiments, the method further comprises directing the subject to obtain (i) additional screening or an additional diagnostic test for the disease if the subject is identified as at risk of developing the disease; or (ii) treatment to reduce, delay, or prevent the onset or progression of the disease.

The present subject matter also includes a method for monitoring whether a disease that comprises aberrant angiogenesis is progressing in a subject who has been diagnosed with the disease, comprising periodically determining the level of PPIF or CD44 protein or mRNA in the subject, and (1) identifying the disease as worsening if the level of PPIF or CD44 protein or mRNA increases over time; (2) identifying the disease as improving if the level of PPIF or CD44 protein or mRNA decreases over time; or (3) identifying the disease as neither worsening nor improving if the level of PPIF or CD44 protein or mRNA remains the same or about the same over time, wherein determining the level of PPIF or CD44 protein or mRNA comprises (a) providing a test sample from the subject; and (b) assaying the level of PPIF or CD44 protein or mRNA in the test sample. In some embodiments, the level of PPIF or CD44 protein or mRNA is determined at least about 1, 2, 3, 4, 5, 6, 7, 8, 9, 10 or more times and/or at least once every 1, 2, 3, or 4 weeks; at least once every 1, 2, 3, 4, 5, or 6 weeks; or at least once every 1, 2, 3, 4, or 5 years.

Aspects of the present subject matter also provide a method of prophylaxis for a disease comprising aberrant angiogenesis, comprising identifying whether a subject is at risk of suffering from the disease, and administering to the subject a treatment for the disease if the subject is identified as at risk of suffering from the disease.

Also included is a method for adjusting the dose of a compound that is administered to a subject during a treatment regimen for a disease that comprises aberrant angiogenesis, comprising periodically determining the level of PPIF or CD44 protein or mRNA in the subject, and (1) increasing the dose of the compound if the level of PPIF or CD44 protein or mRNA increases over time; (2) maintaining or decreasing the dose of the compound if the level of PPIF or CD44 protein or mRNA decreases over time; or (3) maintaining or increasing the dose of the compound if the level of PPIF or CD44 protein or mRNA remains the same or about the same over time, wherein determining the level of PPIF or CD44 protein or mRNA comprises (a) providing a test sample from the subject; and (b) assaying the level of PPIF or CD44 protein or mRNA in the test sample.

The present subject matter further includes a method for identifying whether a therapy has reduced or ameliorated a disease that comprises aberrant angiogenesis in a subject comprising (a) providing a pre-therapy test sample from the subject; (b) assaying the pre-therapy level of PPIF or CD44 protein or mRNA in the pre-therapy test sample; (c) administering the therapy to the subject; (d) providing a post-therapy test sample from the subject; (e) assaying the post-therapy level of PPIF or CD44 protein or mRNA in the post-therapy test sample; and (f) identifying the therapy as having reduced or ameliorated said disease if the level of PPIF or CD44 protein or mRNA in the post-therapy test sample is lower than the level of PPIF or CD44 protein or mRNA in the pre-therapy test sample.

In various embodiments, PPIF and CD44 are downstream targets of RUNX1. In embodiments, the CD44 is present on the plasma membrane of a cell.

In some embodiments, the test sample comprises a bodily fluid from said subject. Non-limiting examples of bodily fluids include whole blood, a component of whole blood, plasma, or serum. Alternatively or in addition, the test sample comprises a tissue biopsy.

In various embodiments, assaying the level of RUNX1, PIM3, IGFBP3, RUNX1, PIM3, IGFBP3, PPIF, or CD44 (e.g., RUNX1, PIM3, or IGFBP3) protein or mRNA comprises contacting the RUNX1, PIM3, or IGFBP3 protein or mRNA with a specific binding agent. In some embodiments, the binding agent comprises oligonucleotide probe or primer, an antibody or a fragment thereof, or a polypeptide or a fragment thereof. In certain embodiments, the binding agent is attached to a solid support.

In some embodiments, assaying comprises an enzyme immunoassay (EIA) or a reverse transcriptase polymerase chain reaction (RT-PCR). In certain embodiments, assaying comprises an enzyme-linked immunosorbent assay (ELISA), a Western blot, a mass spectrometry assay, a radioimmunoassay, or a fluoroimmunoassay.

Biomarker changes that may be detected also include the redistribution of biomarkers between different compartments of a body, such as between a vessel and blood or between cerebrospinal fluid (CSF) and blood. Therefore, assaying of one or more of the biomarkers provided herein may be performed using a specific binding agent that may be detected with via imaging. Non-limiting examples of imaging technologies include positron emission tomography (PET) and single-photon emission computed tomography (SPECT).

Embodiments of the present subject matter relate to kits that detect two or more of the biomarkers disclosed herein (e.g., at the same time) and/or protein-protein interactions between them. In some embodiments, the biomarkers include 1, 2, 3, or 4 of any combination of RUNX1, PIM3, IGFBP3, PPIF, and CD44, or all 5 of RUNX1, PIM3, IGFBP3, PPIF, and CD44. Aspects of the present subject matter provide a kit comprising (a) (i) an agent for detecting the level of RUNX1; (ii) an agent for detecting the level of PIM3; or (iii) an agent for detecting the level of IGFBP3, and (b) instructions for using the agent for diagnosing or detecting aberrant angiogenesis, for identifying whether a subject is at risk of developing a disease that comprises aberrant angiogenesis, for determining the progression of the disease, for assessing the efficacy of a treatment for the disease, and/or for adjusting the dose of a compound during the treatment of disease. Also provided is a kit comprising (a) (i) an agent for detecting the level of PPIF; (ii) an agent for detecting the level of CD44; and/or (iii) an agent for detecting the level of RUNX1, PIM3, and/or IGFBP3, and (b) instructions for using the agent for diagnosing or detecting aberrant angiogenesis, for identifying whether a subject is at risk of developing a disease that comprises aberrant angiogenesis, for determining the progression of the disease, for assessing the efficacy of a treatment for the disease, and/or for adjusting the dose of a compound during the treatment of disease. In some embodiments, the agent for detecting the level of RUNX1 detects the level of pRUNX1. In certain embodiments, the level of pRUNX1 comprises pRUNX1 that is phosphorylated at S249.

The present subject matter also provides a diagnostic system comprising (a) an assortment, collection, or compilation of test results data representing the level of RUNX1, PIM3, and/or IGFBP3 in a plurality of test samples; (b) a means for computing an index value using said level, wherein the index value comprises a diagnostic, prognostic, progression, or treatment score; and (c) a means for reporting the index value. Also included is a diagnostic system comprising (a) an assortment, collection, or compilation of test results data representing the level of RUNX1, PIM3, IGFBP3, PPIF, and/or CD44 in a plurality of test samples; (b) a means for computing an index value using said level, wherein the index value comprises a diagnostic, prognostic, progression, or treatment score; and (c) a means for reporting the index value. In some embodiments, the agent for detecting the level of RUNX1 detects the level of pRUNX1. In certain embodiments, the level of pRUNX1 comprises pRUNX1 that is phosphorylated at S249.

In some embodiments, the level of RUNX1, PIM3, IGFBP3, PPIF, and/or CD44 (e.g., RUNX1, PIM3, and/or IGFBP3) is measured in one or more biological fluids as part of a diagnostic or prognostic test for aberrant angiogenesis. Measurements of RUNX1, PIM3, IGFBP3, PPIF, and/or CD44 (e.g., RUNX1, PIM3, and/or IGFBP3) in biological fluids or tissue samples can be used as diagnostic or prognostic readouts for diseases comprising aberrant angiogenesis. In certain embodiments, a method disclosed herein is part of a battery of testing for a disease comprising aberrant angiogenesis. For example, a subject may be screened/tested and/or directed to receive additional screening/testing for a disease based on the level of RUNX1, PIM3, IGFBP3, PPIF, and/or CD44 (e.g., RUNX1, PIM3, and/or IGFBP3) in one or more bodily fluids or tissue samples.

In various embodiments, the level of RUNX1, PIM3, IGFBP3, PPIF, and/or CD44 (e.g., RUNX1, PIM3, and/or IGFBP3) is measured in one or more biological fluids or tissue samples as part of a method for evaluating the effectiveness of a treatment or the progression of a disease. Measures of RUNX1, PIM3, IGFBP3, PPIF, and/or CD44 (e.g., RUNX1, PIM3, and/or IGFBP3) in biological samples can be used as biomarkers to determine the efficacy of a treatment in an animal model or human. For example, a subject may be administered and/or directed to receive a different treatment, an increased dose of a therapeutic compound, or a decreased dose of a therapeutic compound based on the level of RUNX1, PIM3, IGFBP3, PPIF, and/or CD44 (e.g., RUNX1, PIM3, and/or IGFBP3) in one or more samples. In some embodiments, the therapeutic compound is a test compound being evaluated in a clinical trial. In certain embodiments, the therapeutic compound is a compound that has been approved for use in humans by a regulatory body such as the United States Food and Drug Administration. In some embodiments, the level of RUNX1 protein is the level of pRUNX1. In certain embodiments, the level of pRUNX1 comprises pRUNX1 that is phosphorylated at S249.

In instances where a disease cannot be specifically treated, the diagnostic and prognostic methods of the present subject matter provide valuable information to subjects that will allow them to make relevant lifestyle decisions and plan for the onset of likely symptoms. Thus, the present subject matter provides valuable tools, resources, and information to subjects with incurable diseases.

Methods described herein represent a non-invasive (or minimally invasive) test assay. For example, the test sample such as blood is obtained (e.g., by venipuncture), and the sample comprises a bodily fluid such as blood, serum, or plasma. In another example, the test sample comprises saliva, tears, vitreous, urine, or sweat.

In various implementations, the methods described herein may also include computing a level of RUNX1, PIM3, IGFBP3, PPIF, and/or CD44 (e.g., RUNX1, PIM3, and/or IGFBP3) in a process that includes the use of a binding agent. An exemplary example of a binding agent includes an antibody (or a fragment thereof) or a detectable protein (or a fragment thereof). The antibody may be labeled with a detectable moiety, e.g., a fluorescent compound or a radioactive agent (e.g., technetium-99m, iodine-123, iodine-125, iodine-131, indium-111, carbon-11, nitrogen-13, oxygen-15, fluorine-18, gallium-68, zirconium-89, or rubidium-82). When the fluorescently labeled antibody is exposed to light of the proper wavelength, its presence can then be detected due to fluorescence. Non-limiting examples of fluorescent labeling compounds include fluorescein isothiocyanate, rhodamine, phycoerythrin, phycocyanin, allophycocyanin, p-phthaldehyde, and fluorescamine. The antibody can also be detectably labeled using fluorescence emitting metals such as europium-152, or others of the lanthanide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. The presence of the chemiluminescent-tagged antibody is then determined by detecting the presence of luminescence that arises during the course of chemical reaction. Non-limiting examples of particularly useful chemiluminescent labeling compounds include luminol, isoluminol, theromatic acridinium ester, imidazole, acridinium salt, and oxalate ester.

As used herein, a "specific binding agent" describes an agent having a greater than 10-fold, preferably greater than 100-fold, and most preferably, greater than 1000-fold affinity for a target molecule as compared to another molecule. As the skilled artisan will appreciate, the term "specific" is used to indicate that other biomolecules present in the sample do not significantly bind to the binding agent specific for the target molecule. In various embodiments, the level of binding to a biomolecule other than the target molecule results in a binding affinity which is at most only 10% or less, only 5% or less only 2% or less or only 1% or less of the affinity to the target molecule, respectively. A preferred specific binding agent will fulfill both the above minimum criteria for affinity as well as for specificity. For example, an antibody has a binding affinity in the low micromolar ($10^{-6}$), nanomolar ($10^{-7}$-$40^{-9}$), with high affinity antibodies in the low nanomolar ($10^{-9}$) or pico molar ($10^{-12}$) range for its specific target ligand.

The present subject matter describes a composition utilizing a binding agent, wherein the binding agent is attached to a solid support, (e.g., a strip, a polymer, a bead, or a nanoparticle). Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present subject matter. The support material may have virtually any possible structural configuration so long as the target molecule (e.g., a RUNX1, PIM3, or IGFBP3 protein) is capable of binding to a binding agent (e.g., an antibody). Thus, the support configuration may be spherical, as in a bead, or cylindrical, as in the inside surface of a test tube, or the external surface of a rod. Alternatively, the surface may be flat such as a sheet, or test strip, etc. In some embodiments, the support includes polystyrene beads. Those skilled in the art will know many other suitable carriers and supports, or will be able to ascertain the same by use of routine experimentation.

In some aspects, the solid support comprises a polymer, to which an agent is chemically bound, immobilized, dispersed, or associated. A polymer support may be a network of polymers, and may be prepared in bead form (e.g., by suspension polymerization). The location of active sites introduced into a polymer support depends on the type of polymer support. For example, in a swollen-gel-bead polymer support the active sites are distributed uniformly throughout the beads, whereas in a macroporous-bead polymer support they are predominantly on the internal surfaces of the macropores. In various embodiments, the solid support contains a RUNX1 binding agent alone or together with a binding agent for PIM3 and/or IGFBP3. In some embodiments, the solid support contains a PIM3 binding agent alone. In certain embodiments, the solid support contains an IGFBP3 binding agent alone. In various embodiments, the solid support contains a binding agent for any of, or any combination of 2, 3, or 4 of, or all of RUNX1, PIM3, IGFBP3, PPIF, and CD44.

In various embodiments, a test (e.g., assay) is carried out on a bodily fluid such as blood, serum, or plasma. The level of a protein may be measured using any applicable method known in the art, such as an immunoassay such as an enzyme-linked immunosorbent assay (ELISA), Western blot, radioimmunoassay (RIA), fluoroimmunoassay, or mass spectrometry. Non-limiting examples of mass spectrometry techniques include electrospray ionization (ESI), matrix assisted laser desorption (MALDI), MALDI-TOF (Time of flight), Fourier transform ion cyclotron resonance (FTIC), and surface-enhanced laser desorption (SELDI). Non-limiting examples of live imaging techniques for detecting the level and/or location (e.g., expression or localization changes) of a biomarker in the body of a subject include PET and SPECT.

As used herein, the term "assay" is intended to exclude the mere reading of a report or database entry. An assay is an investigative (analytic) procedure for qualitatively assessing or quantitatively measuring presence or amount or the functional activity of a target entity (e.g., the amount or level of RUNX1, PIM3, or IGFBP3 protein or mRNA in a test sample).

The term "sample" as used herein refers to a biological sample obtained for the purpose of evaluation in vitro. With regard to the methods disclosed herein, the sample or patient sample preferably may comprise any body fluid. In some embodiments, the body fluid includes, but is not limited to, whole blood, plasma, serum, lymph, breast milk, saliva, mucous, semen, cellular extracts, inflammatory fluids, cerebrospinal fluid, vitreous humor, tears, vitreous, aqueous humor, or urine obtained from the subject. In some aspects, the sample is a composite panel of two or more body fluids. In exemplary aspects, the sample comprises blood or a fraction thereof (e.g., plasma, serum, fraction obtained via leukopheresis).

Various methods disclosed herein comprise repeating providing, contacting, detecting, assaying, identifying, and/or computing steps over time.

Additionally, a progressive increase over time in the level of RUNX1, PIM3, or IGFBP3 indicates a progressive worsening of the severity of a disease. A progressive decrease over time in the level of RUNX1, PIM3, or IGFBP3 indicates an amelioration of a disease associated with aberrant angiogenesis. In some embodiments, a method may include the step of treatment following risk stratification as described herein. For example, a method further comprises identifying a subject with a high risk of a particular symptom or disease and administering to that subject a therapeutic regimen to inhibit, treat, or prevent the symptom or disease.

Also disclosed herein is a kit comprising RUNX1, PIM3, and/or IGFBP3 binding agent(s) and instructions for using the agent(s) for diagnosing a subject, evaluating a subject's prognosis, or determining the efficacy of a therapeutic regimen. In some embodiments, the agent is attached to a solid support such a test strip. The kit optionally contains buffers, enzymes, salts, stabilizing agents, preservatives, and a container for receiving a test sample of bodily fluid or cell. In some cases, such a container contains an anti-coagulant or a cell separation agent (e.g., to separate white cells from red blood cells). In various embodiments, the agent is attached to a solid support (e.g., a test strip). Various embodiments of the invention relate to a kit comprising agents for measuring a group of markers, wherein the group of markers are defined as described in any of the paragraphs, or panels containing figures, or other descriptions of preferred sets or panels of markers found herein. In some variations, such agents are packaged together. In some variations, the kit further includes an analysis tool for evaluating risk of an individual developing a disease or a symptom thereof from measurements of the group of markers from at least one biological sample from the subject.

The diagnostic or prognostic assay is optionally formulated in a two-antibody binding format in which one RUNX1, PIM3, or IGFBP3 protein-specific antibody captures RUNX1, PIM3, or IGFBP3 protein, e.g., in a patient sample and another anti-RUNX1, anti-PIM3, or anti-IGFBP3 antibody is used to detect captured protein. For example, the capture antibody is immobilized on a solid phase, e.g., an assay plate, an assay well, a nitrocellulose membrane, a bead, a dipstick, or a component of an elution column. The second antibody, i.e., the detection antibody, is typically tagged with a detectable label such as a colorimetric agent or radioisotope.

The present subject matter also describes diagnostic test system that obtains test results data representing levels of a marker in at least one biological sample. In various embodiments, the results are collected and tracked by the system. In some embodiments, the system comprises a means for computing an index value from said marker, wherein the index value comprises a disease risk score or a disease symptom risk score. The system may also include a means of reporting the index value.

Aspects of the present subject matter relate to a diagnostic test system comprising a means for obtaining test results data representing levels of a marker (e.g., the level of RUNX1, PIM3, or IGFBP3 protein or mRNA) in at least one biological sample; a means for collecting and tracking test results data for one or more individual biological samples; a means for computing an index value from marker measurement data, wherein said biomarker measurement data is representative of measured levels of markers, wherein said measured levels of markers comprise the levels of a set or panel of markers; and a means for reporting said index value. In some variations of the diagnostic test system, the index value is a disease risk score or a symptom risk score. In certain variations, the risk score is computed according to the methods described herein for computing such scores. In some variations, the means for collecting and tracking test results data representing information and/or index values for one or more individuals comprises a data structure or database. In various embodiments, the means for computing a risk score comprises a computer or microprocessor, comprising a visible display, an audio output, a link to a data structure or database, or a printer.

Methods, compositions, kits, and systems disclosed herein may be used to indicate that the method according to the present invention will, alone or together with other variables, establish or confirm the absence or presence of a disease, or aid a physician in the prognosis, and or the monitoring of treatment. The skilled artisan will appreciate that any such evaluation or assessment is made using an in vitro assay. The patient sample is solely used for the in vitro diagnostic method of the invention and the material of the patient sample is not transferred back into the patient's body. Typically, the sample is a liquid sample, e.g., whole blood, serum or plasma, or a biopsy sample.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

FIG. 3A: Gene expression of Chemokine (C-X-C Motif) Ligand 10 (CXCL10) (negative control gene), PIM3 Proto-Oncogene, Serine/Threonine Kinase (PIM3), Peptidylprolyl Isomerase F (PPIF), RUNX1, and CD44 was measured by qRT-PCR (NG: normal (5 mM) D-glucose, HG: high (30 mM) D-glucose). Each candidate gene had a marked increase in response to D-glucose but no statistically significant changes in response to osmotic controls (L-glucose or mannitol). CXCL10 is not glucose responsive, consistent with RNA-sequencing (n=3; the experiment was performed in triplicate).

FIG. 4A: Increasing D-glucose led to a dose-dependent increase of RUNX1 protein expression in HRMEC (top) and HUVECs (bottom) as determined by western blot (n=3; experiment performed in triplicate).

FIGS. 5A-E are images showing the immunohistochemical localization of RUNX1 in FVMs. FIG. 5A: Normal retinal vessels showed no staining (RPE=retinal pigment epithelium, L=vessel lumen). FIG. 5B: A subset of vessels in FVM stained positively for RUNX1 (arrows). Asterisk denotes non-staining vessels (scale bar=100 µm). (FIG. 5C) Higher magnification view of normal retinal vessel negative for RUNX1 staining and (FIG. 5D) positively stained vessels in FVM (arrows) (scale bar=50 µm). FIG. 5E shows a larger version of FIGS. 5A and 5D.

FIG. 6A (upper left panel): Merged image of isolectin B4 and Runx1 staining of OIR retina showing distribution of RUNX1 in neovascular tufts. FIG. 6A (upper middle panel): Isolectin B4 staining (green) visualizes both normal vascular networks and pathologic neovascular tufts in retina from pups with OIR. FIG. 6A (right panel): Positive RUNX1 immunostaining (red) conforms to the shape of neovascular tufts only (scale bar=50 µm). FIG. 6B: Section of human melanoma inoculated subdermally in nude mice showing no staining for RUNX1 in normal capillary of the hypodermis. FIGS. 6B-D: Positive RUNX1 immunostaining (red) in melanoma sections conforming to vessel walls, particularly in capillaries (scale bar=50 µm).

FIGS. 7A and B are a set of images and a graph, respectively, showing the role of RUNX1 in HRMEC migration. FIG. 7A: Scratch-wound assay using HRMEC cells at 0 h (left column), 6 h (mid column) and 12 h (right column) with control (top row), scramble siRNA (mid row) or RUNX1 siRNA (bottom row) treatment. Dark grey regions denote wound areas (scale bar=400 µm). FIG. 7B: Quantification of wound closure rates shows that knockdown of RUNX1 effectively inhibits wound closure. There was no significant difference between transfection reagent alone (control) and scramble siRNA treatment. * $p<0.05$.

FIG. 8A: Ki67 staining 48 h post transfection demonstrates significant reduction in cell number and proliferative capacity of RUNX1 siRNA treated cells compared to cells treated with transfection reagent alone or scramble siRNA (scale bar=200 µm).

FIGS. 9A-C is a set of images showing the isolation and culture of endothelial cells from surgical specimens of FVM. FIG. 9A: Representative pre-surgical fundus photograph of a right eye exhibiting a FVM encroaching on the optic nerve (dashed line) causing tractional retinal detachment with blot hemorrhages throughout the retina (arrowheads). FIG. 9B: Magnetic beads (arrows) allow for separation and culturing of enriched cell populations from surgical specimens (Scale bar=100 µm). FIG. 9C: Cultures of isolated cells stained positively for CD31 representing a successfully isolated enriched population (Scale bar=40 µm).

FIG. 10A (left graph): RUNX1 siRNA induced a 60% reduction of RUNX1 expression measured by qRT-PCR 48 hours post-transfection whereas expression of RUNX2 and RUNX3, the two other mammalian RUNX orthologues, showed no significant changes, indicating specificity of the siRNA. FIG. 10A (right graph): Functional inhibition of RUNX1 signaling was demonstrated by a 330% increase in the mRNA expression of a canonical target named IGFBP3, a known target of RUNX1 inhibition. Western blot demonstrated similar reduction in protein levels (FIG. 10B). FIG. 10C: siRNA-2's effect on RUNX1 was validated by qRT-PCR and western blot, demonstrating a similar reduction in both RNA and protein. Scratch assay demonstrates functional inhibition of RUNX1 by siRNA-2. ns: not significant, * $p<0.05$, *** $p<0.001$.

DETAILED DESCRIPTION

Aspects of the present subject matter relate to the surprising discovery that RUNX1 inhibition reduces aberrant angiogenesis. Blood vessel growth may occur via the process of angiogenesis and/or vasculogenesis. The processes are distinct, and the involvement of a protein or pathway in vasculogenesis (e.g., during embryonic development) does not necessarily indicate that the protein or pathway is relevant to angiogenesis, much less aberrant angiogenesis. Moreover, the involvement of a protein or pathway in embryonic angiogenesis does not indicate that targeting the protein or pathway would be capable of reducing the aberrant angiogenesis, much less sufficient for inhibiting aberrant angiogenesis or safe for targeting in an infant, child, or adult.

As used herein, "angiogenesis" means the physiological process through which new blood vessels form from pre-existing vessels. Angiogenesis is particularly relevant to aberrant vessel growth in infants, children, adults, such as during tumor growth and in PDR. "Vasculogenesis" means the process of blood vessel formation occurring by a de novo production of endothelial cells. Vasculogenesis is particularly relevant to embryonic blood vessel formation. Vasculogenesis and angiogenesis are distinct from each other in that angiogenesis relates to the development of new blood vessels from (e.g., sprouting or extending from) pre-existing blood vessels, whereas vasculogenesis relates to the formation of new blood vessels that have not extended/sprouted from pre-existing blood vessels (e.g., where there are no pre-existing vessels). For example, if a monolayer of endothelial cells begins sprouting to form capillaries, angiogenesis is occurring. Vasculogenesis, in contrast, is when endothelial precursor cells (angioblasts) migrate and differentiate in response to local cues (such as growth factors and extracellular matrices) to form new blood vessels. These new blood vessels formed by vasculogenesis are then pruned and extended through angiogenesis.

RUNX1 has been implicated in other biological processes including endothelial-cell derived blood vessel formation during embryonic development and normal angiogenesis. However, a role for RUNX1 in pathogenic angiogenesis has not previously been described.

Figure 6A:
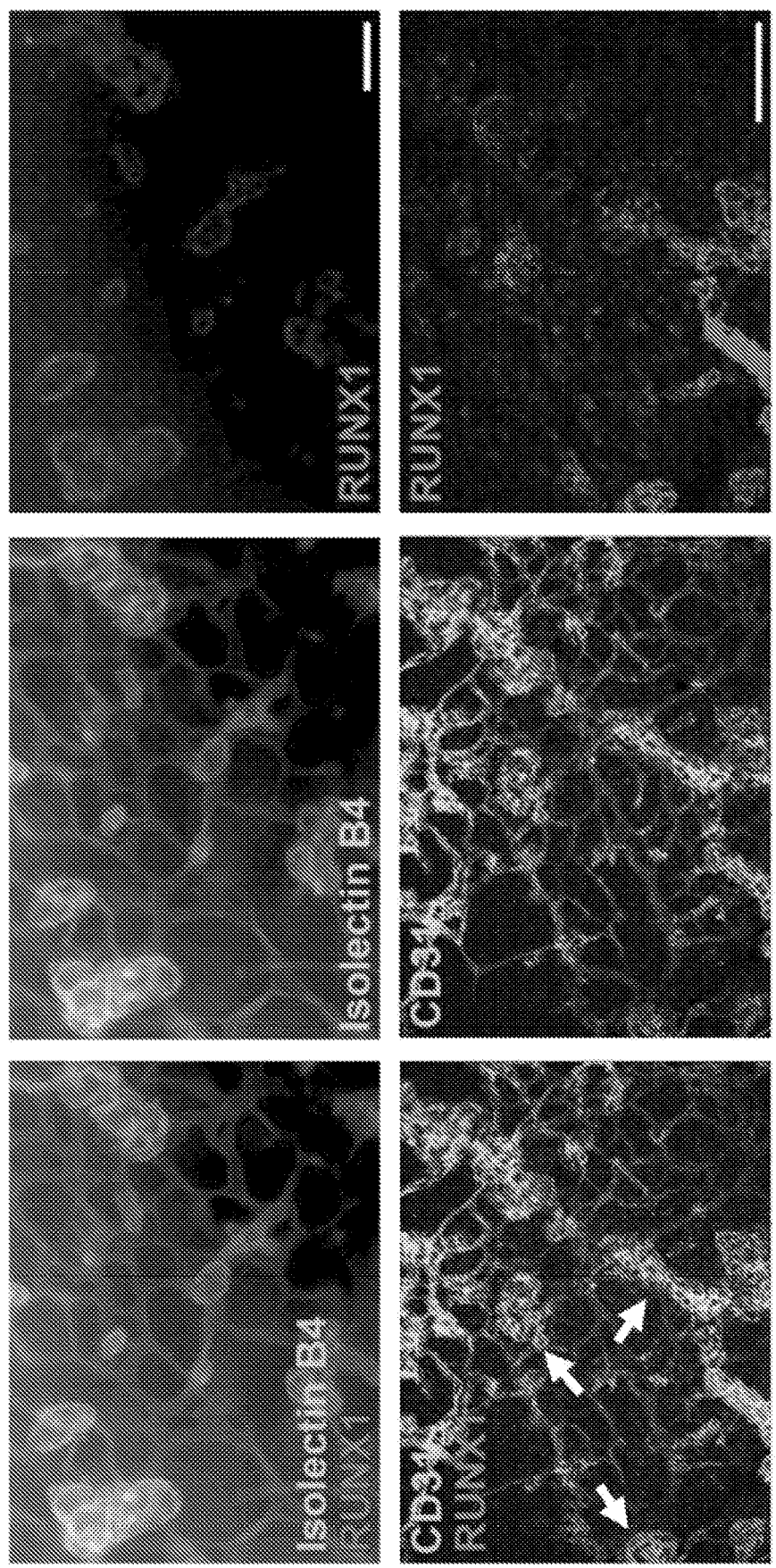
FIG. 6A is a set of are images showing the retina of P17 C57BL/6J mice with oxygen-induced retinopathy (OIR) co-stained for RUNX1 and vessels (IB4 or CD31) showing positive RUNX1 staining conforming to neovascular tufts and not to normal underlying vasculature (scale bar=50 µm).
Figure 6E:
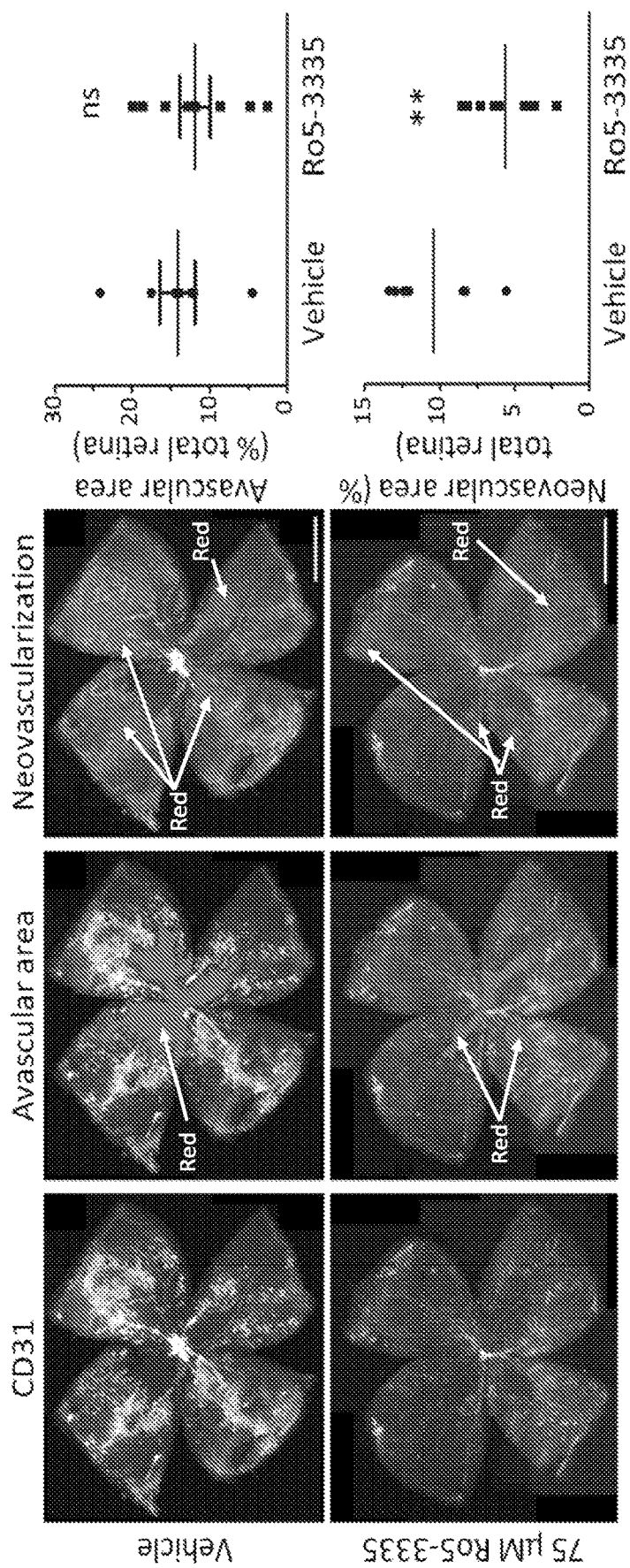
FIG. 6E is a set of images and graphs showing the effectiveness of treatment using a RUNX1 inhibitor in a model of aberrant retinal angiogenesis. Retinal flat mounts of P17 C57BL/6J mice following OIR induction and intravitreal injection of 75 µM Ro5-3335 or vehicle at P13 and P15 (red overlay identifies the avascular area and neovascularization respectively. Scale bar=1 mm). There was a non-significant downward trend in avascular area but a significant reduction in neovascularization in the treated group compared to vehicle treated ($n_{vehicle}$=7; $n_{Ro5\text{-}3335}$=9. Experiment performed in triplicate). ns: not significant, ** $p<0.01$.

In various embodiments, RUNX1 is used as a therapeutic target for diabetic retinopathy (a common complication of diabetes) and other conditions characterized by aberrant angiogenesis. As shown in FIG. 6E, treatment using a RUNX1 inhibitor was effective at reducing neovascularization in an animal model of aberrant retinal angiogenesis. In some embodiments, the diabetic retinopathy comprises PDR. There are currently no non-surgical methods for the management of PDR. RUNX1 pathway represents an alternative target for PDR. Current management of fibrovascular membranes includes the use of laser photocoagulation (which is a destructive method that ablates the peripheral retina) or potentially risky and invasive surgical methods for removing fibrovascular membranes directly from the eye.

Targeting RUNX1 allows for targeted medical management of fibrovascular membranes, and causes their regression and/or impedes the growth of such membranes, which avoids the need for surgery. Other conditions including cancer that are characterized and/or made worse by aberrant angiogenesis may be inhibited, treated, or prevented using RUNX1 regulation. In addition to PDR, RUNX1 regulation is used as a target for the treatment of a wide variety of retinal neovascular disorders including but not limited to: retinal vein occlusions, ocular ischemic syndrome, neovascular glaucoma, retinal hemangiomas, and retinopathy of prematurity in addition to other ocular neovascular disorders such as corneal graft rejection and other pathologic neovascularization in the anterior segment of the eye, as well as other conditions characterized by aberrant angiogenesis, such as cancer.

Also provided herein, inter alia, are methods and compositions for reducing aberrant angiogenesis by inhibiting PIM3. The characterization of transcriptomes from endothelial cells obtained from human fibrovascular membranes derived from fresh surgical specimens identified PIM3—a serine/threonine kinase—as a candidate gene in PDR (the PIM3 gene is overexpressed). Consistent with this finding, upregulation of PIM3 in human retinal microvascular endothelial cells (HRMEC) exposed to high glucose in vitro. PIM kinases have pleiotropic pro-survival and anti-apoptotic effects.

RUNX1 is phosphorylated in the vessels of individuals with proliferative diabetic retinopathy. A different PIM kinase can phosphorylate and stabilize a different RUNX protein. See, e.g., Kim et al. (2008) *J Cell Biochem* 105(4): 1048-58. In some embodiments, one way to inhibit RUNX1 is to inhibit its phosphorylation by inhibiting PIM3. In certain embodiments, PIM kinase inhibition impacts RUNX1 function via diminished phosphorylation.

Surprisingly, and without being limited by any scientific theory, in various embodiments there is a direct functional link between PIM3 and RUNX1. In some embodiments, PIM3 inhibition results in RUNX1 inhibition (e.g., downregulation). In certain embodiments, a RUNX1 inhibitor and/or a PIM3 inhibitor is administered in a formulation such as an eyedrop formulation (e.g., topically). In various embodiments, PIM3 inhibition using a small molecule inhibitor that binds to PIM3 leads to significant RUNX1 downregulation. In some embodiments, PIM3 knockdown or inhibition via small molecules leads to downregulation of RUNX1. In certain embodiments, an existing PIM3 inhibitor (e.g., a commercially available inhibitor such as a non-limiting example disclosed herein) is administered to treat aberrant angiogenesis in a disease or disorder such as diabetic retinopathy, age-related macular degeneration, retinal vein occlusions, neovascular glaucoma, corneal neovascularization, retinal hemangioma, or cancer. Other non-limiting examples of diseases and disorders are disclosed herein. Alternatively or in addition, compounds are screened and developed to inhibit PIM3 for treating aberrant angiogenesis. In some embodiments, PIM3 inhibition is used as means to inhibit RUNX1 expression or activity.

Preferably, (i) a PIM3 inhibitor binds to a PIM3 protein or a polynucleotide (such as mRNA) that encodes a PIM3 protein; and (ii) a RUNX1 inhibitor binds to a RUNX1 protein or a polynucleotide (such as mRNA) that encodes a RUNX1 protein.

It is surprising that PIM3 inhibition would regulate RUNX1 expression or regulate pathological angiogenesis. It is also surprising that PIM3 is upregulated in PDR. In some embodiments, PIM3 inhibition is used to treat aberrant angiogenesis. In various embodiments, PIM3 inhibition is used as means to inhibit RUNX1 to treat aberrant angiogenesis.

In certain embodiments, PIM3 inhibition is used in combination with RUNX1 inhibition and/or other compounds to treat aberrant angiogenesis. In various embodiments, the level of activity of PIM3 is used as a biomarker for aberrant angiogenesis. In certain embodiments, a disease that impacts the anterior segment of the eye is treated or prevented. In various embodiments, a disease that impacts the posterior segment of the eye is treated or prevented. In some embodiments, PIM3 inhibition reduces oxygen-induced retinopathy. In certain embodiments, PIM3 inhibition reduces corneal neovascularization. Non-limiting examples of diseases involving aberrant angiogenesis that may be treated with PIM3 inhibitors are disclosed herein, and include retinopathy of prematurity, wet-age related macular degeneration, proliferative diabetic retinopathy, retinal vein occlusion, cancer and other conditions.

In some embodiments, a PIM3 inhibitor is used to treat PDR. As noted above, PIM3 expression is increased in vascular endothelial cells from proliferative diabetic retinopathy fibrovascular membranes. PDR, a condition characterized by aberrant angiogenesis in the eye, is a common cause of blindness in working adults in the United States. In severe cases, the angiogenic sprouts develop into fibrovascular membranes (FVM), which may contract, triggering tractional retinal detachment and blindness.

Anti-VEGF therapy is infrequently used in PDR because it may trigger hemorrhage and retinal detachment by precipitating the angio-fibrotic switch. Additionally, anti-VEGF therapy often requires intravitreal injection. Non-VEGF-related pathways in PDR that could be targeted with drugs are needed. As disclosed herein, RUNX1 and PIM3 inhibition and or IGFBP3 activation is useful for treating PDR that has important advantages compared to anti-VEGF therapy. For example, in some embodiments the RUNX1 or PIM3 inhibitor is a small molecule inhibitor. In certain embodiments, the inhibitor is administered by a method other than intravitreal injection. For example, in some embodiments the IGFBP3 activator is a small molecular activator. In certain embodiments, the activator is administered by a method other than intravitreal injection.

In some embodiments, IGFBP3, PIM3, and/or RUNX1 is expressed in a blood cell. In certain embodiments, the level of IGFBP3, PIM3, and/or RUNX1 expression is measured in a blood cell. In various embodiments, the level of IGFBP3, PIM3, and/or RUNX1 expression is measured in a cell from an affected tissue. In some embodiments, the affected tissue is a fibrovascular membrane. In certain embodiments, cells are obtained from specific ocular fluids (e.g. vitreous fluid), and the level of IGFBP3, PIM3, and/or RUNX1 mRNA and/or protein is measured in the cells. In various embodiments, the level of PIM3 and/or RUNX1 expression (e.g., as measured by the level of mRNA and/or protein) will be higher compared to a control (such as the level in a corresponding fluid, tissue, or cell from a healthy subject) by at least about 10%, 20%, 30%, 40%, 50%, 60%, 70%, 80%, 90%, or 100%. In some embodiments, the level of IGFBP3 is assessed in a bodily fluid such as blood, plasma, or serum. In certain embodiments, the level of IGFBP3 expression (e.g., as measured by the level of mRNA and/or protein) will be lower compared to a control (such as the level in a corresponding fluid, tissue, or cell from a healthy subject) by at least about 10%, 20%, 30%, 40%, 50%, 60%, 70%, 80%, 90%, or 100%.

Aberrant Angiogenesis

Aberrant angiogenesis is observed in numerous diseases, such as proliferative diabetic retinopathy, ROP, DR, AMD, retinal vein occlusions, ocular ischemic syndrome, neovascular glaucoma, retinal hemangiomas, and cancer (especially in solid tumors). It is also observed in genetic diseases such as Coats disease, Norrie's Disease, FEVR and Von Hippel Lindau. Aberrant angiogenesis includes any angiogenesis that is not a normal (nonpathological) part of an organism's development, growth, or healing. Ocular neovascularization includes retinal neovascularization as well as neovascularization in the anterior segment of the eye.

In some instances, aberrant angiogenesis may manifest itself as anterior ocular neovascularization, e.g., aberrant angiogenesis that occurs as a part of corneal graft rejection. Corneal angiogenesis is involved in corneal graft rejection. Thus, inhibition of RUNX expression or activity, (e.g., anti-RUNX1 treatment) is also useful to prevent or reduce corneal graft rejection.

Diabetic Retinopathy

Diabetic retinopathy is a condition that occurs in people who have diabetes. It causes progressive damage to the retina, which is the light-sensitive lining at the back of the eye. Diabetic retinopathy is a serious sight-threatening complication of diabetes. See, e.g., American Optometric Association, Diabetic Retinopathy, available from www.aoa.org/patients-and-public/eye-and-vision-problems/glossary-of-eye-and-vision-conditions/diabetic-retinopathy?sso=y, the entire contents of which are incorporated herein by reference.

Diabetes interferes with the body's ability to use and store sugar (glucose). The disease is characterized by too much sugar in the blood, which can cause damage throughout the body, including the eyes. Over time, diabetes damages the blood vessels in the retina. Diabetic retinopathy occurs when these tiny blood vessels leak blood and other fluids. This causes the retinal tissue to swell, resulting in cloudy or blurred vision. The condition usually affects both eyes. The longer a person has diabetes, the more likely they will develop diabetic retinopathy. If left untreated, diabetic retinopathy can cause blindness.

Symptoms of diabetic retinopathy include (i) seeing spots or floaters; (ii) blurred vision; (iii) having a dark or empty spot in the center of vision; and (iv) difficulty seeing well at night.

Often the early stages of diabetic retinopathy have no visual symptoms. Early detection and treatment can limit the potential for significant vision loss from diabetic retinopathy. In some embodiments, a subject with diabetes or early stage diabetic retinopathy is administered a RUNX1 inhibitor to halt, prevent, inhibit, or treat the progression of diabetic retinopathy. In certain embodiments, visual symptoms are delayed or prevented.

PDR is a more advanced form of the disease. At this stage, new fragile blood vessels can begin to grow in the retina and into the vitreous (the gel-like fluid that fills the back of the eye). The new blood vessels may leak blood into the vitreous, clouding vision.

Without wishing to be bound by any scientific theory, diabetic retinopathy results from the damage diabetes causes to the small blood vessels located in the retina. These damaged blood vessels can cause vision loss. For example, fluid can leak into the macula, the area of the retina responsible for clear central vision. Although small, the macula is the part of the retina that allows us to see colors and fine detail. The fluid causes the macula to swell, resulting in blurred vision. In an attempt to improve blood circulation in the retina, new blood vessels may form on its surface. These fragile, abnormal blood vessels can leak blood into the back of the eye and block vision.

Diabetic retinopathy is classified into two types:
(1) Non-proliferative diabetic retinopathy (NPDR) is the early stage of the disease in which symptoms will be mild or nonexistent. In NPDR, the blood vessels in the retina are weakened. Tiny bulges in the blood vessels, called microaneurysms, may leak fluid into the retina. This leakage may lead to swelling of the macula.
(2) PDR is the more advanced form of the disease. At this stage, circulation problems deprive the retina of oxygen. As a result new, fragile blood vessels can begin to grow in the retina and into the vitreous, the gel-like fluid that fills the back of the eye. The new blood vessels may leak blood into the vitreous, clouding vision.

Both NPDR and PDR may also result in macular edema. Embodiments of the present subject matter relate to the reduction of macular edema in subjects with diabetic retinopathy.

Other complications of PDR include detachment of the retina due to scar tissue formation and the development of neovascular glaucoma. Glaucoma is an eye disease in which there is progressive damage to the optic nerve. In PDR, new blood vessels grow into the area of the eye that drains fluid from the eye. This greatly raises the eye pressure, which damages the optic nerve. If left untreated, PDR can cause severe vision loss and even blindness.

In some embodiments, a subject who is at risk of developing diabetic retinopathy is administered a RUNX1 inhibitor to delay, prevent, or ameliorate the onset of the disease (e.g., NPDR and/or PDR and/or macular edema). Risk factors for diabetic retinopathy include:
(i) Diabetes. People with type 1 or type 2 diabetes are at risk for developing diabetic retinopathy. The longer a person has diabetes, the more likely he or she is to develop diabetic retinopathy, particularly if the diabetes is poorly controlled.
(ii) Race. Hispanics and African Americans are at greater risk for developing diabetic retinopathy.
(iii) Medical conditions. People with other medical conditions, such as high blood pressure and high cholesterol, are at greater risk.
(iv) Pregnancy. Pregnant women face a higher risk for developing diabetes and diabetic retinopathy. If a woman develops gestational diabetes, she has a higher risk of developing diabetes as she ages.

Non-limiting examples of methods for diagnosing diabetic retinopathy include dilated eye examination, visual acuity tests, slit-lamp examination, fluorescein angiography, optical coherence tomography (OCT), and ultrasound. See, e.g., Kierstan Boyd (2013) "Diabetic Retinopathy Diagnosis" American Academy of Ophthamology (available at www.aao.org/eye-health/diseases/diabetic-retinopathy-diagnosis); and Mayo Clinic (2015) "Diabetic retinopathy, Tests and diagnosis" (available at www.mayoclinic.org/diseases-conditions/diabetic-retinopathy/basics/tests-diagnosis/con-20023311) the entire content of each of which is hereby incorporated by reference.

Any symptom, type, or stage of diabetic retinopathy may be inhibited, treated, or prevented using methods and compositions disclosed herein.

Retinopathy of Prematurity

Retinopathy of prematurity (ROP) is a potentially blinding eye disorder that primarily affects premature infants weighing about 23/4 pounds (1250 grams) or less that are born before 31 weeks of gestation (a full-term pregnancy has a gestation of 38-42 weeks). The smaller a baby is at birth, the more likely that baby is to develop ROP. This disorder, which usually develops in both eyes, is one of the most common causes of visual loss in childhood and can lead to lifelong vision impairment and blindness. See, e.g., National Eye Institute, Facts About Retinopathy of Prematurity (ROP), available from nei.nih.gov/health/rop/rop, the entire contents of which are incorporated herein by reference.

Today, with advances in neonatal care, smaller and more premature infants are being saved. These infants are at a much higher risk for ROP. Not all babies who are premature develop ROP. There are approximately 3.9 million infants born in the U.S. each year; of those, about 28,000 weigh 23/4 pounds or less. About 14,000-16,000 of these infants are affected by some degree of ROP. The disease improves and leaves no permanent damage in milder cases of ROP.

About 90 percent of all infants with ROP are in the milder category and do not need treatment. However, infants with more severe disease can develop impaired vision or even blindness. About 1,100-1,500 infants annually develop ROP that is severe enough to require medical treatment. About 400-600 infants each year in the US become legally blind from ROP.

ROP is classified in five stages, ranging from mild (stage I) to severe (stage V):

Stage I—Mildly abnormal blood vessel growth. Many children who develop stage I improve with no treatment and eventually develop normal vision. The disease resolves on its own without further progression.

Stage II—Moderately abnormal blood vessel growth. Many children who develop stage II improve with no treatment and eventually develop normal vision. The disease resolves on its own without further progression.

Stage III—Severely abnormal blood vessel growth. The abnormal blood vessels grow toward the center of the eye instead of following their normal growth pattern along the surface of the retina. Some infants who develop stage III improve with no treatment and eventually develop normal vision. However, when infants have a certain degree of Stage III and "plus disease" develops, treatment is considered. "Plus disease" means that the blood vessels of the retina have become enlarged and twisted, indicating a worsening of the disease. Treatment at this point has a good chance of preventing retinal detachment.

Stage IV—Partially detached retina. Traction from the scar produced by bleeding, abnormal vessels pulls the retina away from the wall of the eye.

Stage V—Completely detached retina and the end stage of the disease. If the eye is left alone at this stage, the baby can have severe visual impairment and even blindness.

Most babies who develop ROP have stages I or II. However, in a small number of babies, ROP worsens, sometimes very rapidly. Untreated ROP threatens to destroy vision.

ROP occurs when abnormal blood vessels grow and spread throughout the retina, the tissue that lines the back of the eye. These abnormal blood vessels are fragile and can leak, scarring the retina and pulling it out of position. This causes a retinal detachment. Retinal detachment is the main cause of visual impairment and blindness in ROP.

Without wishing to be bound by any scientific theory, several complex factors may be responsible for the development of ROP. The eye starts to develop at about 16 weeks of pregnancy, when the blood vessels of the retina begin to form at the optic nerve in the back of the eye. The blood vessels grow gradually toward the edges of the developing retina, supplying oxygen and nutrients. During the last 12 weeks of a pregnancy, the eye develops rapidly. When a baby is born full-term, the retinal blood vessel growth is mostly complete (the retina usually finishes growing a few weeks to a month after birth). But if a baby is born prematurely, before these blood vessels have reached the edges of the retina, normal vessel growth may stop. The edges of the retina (the periphery) may not get enough oxygen and nutrients. The periphery of the retina may then send out signals to other areas of the retina for nourishment. As a result, new abnormal vessels begin to grow. These new blood vessels are fragile and weak and can bleed, leading to retinal scarring. When these scars shrink, they pull on the retina, causing it to detach from the back of the eye.

A non-limiting example of a method for diagnosing ROP includes dilated eye examination. See, e.g., American Association for Pediatric Ophthalmology and Strabismus (2016) *Retinopathy of Prematurity* (available at aapos.org/terms/conditions/94), the entire content of which is incorporated herein by reference.

Aspects of the present invention relate to inhibiting, preventing, or treating the onset of or the progression of a ROP in a premature infant. Any symptom or stage of ROP may be inhibited, treated, or prevented using methods and compositions disclosed herein.

Age-Related Macular Degeneration

Age-related macular degeneration (AMD) is an eye disease that is a leading cause of vision loss in older people in developed countries. The vision loss usually becomes noticeable in a person's sixties or seventies and tends to worsen over time. See, e.g., the U.S. National Library of Medicine Genetics Home Reference, Age-Related Macular Degeneration, available at ghr.nlm.nih.gov/condition/age-related-macular-degeneration, the entire contents of which are incorporated herein by reference.

Age-related macular degeneration mainly affects central vision, which is needed for detailed tasks such as reading, driving, and recognizing faces. The vision loss in this condition results from a gradual deterioration of light-sensing cells in the tissue at the back of the eye that detects light and color (the retina). Specifically, age-related macular degeneration affects a small area near the center of the retina, called the macula, which is responsible for central vision. Side (peripheral) vision and night vision are generally not affected.

Researchers have described two major types of age-related macular degeneration, known as the dry form and the wet form. The dry form is much more common, accounting for 85 to 90 percent of all cases of AMD. It is characterized by a buildup of yellowish deposits called drusen beneath the retina and slowly progressive vision loss. The condition typically affects vision in both eyes, although vision loss often occurs in one eye before the other.

The wet form of age-related macular degeneration is associated with severe vision loss that can worsen rapidly. This form of the condition is characterized by the growth of abnormal, fragile blood vessels underneath the macula. These vessels leak blood and fluid, which damages the macula and makes central vision appear blurry and distorted.

In some embodiments, a subject who is at risk of developing AMD is administered a RUNX1 inhibitor to delay, prevent, or ameliorate the onset of AMD. AMD results from a combination of genetic and environmental factors. Many of these factors have been identified, but some remain unknown.

Researchers have considered changes in many genes as possible risk factors for AMD. The best-studied of these genes are involved in a part of the body's immune response known as the complement system. This system is a group of proteins that work together to destroy foreign invaders (such as bacteria and viruses), trigger inflammation, and remove debris from cells and tissues. Genetic changes in and around several complement system genes, including the complement factor H (CFH) gene, contribute to a person's risk of developing AMD. It is unclear how these genetic changes are related to the retinal damage and vision loss characteristic of this condition.

Changes on the long (q) arm of chromosome 10 in a region known as 10q26 are also associated with an increased risk of AMD. The 10q26 region contains two genes of interest, age-related maculopathy susceptibility 2 (ARMS2) and HtrA Serine Peptidase 1 (HTRA1). Changes in both genes have been studied as possible risk factors for the disease. However, because the two genes are so close together, it is difficult to tell which gene is associated with AMD risk, or whether increased risk results from variations in both genes. An estimated 15 to 20 percent of people with AMD have at least one first-degree relative (such as a sibling) with the condition.

Other genes that are associated with AMD include genes involved in transporting and processing high-density lipoprotein (HDL) and genes that have been associated with other forms of macular disease.

Nongenetic factors also contribute to the risk of age-related macular degeneration. Age appears to be the most important risk factor; the chance of developing the condition increases significantly as a person gets older. Smoking is another established risk factor for AMD.

Aspects of the present subject matter relate to administering a RUNX1 inhibitor or a PIM3 inhibitor to a subject who is diagnosed with or determined to be at risk of developing AMD. Subjects at risk of developing AMD include subjects with high blood pressure, heart disease, a high-fat diet or a diet that is low in certain nutrients (such as antioxidants and zinc), obesity, repeated and/or prolonged exposure to ultraviolet (UV) rays from sunlight, and/or who smoke or have smoked for at least about 1, 5, 10, or more years, and/or who are at least about 50, 55, 60, 65, 70, 75, 80, 85, or 90 years old. Subjects at risk of developing AMD and/or a symptom or complication thereof also include subjects with at least 1 or 2 grandparents, parents, or siblings who suffer from AMD, and/or the symptom or complication thereof. In various embodiments, a subject who carries a mutation in a CFH, ARMS2, HTRA1 gene, or a gene involved in transporting or processing HDL.

Non-limiting examples of methods for diagnosing AMD include examination of the back of the eye (e.g., with an ophthalmoscope), tests for defects in the center of a subject's vision, fluorescein angiography, indocyanine green angiography, and optical coherence tomography. See, e.g., Mayo Clinic (2015) "Dry Macular Degeneration" (available at www.mayoclinic.org/diseases-conditions/dry-macular-degeneration/diagnosis-treatment/diagnosis/dxc-20165013); Mayo Clinic (2015) "Wet macular degeneration" (available at www.mayoclinic.org/diseases-conditions/wet-macular-degeneration/diagnosis-treatment/diagnosis/dxc-20164284), the entire contents of each of which are incorporated herein by reference.

Any symptom, type, or stage of AMD may be inhibited, treated, or prevented using methods and compositions disclosed herein.

Retinal Vein Occlusion

Retinal vein occlusion (RVO) is a blockage of the small veins that carry blood away from the retina. Retinal vein occlusion is most often caused by hardening of the arteries (atherosclerosis) and the formation of a blood clot. Blockage of smaller veins (branch veins or BRVO) in the retina often occurs in places where retinal arteries that have been thickened or hardened by atherosclerosis cross over and place pressure on a retinal vein. See, e.g., U.S. National Library of Medicine, Retinal vein occlusion, available at www.nlm.nih.gov/medlineplus/ency/article/007330.htm, the entire contents of which are incorporated herein by reference.

Risk factors for retinal vein occlusion include: (i) atherosclerosis; (ii) diabetes; (iii) high blood pressure (hypertension; e.g., a systolic pressure of at least 140 mmHg or a diastolic pressure of at least 90 mmHg); and (iv) other eye conditions, such as glaucoma, macular edema, or vitreous hemorrhage. The risk of these disorders increases with age, therefore retinal vein occlusion most often affects older people.

Blockage of retinal veins may cause other eye problems, including: (i) glaucoma (high pressure in the eye), caused by new, abnormal blood vessels growing in the front part of the eye; (ii) neovascularization (RVO can cause the retina to develop new, abnormal blood vessels, a condition called neovascularization. These new vessels may leak blood or fluid into the vitreous, the jelly-like substance that fills the inside of the eye. Small spots or clouds, called floaters, may appear in the field of vision. With severe neovascularization, the retina may detach from the back of the eye.); (iii) macular edema, caused by the leakage of fluid in the retina; and (iv) neovascular glaucoma (New blood vessels in certain parts of the eye can cause pain and a dangerous increase in pressure inside the eye.).

Non-limiting examples of methods for diagnosing RVO include optical coherence tomography, ophthalmoscopy, and fluorescein angiography. See, e.g., Cleveland Clinic (2015) "Retinal Vein Occlusion" (available at my.clevelandclinic.org/services/cole-eye/diseases-conditions/hic-retinal-vein-occlusion), the entire content of which is incorporated herein by reference.

Any symptom, type, or stage of retinal vein occlusion may be inhibited, treated, or prevented using methods and compositions disclosed herein.

Ocular Ischemic Syndrome

Ocular ischemic syndrome (OIS) encompasses the ocular signs and symptoms that result from chronic vascular insufficiency. Common anterior segment findings include advanced cataract, anterior segment inflammation, and iris neovascularization. Posterior segment signs include narrowed retinal arteries, dilated but nontortuous retinal veins, midperipheral dot-and-blot retinal hemorrhages, cotton-wool spots, and optic nerve/retinal neovascularization. The presenting symptoms include ocular pain and abrupt or gradual visual loss. See, e.g., Medscape, Ocular Ischemic Syndrome, available at emedicine.medscape.com/article/1201678-overview#a6.

Without wishing to be bound by any scientific theory, the most common etiology of OIS is severe unilateral or bilateral atherosclerotic disease of the internal carotid artery or marked stenosis at the bifurcation of the common carotid artery. OIS may also be caused by giant cell arteritis. The decreased vascular perfusion results in tissue hypoxia and increased ocular ischemia, leading to neovascularization.

Non-limiting examples of methods for diagnosing OIS include imaging studies of the carotid arteries (such as fluorescein angiography) and ultrasound. See, e.g., Terelak-Borys et al., Med Sci Monit. 2012; 18(8): RA138-RA144, the entire content of which is incorporated herein by reference.

Any symptom, type, or stage of ocular ischemic syndrome may be inhibited, treated, or prevented using methods and compositions disclosed herein.

Neovascular Glaucoma Neovascular glaucoma (NVG) is classified as a secondary glaucoma. First documented in 1871, historically, it has been referred to as hemorrhagic glaucoma, thrombotic glaucoma, congestive glaucoma, rubeotic glaucoma, and diabetic hemorrhagic glaucoma. Numerous secondary ocular and systemic diseases that share one common element, retinal ischemia/hypoxia and subsequent release of an angiogenesis factor, cause NVG. This angiogenesis factor causes new blood vessel growth from preexisting vascular structure. Depending on the progression of NVG, it can cause glaucoma either through secondary open-angle or secondary closed-angle mechanisms. This is accomplished through the growth of a fibrovascular membrane over the trabecular meshwork in the anterior chamber angle, resulting in obstruction of the meshwork and/or associated peripheral anterior synechiae. See, e.g., Medscape, Neovascular Glaucoma, available at emedicine.medscape.com/article/1205736-overview#a6, the entire contents of which are hereby incorporated herein by reference.

NVG is a potentially devastating glaucoma, where delayed diagnosis or poor management can result in complete loss of vision or, quite possibly, loss of the globe itself. Early diagnosis of the disease, followed by immediate and aggressive treatment, is imperative. In managing NVG, it is essential to treat both the elevated intraocular pressure (TOP) and the underlying cause of the disease.

Retinal ischemia is the most common and important mechanism in most, if not all, cases that result in the anterior segment changes causing NVG. Various predisposing conditions cause retinal hypoxia and, consequently, production of an angiogenesis factor.

Without wishing to be bound by any scientific theory, several angiogenesis factors have been identified as potential agents causing ocular neovascularization. Recent studies suggest that VEGF might play a central role in angiogenesis. Once released, the angiogenic factor(s) diffuses into the aqueous and the anterior segment and interacts with vascular structures in areas where the greatest aqueous-tissue contact occurs. The resultant growth of new vessels at the pupillary border and iris surface [neovascularization of the iris (NVI)] and over the iris angle [neovascularization of the angle (NVA)] ultimately leads to formation of fibrovascular membranes. The fibrovascular membranes, which may be invisible on gonioscopy, accompany NVA and progressively obstruct the trabecular meshwork. This causes secondary open-angle glaucoma.

As the disease process continues, the fibrovascular membranes along the NVA tend to mature and contract, thereby tenting the iris toward the trabecular meshwork and resulting in peripheral anterior synechiae and progressive synechial angle closure. Elevated TOP is a direct result of this secondary angle-closure glaucoma.

Non-limiting methods for diagnosing neovascular glaucoma may include, e.g., examination of the iris and aqueous humor outflow and measuring intraocular pressure. See, e.g., Shazly and Latina, (2009) "Neovascular Glaucoma: Etiology, Diagnosis and Prognosis" Seminars in Ophthalmology, Volume 24, Issue 2, pages 113-121, the entire content of which is incorporated herein by reference.

Any symptom, type, or stage of neovascular glaucoma may be inhibited, treated, or prevented using methods and compositions disclosed herein.

Retinal Hemangiomas

Retinal hemangiomas, also known as retinal capillary hemangiomas (RCHs) and retinal hemangioblastomas, occur most frequently in conjunction with von Hippel-Lindau (VHL) syndrome. These lesions are characterized by plump, but otherwise normal, retinal capillary endothelial cells with normal pericytes and basement membrane. Astrocytes with lipid vacuoles are found in the tumor interstitia. Isolated RCH outside of VHL do occur, although they are more likely to be single, unilateral, and present later. See, e.g., American Academy of Ophthamology, Retinal Capillary Angioma, available at www.aao.org/munnerlyn-laser-surgery-center/retinal-capillary-angioma, the entire content of which is incorporated herein by reference.

Von Hippel-Lindau syndrome has an autosomal dominant inheritance pattern, with an incidence of 1 in 36,000 live births. These lesions can occur either singly, or more often, multiply and bilaterally, with a greater than 80% predilection for peripheral location. Vision loss can occur from exudation, strabismus, hemorrhage, and retinal detachment, as well secondary causes such as macular edema, lipid maculopathy, and epiretinal membrane. Early lesions often present as indistinct areas of redness in the retina, which appear to be retinal hemorrhages. Patients may be relatively asymptomatic until the lesions achieve larger size, and it is imperative to perform life-long surveillance of even asymptomatic individuals with VHL because smaller lesions are more easily eradicated than larger lesions. In VHL patients, RCH is diagnosed at a mean of 25 years.

In VHL syndrome, the stromal cells have a mutation on chromosome 3p25-26, which leads to dysfunctional VHL protein. These cells cannot degrade hypoxia-inducible factor 1a (HIF-1a), so this factor accumulates and causes production of VEGF, platelet-derived growth factor (PDGF), erythropoietin, and transforming growth factor-alpha, all of which lead to proliferation and vascularization of the tumor. There are three types of mutation in the VHL gene: type 1, with deletion or nonsense mutation and manifesting mainly hemangioblastomas only; type 2, with missense mutation at risk for hemangioblastomas and pheochromocytomas (type 2A), additional renal cell carcinoma (type 2B), or only pheochromocytoma (type 2C); and type 3, with risk for polycythemia.

Non-limiting examples of methods or diagnosing retinal hemangiomas include ophthalmoscopic examination. See, e.g., Turell and Singh (2010) "Vascular Tumors of the Retina and Choroid: Diagnosis and Treatment" Middle East Afr J Ophthalmol. 17(3): 191-200, the entire content of which is incorporated herein by reference.

Any symptom, type, or stage of retinal hemangioma may be inhibited, treated, or prevented using methods and compositions disclosed herein. In some embodiments, a subject at risk of developing a retinal hemangioma, such as a subject with VHL, is treated to delay or prevent the onset of a retinal hemangioma.

Hemangiomas

A hemangioma is an abnormal buildup of blood vessels in the skin or internal tissue/organs. Symptoms of a hemangioma include a red to reddish-purple, raised sore (lesion) on the skin; a massive, raised, tumor with blood vessels; bleeding; problems with breathing or eating; psychological distress from skin appearance; secondary infections and sores; visible changes in the skin; and vision problems. Hemangiomas can grow, e.g., in/on the skin, the liver, the lungs, the colon, or the brain. However, many hemangiomas are on the face and neck.

In some instances, a hemangioma may be associated with a pathologic processes, such as the consumptive coagulopathy of Kasabach-Merritt syndrome and tumor-induced osteomalacia. Gorham disease is a process of massive osteolysis, which is believed to be within the spectrum of hemangiomatous disease. Hemangiomas occurring in the setting of multiple enchondromatosis are part of the spectrum of Maffucci syndrome.

Cavernous hemangiomas that involve the eyelid and block vision can be treated with lasers or steroid injections to shrink them. This allows vision to develop normally. Large cavernous hemangiomas or mixed hemangiomas may be treated with steroids, taken by mouth or injected into the hemangioma. Taking beta-blocker medicines may also help reduce the size of a hemangioma.

Any symptom, type, or stage of hemangioma may be inhibited, treated, or prevented using methods and compositions disclosed herein. In some embodiments, a subject at risk of developing a hemangioma is treated to delay or prevent the onset of the hemangioma.

Cerebral Cavernous Malformations

Cerebral cavernous malformations (CCMs) are vascular lesions comprising clusters of tightly packed, abnormally thin-walled small blood vessels (capillaries) that displace normal neurological tissue in the brain or spinal cord. The vessels are often filled with slow-moving or stagnant blood that is usually clotted or in a state of decomposition. Cavernous malformations can occur in the brain, spinal cord, and other body regions. In the brain and spinal cord these cavernous lesions are quite fragile and are prone to bleeding, causing hemorrhagic strokes (bleeding into the brain), seizures, and neurological deficits. CCMs can range in size from a few fractions of an inch to several inches in diameter, depending on the number of blood vessels involved. Some people develop multiple lesions while others never experience related medical problems. Hereditary forms of CCM are caused by mutations in one of three CCM disease genes: cerebral cavernous malformation protein 1 (CCM1), cerebral cavernous malformation protein 2 (CCM2), and cerebral cavernous malformation protein 3 (CCM3). A large population with hereditary CCM disease is found in New Mexico and the Southwestern United States, in which the disease is caused by mutations in the gene CCM1.

Any symptom, type, or stage of a CCM may be inhibited, treated, or prevented using methods and compositions disclosed herein. In some embodiments, a subject at risk of developing a CCM is treated to delay or prevent the onset of the CCM.

Tumor Angiogenesis

As tumors grow in size, they require blood vessels to provide oxygen and nutrients to cancer cells, as well as to clear waste from the tumor. Disrupting the growth of vessels may reduce the growth and size of a tumor.

Cancer cells are cells that have lost their ability to divide in a controlled fashion. A malignant tumor consists of a population of rapidly dividing and growing cancer cells that progressively accrues mutations. However, tumors need a blood supply to provide the oxygen and other essential nutrients they require in order to grow beyond a certain size (generally 1-2 $mm^3$).

Without wishing to be bound by any scientific theory, tumors may induce blood vessel growth (angiogenesis) by secreting various growth factors (e.g. VEGF). Growth factors such as basic fibroblast growth factor (bFGF) and VEGF can induce capillary growth into the tumor, which may supply required nutrients, allowing for tumor expansion. Unlike normal blood vessels, tumor blood vessels are dilated with an irregular shape. Angiogenesis may also serve as a waste pathway, taking away the biological end products secreted by rapidly dividing cancer cells. In either case, angiogenesis is a necessary and required step for transition from a small harmless cluster of cells, often said to be about the size of the metal ball at the end of a ball-point pen, to a large tumor. Angiogenesis is also required for the spread of a tumor, or metastasis. Single cancer cells can break away from an established solid tumor, enter a blood vessel, and be carried to a distant site, where they can implant and begin the growth of a secondary tumor. Evidence now suggests the blood vessel in a given solid tumor may, in fact, be mosaic vessels, composed of endothelial cells and tumor cells. This mosaicity allows for substantial shedding of tumor cells into the vasculature, possibly contributing to the appearance of circulating tumor cells in the peripheral blood of patients with malignancies. The subsequent growth of such metastases will also require a supply of nutrients and oxygen and a waste disposal pathway.

Aspects of the present subject matter relate to the use of RUNX1 inhibitors to inhibit, treat, or prevent angiogenesis by cancer cells and tumors, and/or to inhibit, treat, or prevent tumor metastasis. RUNX1 inhibition may also lead to vessel stabilization, which can improve access of the chemotherapeutic agents to tumor.

Coats' Disease

Coats' disease, (also known as exudative retinitis or retinal telangiectasis, sometimes spelled Coates' disease), is a rare congenital, nonhereditary eye disorder, causing full or partial blindness, characterized by abnormal development of blood vessels behind the retina. Coats' usually affects only one eye (unilateral) and occurs predominantly in young males $1/100,000$, with the onset of symptoms generally appearing in the first decade of life. Peak age of onset is between 6-8 years of age, but onset can range from 5 months to 71 years.

Coats' disease results in a gradual loss of vision. Blood leaks from the abnormal vessels into the back of the eye, leaving behind cholesterol deposits and damaging the retina. Coats' disease normally progresses slowly. At advanced stages, retinal detachment is likely to occur. Glaucoma, atrophy, and cataracts can also develop secondary to Coats' disease. In some cases, removal of the eye may be necessary (enucleation).

The most common sign at presentation is leukocoria (abnormal white reflection of the retina). Symptoms typically begin as blurred vision, usually pronounced when one eye is closed (due to the unilateral nature of the disease). Often the unaffected eye will compensate for the loss of vision in the other eye; however, this results in some loss of depth perception and parallax. Deterioration of sight may begin in either the central or peripheral vision. Deterioration is likely to begin in the upper part of the vision field as this corresponds with the bottom of the eye where blood usually pools. Flashes of light, known as photopsia, and floaters are common symptoms. Persistent color patterns may also be perceived in the affected eye. Initially, these may be mistaken for psychological hallucinations, but are actually the result of both retinal detachment and foreign fluids mechanically interacting with the photoreceptors located on the retina.

One early warning sign of Coats' disease is yellow-eye in flash photography. Just as the red-eye effect is caused by a reflection of blood vessels in the back of a normal eye, an eye affected by Coats' will glow yellow in photographs as light reflects off cholesterol deposits. Children with yellow-eye in photographs are typically advised to immediately seek evaluation from an optometrist or ophthalmologist, who will assess and diagnose the condition and refer to a vitreo-retinal specialist.

Coats' disease itself is painless. Pain may occur if fluid is unable to drain from the eye properly, causing the internal pressure to swell, resulting in painful glaucoma.

Coats' disease is thought to result from breakdown of the blood-retinal barrier in the endothelial cell, resulting in leakage of blood products containing cholesterol crystals and lipid-laden macrophages into the retina and subretinal space. Over time, the accumulation of this proteinaceous exudate thickens the retina, leading to massive, exudative retinal detachment.

On funduscopic eye examination, the retinal vessels in early Coats' disease appear tortuous and dilated, mainly confined to the peripheral and temporal portions of retina. In moderate to severe Coats' disease, massive retinal detachment and hemorrhage from the abnormal vessels may be seen.

Imaging studies such as ultrasonography (US), Computerized Tomography (CT) and Magnetic Resonance Imaging (MRI) can aid diagnosis. On ultrasound, Coats' disease appears as a hyperechoic mass in the posterior vitreous without posterior acoustic shadowing; vitreous and subretinal hemorrhage may often be observed. On CT, the globe appears hyperdense compared to normal vitreous due to the proteinaceous exudate, which may obliterate the vitreous space in advanced disease. The anterior margin of the subretinal exudate enhances with contrast. Since the retina is fixed posteriorly at the optic disc, this enhancement has a V-shaped configuration. On MRI, the subretinal exudate shows high signal intensity on both T1- and T2-weighted images. The exudate may appear heterogeneous if hemorrhage or fibrosis is present. The subretinal space does not enhance with gadolinium contrast. Mild to moderate linear enhancement may be seen between the exudate and the remaining vitreous. The exudate shows a large peak at 1-1.6 ppm on proton MR spectroscopy.

Any symptom, type, or stage of Coats' disease may be inhibited, treated, or prevented using methods and compositions disclosed herein. In some embodiments, a subject at risk of developing Coats' disease is treated to delay or prevent the onset of Coats' disease.

Norrie Disease

Norrie disease is an inherited eye disorder that leads to blindness in male infants at birth or soon after birth. It causes abnormal development of the retina, the layer of sensory cells that detect light and color, with masses of immature retinal cells accumulating at the back of the eye. As a result, the pupils appear white when light is shone on them, a sign called leukocoria. The irises (colored portions of the eyes) or the entire eyeballs may shrink and deteriorate during the first months of life, and cataracts (cloudiness in the lens of the eye) may eventually develop.

About one third of individuals with Norrie disease develop progressive hearing loss, and more than half experience developmental delays in motor skills such as sitting up and walking. Other problems may include mild to moderate intellectual disability, often with psychosis, and abnormalities that can affect circulation, breathing, digestion, excretion, or reproduction.

Mutations in the norrin cystine knot growth factor (NDP) gene cause Norrie disease. The NDP gene provides instructions for making a protein called norrin. Norrin participates in the Wnt cascade, a sequence of steps that affect the way cells and tissues develop. In particular, norrin seems to play a critical role in the specialization of retinal cells for their unique sensory capabilities. It is also involved in the establishment of a blood supply to tissues of the retina and the inner ear, and the development of other body systems. In order to initiate the Wnt cascade, norrin must bind (attach) to another protein called frizzled-4. Mutations in the norrin protein interfere with its ability to bind to frizzled-4, resulting in the signs and symptoms of Norrie disease. This condition is inherited in an X-linked recessive pattern. A condition is considered X-linked if the mutated gene that causes the disorder is located on the X chromosome, one of the two sex chromosomes. In males (who have only one X chromosome), one altered copy of the gene in each cell is sufficient to cause the condition. In females (who have two X chromosomes), a mutation must be present in both copies of the gene to cause the disorder. Males are affected by X-linked recessive disorders much more frequently than females. A characteristic of X-linked inheritance is that fathers cannot pass X-linked traits to their sons. In X-linked recessive inheritance, a female with one altered copy of the gene in each cell is called a carrier. She can pass on the gene, but generally does not experience signs and symptoms of the disorder. In rare cases, however, carrier females have shown some retinal abnormalities or mild hearing loss associated with Norrie disease.

Norrie disease is diagnosed if an individual has the symptoms suggesting this disorder (primarily congenital blindness). Most often the Norrie gene mutation can be identified by DNA analysis in the affected individual. Mutations in the Norrie gene are often unique to a family and have been described throughout the extent of the Norrie gene. About 15-20% of mutations are a gene deletion involving at least some part of the Norrie gene and sometimes extending out beyond the Norrie gene to affect other adjacent genes.

Clinical genetic lab testing is available to help make the diagnosis, assess genetic risk in family members and for prenatal testing. Although Norrie disease itself does not seem to shorten lifespan, individuals with blindness, deafness and/or mental disability may have a reduced lifespan as a result of these conditions. Norrie disease affects each individual differently, even within the same family, as there is a spectrum of symptoms and severity.

Patients who have not completely lost their vision may be treated with surgery or laser therapy in infancy. Hearing loss can be treated with hearing aids and cochlear implants. Behavioral abnormalities and mental disability can be treated through counseling, medications, and care by special education professionals. Men with Norrie disease may need varying degrees of assistance from family, friends and caretakers, but lead full and rewarding lives.

Any symptom, type, or stage of Norrie disease may be inhibited, treated, or prevented using methods and compositions disclosed herein.

Von Hippel-Lindau Disease

Von Hippel-Lindau disease is an inherited disorder characterized by the formation of tumors and fluid-filled sacs (cysts) in many different parts of the body. Tumors may be either noncancerous or cancerous and most frequently appear during young adulthood; however, the signs and symptoms of von Hippel-Lindau disease can occur throughout life.

Tumors called hemangioblastomas are characteristic of von Hippel-Lindau disease. These growths are made of newly formed blood vessels. Although they are typically noncancerous, they can cause serious or life-threatening complications. Hemangioblastomas that develop in the brain and spinal cord can cause headaches, vomiting, weakness, and a loss of muscle coordination (ataxia). Hemangioblastomas can also occur in the light-sensitive tissue that lines the back of the eye (the retina). These tumors, which are also called retinal angiomas, may cause vision loss.

People with von Hippel-Lindau disease commonly develop cysts in the kidneys, pancreas, and genital tract. They are also at an increased risk of developing a type of kidney cancer called clear cell renal cell carcinoma and a type of pancreatic cancer called a pancreatic neuroendocrine tumor.

Von Hippel-Lindau disease is associated with a type of tumor called a pheochromocytoma, which most commonly occurs in the adrenal glands (small hormone-producing glands located on top of each kidney). Pheochromocytomas are usually noncancerous. They may cause no symptoms, but in some cases they are associated with headaches, panic attacks, excess sweating, or dangerously high blood pressure that may not respond to medication. Pheochromocytomas are particularly dangerous if they develop during pregnancy.

About 10 percent of people with von Hippel-Lindau disease develop endolymphatic sac tumors, which are non-cancerous tumors in the inner ear. These growths can cause hearing loss in one or both ears, as well as ringing in the ears (tinnitus) and problems with balance. Without treatment, these tumors can cause sudden profound deafness.

Mutations in the von Hippel-Lindau tumor suppressor (VHL) gene cause von Hippel-Lindau disease. The VHL gene is a tumor suppressor gene, which means it keeps cells from growing and dividing too rapidly or in an uncontrolled way. Mutations in this gene prevent production of the VHL protein or lead to the production of an abnormal version of the protein. An altered or missing VHL protein cannot effectively regulate cell survival and division. As a result, cells grow and divide uncontrollably to form the tumors and cysts that are characteristic of von Hippel-Lindau disease.

Mutations in the VHL gene are inherited in an autosomal dominant pattern, which means that one copy of the altered gene in each cell is sufficient to increase the risk of developing tumors and cysts. Most people with von Hippel-Lindau disease inherit an altered copy of the gene from an affected parent. In about 20 percent of cases, however, the altered gene is the result of a new mutation that occurred during the formation of reproductive cells (eggs or sperm) or very early in development.

Unlike most autosomal dominant conditions, in which one altered copy of a gene in each cell is sufficient to cause the disorder, two copies of the VHL gene must be altered to trigger tumor and cyst formation in von Hippel-Lindau disease. A mutation in the second copy of the VHL gene occurs during a person's lifetime in certain cells within organs such as the brain, retina, and kidneys. Cells with two altered copies of this gene make no functional VHL protein, which allows tumors and cysts to develop. Almost everyone who inherits one VHL mutation will eventually acquire a mutation in the second copy of the gene in some cells, leading to the features of von Hippel-Lindau disease.

The detection of tumors specific to VHL disease is important in the disease's diagnosis. In individuals with a family history of VHL disease, one hemangioblastoma, pheochromocytoma or renal cell carcinoma may be sufficient to make a diagnosis. As all the tumors associated with VHL disease can be found sporadically, at least two tumors must be identified to diagnose VHL disease in a person without a family history.

Genetic diagnosis is also useful in VHL disease diagnosis. In hereditary VHL, disease techniques such as southern blotting and gene sequencing can be used to analyze DNA and identify mutations. These tests can be used to screen family members of those afflicted with VHL disease; de novo cases that produce genetic mosaicism are more difficult to detect because mutations are not found in the white blood cells that are used for genetic analysis. Any symptom, type, or stage of Von Hippel-Lindau disease may be inhibited, treated, or prevented using methods and compositions disclosed herein. In some embodiments, a subject at risk of developing Von Hippel-Lindau disease is treated to delay or prevent the onset of Von Hippel-Lindau disease.

Familial Exudative Vitreoretinopathy

Familial exudative vitreoretinopathy (FEVR) is a rare hereditary ocular disorder characterized by a failure of peripheral retinal vascularization which may be abnormal or incomplete. FEVR is a condition with fundus changes similar to those in retinopathy of prematurity, but appearing in children who had been born full-term with normal birth-weight. With respect to genetics, about 50% of cases can be linked to 4 causative genes (NDP, LRP5, FZD4, and TSPAN12), all of which form part of the Wnt signaling pathway, which is vital for normal retinal vascular development.

Any symptom, type, or stage of FEVR may be inhibited, treated, or prevented using methods and compositions disclosed herein. In some embodiments, a subject at risk of developing FEVR is treated to delay or prevent the onset or progression of FEVR. In some embodiments, a subject at risk of developing FEVR is treated to delay or prevent the onset or progression of aberrant angiogenesis due to FEVR.

Runt-Related Transcription Factor 1

Runt-related transcription factor 1 (RUNX1), also known as acute myeloid leukemia 1 protein (AML1) or core-binding factor subunit alpha-2 (CBFA2), is a protein that in humans is encoded by the RUNX1 gene.

RUNX1 is a transcription factor that regulates the differentiation of hematopoietic stem cells into mature blood cells. RUNX1 also plays a role in the development of the neurons that transmit pain. It belongs to the Runt-related transcription factor (RUNX) family of genes which are also called core binding factor-α (CBFα).

RUNX1 may form part of a complex called Core Binding Factor (CBF), corresponding to a group of heterodimeric transcription factors. Core Binding Factors are comprised of (i) a non DNA-binding CBFβ chain (encoded by the CBFB gene); and (ii) a DNA-binding CBFα chain (such as RUNX1, RUNX2, or RUNX3). CBFB is a gene. RUNX1 is another gene. RUNX2 is another gene. RUNX3 is another gene. Due to alternative splicing RUNX1 has many true isoforms. CBFB and RUNX1 proteins can form a complex in which the CBFB protein is the beta subunit and RUNX1 is the alpha subunit. RUNX proteins form a heterodimeric complex with core binding factor β (CBFβ) which confers increased deoxyribonucleic acid (DNA) binding and stability to the complex.

In humans, the RUNX1 gene is 260 kilobases (kb) in length, and is located on chromosome 21 (21q22.12). The gene can be transcribed from 2 alternative promoters, promoter 1 (distal) or promoter 2 (proximal). As a result, various isoforms of RUNX1 can be synthesized, facilitated by alternative splicing. The full-length RUNX1 protein is encoded by 12 exons. Among the exons are two defined domains, namely the runt homology domain (RHD) or the runt domain (exons 2, 3 and 4), and the transactivation domain (TAD) (exon 6). These domains are necessary for RUNX1 to mediate DNA binding and protein-protein interactions respectively. The transcription of RUNX1 is regulated by 2 enhancers (regulatory element 1 and regulatory element 2), and these tissue specific enhancers enable the binding of lymphoid or erythroid regulatory proteins, therefore the gene activity of RUNX1 is highly active in the hematopoietic system.

An exemplary isoform of RUNX1 (Q01196-1) has 453 amino acids. As a transcription factor (TF), its DNA binding ability is encoded by the runt domain (residues 50-177), which is homologous to the p53 family. Without wishing to be bound by any scientific theory, the runt domain of RUNX1 is believed to bind to the core consensus sequence TGTGGNNN (where NNN can represent either TTT or TCA). DNA recognition is achieved by loops of the 12-stranded β-barrel and the C-terminus "tail" (residues 170-177), which clamp around the sugar phosphate backbone and fits into the major and minor grooves of DNA. Specificity is achieved by making direct or water-mediated contacts with the bases. RUNX1 can bind DNA as a monomer, but its DNA binding affinity is enhanced by 10 fold if it heterodimerizes with the CBFβ, also via the runt domain.

The RUNX family is often referred to as α-subunits, together with binding of a common β-subunit CBFβ, RUNX can behave as heterodimeric transcription factors collectively called the core binding factors (CBFs).

An amino acid sequence for human RUNX1b is publically available in the UniProt database under accession number Q01196-1 (SEQ ID NO: 1) and is as follows:

MRIPVDASTSRRFTPPSTALSPGKMSEALPLGAPDAGAALAGKLRSGDRS

MVEVLADHPGELVRTDSPNFLCSVLPTHWRCNKTLPIAFKVVALGDVPDG

TLVTVMAGNDENYSAELRNATAAMKNQVARFNDLRFVGRSGRGKSFTLTI

TVFTNPPQVATYHRAIKITVDGPREPRRHRQKLDDQTKPGSLSFSERLSE

LEQLRRTAMRVSPHHPAPTPNPRASLNHSTAFNPQPQSQMQDTRQIQPSP

PWSYDQSYQYLGSIASPSVHPATPISPGRASGMTTLSAELSSRLSTAPDL

TAFSDPRQFPALPSISDPRMHYPGAFTYSPTPVTSGIGIGMSAMGSATRY

HTYLPPPYPGSSQAQGGPFQASSPSYHLYYGASAGSYQFSMVGGERSPPR

ILPPCTNASTGSALLNPSLPNQSDVVEAEGSHSNSPTNMAPSARLEEAVW

RPY

Positions 80 through 84, 135 through 143, and 168 through 177 of SEQ ID NO: 1 have been predicted to relate to interactions with DNA. Positions 291 through 371 have been predicted to relate to interaction with Lysine Acetyltransferase 6A (KAT6A). Positions 307 through 400 have been predicted to relate to interaction with Lysine Acetyltransferase 6B (KAT6B). Positions 362 through 402 have been predicted to relate to interaction with Forkhead Box P3 (FOXP3).

Amino acid sequences of additional isoforms are publically available in the UniProt database under accession numbers Q01196-2 (SEQ ID NO: 2); Q01196-3 (SEQ ID NO: 3); Q01196-4 (SEQ ID NO: 4); Q01196-5 (SEQ ID NO: 5); Q01196-6 (SEQ ID NO: 6); Q01196-7 (SEQ ID NO: 7); Q01196-8 (SEQ ID NO: 8); Q01196-9 (SEQ ID NO: 9); Q01196-10 (SEQ ID NO: 10); and Q01196-11 (SEQ ID NO: 11).

A nucleotide sequence that encodes human RUNX1 is publically available in the GenBank database under accession number NM_001001890.2 (SEQ ID NO: 12) and is as follows (start and stop codon are bolded and underlined):

CATAGAGCCAGCGGGCGCGGGCGGGACGGGCGCCCCGCGGCCGGACCCAG

CCAGGGCACCACGCTGCCCGGCCCTGCGCCGCCAGGCACTTCTTTCCGGG

GCTCCTAGGGACGCCAGAAGGAAGTCAACCTCTGCTGCTTCTCCTTGGCC

TGCGTTGGACCTTCCTTTTTTTGTTGTTTTTTTTGTTTTTCCCCTTTCT

TCCTTTTGAATTAACTGGCTTCTTGGCTGGATGTTTTCAACTTCTTTCCT

GGCTGCGAACTTTTCCCCAATTGTTTTCCTTTTACAACAGGGGGAGAAAG

TGCTCTGTGGTCCGAGGCGAGCCGTGAAGTTGCGTGTGCGTGGCAGTGTG

CGTGGCAGGATGTGCGTGCGTGTGTAACCCGAGCCGCCCGATCTGTTTCG

ATCTGCGCCGCGGAGCCCTCCCTCAAGGCCCGCTCCACCTGCTGCGGTTA

CGCGGCGCTCGTGGGTGTTCGTGCCTCGGAGCAGCTAACCGGCGGGTGCT

GGGCGACGGTGGAGGAGTATCGTCTCGCTGCTGCCCGAGTCAGGGCTGAG

TCACCCAGCTGATGTAGACAGTGGCTGCCTTCCGAAGAGTGCGTGTTTGC

ATGTGTGTGACTCTGCGGCTGCTCAACTCCCAACAAACCAGAGGACCAGC

CACAAACTTAACCAACATCCCCAAACCCGAGTTCACAGATGTGGGAGAGC

TGTAGAACCCTGAGTGTCATCGACTGGGCCTTCTTATGATTGTTGTTTTA

AGATTAGCTGAAGATCTCTGAAACGCTGAATTTTCTGCACTGAGCGTTTT

GACAGAATTCATTGAGAGAACAGAGAACATGACAAGTACTTCTAGCTCAG

CACTGCTCCAACTACTGAAGCTGATTTTCAAGGCTACTTAAAAAAATCTG

CAGCGTACATTAATGGATTTCTGTTGTGTTTAAATTCTCCACAGATTGTA

TTGTAAATATTTTATGAAGTAGAGCATATGTATATATTTATATATACGTG

CACATACATTAGTAGCACTACCTTTGGAAGTCTCAGCTCTTGCTTTTCGG

GACTGAAGCCAGTTTTGCATGATAAAAGTGGCCTTGTTACGGGAGATAAT

TGTGTTCTGTTGGGACTTTAGACAAAACTCACCTGCAAAAAACTGACAGG

CATTAACTACTGGAACTTCCAAATAATGTGTTTGCTGATCGTTTTACTCT

TCGCATAAATATTTTAGGAAGTGTATGAGAATTTTGCCTTCAGGAACTTT

TCTAACAGCCAAAGACAGAACTTAACCTCTGCAAGCAAGATTCGTGGAAG

ATAGTCTCCACTTTTTAATGCACTAAGCAATCGGTTGCTAGGAGCCCATC

CTGGGTCAGAGGCCGATCCGCAGAACCAGAACGTTTTCCCCTCCTGGACT

GTTAGTAACTTAGTCTCCCTCCTCCCCTAACCACCCCGCCCCCCCCAC

CCCCCGCAGTAATAAAGGCCCCTGAACGTGTATGTTGGTCTCCCGGGAGC

TGCTTGCTGAAGATCCGCGCCCTGTCGCCGTCTGGTAGGAGCTGTTTGC

AGGGTCCTAACTCAATCGGCTTGTTGTGATGCGTATCCCCGTAGATGCCA

GCACGAGCCGCCGCTTCACGCCGCCTTCCACCGCGCTGAGCCCAGGCAAG

ATGAGCGAGGCGTTGCCGCTGGGCGCCCCGGACGCCGGCGCTGCCCTGGC

CGGCAAGCTGAGGAGCGGCGACCGCAGCATGGTGGAGGTGCTGGCCGACC

ACCCGGGCGAGCTGGTGCGCACCGACAGCCCCAACTTCCTCTGCTCCGTG

CTGCCTACGCACTGGCGCTGCAACAAGACCCTGCCCATCGCTTTCAAGGT

GGTGGCCCTAGGGGATGTTCCAGATGGCACTCTGGTCACTGTGATGGCTG

GCAATGATGAAAACTACTCGGCTGAGCTGAGAAATGCTACCGCAGCCATG

AAGAACCAGGTTGCAAGATTTAATGACCTCAGGTTTGTCGGTCGAAGTGG

AAGAGGGAAAAGCTTCACTCTGACCATCACTGTCTTCACAAACCCACCGC

AAGTCGCCACCTACCACAGAGCCATCAAAATCACAGTGGATGGGCCCCGA

GAACCTCGAAGACATCGGCAGAAACTAGATGATCAGACCAAGCCCGGGAG

CTTGTCCTTTTCCGAGCGGCTCAGTGAACTGGAGCAGCTGCGGCGCACAG

CCATGAGGGTCAGCCCACACCACCCAGCCCCACGCCCAACCCTCGTGCC

TCCCTGAACCACTCCACTGCCTTTAACCCTCAGCCTCAGAGTCAGATGCA

GGATACAAGGCAGATCCAACCATCCCCACCGTGGTCCTACGATCAGTCCT

ACCAATACCTGGGATCCATTGCCTCTCCTTCTGTGCACCCAGCAACGCCC

ATTTCACCTGGACGTGCCAGCGGCATGACAACCCTCTCTGCAGAACTTTC

CAGTCGACTCTCAACGGCACCCGACCTGACAGCGTTCAGCGACCCGCGCC

AGTTCCCCGCGCTGCCCTCCATCTCCGACCCCCGCATGCACTATCCAGGC

GCCTTCACCTACTCCCCGACGCCGGTCACCTCGGGCATCGGCATCGGCAT

GTCGGCCATGGGCTCGGCCACGCGCTACCACACCTACCTGCCGCCGCCCT

ACCCCGGCTCGTCGCAAGCGCAGGGAGGCCCGTTCCAAGCCAGCTCGCCC

TCCTACCACCTGTACTACGGCGCCTCGGCCGGCTCCTACCAGTTCTCCAT

GGTGGGCGGCGAGCGCTCGCCGCCGCGCATCCTGCCGCCCTGCACCAACG

CCTCCACCGGCTCCGCGCTGCTCAACCCCAGCCTCCCGAACCAGAGCGAC

GTGGTGGAGGCCGAGGGCAGCCACAGCAACTCCCCCACCAACATGGCGCC

CTCCGCGCGCCTGGAGGAGGCCGTGTGGAGGCCCTACTGAGGCGCCAGGC

CTGGCCCGGCTGGGCCCCGCGGGCCGCCGCCTTCGCCTCCGGGCGCGCGG

GCCTCCTGTTCGCGACAAGCCCGCCGGGATCCCGGGCCCTGGGCCCGGCC

ACCGTCCTGGGGCCGAGGGCGCCCGACGGCCAGGATCTCGCTGTAGGTCA

GGCCCGCGCAGCCTCCTGCGCCCAGAAGCCCACGCCGCCGCCGTCTGCTG

GCGCCCCGGCCCTCGCGGAGGTGTCCGAGGCGACGCACCTCGAGGGTGTC

CGCCGGCCCCAGCACCCAGGGGACGCGCTGGAAAGCAAACAGGAAGATTC

CCGGAGGGAAACTGTGAATGCTTCTGATTTAGCAATGCTGTGAATAAAAA

GAAAGATTTTATACCCTTGACTTAACTTTTTAACCAAGTTGTTTATTCCA

AAGAGTGTGGAATTTTGGTTGGGGTGGGGGGAGAGGAGGGATGCAACTCG

CCCTGTTTGGCATCTAATTCTTATTTTTAATTTTTCCGCACCTTATCAAT

TGCAAAATGCGTATTTGCATTTGGGTGGTTTTATTTTTATATACGTTTA

TATAAATATATATAAATTGAGCTTGCTTCTTTCTTGCTTTGACCATGGAA

AGAAATATGATTCCCTTTTCTTTAAGTTTTATTTAACTTTTCTTTTGGAC

TTTTGGGTAGTTGTTTTTTTTGTTTTGTTTTGTTTTTTGAGAAACAGC

TACAGCTTTGGGTCATTTTTAACTACTGTATTCCCACAAGGAATCCCCAG

ATATTTATGTATCTTGATGTTCAGACATTTATGTGTTGATAATTTTTAA

TTATTTAAATGTACTTATATTAAGAAAAATATCAAGTACTACATTTTCTT

TTGTTCTTGATAGTAGCCAAAGTTAAATGTATCACATTGAAGAAGGCTAG

AAAAAAAGAATGAGTAATGTGATCGCTTGGTTATCCAGAAGTATTGTTTA

CATTAAACTCCCTTTCATGTTAATCAAACAAGTGAGTAGCTCACGCAGCA

ACGTTTTTAATAGGATTTTTAGACACTGAGGGTCACTCCAAGGATCAGAA

GTATGGAATTTTCTGCCAGGCTCAACAAGGGTCTCATATCTAACTTCCTC

CTTAAAACAGAGAAGGTCAATCTAGTTCCAGAGGGTTGAGGCAGGTGCCA

ATAATTACATCTTTGGAGAGGATTTGATTTCTGCCCAGGGATTTGCTCAC

CCCAAGGTCATCTGATAATTTCACAGATGCTGTGTAACAGAACACAGCCA

AAGTAAACTGTGTAGGGAGCCACATTTACATAGGAACCAAATCAATGAA

TTTAGGGGTTACGATTATAGCAATTTAAGGGCCCACCAGAAGCAGGCCTC

GAGGAGTCAATTTGCCTCTGTGTGCCTCAGTGGGACAAGTGGGAAAACA

TGGTCCCACCTGTGCGAGACCCCTGTCCTGTGCTGCTCACTCAACAACA

TCTTTGTGTTGCTTTCACCAGGCTGAGACCCTACCCTATGGGGTATATGG

GCTTTTACCTGTGCACCAGTGTGACAGGAAAGATTCATGTCACTACTGTC

CGTGGCTACAATTCAAAGGTATCCAATGTCGCTGTAAATTTTATGGCACT

ATTTTTATTGGAGGATTTGGTCAGAATGCAGTTGTTGTACAACTCATAAA

TACTAACTGCTGATTTTGACACATGTGTGCTCCAAATGATCTGGTGGTTA

TTTAACGTACCTCTTAAAATTCGTTGAAACGATTTCAGGTCAACTCTGAA

GAGTATTTGAAAGCAGGACTTCAGAACAGTGTTTGATTTTTATTTTATAA

ATTTAAGCATTCAAATTAGGCAAATCTTTGGCTGCAGGCAGCAAAAACAG

CTGGACTTATTTAAAACAACTTGTTTTTGAGTTTTCTTATATATATATTG

ATTATTTGTTTTACACACATGCAGTAGCACTTTGGTAAGAGTTAAAGAGT

AAAGCAGCTTATGTTGTCAGGTCGTTCTTATCTAGAGAAGAGCTATAGCA

GATCTCGGACAAACTCAGAATATATTCACTTTCATTTTTGACAGGATTCC

CTCCACAACTCAGTTTCATATATTATTCCGTATTACATTTTTGCAGCTAA

ATTACCATAAAATGTCAGCAAATGTAAAAATTTAATTTCTGAAAAGCACC

ATTAGCCCATTTCCCCCAAATTAAACGTAAATGTTTTTTTTCAGCACATG

TTACCATGTCTGACCTGCAAAAATGCTGGAGAAAAATGAAGGAAAAATT

ATGTTTTTCAGTTTAATTCTGTTAACTGAAGATATTCCAACTCAAAACCA

GCCTCATGCTCTGATTAGATAATCTTTTACATTGAACCTTTACTCTCAAA

GCCATGTGTGGAGGGGCTTGTCACTATTGTAGGCTCACTGGATTGGTCA

TTTAGAGTTTCACAGACTCTTACCAGCATATATAGTATTTAATTGTTTCA

AAAAAAATCAAACTGTAGTTGTTTTGGCGATAGGTCTCACGCAACACATT

TTTGTATGTGTGTGTGTGCGTGTGTGTGTGTGTGTGAAAAATTGCA

TTCATTGACTTCAGGTAGATTAAGGTATCTTTTTATTCATTGCCCTCAGG

AAAGTTAAGGTATCAATGAGACCCTTAAGCCAATCATGTAATAACTGCAT

GTGTCTGGTCCAGGAGAAGTATTGAATAAGCCATTTCTACTGCTTACTCA

TGTCCCTATTTATGATTTCAACATGGATACATATTTCAGTTCTTTCTTTT

TCTCACTATCTGAAAATACATTTCCCTCCCTCTCTTCCCCCCAATATCTC

CCTTTTTTTCTCTCTTCCTCTATCTTCCAAACCCCACTTTCTCCCTCCTC

CTTTTCCTGTGTTCTCTTAAGCAGATAGCACATACCCCCACCCAGTACCA

AATTTCAGAACACAAGAAGGTCCAGTTCTTCCCCCTTCACATAAAGGAAC

ATGGTTTGTCAGCCTTTCTCCTGTTTATGGGTTTCTTCCAGCAGAACAGA

GACATTGCCAACCATATTGGATCTGCTTGCTGTCCAAACCAGCAAACTTT

CCTGGGCAAATCACAATCAGTGAGTAAATAGACAGCCTTTCTGCTGCCTT

GGGTTTCTGTGCAGATAAACAGAAATGCTCTGATTAGAAAGGAAATGAAT

GGTTCCACTCAAATGTCCTGCAATTTAGGATTGCAGATTTCTGCCTTGAA

ATACCTGTTTCTTTGGGACATTCCGTCCTGATGATTTTATTTTTGTTGG

TTTTTATTTTTGGGGGGAATGACATGTTTGGGTCTTTTATACATGAAAAT

TTGTTTGACAATAATCTCACAAAACATATTTTACATCTGAACAAAATGCC

TTTTTGTTTACCGTAGCGTATACATTTGTTTTGGGATTTTTGTGTGTTTG

TTGGGAATTTTGTTTTTAGCCAGGTCAGTATTGATGAGGCTGATCATTTG

GCTCTTTTTTTCCTTCCAGAAGAGTTGCATCAACAAAGTTAATTGTATTT

ATGTATGTAAATAGATTTTAAGCTTCATTATAAAATATTGTTAATGCCTA

TAACTTTTTTTCAATTTTTTTGTGTGTGTTTCTAAGGACTTTTTCTTAGG

TTTGCTAAATACTGTAGGGAAAAAAATGCTTCTTTCTACTTTGTTTATTT

TAGACTTTAAAATGAGCTACTTCTTATTCACTTTTGTAAACAGCTAATAG

-continued

```
CATGGTTCCAATTTTTTTTAAGTTCACTTTTTTTGTTCTAGGGGAAATGA

ATGTGCAAAAAAAGAAAAAGAACTGTTGGTTATTTGTGTTATTCTGGATG

TATAAAAATCAATGGAAAAAAATAAACTTTCAAATTGAAATGACGGTATA

ACACATCTACTGAAAAAGCAACGGGAAATGTGGTCCTATTTAAGCCAGCC

CCCACCTAGGGTCTATTTGTGTGGCAGTTATTGGGTTTGGTCACAAAACA

TCCTGAAAATTCGTGCGTGGGCTTCTTTCTCCCTGGTACAAACGTATGGA

ATGCTTCTTAAAGGGGAACTGTCAAGCTGGTGTCTTCAGCCAGATGACAT

GAGAGAATATCCCAGAACCCTCTCTCCAAGGTGTTTCTAGATAGCACAGG

AGAGCAGGCACTGCACTGTCCACAGTCCACGGTACACAGTCGGGTGGGCC

GCCTCCCCTCTCCTGGGAGCATTCGTCGTGCCCAGCCTGAGCAGGGCAGC

TGGACTGCTGCTGTTCAGGAGCCACCAGAGCCTTCCTCTCTTTGTACCAC

AGTTTCTTCTGTAAATCCAGTGTTACAATCAGTGTGAATGGCAAATAAAC

AGTTTGACAAGTACATACACCATA
```

Additional RUNX1-encoding nucleotide sequences are publically available in the GenBank database under accession numbers NM_001754.4 (SEQ ID NO: 13); NM_001122607.1 (SEQ ID NO: 14); XM_005261068.3 (SEQ ID NO: 15); XM_011529770.2 (SEQ ID NO: 16); XR_937576.2 (SEQ ID NO: 17); XM_011529768.2 (SEQ ID NO: 18); XM_005261069.4 (SEQ ID NO: 19); XM_017028487.1 (SEQ ID NO: 20); XM_011529767.2 (SEQ ID NO: 21); and XM_011529766.2 (SEQ ID NO: 22).

In some embodiments, the RUNX1 is RUNX1a. In certain embodiments, the RUNX1 is RUNXb. In various embodiments, the RUNX1 is RUNX1a and RUNX1b. In some embodiments, the level of RUNX1 expression is measured in CD31+ cells, and the RUNX1 is RUNX1b. In certain embodiments, the RUNX1 is any combination of 2, 3, 4, 5, 6, 7, 8, 9, 10, or 11 of RUNX1a, RUNX1b, RUNX1c, RUNX1e, RUNX1fa, RUNX1fb, RUNX1fc, RUNX1g, RUNX1h, RUNX1i, and/or RUNX1l. In some embodiments, the RUNX1 is RUNX1a, RUNX1b, RUNX1c, RUNX1e, RUNX1fa, RUNX1fb, RUNX1fc, RUNX1g, RUNX1h, RUNX1i, and RUNX1l. In various embodiments, the RUNX1 comprises RUNX1a. In some embodiments, the RUNX1 comprises RUNX1b. In certain embodiments, the RUNX1 comprises RUNX1c. In various embodiments, the RUNX1 comprises RUNX1e. In some embodiments, the RUNX1 comprises RUNX1fa. In certain embodiments, the RUNX1 comprises RUNX1fb. In various embodiments, the RUNX1 comprises RUNX1fc. In some embodiments, the RUNX1 comprises RUNX1g. In certain embodiments, the RUNX1 comprises RUNX1h. In various embodiments, the RUNX1 comprises RUNX1i. In come embodiments, the RUNX1 comprises RUNX1l.

An amino acid sequence for human RUNX1a is publically available in the UniProt database under accession number Q01196-2 (SEQ ID NO: 2) and is as follows:

```
MRIPVDASTSRRFTPPSTALSPGKMSEALPLGAPDAGAALAGKLRSGDRS

MVEVLADHPGELVRTDSPNFLCSVLPTHWRCNKTLPIAFKVVALGDVPDG

TLVTVMAGNDENYSAELRNATAAMKNQVARFNDLRFVGRSGRGKSFTLTI

TVFTNPPQVATYHRAIKITVDGPREPRRHRQKLDDQTKPGSLSFSERLSE

LEQLRRTAMRVSPHHPAPTPNPRASLNHSTAFNPQPQSQMQDTRQIQPSP

PWSYDQSYQYLGSIASPSVHPATPISPGRASGMTTLSAELSSRLSTAPDL

TAFSDPRQFPALPSISDPRMHYPGAFTYSPTPVTSGIGIGMSAMGSATRY

HTYLPPPYPGSSQAQGGPFQASSPSYHLYYGASAGSYQFSMVGGERSPPR

ILPPCTNASTGSALLNPSLPNQSDVVEAEGSHSNSPTNMGGASCSRQARR

DPGPWARTPSWGRGRPTDRISL
```

An amino acid sequence for human RUNX1c is publically available in the UniProt database under accession number Q01196-3 (SEQ ID NO: 3) and is as follows:

```
MRIPVDASTSRRFTPPSTALSPGKMSEALPLGAPDAGAALAGKLRSGDRS

MVEVLADHPGELVRTDSPNFLCSVLPTHWRCNKTLPIAFKVVALGDVPDG

TLVTVMAGNDENYSAELRNATAAMKNQVARFNDLRFVGRSGRGKSFTLTI

TVFTNPPQVATYHRAIKITVDGPREPRRHRQKLDDQTKPGSLSFSERLSE

LEQLRRTAMRVSPHHPAPTPNPRASLNHSTAFNPQPQSQMQEEDTAPWRC
```

An amino acid sequence for human RUNX1e is publically available in the UniProt database under accession number Q01196-4 (SEQ ID NO: 4) and is as follows:

```
MRIPVDASTSRRFTPPSTALSPGKMSEALPLGAPDAGAALAGKLRSGDRS

MVEVLADHPGELVRTDSPNFLCSVLPTHWRCNKTLPIAFKVVALGDVPDG

TLVTVMAGNDENYSAELRNATAAMKNQVARFNDLRFVGRSGRGKSFTLTI

TVFTNPPQVATYHRAIKITVDGPREPRRHRQKLDDQTKPGSLSFSERLSE

LEQLRRTAMRVSPHHPAPTPNPRASLNHSTAFNPQPQSQMQDTRQIQPSP

PWSYDQS
```

An amino acid sequence for human RUNX1fa is publically available in the UniProt database under accession number Q01196-5 (SEQ ID NO: 5) and is as follows:

```
MRIPVDASTSRRFTPPSTALSPGKMSEALPLGAPDAGAALAGKLRSGDRS

MVEVLADHPGELVRTDSPNFLCSVLPTHWRCNKTLPIAFKVVALGDVPDG

TLVTVMAGNDENYSAELRNATAAMKNQVARFNDLRFVGRSGRGKSFTLTI

TVFTNPPQVATYHRAIKITVDGPREPRSKCIHLGLVHPPGWYTLQAGILR

DHVSDSLGSTFPPGGWQAPVKPKS
```

An amino acid sequence for human RUNX1fb is publically available in the UniProt database under accession number Q01196-6 (SEQ ID NO: 6) and is as follows:

```
MRIPVDASTSRRFTPPSTALSPGKMSEALPLGAPDAGAALAGKLRSGDRS

MVEVLADHPGELVRTDSPNFLCSVLPTHWRCNKTLPIAFKVVALGDVPDG

TLVTVMAGNDENYSAELRNATAAMKNQVARFNDLRFVGRSGRGKSFTLTI

TVFTNPPQVATYHRAIKITVDGPREPRNSLTWPRYPHI
```

An amino acid sequence for human RUNX1fc is publically available in the UniProt database under accession number Q01196-7 (SEQ ID NO: 7) and is as follows:

MRIPVDASTSRRFTPPSTALSPGKMSEALPLGAPDAGAALAGKLRSGDRS

MVEVLADHPGELVRTDSPNFLCSVLPTHWRCNKTLPIAFKVVALGDVPDG

TLVTVMAGNDENYSAELRNATAAMKNQVARFNDLRFVDGPREPRRHRQKL

DDQTKPGSLSFSERLSELEQLRRTAMRVSPHHPAPTPNPRASLNHSTAFN

PQPQSQMQDTRQIQPSPPWSYDQSYQYLGSIASPSVHPATPI

An amino acid sequence for human RUNX1g is publically available in the UniProt database under accession number O01196-8 (SEQ ID NO: 8) and is as follows:

MASDSIFESFPSYPQCFMRECILGMNPSRDVHDASTSRRFTPPSTALSPG

KMSEALPLGAPDAGAALAGKLRSGDRSMVEVLADHPGELVRTDSPNFLCS

VLPTHWRCNKTLPIAFKVVALGDVPDGTLVTVMAGNDENYSAELRNATAA

MKNQVARFNDLRFVGRSGRGKSFTLTITVFTNPPQVATYHRAIKITVDGP

REPRRHRQKLDDQTKPGSLSFSERLSELEQLRRTAMRVSPHHPAPTPNPR

ASLNHSTAFNPQPQSQMQDTRQIQPSPPWSYDQSYQYLGSIASPSVHPAT

PISPGRASGMTTLSAELSSRLSTAPDLTAFSDPRQFPALPSISDPRMHYP

GAFTYSPTPVTSGIGIGMSAMGSATRYHTYLPPPYPGSSQAQGGPFQASS

PSYHLYYGASAGSYQFSMVGGERSPPRILPPCTNASTGSALLNPSLPNQS

DVVEAEGSHSNSPTNMAPSARLEEAVWRPY

An amino acid sequence for human RUNX1h is publically available in the UniProt database under accession number Q01196-9 (SEQ ID NO: 9) and is as follows:

MNPSRDVHDASTSRRFTPPSTALSPGKMSEALPLGAPDAGAALAGKLRSG

DRSMVEVLADHPGELVRTDSPNFLCSVLPTHWRCNKTLPIAFKVVALGDV

PDGTLVTVMAGNDENYSAELRNATAAMKNQVARFNDLRFVGRSGRGKSFT

LTITVFTNPPQVATYHRAIKITVDGPREPRRHRQKLDDQTKPGSLSFSER

LSELEQLRRTAMRVSPHHPAPTPNPRASLNHSTAFNPQPQSQMQDTRQIQ

PSPPWSYDQSYQYLGSIASPSVHPATPISPGRASGMTTLSAELSSRLSTA

PDLTAFSDPRQFPALPSISDPRMHYPGAFTYSPTPVTSGIGIGMSAMGSA

TRYHTYLPPPYPGSSQAQGGPFQASSPSYHLYYGASAGSYQFSMVGGERS

PPRILPPCTNASTGSALLNPSLPNQSDVVEAEGSHSNSPTNMAPSARLEE

AVWRPY

An amino acid sequence for human RUNX1i is publically available in the UniProt database under accession number Q01196-10 (SEQ ID NO: 10) and is as follows:

MPAAPRGPAQGEAAARTRSRDASTSRRFTPPSTALSPGKMSEALPLGAPD

AGAALAGKLRSGDRSMVEVLADHPGELVRTDSPNFLCSVLPTHWRCNKTL

PIAFKVVALGDVPDGTLVTVMAGNDENYSAELRNATAAMKNQVARFNDLR

FVGRSGRGKSFTLTITVFTNPPQVATYHRAIKITVDGPREPRRHRQKLDD

QTKPGSLSFSERLSELEQLRRTAMRVSPHHPAPTPNPRASLNHSTAFNPQ

PQSQMQDTRQIQPSPPWSYDQSYQYLGSIASPSVHPATPISPGRASGMTT

LSAELSSRLSTAPDLTAFSDPRQFPALPSISDPRMHYPGAFTYSPTPVTS

GIGIGMSAMGSATRYHTYLPPPYPGSSQAQGGPFQASSPSYHLYYGASAG

SYQFSMVGGERSPPRILPPCTNASTGSALLNPSLPNQSDVVEAEGSHSNS

PTNMAPSARLEEAVWRPY

An amino acid sequence for human RUNX1l is publically available in the UniProt database under accession number Q01196-11 (SEQ ID NO: 11) and is as follows:

MAGNDENYSAELRNATAAMKNQVARFNDLRFVGRSGRGKSFTLTITVFTN

PPQVATYHRAIKITVDGPREPRRHRQKLDDQTKPGSLSFSERLSELEQLR

RTAMRVSPHHPAPTPNPRASLNHSTAFNPQPQSQMQDTRQIQPSPPWSYD

QSYQYLGSIASPSVHPATPISPGRASGMTTLSAELSSRLSTAPDLTAFSD

PRQFPALPSISDPRMHYPGAFTYSPTPVTSGIGIGMSAMGSATRYHTYLP

PPYPGSSQAQGGPFQASSPSYHLYYGASAGSYQFSMVGGERSPPRILPPC

TNASTGSALLNPSLPNQSDVVEAEGSHSNSPTNMAPSARLEEAVWRPY

Serine/Threonine-Protein Kinase PIM3

PIM3 (PIM3 Proto-Oncogene, Serine/Threonine Kinase) is a protein that in humans is encoded by the PIM3 gene. The PIM3 gene has been reported to be overexpressed in hematological and epithelial tumors, and has been associated with MYC coexpression. It plays a role in the regulation of signal transduction cascades, contributing to both cell proliferation and survival, and provides a selective advantage in tumorigenesis.

An amino acid sequence for human PIM3 is publically available in the UniProt database under accession number Q86V86 (SEQ ID NO: 23) and is as follows:

MLLSKFGSLAHLCGPGGVDHLPVKILQPAKADKESFEKAYQVGAVLGSGG

FGTVYAGSRIADGLPVAVKHVVKERVTEWGSLGGATVPLEVVLLRKVGAA

GGARGVIRLLDWFERPDGFLLVLERPEPAQDLFDFITERGALDEPLARRF

FAQVLAAVRHCHSCGVVHRDIKDENLLVDLRSGELKLIDFGSGALLKDTV

YTDFDGTRVYSPPEWIRYHRYHGRSATVWSLGVLLYDMVCGDIPFEQDEE

ILRGRLLFRRRVSPECQQLIRWCLSLRPSERPSLDQIAAHPWMLGADGGV

PESCDLRLCTLDPDDVASTTSSSESL

Positions 40 through 293 of SEQ ID NO: 23 have been predicted to be a protein kinase domain.

Additional amino acid sequences for human PIM3 are publically available in the European Nucleotide Archive database under accession numbers BAD42438.1 (SEQ ID NO: 24), BAF84694.1 (SEQ ID NO: 25), and AAI41856.1 (SEQ ID NO: 26).

A nucleotide sequence that encodes human PIM3 is publically available in the GenBank database under accession number NM_001001852 (SEQ ID NO: 27) and is as follows (start and stop codon are bolded and underlined):

GAGAGCGTGAGCGCGGAGAGCGGACCGACGCGACACGCCGTGCGCCTCCG

CGGCTGCGCTACGAAAACGAGTCCCGGAGCGGCCCCGCGCCCGCCGCACC

CGGCCCTCGCCCGCCCGAAGACAGGCGCCAAGCTGCCCCGCCGTCTCCCC

```
AGCTAGCGCCCGGCCGCCGCCGCCTCGCGGGCCCCGGGCGGAAGGGGCG

GGGTCCCGATTCGCCCCGCCCCGCGGAGGGATACGCGGCGCCGCGCCC

AAAACCCCGGGCGAGGCGGCCGGGGCGGGTGAGGCGCTCCGCCTGCTGC

GCGTCTACGCGGTCCCCGCGGGCCTTCCGGGCCCACTGCGCCGCGCGGAC

CGCCTCGGGCTCGGACGGCCGGTGTCCCCGGCGCGCCGCTCGCCCGGATC

GGCCGCGGCTTCGGCGCCTGGGGCTCGGGGCTCCGGGGAGGCCGTCGCCC

GCGATGCTGCTCTCCAAGTTCGGCTCCCTGGCGCACCTCTGCGGGCCCGG

CGGCGTGGACCACCTCCCGGTGAAGATCCTGCAGCCAGCCAAGGCGGACA

AGGAGAGCTTCGAGAAGGCGTACCAGGTGGGCGCCGTGCTGGGTAGCGGC

GGCTTCGGCACGGTCTACGCGGGTAGCCGCATCGCCGACGGGCTCCCGGT

GGCTGTGAAGCACGTGGTGAAGGAGCGGGTGACCGAGTGGGGCAGCCTGG

GCGGCGCGACCGTGCCCCTGGAGGTGGTGCTGCTGCGCAAGGTGGGCGCG

GCGGGCGGCGCGCGCGGCGTCATCCGCCTGCTGGACTGGTTCGAGCGGCC

CGACGGCTTCCTGCTGGTGCTGGAGCGGCCCGAGCCGGCGCAGGACCTCT

TCGACTTTATCACGGAGCGCGGCGCCCTGGACGAGCCGCTGGCGCGCCGC

TTCTTCGCGCAGGTGCTGGCCGCCGTGCGCCACTGCCACAGCTGCGGGGT

CGTGCACCGCGACATTAAGGACGAAAATCTGCTTGTGGACCTGCGCTCCG

GAGAGCTCAAGCTCATCGACTTCGGTTCGGGTGCGCTGCTCAAGGACACG

GTCTACACCGACTTCGACGGCACCCGAGTGTACAGCCCCCGGAGTGGAT

CCGCTACCACCGCTACCACGGGCGCTCGGCCACCGTGTGGTCGCTGGGCG

TGCTTCTCTACGATATGGTGTGTGGGGACATCCCCTTCGAGCAGGACGAG

GAGATCCTCCGAGGCCGCCTGCTCTTCCGGAGGAGGGTCTCTCCAGAGTG

CCAGCAGCTGATCCGGTGGTGCCTGTCCCTGCGGCCCTCAGAGCGGCCGT

CGCTGGATCAGATTGCGGCCCATCCCTGGATGCTGGGGGCTGACGGGGGC

GTCCCGGAGAGCTGTGACCTGCGGCTGTGCACCCTCGACCCTGATGACGT

GGCCAGCACCACGTCCAGCAGCGAGAGCTTGTGAGGAGCTGCACCTGACT

GGGAGCTAGGGGACCACCTGCCTTGGCCAGACCTGGGACGCCCCAGACC

CTGACTTTCTCCTGCGTGGGCCGTCTCCTCCTGCGGAAGCAGTGACCTCT

GACCCCTGGTGACCTTCGCTTTGAGTGCCTTTTGAACGCTGGTCCCGCGG

GACTTGGTTTTCTCAAGCTCTGTCTGTCCAAAGACGCTCCGGTCGAGGTC

CCGCCTGCCCTGGGTGGATACTTGAACCCCAGACGCCCCTCTGTGCTGCT

GTGTCCGGAGGCGGCCTTCCCATCTGCCTGCCCACCCGGAGCTCTTTCCG

CCGGCGCAGGGTCCCAAGCCCACCTCCCGCCCTCAGTCCTGCGGTGTGCG

TCTGGGCACGTCCTGCACACAATGCAAGTCCTGGCCTCCGCGCCCGCC

CGCCCACGCGAGCCGTACCCGCCGCCAACTCTGTTATTTATGGTGTGACC

CCCTGGAGGTGCCCTCGGCCCACCGGGGCTATTTATTGTTTAATTTATTT

GTTGAGGTTATTTCCTCTGAGCAGTCTGCCTCTCCCAAGCCCCAGGGGAC

AGTGGGGAGGCAGGGGAGGGGGTGGCTGTGGTCCAGGGACCCCAGGCCCT

GATTCCTGTGCCTGGCGTCTGTCCCGGCCCCGCCTGTCAGAAGATGAACA

TGTATAGTGGCTAACTTAAGGGGAGTGGGTGACCCTGACACTTCCAGGCA

CTGTGCCCAGGGTTTGGGTTTTAAATTATTGACTTTGTACAGTCTGCTTG
```

```
TGGGCTCTGAAAGCTGGGGTGGGGCCAGAGCCTGAGCGTTTAATTTATTC

AGTACCTGTGTTTGTGTGAATGCGGTGTGTGCAGGCATCGCAGATGGGG

TTCTTTCAGTTCAAAAGTGAGATGTCTGGAGATCATATTTTTTTATACAG

GTATTTCAATTAAAATGTTTTTGTACATAAAAAAAAAAAAAAAAAAAAAA

AAAAAAAAAA
```

Additional PIM3-encoding nucleotide sequences are publically available in the GenBank database under accession number BC141855.1 (SEQ ID NO: 28) as well as in the European Nucleotide Archive under accession numbers AB114795.1 (SEQ ID NO: 29), and AK292005.1 (SEQ ID NO: 30).

Insulin-Like Growth Factor-Binding Protein 3 (IGFBP3)

IGFBP3 is a protein that in humans is encoded by the IGFBP3 gene. IGFBP-3 has been reported to exert antiproliferative effects in many cell types by blocking the ability of IGF-1 and IGF-2 to activate the IGF1R (which stimulates cell proliferation). For example, in esophageal epithelial cells, responsiveness to IGF-1 stimulation is suppressed by secreted IGFBP-3 and restored when IGFBP-3 is downregulated by epidermal growth factor.

An amino acid sequence for human IGFBP3 is publically available in the UniProt database under accession number P17936-1 (SEQ ID NO: 31) and is as follows:

```
MQRARPTLWAAALTLLVLLRGPPVARAGASSAGLGPVVRCEPCDARALAQ

CAPPPAVCAELVREPGCGCCLTCALSEGQPCGIYTERCGSGLRCQPSPDE

ARPLQALLDGRGLCVNASAVSRLRAYLLPAPPAPGNASESEEDRSAGSVE

SPSVSSTHRVSDPKFHPLHSKIIIIKKGHAKDSQRYKVDYESQSTDTQNF

SSESKRETEYGPCRREMEDTLNHLKFLNVLSPRGVHIPNCDKKGFYKKKQ

CRPSKGRKRGFCWCVDKYGQPLPGYTTKGKEDVHCYSMQSK
```

Positions 28 through 134 of SEQ ID NO: 31 have been predicted to be an IGF-binding domain. Positions 210 through 285 of SEQ ID NO: 31 have been predicted to be a thyroglobulin type-1 domain.

Additional amino acid sequences for human IGFBP3 are publically available in the UniProt database under accession number P17936-2 (SEQ ID NO: 32), as well as the NCBI database under accession numbers NP_000589.2 (SEQ ID NO: 33) and NP_001013416.1 (SEQ ID NO: 34).

A nucleotide sequence that encodes human IGFBP3 is publically available in the GenBank database under accession number NM_001013398.1 SEQ ID NO: 35) and is as follows (start and stop codon are bolded and underlined):

```
AGATGCGAGCACTGCGGCTGGGCGCTGAGGATCAGCCGCTTCCTGCCTGG

ATTCCACAGCTTCGCGCCGTGTACTGTCGCCCCATCCCTGCGCGCCCAGC

CTGCCAAGCAGCGTGCCCCGGTTGCAGGCGTCATGCAGCGGGCGCGACCC

ACGCTCTGGGCCGCTGCGCTGACTCTGCTGGTGCTGCTCCGCGGGCCGCC

GGTGGCGCGGGCTGGCGCGAGCTCGGCGGGCTTGGGTCCCGTGGTGCGCT

GCGAGCCGTGCGACGCGCGTGCACTGGCCCAGTGCGCGCCTCCGCCCGCC

GTGTGCGCGGAGCTGGTGCGCGAGCCGGGCTGCGGCTGCTGCCTGACGTG
```

```
CGCACTGAGCGAGGGCCAGCCGTGCGGCATCTACACCGAGCGCTGTGGCT

CCGGCCTTCGCTGCCAGCCGTCGCCCGACGAGGCGCGACCGCTGCAGGCG

CTGCTGGACGGCCGCGGGCTCTGCGTCAACGCTAGTGCCGTCAGCCGCCT

GCGCGCCTACCTGCTGCCAGCGCCGCCAGCTCCAGGTGAGCCGCCCGCGC

CAGGAAATGCTAGTGAGTCGGAGGAAGACCGCAGCGCCGGCAGTGTGGAG

AGCCCGTCCGTCTCCAGCACGCACCGGGTGTCTGATCCCAAGTTCCACCC

CCTCCATTCAAAGATAATCATCATCAAGAAAGGGCATGCTAAAGACAGCC

AGCGCTACAAAGTTGACTACGAGTCTCAGAGCACAGATACCCAGAACTTC

TCCTCCGAGTCCAAGCGGGAGACAGAATATGGTCCCTGCCGTAGAGAAAT

GGAAGACACACTGAATCACCTGAAGTTCCTCAATGTGCTGAGTCCCAGGG

GTGTACACATTCCCAACTGTGACAAGAAGGGATTTTATAAGAAAAAGCAG

TGTCGCCCTTCCAAAGGCAGGAAGCGGGGCTTCTGCTGGTGTGTGGATAA

GTATGGGCAGCCTCTCCCAGGCTACACCACCAAGGGGAAGGAGGACGTGC

ACTGCTACAGCATGCAGAGCAAGTAGACGCCTGCCGCAAGGTTAATGTGG

AGCTCAAATATGCCTTATTTTGCACAAAAGACTGCCAAGGACATGACCAG

CAGCTGGCTACAGCCTCGATTTATATTTCTGTTTGTGGTGAACTGATTTT

TTTTAAACCAAAGTTTAGAAAGAGGTTTTTGAAATGCCTATGGTTTCTTT

GAATGGTAAACTTGAGCATCTTTTCACTTTCCAGTAGTCAGCAAAGAGCA

GTTTGAATTTTCTTGTCGCTTCCTATCAAAATATTCAGAGACTCGAGCAC

AGCACCCAGACTTCATGCGCCCGTGGAATGCTCACCACATGTTGGTCGAA

GCGGCCGACCACTGACTTTGTGACTTAGGCGGCTGTGTTGCCTATGTAGA

GAACACGCTTCACCCCCACTCCCCGTACAGTGCGCACAGGCTTTATCGAG

AATAGGAAAACCTTTAAACCCCGGTCATCCGGACATCCCAACGCATGCTC

CTGGAGCTCACAGCCTTCTGTGGTGTCATTTCTGAAACAAGGGCGTGGAT

CCCTCAACCAAGAAGAATGTTTATGTCTTCAAGTGACCTGTACTGCTTGG

GGACTATTGGAGAAAATAAGGTGGAGTCCTACTTGTTTAAAAAATATGTA

TCTAAGAATGTTCTAGGGCACTCTGGGAACCTATAAAGGCAGGTATTTCG

GGCCCTCCTCTTCAGGAATCTTCCTGAAGACATGGCCCAGTCGAAGGCCC

AGGATGGCTTTTGCTGCGGCCCCGTGGGGTAGGAGGGACAGAGAGACAGG

GAGAGTCAGCCTCCACATTCAGAGGCATCACAAGTAATGGCACAATTCTT

CGGATGACTGCAGAAAATAGTGTTTTGTAGTTCAACAACTCAAGACGAAG

CTTATTTCTGAGGATAAGCTCTTTAAAGGCAAAGCTTTATTTTCATCTCT

CATCTTTTGTCCTCCTTAGCACAATGTAAAAAAGAATAGTAATATCAGAA

CAGGAAGGAGGAATGGCTTGCTGGGGAGCCCATCCAGGACACTGGGAGCA

CATAGAGATTCACCCATGTTTGTTGAACTTAGAGTCATTCTCATGCTTTT

CTTTATAATTCACACATATATGCAGAGAAGATATGTTCTTGTTAACATTG

TATACAACATAGCCCCAAATATAGTAAGATCTATACTAGATAATCCTAGA

TGAAATGTTAGAGATGCTATATGATACAACTGTGGCCATGACTGAGGAAA

GGAGCTCACGCCCAGAGACTGGGCTGCTCTCCCGGAGGCCAAACCCAAGA

AGGTCTGGCAAAGTCAGGCTCAGGGAGACTCTGCCCTGCTGCAGACCTCG

GTGTGGACACACGCTGCATAGAGCTCTCCTTGAAAACAGAGGGGTCTCAA

GACATTCTGCCTACCTATTAGCTTTTCTTTATTTTTTTAACTTTTTGGGG

GGAAAAGTATTTTTGAGAAGTTTGTCTTGCAATGTATTTATAAATAGTAA

ATAAAGTTTTTACCATTAAAAAAATATCTTTCCCTTTGTTATTGACCATC

TCTGGGCTTTGTATCACTAATTATTTTATTTTATTATATAATAATTATTT

TATTATAATAAAATCCTGAAAGGGGAAAATAAAAAAAA
```

An additional IGFBP3-encoding nucleotide sequence is publically available in the GenBank database under accession number NM_000598.4 (SEQ ID NO: 36).

Exemplary Inhibitors

Aspects of the present subject matter relate to the administration of an RUNX1 inhibitor and/or a PIM3 inhibitor. In various embodiments, an inhibitor may be, e.g., an aptamer, an oligonucleotide (e.g., an antisense oligonucleotide, a ribozyme, or an RNA interfering molecule), a peptide, an antibody or a fragment thereof, or a small molecule, that specifically binds to RUNX1 or PIM3 or a polynucleotide that encodes RUNX1 or PIM3.

Small Molecules

In various embodiments, the RUNX1 inhibitor is a small molecule inhibitor. Non-limiting examples include:

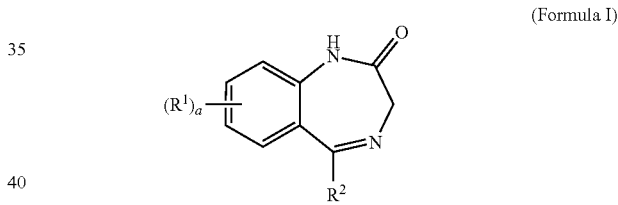

(Formula I)

or pharmaceutically acceptable salts or esters thereof, wherein each $R^1$ is individually selected from halogen, alkyl, aryl, heteroaryl, or alkoxy; $R^2$ is selected from aryl or heteroaryl; and a is 0 to 4;

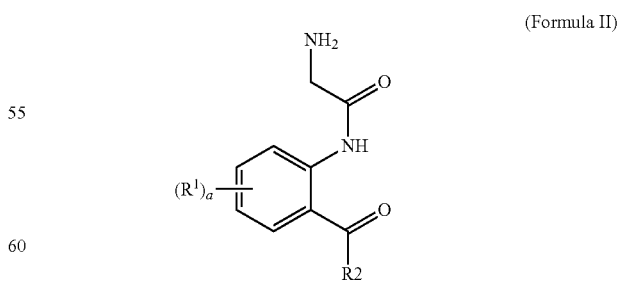

(Formula II)

or a pharmaceutically acceptable salt or ester thereof, wherein each $R^1$ is individually selected from halogen, alkyl, aryl, heteroaryl, or alkoxy; $R^2$ is selected from aryl or heteroaryl; and a is 0 to 4; or

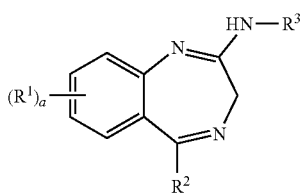

(Formula III)

or a pharmaceutically acceptable salt or ester thereof, wherein each $R^1$ is individually selected from halogen, alkyl, aryl, heteroaryl, or alkoxy; R2 is selected from aryl or heteroaryl; $R^3$ is alkyl or aryl; and a is 0 to 4.

In certain embodiments of formulae I-III, $R^2$ is a heteroaryl, particularly pyrrolyl, and especially pyrrol-2-yl. In certain embodiments of formulae I-III, $R^1$ is a halogen, particularly Cl or F. In certain embodiments of formula III, $R^3$ is a lower alkyl. In certain embodiments of formulae I-III, $R^2$ is a heteroaryl, particularly pyrrolyl, and especially pyrrol-2-yl; and $R^1$ is a halogen, particularly Cl or F. In certain embodiments of formula III, R2 is a heteroaryl, particularly pyrrolyl, and especially pyrrol-2-yl; $R^1$ is a halogen, particularly Cl or F; and $R^3$ is a lower alkyl.

The term "alkoxy" refers to a group of the formula —OR, wherein R is an organic group such as an alkyl group, optionally substituted with an alkenyl, alkynyl, aryl, aralkyl, cycloalkyl, halogenated alkyl, or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Alkyl groups may be substituted alkyls wherein one or more hydrogen atoms are substituted with a substituent such as halogen, cycloalkyl, alkoxy, amino, hydroxyl, aryl, or carboxyl. For example, an "alkoxyalkyl" has the structure —ROR, wherein R is an alkyl group.

The term "aryl" refers to any carbon-based aromatic group including, but not limited to, benzyl, naphthyl, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be optionally substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "heteroaryl" refers to a mono- or poly-cyclic (e.g., bi-, or tri-cyclic or more) fused or non-fused, radical or ring system having at least one aromatic ring, having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "derivative" refers to a compound or portion of a compound that is derived from or is theoretically derivable from a parent compound.

The term "pharmaceutically acceptable salt or ester" refers to salts or esters prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., J. Pharm. Sci. 66:1 (1977). "Pharmaceutically acceptable esters" includes those derived from compounds described herein that are modified to include a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$ alkoxymethyl esters for example methoxy-methyl, $C_{1-6}$ alkanoyloxymethyl esters for example pivaloyloxymethyl, phthalidyl esters, $C_{3-8}$ cycloalkoxycarbonyloxy $C_{1-6}$ alkyl esters for example 1-cyclohexylcarbonyl-oxyethyl; 1,3-dioxolen-2-onylmethyl esters for example 5-methyl-1,3-dioxolen-2-onylmethyl; and $C_{1-6}$ alkoxycarbonyloxyethyl esters for example 1-methoxycarbonyl-oxyethyl which may be formed at any carboxy group in the compounds.

In some embodiments relating to a small molecule inhibitor that binds RUNX1, the small molecule inhibitor comprises Ro5-3335, Ro24-7429, NSC140873, MLS000548294, MLS001048862, or NSC156594. See, e.g., Cunningham et al. (2012) Proc Natl Acad Sci USA, 109(36): 14592-14597 and U.S. Patent Application Publication No. 2014/0004082, the entire contents of each of which are incorporated herein by reference. Additional examples of RUNX1 inhibitors are described in U.S. Pat. Nos. 5,641,773; 5,164,376; 5,141,735; 5,041,438; 5,036, 101; and 3,405,122, as well as U.S. Patent Application Publication No. 2014/0004082, the entire contents of each of which are hereby incorporated herein by reference.

Ro5-3335 has the following structure:

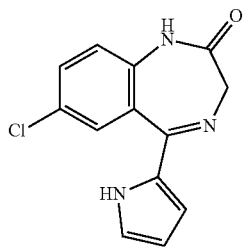 [SMILES: O=C1CN=C(c2ccc[nH]2)c2cc(Cl)ccc2N1]

The CAS Registry Number for Ro5-3335 is 30195-30-3.
Ro24-7429 has the following structure:

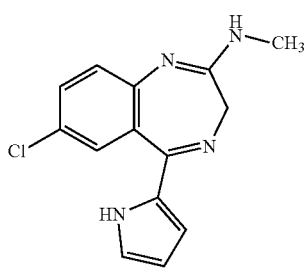 [SMILES: CNC1=Nc2ccc(Cl)cc2C(c2ccc[nH]2)=NC1]

The CAS Registry Number for Ro24-7429 is 139339-45-0. Additional non-limiting descriptions showing that Ro24-7429 was found to be safe in a clinical trial relating to human immunodeficiency virus (HIV) treatment are provided in Haubrich et al. (1995) *J Infect Dis.* 172(5):1246-52, the entire content of which is incorporated herein by reference.

NSC140873 has the following structure:

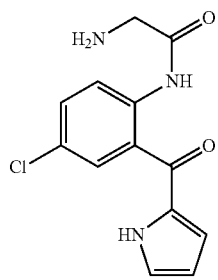 [SMILES: NCC(=O)Nc1ccc(Cl)cc1C(=O)c1ccc[nH]1]

The CAS Registry Number for NSC140873 is 106410-13-3.

MLS000548294 has the following structure:

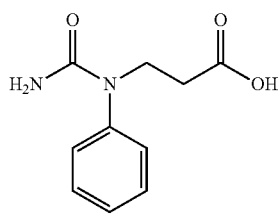 [SMILES: NC(=O)N(CCC(=O)O)c1ccccc1]

The PubChem ID for MLS000548294 is 768985.

MLS001048862 has the following structure:

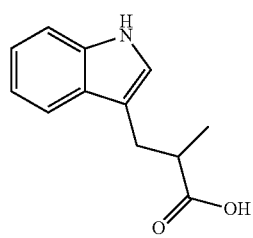

The PubChem ID for MLS001048862 is 2772042.

NSC156594 has the following structure:

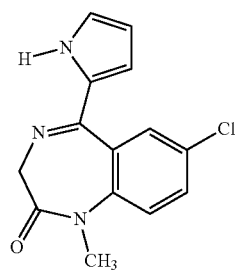 [SMILES: CN1C(=O)CN=C(c2ccc[nH]2)c2cc(Cl)ccc21]

The PubChem ID for NSC156594 is 457993.

The synthesis of several of the compounds disclosed above and analogs thereof have been previously described, for example, in U.S. Pat. Nos. 5,641,773; 5,164,376; 5,141,735; 5,041,438; 5,036,101; and 3,405,122, the entire contents of each of which are incorporated herein by reference.

In some embodiments, the RUNX1 inhibitor inhibits RUNX1 via inhibition of CBFβ, which is the transcriptional partner of RUNX1. In certain embodiments, the CBFβ inhibitor is a pyridyl benzimidazole.

Non-limiting examples of CBFβ inhibitors include:

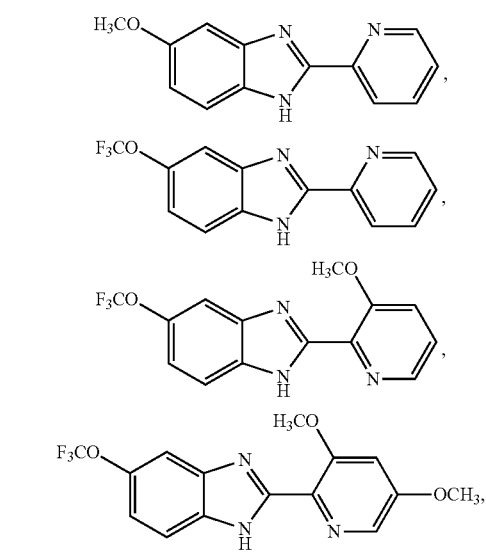

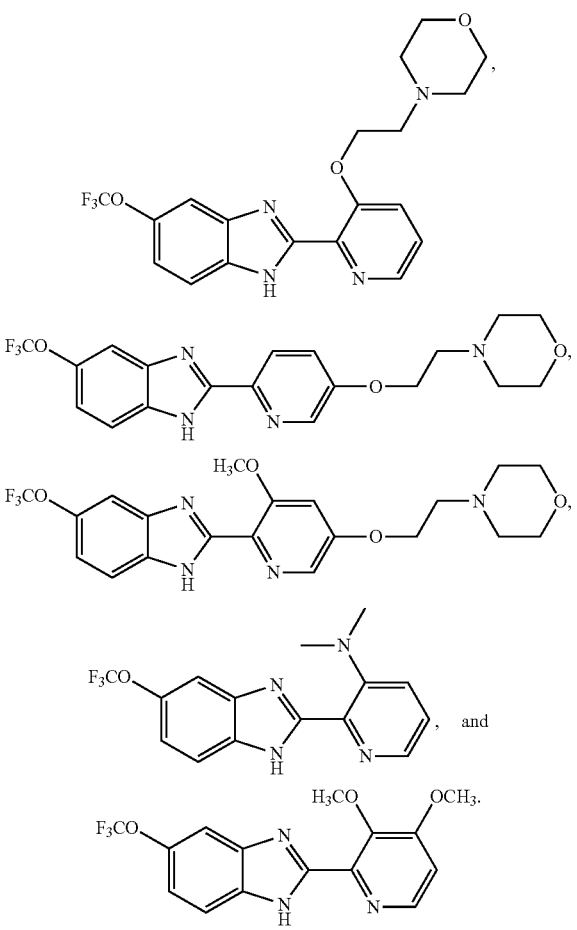

Non-limiting descriptions of CBFβ inhibitors and aspects thereof are described in Illendula et al. (2016) *EBioMedicine* 8: 117-131, the entire content of which is incorporated herein by reference. In some embodiments, the CBFβ inhibitor is

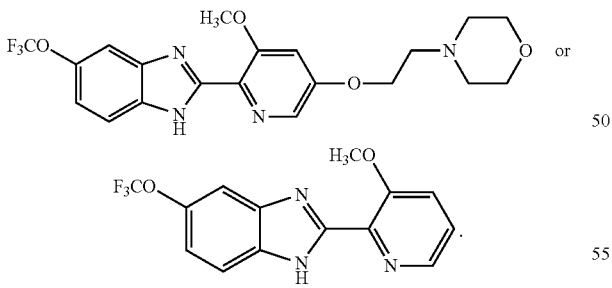

In various embodiments, the RUNX1 inhibitor is a gamma-secretase inhibitor or modulator. In some embodiments, the gamma-secretase inhibitor reduces the expression of RUNX1. In certain embodiments, the gamma-secretase inhibitor is Compound E. The molecular formula for Compound E is $C_{27}H_{24}F_2N_4O_3$. Compound E has the following structure and is commercially available from Cayman Chemical (Ann Arbor, Mich., USA; Item No. 15579; CAS No. 209986-17-4):

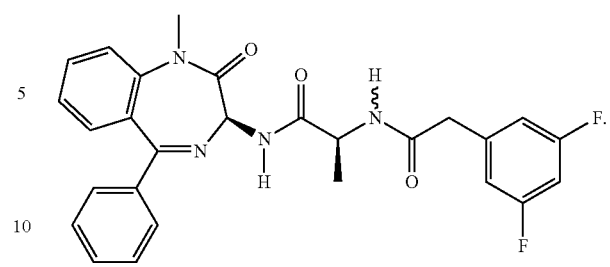

Additional non-limiting examples of gamma-secretase inhibitors include PF-3084014, MK-0752, RO4929079, Semagacestat, BMS-906024, DAPT, and LY411575. Details regarding these inhibitors are described in Ran et al. (2017) *EMBO Molecular Medicine*, 9: 950-966, the entire content of which is incorporated herein by reference. The structures of these inhibitors are as follows:

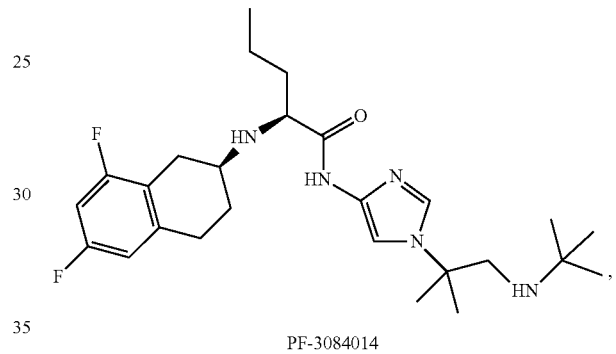

PF-3084014

MK-0752

RO4929079

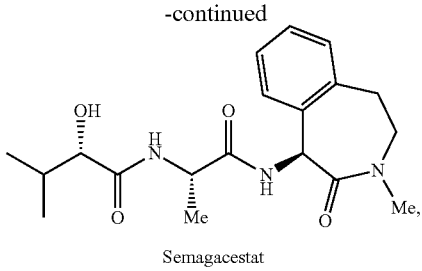

Semagacestat

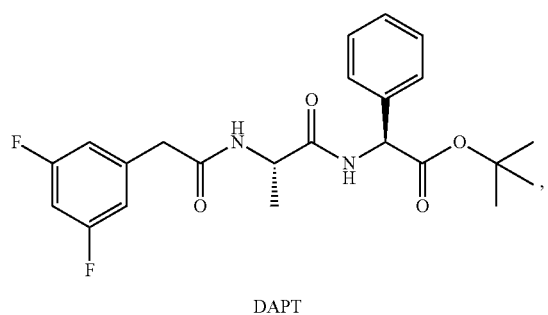

DAPT

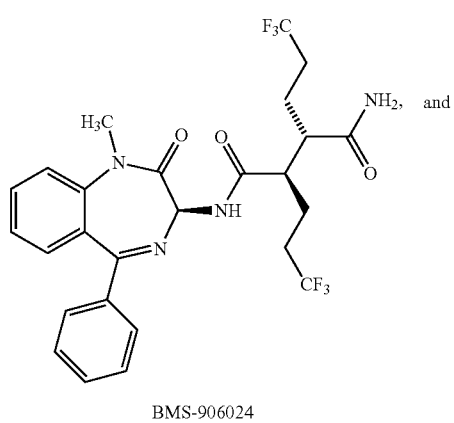

BMS-906024

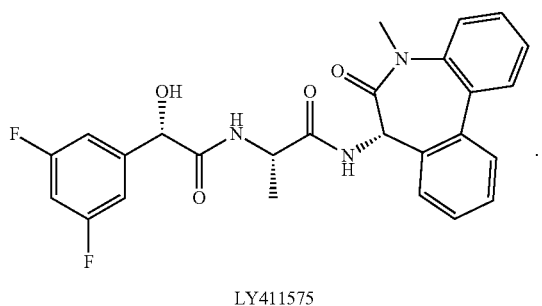

LY411575

In various embodiments, the PIM3 inhibitor is a small molecule inhibitor. Non-limiting examples of small molecule PIM3 inhibitors include AZD1208, CX-6258, SGI-1776, and M-110.

AZD1208 has the following structure:

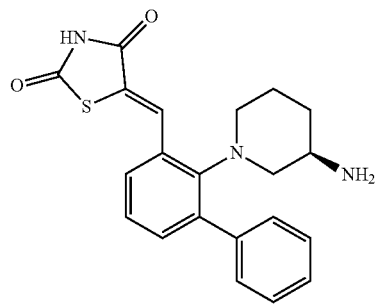 [SMILES: N[C@@H]1CCCN(c2c(/C=C3\SC(=O)NC3=O)cccc2-c2ccccc2)C1]

The CAS Registry Number for AZD1208 is 1204144-28-4. The molecular formula for AZD1208 is $C_{21}H_{21}N_3O_2S$. AZD1208 is commercially available from several sources, including Selleck Chemicals (Houston, Tex., USA).

CX-6258 HCl has the following structure:

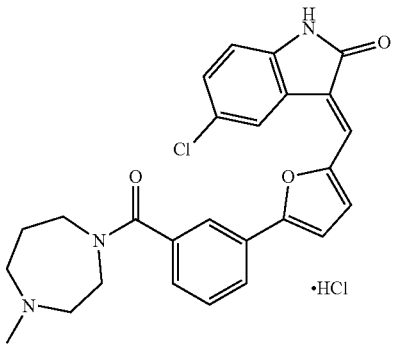 [SMILES: CN1CCCN(C(=O)c2cccc(-c3ccc(/C=C4/C(=O)Nc5ccc(Cl)cc54)o3)c2)CC1 ; Cl]

The CAS Registry Number for CX-6258 is 1353859-00-3.

SGI-1776 has the following structure:

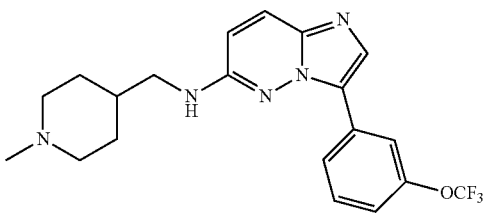 [SMILES: CN1CCC(CNc2ccc3ncc(-c4cccc(OC(F)(F)F)c4)n3n2)CC1]

The CAS Registry Number for SGI-1776 is 1025065-69-3.

M-110 has the following structure:

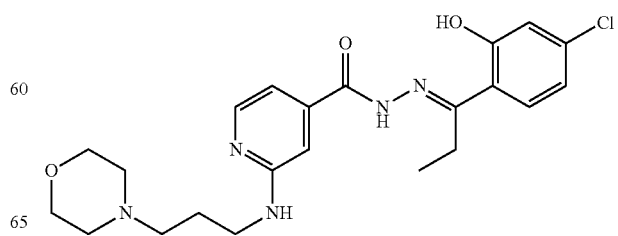

Synonyms for M-110 include N'-(1-(4-Chloro-2-hydroxyphenyl)propylidene)-2-((3-morpholinopropyl)amino)isonicotinohydrazide and PIM3 kinase inhibitor VII. M-110 is available from, e.g., EMD Millipore (Billerica Mass. USA; Cat. No. 526526). Non-limiting descriptions relating to M-110 are provided in Chang, M., et al. 2010. Mol. Cancer Ther. 9, 2478-2487, the entire content of which is incorporated herein by reference.

Additional non-limiting examples of PIM3 inhibitors are described in U.S. Pat. No. 8,053,454, issued Nov. 8, 2011; U.S. Patent Application Publication No. 20140249135, published Sep. 4, 2014; and Nakano et al. Bioorg Med Chem Lett. 2015 Dec. 15; 25(24):5687-93, the entire contents of each of which are incorporated herein by reference in their entireties.

In some embodiments, the PIM3 inhibitor inhibits PIM3 as well as PIM1 and/or PIM2. In certain embodiments, the PIM3 inhibitor inhibits PIM3 as well as PIM1. In various embodiments, the PIM3 inhibitor inhibits PIM3 as well as PIM2. In some embodiments, the PIM3 inhibitor inhibits PIM3 as well as PIM1 and PIM2. In certain embodiments, the PIM3 inhibitor is a pan-PIM inhibitor.

Non-limiting examples of pan-PIM inhibitors such as N-substituted 7-azaindoles that may be used as PIM3 inhibitors are described in Barberis et al. (2017) *Bioorganic & Medicinal Chemistry Letters* 27:4735-4740, and include:

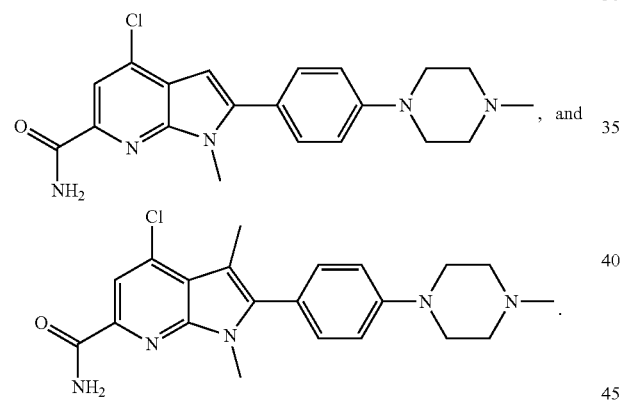

The entire content of Barberis et al. (2017) *Bioorganic & Medicinal Chemistry Letters* 27:4735-4740 is incorporated herein by reference.

Additional non-limiting example of PIM inhibitors that can be used as PIM3 inhibitors include:

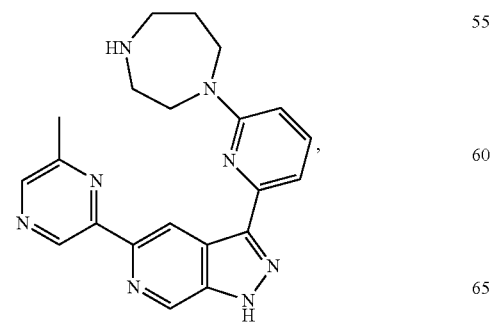

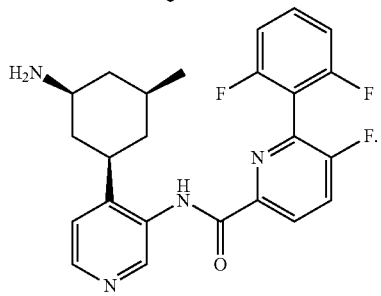

These and other PIM inhibitors that may be used as PIM3 inhibitors are described in Wang et al. (2017) *J. Med. Chem.* 60, 4458-4473, the entire content of which is incorporated herein by reference.

Non-limiting examples of PIM inhibitors that may be used as PIM3 inhibitors also include:

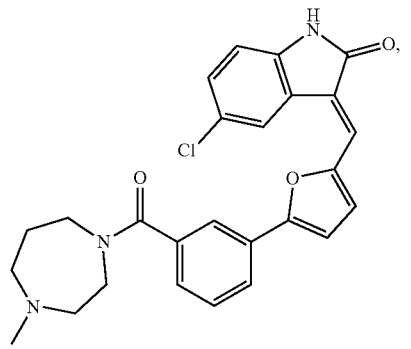

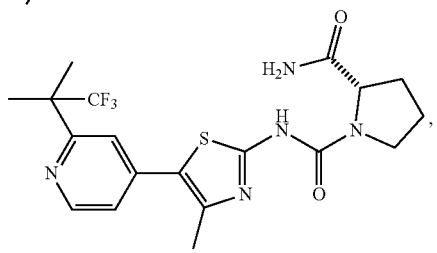

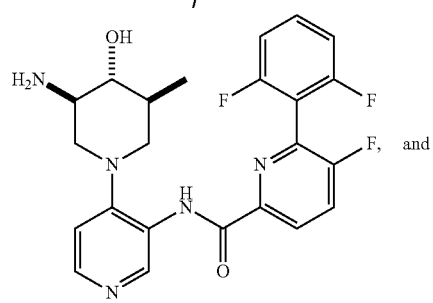

-continued

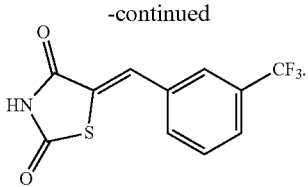

These and other PIM inhibitors that may be used as PIM3 inhibitors are described in Bataille et al. (2017) *Bioorganic & Medicinal Chemistry* 25:2657-2665, the entire content of which is incorporated herein by reference.

Additional non-limiting examples of PIM inhibitors that may be used as PIM3 inhibitors include:

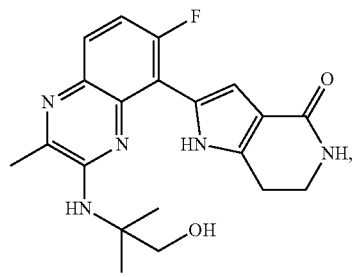

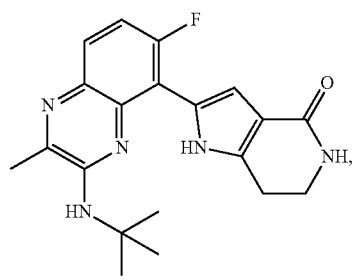

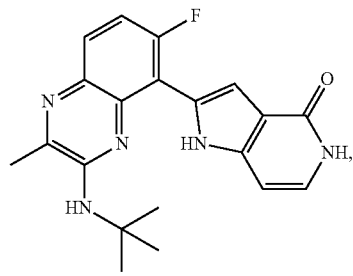

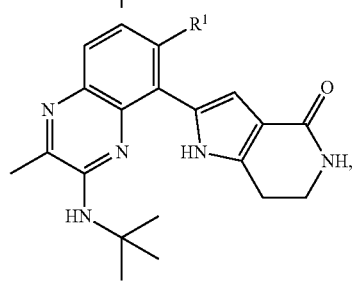

1: $R^1$ = F
4: $R^1$ = H

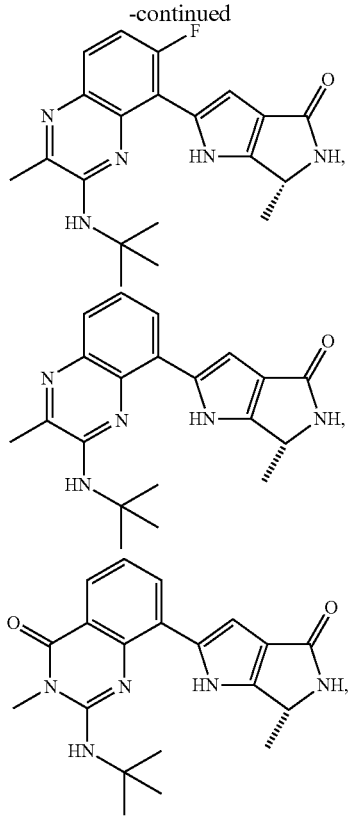

which are described together with others in Pettus et al. (2016) *J. Med. Chem.* 59, 6407-6430, the entire content of which is incorporated herein by reference.

In various embodiments, a PIM3 inhibitor is co-administered with an USP7 inhibitor. Non-limiting aspects and descriptions of USP7 inhibitors are described in Kategaya et al. (2017) *Nature,* 550:534-538, the entire content of which (including all supplemental information and data) is incorporated herein by reference. Examples of USP7 inhibitors shown in Kategaya et al. (2017) include:

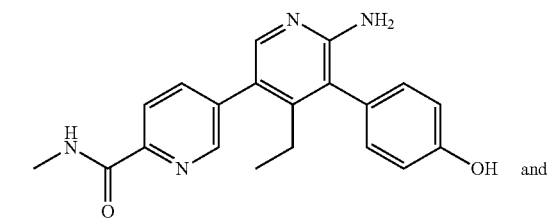

and

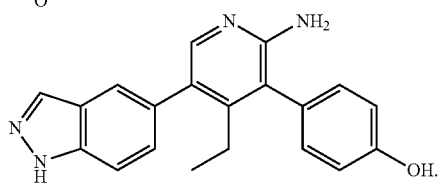

Proteins and Peptides

In some embodiments, a protein, peptide, or a fragment thereof is used to inhibit RUNX1 or PIM3. A non-limiting example of such an inhibitor for RUNX1 is a dominant negative CBF-Beta protein (CBFB-MYH11). See, e.g., Castilla et al. (1996) *Cell.* 1996; 87:687-696, the entire content of which is hereby incorporated herein by reference.

Aptamers

Aptamers are small, single stranded biomolecules, typically oligonucleotides (either DNA or RNA) or peptides, that bind to a specific target molecule (e.g. a protein or small molecule such as a steroid). They can be considered analogous to antibodies in their specificity but, unlike antibodies, aptamers are have a relatively low molecular weight. Peptide-based aptamers are generally less than thirty residues long while nucleotide-based aptamers are typically less than one hundred residues long.

Non-limiting examples of methods that are useful for designing aptamers that target a particular protein, such as RUNX1 or PIM3, are described in U.S. Pat. Nos. 8,484,010; 5,582,981; PCT International Patent Application No. WO 2015/049356; Blackwell et al., (1993) Science 250:1104-1110; Blackwell, et al., (1990) Science 250:1149-1152; Tuerk and Gold (1990) Science 249:505-510; and Joyce (1989) Gene 82:83-87, the entire contents of each of which are incorporated herein by reference.

Antisense Oligonucleotides

As used herein, an "antisense oligonucleotide" is an oligonucleotide that inhibits gene expression by a mechanism other than RNAi. Non-limiting examples of antisense oligonucleotides which decrease the amount of RUNX1 or PIM3 produced by cells that can be employed in the methods described herein include antisense oligonucleotides that are complementary (e.g., at least about 90, 95, 96, 97, 98, 99, or 100% complementary) to a stretch of at least about 10, 11, 12, 13, 14, 15, 16, 17, 18, 19, 20, 21, 22, 23, 24, 25, 26, 27, 28, 29 or 30 consecutive nucleotides having a sequence found within a nucleotide sequence that encodes RUNX1 or PIM3, such as any of the RUNX1- or PIM3-encoding nucleotide sequences disclosed herein.

Antisense oligonucleotides comprise nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of RUNX1 or PIM3 gene products in the cell.

Antisense oligonucleotides can comprise deoxyribonucleotides, ribonucleotides, or a combination of both. Antisense oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters.

Modifications of gene expression can be obtained by designing antisense oligonucleotides which will form duplexes to the control, 5', or regulatory regions of the gene. Antisense oligonucleotides that target the transcription initiation site, e.g., between positions −10 and +10 from the start site, are used in some embodiments. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (Nicholls et al., 1993, J Immunol Meth 165:81-91). Antisense oligonucleotides that are complementary to a sequence that includes the translational start site, and/or that are complementary to a portion of a target mRNA within 10 nucleotides of the translational start site, are used in various embodiments. An antisense oligonucleotide also can be designed to block translation of mRNA by preventing the transcript from binding to ribosomes.

Precise complementarity is not required for successful complex formation between an antisense oligonucleotide and the complementary sequence of a RUNX1 or PIM3 polynucleotide. Antisense oligonucleotides which comprise, for example, 2, 3, 4, or 5 or more stretches of contiguous nucleotides which are precisely complementary to a RUNX1 or PIM3 polynucleotide, each separated by a stretch of contiguous nucleotides which are not complementary to adjacent RUNX1 or PIM3 nucleotides, can provide sufficient targeting specificity for RUNX1 or PIM3 mRNA. In some embodiments, each stretch of complementary contiguous nucleotides is at least 4, 5, 6, 7, or 8 or more nucleotides in length. Noncomplementary intervening sequences may be, e.g., 1, 2, 3, or 4 nucleotides in length. One skilled in the art can easily use the calculated melting point of an antisense-sense pair to determine the degree of mismatching which will be tolerated between a particular antisense oligonucleotide and a particular RUNX1 or PIM3 polynucleotide sequence. Antisense oligonucleotides can be modified without affecting their ability to hybridize to a RUNX1 or PIM3 polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3' or 5'-substituted oligonucleotide in which the 3' hydroxyl group and/or the 5' phosphate group is substituted, also can be employed in a modified antisense oligonucleotide. These modified antisense oligonucleotides can be prepared by methods well known in the art.

Ribozymes

Ribozymes are RNA molecules with catalytic activity (Uhlmann et al., 1987, Tetrahedron. Lett. 215, 3539-3542). Ribozymes can be used to inhibit gene function by cleaving an RNA sequence, as is known in the art. The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences. The coding sequence of a polynucleotide can be used to generate ribozymes which will specifically bind to mRNA transcribed from the polynucleotide. Methods of designing and constructing ribozymes which can cleave other RNA molecules in trans in a highly sequence specific manner have been developed and described in the art. For example, the cleavage activity of ribozymes can be targeted to specific RNAs by engineering a discrete "hybridization" region into the ribozyme. The hybridization region contains a sequence complementary to the target RNA and thus specifically hybridizes with the target RNA.

Specific ribozyme cleavage sites within an RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate RNA targets also can be evaluated by testing accessibility to hybridization with complementary oligonucleotides using ribonuclease protection assays. The nucleotide sequences shown in SEQ ID NOs: 12-22 and 27-30 and their complements provide sources of suitable hybridization region sequences. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease RUNX1 or PIM3 expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer element, and a transcriptional terminator signal, for controlling transcription of ribozymes in the cells (U.S. Pat. No. 5,641,673). Ribozymes also can be engineered to provide an additional level of regulation, so that destruction of mRNA occurs only when both a ribozyme and a target gene are induced in the cells.

RNA Interference

As used herein, an "RNA interference" inducing compound refers to a compound capable of inducing RNA interference or "RNAi" of target gene (e.g., RUNX1 or PIM3) expression, depending on the context. RNAi involves mRNA degradation. The use of RNAi has been described in Fire et al. (1998) Nature 19; 391(6669):806-11, Elbashir et al. (2001) EMBO J. 20(23): 6877-6888, and Cheloufi et al. (2010) Nature 465, 584-589, the entire contents of each of which are incorporated herein by reference.

Isolated RNA molecules can mediate RNAi. That is, the isolated RNA molecules of the present subject matter mediate degradation or block expression of mRNA that is the transcriptional product of the gene, which is also referred to as a target gene. For convenience, such mRNA may also be referred to herein as mRNA to be degraded. RNAi molecules may be, e.g., double-stranded RNA, small interfering RNA (siRNA), hairpin RNA, microRNA molecules which may be altered compared to naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the RNA molecules of the present invention can also comprise nonstandard nucleotides, including non-naturally occurring nucleotides or deoxyribonucleotides. Collectively, all such altered RNAi molecules may be referred to as analogs or analogs of naturally-occurring RNA. RNA of the present invention need only be sufficiently similar to natural RNA that it has the ability to mediate RNAi.

As used herein the phrase "mediate RNAi" refers to and indicates the ability to distinguish which mRNA molecules are to be afflicted with the RNAi machinery or process. RNA that mediates RNAi interacts with the RNAi machinery such that it directs the machinery to degrade particular mRNAs or to otherwise reduce the expression of the target protein. In some embodiments, the present invention relates to RNA molecules that direct cleavage of specific mRNA to which their sequence corresponds. It is not necessary that there be perfect correspondence of the sequences, but the correspondence must be sufficient to enable the RNA to direct RNAi inhibition by cleavage or blocking expression of the target mRNA. In some embodiments, an RNAi molecule comprises a stretch of about 16 to 29, 18 to 23, 21-23, or at least 12, 13, 14, 15, 16, 17, 18, 19, 20, 21, 22, 23, 24, or 25 nucleotides having a sequence that is at least about 90, 95, 96, 97, 98, 99, or 100% complementary to a target sequence. As noted above, the RNA molecules of the present invention may comprise an RNA portion and some additional portion, for example a deoxyribonucleotide portion.

Antibodies

In some embodiments, the RUNX1 or PIM3 inhibitor is an antibody or a fragment thereof.

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, an $F_{ab}$ expression library, single-chain antibody molecules (e.g., scFv), and multispecific antibodies formed from antibody fragments. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

An "antibody fragment" refers to a molecule other than an intact antibody that comprises a portion of an intact antibody that binds the antigen to which the intact antibody binds. The terms "full length antibody," "intact antibody," and "whole antibody" are used herein interchangeably to refer to an antibody having a structure substantially similar to a native antibody structure or having heavy chains that contain an Fc region.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs." Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three hypervariable regions (HVRs) of each variable domain interact to define an antigen binding site on the surface of the VH-VL dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

A "Fab" fragment contains a variable and constant domain of the light chain and a variable domain and the first constant domain (CHI) of the heavy chain. F(ab') 2 antibody fragments comprise a pair of Fab fragments which are generally covalently linked near their carboxy termini by hinge cysteines between them. Other chemical couplings of antibody fragments are also known in the art, "Single-chain Fv" or "scFv" antibody fragments comprise the VH and VL domains of an antibody, wherein these domains are present in a single polypeptide chain. Generally the Fv polypeptide further comprises a polypeptide linker between the VH and L domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-31S (1994).

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, BP 404,097; WO 93/11161; and Hollinger et al., Proc. Natl. Acad. Sci. USA, 90:6444-6448 (1993).

The expression "linear antibodies" refers to the antibodies described in Zapata et al., Protein Eng., 8 (10): 1057-1062 (1995). Briefly, these antibodies comprise a pair of tandem segments which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

As used herein, the term "epitope" includes any protein determinant capable of specific binding to an antibody, an antibody fragment, or a T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; preferably <100 nM and most preferably ≤10 nM.

Antibodies can be produced according to any method known in the art.

Methods of preparing monoclonal antibodies are known in the art. For example, monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a full length protein or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) Monoclonal Antibodies: Principles and Practice Academic Press). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some examples, the antibodies to an epitope for an interested protein as described herein or a fragment thereof are humanized antibodies. Humanized forms of non-human (e.g., murine) antibodies are chimeric molecules of immunoglobulins, immunoglobulin chains or fragments thereof (such as Fv, $F_{ab}$, $F_{ab'}$, $F_{(ab')2}$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al. 1986. Nature 321:522-525; Riechmann et al. 1988. Nature 332:323-329; Presta. 1992. Curr. Op. Struct. Biol. 2:593-596). Humanization can be essentially performed following methods of Winter and co-workers (see, e.g., Jones et al. 1986. Nature 321:522-525; Riechmann et al. 1988. Nature 332:323-327; and Verhoeyen et al. 1988. Science 239:1534-1536), by substituting rodent CDRs or CDR sequences for the corresponding sequences of a human antibody. Accordingly, such humanized antibodies are chimeric antibodies (e.g., U.S. Pat. No. 4,816,567), wherein substantially less than an intact human variable domain has been substituted by the corresponding sequence from a non-human species.

In various examples the antibodies to an epitope of an interested protein as described herein or a fragment thereof are human antibodies. Human antibodies can also be produced using various techniques known in the art, including phage display libraries (Hoogenboom and Winter. 1991. J. Mol. Biol. 227:381-388; Marks et al. 1991. J. Mol. Biol. 222:581-597) or the preparation of human monoclonal antibodies [e.g., Cole et al. 1985. Monoclonal Antibodies and Cancer Therapy Liss; Boerner et al. 1991. J. Immunol. 147(1):86-95]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al. 1992. Bio/Technology 10:779-783; Lonberg et al. 1994. Nature 368:856-859; Morrison. 1994. Nature 368: 812-13; Fishwild et al. 1996. Nature Biotechnology 14:845-51; Neuberger. 1996. Nature Biotechnology 14:826; Lonberg and Huszar. 1995. Intern. Rev. Immunol. 13:65-93.

U.S. Pat. No. 6,719,971 also provides guidance to methods of generating humanized antibodies.

In some embodiments, an intrabody is used to inhibit RUNX1 or PIM3. An "intrabody" (from intracellular and antibody) is an antibody that works within the cell to bind to an intracellular antigen. Intrabodies typically lack disulfide bonds and are capable of modulating the expression or activity of target genes through their specific binding activity. Intrabodies include single domain fragments such as isolated VH and VL domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in proteinprotein, protein-DNA, or protein-RNA interactions. In various embodiments, the intrabody is expressed within a target cell, e.g., by a viral or plasmid expression vector that has been introduced into the target cell. An intrabody may remain in the cytoplasm, or it may have a nuclear localization signal, or it may undergo cotranslational translocation across the membrane into the lumen of the endoplasmic reticulum, provided that it is retained in that compartment through a KDEL sequence. Because antibodies ordinarily are designed to be secreted from the cell, intrabodies require special alterations, including the use of single-chain antibodies (scFvs), modification of immunoglobulin VL domains for hyperstability, selection of antibodies resistant to the more reducing intracellular environment, or expression as a fusion protein with maltose binding protein or other stable intracellular proteins. Non-limiting aspects of intrabodies are described, e.g., in U.S. Pat. No. 9,133,269; U.S. Patent Application Publication No. 2006/0034834; Chen et al. (1994) Human gene therapy 5 (5): 595-601; and Shaki-Loewenstein et al. (2005) Journal of immunological methods 303 (1-2): 19-39, the entire contents of each of which are incorporated herein by reference.

Exemplary antibodies against RUNX1 include, but are not limited to, antibodies obtained from Abcam (Cambridge, Mass., USA) (e.g., Cat. Nos. ab23980, ab35962, ab189172, ab189153, and ab91002), antibodies obtained from Novus Biologicals (Littleton, Colo., USA) (e.g., Cat. Nos. NBP1-89105, H00000861-M05, H00000861-M06, MAB2399, and H00000861-M02), and antibodies obtained from ThermoFisher Scientific (Cambridge, Mass., USA) (e.g., 710233, MA5-15814, PA1-41078, OSR00271W, PAS-17434, PAS-19638, PAS-12409, PAS-40076, and PAS-17351).

Exemplary antibodies against PIM3 include, but are not limited to, antibodies obtained from Abcam (Cambridge, Mass., USA) (e.g., Cat. Nos. ab71321, ab198842, and ab108920), and antibodies obtained from ThermoFisher Scientific (Cambridge, Mass., USA) (e.g., Cat. No. PAS-13976).

Exemplary antibodies against IGFBP3 include, but are not limited to, antibodies obtained from Abcam (Cambridge, Mass., USA) (e.g., Cat. Nos. ab76001, ab4248, ab111931, and ab109790), and antibodies obtained from ThermoFisher Scientific (Cambridge, Mass., USA) (e.g., Cat. No. MA1-20185).

Gene Therapy

In some embodiments, a gene editing method is used to modulate (e.g., reduce) RUNX1 and/or PIM3 expression and/or activity. In certain embodiments, a gene editing method is used to modulate (e.g., increase) IGFBP3 expression and/or activity. Non-limiting examples of gene editing systems useful in such embodiments include the clustered regularly interspaced short palindromic repeat (CRISPR)-Cas system; zinc finger nuclease (ZFN) systems, and transcription activator-like effector-based nuclease (TALEN) systems.

Exemplary aspects of the CRISPR-Cas system are described in, e.g., U.S. Pat. No. 9,023,649, issued May 5, 2015; U.S. Pat. No. 9,074,199, issued Jul. 7, 2015; and U.S. Pat. No. 8,697,359, issued Apr. 15, 2014 the entire contents of each of which are incorporated herein by reference.

With their highly flexible but specific targeting, CRISPR-Cas systems can be manipulated and redirected to become powerful tools for genome editing. CRISPR-Cas technology permits targeted gene cleavage and gene editing in a variety of eukaryotic cells, and editing can be directed to virtually any genomic locus. Exemplary CRISPR Cas genes include Cas1, Cas2, Cas3', Cas3", Cas4, Cas5, Cas6, Cas6e (formerly referred to as CasE, Cse3), Cas6f (i.e., Csy4), Cas7, Cas8a1, Cas8a2, Cas8b, Cas8c, Cas9, Cas10, Cas10d, Csy1, Csy2, CPf1, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. These enzymes are known; for example, the amino acid sequence of *Streptococcus pyogenes* Cas9 protein may be found in the SwissProt database under accession number Q99ZW2.

Non-limiting examples of sequences of Guide RNA for CRISPR-Cas9 targeting of RUNX1 are as follows:

RUNX1 guide RNAs: (20 bp). The proto-spacer adjacent motif (PAM) sequences are underlined.

```
                                         (SEQ ID NO: 255)
1. GATGAGCGAGGCGTTGCCGCTGG (exon1)

(SEQ ID NO: 256)
2. TAGATGATCAGACCAAGCCCGGG (exon 4)

(SEQ ID NO: 257)
3. TGGCAATGATGAAAACTACTCGG (exon 2)
```

In the guide RNA sequences shown above, each T may optionally be a U.

Other non-limiting examples of approaches for gene editing include the use of zinc finger nucleases, which are artificial restriction enzymes generated by fusing a zinc finger DNA-binding domain to a DNA-cleavage domain. A zinc finger nuclease is a site-specific endonuclease designed to bind and cleave DNA at specific positions. There are two protein domains. The first domain is the DNA binding domain, which consists of eukaryotic transcription factors and contain the zinc finger. The second domain is the nuclease domain, which consists of the FokI restriction enzyme and is responsible for the catalytic cleavage of DNA. The DNA-binding domains of individual ZFNs typically contain between three and six individual zinc finger repeats and can each recognize between 9 and 18 basepairs. If the zinc finger domains are perfectly specific for their intended target site then even a pair of 3-finger ZFNs that recognize a total of 18 basepairs can, in theory, target a single locus in a mammalian genome. Various strategies have been developed to engineer Cys2His2 zinc fingers to bind desired sequences. These include both "modular assembly" and selection strategies that employ either phage display or cellular selection systems. The most straightforward method to generate new zinc-finger arrays is to combine smaller zinc-finger "modules" of known specificity. The most common modular assembly process involves combining three separate zinc fingers that can each recognize a 3 basepair DNA sequence to generate a 3-finger array that can recognize a 9 basepair target site. Other procedures can utilize either 1-finger or 2-finger modules to generate zinc-finger arrays with six or more individual zinc fingers. Numerous selection methods have been used to generate zinc-finger arrays capable of targeting desired sequences. Initial selection efforts utilized phage display to select proteins that bound a given DNA target from a large pool of partially randomized zinc-finger arrays. More recent efforts have utilized yeast one-hybrid systems, bacterial one-hybrid and two-hybrid systems, and mammalian cells. The non-specific cleavage domain from the type IIs restriction endonuclease FokI is typically used as the cleavage domain in ZFNs. This cleavage domain must dimerize in order to cleave DNA and thus a pair of ZFNs are required to target non-palindromic DNA sites. Standard ZFNs fuse the cleavage domain to the C-terminus of each zinc finger domain. In order to allow the two cleavage domains to dimerize and cleave DNA, the two individual ZFNs must bind opposite strands of DNA with their C-termini a certain distance apart. The most commonly used linker sequences between the zinc finger domain and the cleavage domain requires the 5' edge of each binding site to be separated by 5 to 7 bp.

TALENs are restriction enzymes that can be engineered to cut specific sequences of DNA. They are made by fusing a TAL effector DNA-binding domain to a DNA cleavage domain. Transcription activator-like effectors (TALEs) can be engineered to bind practically any desired DNA sequence, so when combined with a nuclease, DNA can be cut at specific locations. The restriction enzymes can be introduced into cells, for use in gene editing or for genome editing in situ. Alongside zinc finger nucleases and CRISPR/Cas9, TALEN is a prominent tool in the field of genome editing.

NOTCH Signaling Inhibition

NOTCH signaling is an upstream regulator of the expression of Runx genes (Burns C E, et al., Genes and Development, 2005, 19:2331-2342). Modalities of treatment for aberrant angiogenesis conditions based on inhibition of the Notch receptors (NOTCH 1, NOTCH 2, NOTCH 3, NOTCH 4) and or any of their ligands (Delta like 1, Delta like 3, Delta like 4, Jagged 1 and Jagged 2) or other modulators of the NOTCH pathway operate via regulation of RUNX1. These modalities of treatment include inhibition or modulation of gamma-secretase, modulating antibodies against the receptors and the ligands, and other small molecules, biologicals and genetic approaches that inhibit RUNX1 expression via modulation of NOTCH signaling activity.

In some embodiments, a gamma-secretase inhibitor or modulator is used to modulate RUNX1 activity or expression.

In various embodiments, inhibition of any of the NOTCH receptors including NOTCH 1, NOTCH 2, NOTCH 3, and/or NOTCH 4, and/or any of the NOTCH ligands including Jagged 1, Jagged 2, Delta-like 1, Delta-like 3, Delta-like 4, and/or Delta like 5 may be used as means to modulate RUNX1. In some embodiments, NOTCH signaling is modulated to reduce RUNX1 function. For example, a NOTCH inhibitor is used to reduce RUNX1 expression or activity.

Non-limiting examples of NOTCH inhibitors include aptamers, oligonucleotides (e.g., antisense oligonucleotides, ribozymes, and RNAi molecules), peptides (e.g., a portion of or the entire extracellular domain of a NOTCH protein), antibodies, antibody fragments, and small molecules that specifically bind to a NOTCH protein or a polynucleotide that encodes a NOTCH protein. Non-limiting examples of small molecule inhibitors for NOTCH proteins include compounds having the following structures:

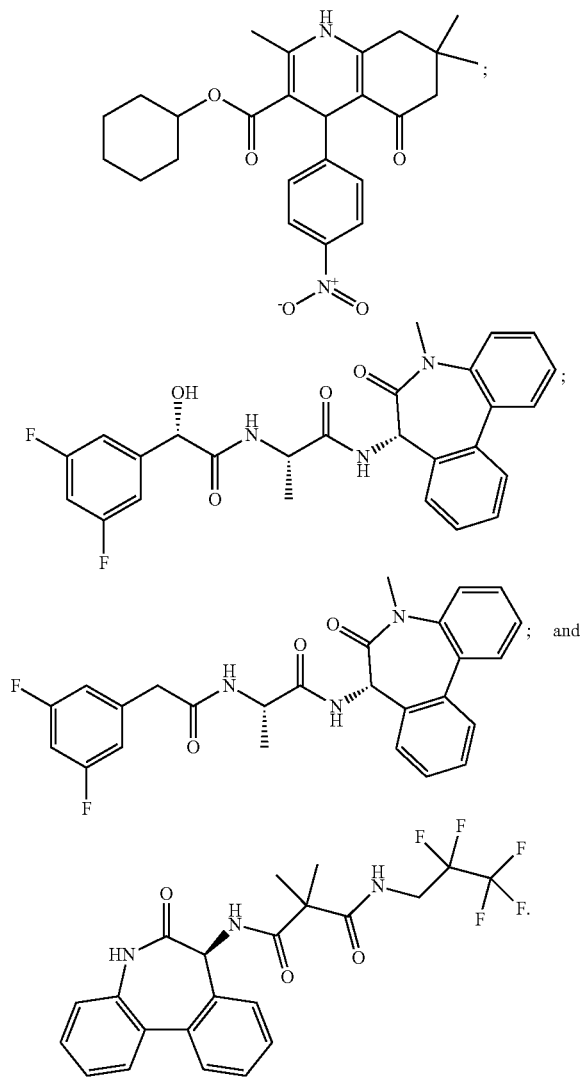

Additional non-limiting examples of NOTCH inhibitors (as well as aspects of NOTCH signaling) are described in Espinoza and Miele, *Pharmacol Ther.* 2013, 139(2): 95-110; and Yuan et al., *Cancer Letters* 2015, 369(1) 20-27, the entire contents of each of which are incorporated herein in their entireties.

In some embodiments RUNX1 signaling is modulated to reduce NOTCH signaling or function. For example, a RUNX1 inhibitor is used to reduce NOTCH signaling or function.

Pharmaceutical Formulations and Delivery

Dosages, formulations, dosage volumes, regimens, and methods for administering a RUNX1 inhibitor may vary. Thus, minimum and maximum effective dosages vary depending on the method of administration.

"Administering" an inhibitor described herein can be effected or performed using any of the various methods and delivery systems known to those skilled in the art. The administering can be, for example, intravenous, oral, ocular (e.g., subconjunctival, intravitreal, retrobulbar, or intracameral), intramuscular, intravascular, intra-arterial, intracoronary, intramyocardial, intraperitoneal, subcutaneous, inhaled, or intrathecal. Other non-limiting examples include topical administration, or coating of a device to be placed within the subject. Topical administration also includes administration of the inhibitor(s) by eye drop, e.g., contacting the surface of the eye with a liquid (aqueous, lipid, or combination thereof) or gel formulation. In other embodiments, administration is carried by injection, e.g., using a needle, or via a catheter.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

As used herein, a "monotherapy" is therapy that is administered to inhibit, treat, or prevent a disorder, such as aberrant angiogenesis (or a disease that includes aberrant angiogenesis such as cancer or PDR), without any other therapy that is used to treat the disorder. A monotherapy for treating a disorder may optionally be combined with another treatment that is used to ameliorate a symptom of the disorder while not being directed against the disorder, for example an analgesic compound, an antipyretic compound, and/or an anti-inflammatory compound (e.g., aspirin, ibuprofen, naproxen, or acetaminophen) may be administered concurrently with the monotherapy.

In various embodiments of the invention, a composition comprising a RUNX1 inhibitor may be administered only once or multiple times. For example, a RUNX1 inhibitor may be administered using a method disclosed herein at least about once, twice, three times, four times, five times, six times, or seven times per day, week, month, or year. In some embodiments, a composition comprising a RUNX1 inhibitor is administered once per month. In certain embodiments, the composition is administered once per month via intravitreal injection. In various embodiments, such as embodiments involving eye drops, a composition is self-administered.

For the treatment of an ocular disorder, a RUNX1 inhibitor (e.g., a pharmaceutical composition comprising a RUNX1 inhibitor) may be administered locally, e.g., as a topical eye drop, peri-ocular injection (e.g., sub-tenon), intraocular injection, intravitreal injection, retrobulbar injection, intraretinal injection, subretinal injection, subconjunctival injection, or using iontophoresis, or peri-ocular devices which can actively or passively deliver drug.

Sustained release of drug may be achieved by the use of technologies such as implants (e.g., solid implants) (which may or may not be bio-degradable) or bio-degradable polymeric matrices (e.g., micro-particles). These may be administered, e.g., peri-ocularly or intravitreally.

Pharmaceutical formulations adapted for topical administration may be formulated as aqueous solutions, ointments, creams, suspensions, lotions, powders, solutions, pastes, gels, sprays, aerosols, liposomes, microcapsules, microspheres, or oils.

For treatments of the eye or other external tissues, such as the mouth or skin, the formulations (e.g., a pharmaceutical composition comprising a RUNX1 inhibitor) may be applied as a topical ointment or cream. When formulated in an ointment, a RUNX1 inhibitor may be employed with either a paraffinic or a water-miscible ointment base. Alternatively, a RUNX1 inhibitor may be formulated in a cream with an oil-in-water cream base or a water-in-oil base.

The present subject matter provides compositions comprising a RUNX1 inhibitor and a carrier or excipient suitable for administration to ocular tissue. Such carriers and excipients are suitable for administration to ocular tissue (e.g., sclera, lens, iris, cornea, uvea, retina, macula, or vitreous tissue) without undue adverse side effects (such as toxicity, irritation, and allergic response) commensurate with a reasonable benefit/risk ratio.

Pharmaceutical formulations adapted for topical administrations to the eye include eye drops wherein a RUNX1 inhibitor is dissolved or suspended in a suitable carrier, especially an aqueous solvent. Formulations to be administered to the eye will have ophthalmically compatible pH and osmolality. The term "ophthalmically acceptable vehicle" means a pharmaceutical composition having physical properties (e.g., pH and/or osmolality) that are physiologically compatible with ophthalmic tissues.

In some embodiments, an ophthalmic composition of the present invention is formulated as sterile aqueous solutions having an osmolality of from about 200 to about 400 milliosmoles/kilogram water ("mOsm/kg") and a physiologically compatible pH. The osmolality of the solutions may be adjusted by means of conventional agents, such as inorganic salts (e.g., NaCl), organic salts (e.g., sodium citrate), polyhydric alcohols (e.g., propylene glycol or sorbitol) or combinations thereof.

In various embodiments, the ophthalmic formulations of the present invention may be in the form of liquid, solid or semisolid dosage form. The ophthalmic formulations of the present invention may comprise, depending on the final dosage form, suitable ophthalmically acceptable excipients. In some embodiments, the ophthalmic formulations are formulated to maintain a physiologically tolerable pH range. In certain embodiments, the pH range of the ophthalmic formulation is in the range of from about 5 to about 9. In some embodiments, pH range of the ophthalmic formulation is in the range of from about 6 to about 8, or is about 6.5, about 7, or about 7.5.

In some embodiments, the composition is in the form of an aqueous solution, such as one that can be presented in the form of eye drops. By means of a suitable dispenser, a desired dosage of the active agent can be metered by administration of a known number of drops into the eye, such as by one, two, three, four, or five drops.

One or more ophthalmically acceptable pH adjusting agents and/or buffering agents can be included in a composition of the invention, including acids such as acetic, boric, citric, lactic, phosphoric, and hydrochloric acids; bases such as sodium hydroxide, sodium phosphate, sodium borate, sodium citrate, sodium acetate, and sodium lactate; and buffers such as citrate/dextrose, sodium bicarbonate, and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium, or ammonium cations and chloride, citrate, ascorbate, borate, phosphate, bicarbonate, sulfate, thiosulfate, or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g., poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition, and polymeric coatings that will enhance drug diffusion, erosion, dissolution, and osmosis.

Formulations for drug delivery using ocular devices may combine one or more active agents and adjuvants appropriate for the indicated route of administration. For example, a RUNX1 inhibitor (optionally with another agent) may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers, and a carrier or diluent that has a time delay property. Representative examples of biodegradable compositions can include albumin, gelatin, starch, cellulose, dextrans, polysaccharides, poly (D,L-lactide), poly (D,L-lactide-co-glycolide), poly (glycolide), poly (hydroxybutyrate), poly (alkylcarbonate) and poly (orthoesters), and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig, Adv. Drug Deliv. Rev. 3; 57:1595-639 (2005), the entire content of which is incorporated herein by reference.

Biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661;

6,331,313; 6,369,116; 6,699,493; and 8,293,210, the entire contents of each of which are incorporated herein by reference.

The implants may be monolithic, i.e. having the active agent (e.g., a RUNX1 inhibitor) or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including a RUNX1 inhibitor, may be distributed in a non-homogenous pattern in the matrix. For example, the implant may include a portion that has a greater concentration of a RUNX1 inhibitor relative to a second portion of the implant.

The intraocular implants disclosed herein may have a size of between about 5 um and about 2 mm, or between about 10 um and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 ug, more preferably about 500-1000 ug. For example, an implant may be about 500 ug, or about 1000 ug. For non-human subject, the dimensions and total weight of the implant(s) may be larger or smaller, depending on the type of subject. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques, and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of 0.5 u.m to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Microspheres for ocular delivery are described, for example, in U.S. Pat. Nos. 5,837,226; 5,731,005; 5,641,750; 7,354,574; and U.S. Pub. No. 2008-0131484, the entire contents of each of which are incorporated herein by reference.

For oral or enteral formulations for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. Nos. 4,704,295; 4, 556,552; 4,309, 404; and 4,309,406, the entire contents of each of which are incorporated herein by reference.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (RNA or DNA) is free of the genes or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. An individual described as a "subject," "patient," "individual," and the like does not necessarily have a given disease, but may be merely seeking medical advice. The terms "subject," "patient," "individual," and the like as used herein include all members of the animal kingdom that may suffer from the indicated disorder. In some aspects, the subject is a mammal, and in some aspects, the subject is a human. In some embodiments, a subject is a mouse, rat, guinea pig, primate (such as a monkey, a chimpanzee, a gorilla, or a baboon), a cat, a dog, a cow, a camel, a sheep, a horse, an ox, a reindeer, an elephant, a work animal, a zoo animal, a reptile, an amphibian, or a fish.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. For purposes of this disclosure, beneficial or desired clinical results include, but are not limited to, alleviation or amelioration of any symptom or symptoms, diminishment of extent of disease, stabilized (i.e., not worsening) state of disease, preventing spread of disease, delay or slowing of disease progression, amelioration or palliation of the disease state, and recovery (whether partial or total), whether detectable or undetectable. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

A "control" sample or value refers to a sample that serves as a reference, usually a known reference, for comparison to a test sample. For example, a test sample can be taken from a test subject, e.g., a subject in need of diagnosis for a disease, and compared to samples from known conditions, e.g., a subject (or subjects) that does not have the disease (a negative or normal control), or a subject (or subjects) who does have the disease (positive control). A control can also represent an average value gathered from a number of tests or results. One of skill in the art will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are variable in controls, variation in test samples will not be considered as significant.

The term, "normal amount" with respect to a compound (e.g., a protein) refers to a normal amount of the protein in an individual known not to be diagnosed with a disease that comprises aberrant angiogenesis. The amount of a protein can be measured in a test sample and compared to the "normal control" level, utilizing techniques such as reference limits, discrimination limits, or risk defining thresholds to define cutoff points and abnormal values (e.g., for a particular neovascularization disorder or a symptom thereof). The normal control level means the level of one or more proteins or combined protein indices typically found in a subject known not suffering from a disease that comprises aberrant angiogenesis. Such normal control levels and cutoff points may vary based on whether a protein is used alone or in a formula combining with other proteins into an index. Alternatively, the normal control level can be a database of protein patterns from previously tested subjects who did not develop a disease that comprises aberrant angiogenesis or a particular symptom thereof (e.g., in the event the disease develops or a subject already having the disease is tested) over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease (or a symptom thereof) in question or is not at risk for the disease.

Relative to a control level, the level that is determined may an increased level. As used herein, the term "increased" with respect to level (e.g., protein level) refers to any % increase above a control level. In various embodiments, the increased level may be at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level.

Relative to a control level, the level that is determined may a decreased level. As used herein, the term "decreased" with respect to level (e.g., protein level) refers to any % decrease below a control level. In various embodiments, the decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

"Risk" in the context of the present disclosure, relates to the probability that an event will occur over a specific time period, as in the development of a neovascularization disorder or a symptom thereof, and can mean a subject's "absolute" risk or "relative" risk. In various embodiments, a "high risk" subject is a subject who is likely to develop a disease that comprises aberrant angiogenesis or a symptom thereof within, e.g., about 1, 2, 3, 4, or 5 years. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used [odds are according to the formula p/(1−p) where p is the probability of event and (1−p) is the probability of no event] to no-conversion.

Embodiments and examples are provided below to facilitate a more complete understanding of the invention. The following embodiments and examples illustrate the exemplary modes of making and practicing the invention. However, the scope of the invention is not limited to specific embodiments disclosed in these embodiments and examples, which are for purposes of illustration only, since alternative methods can be utilized to obtain similar results.

EMBODIMENTS

Embodiments include Embodiments P1 to P50 following.

Embodiment P1

A method for inhibiting, treating, or preventing aberrant angiogenesis in a subject in need thereof, comprising administering to said subject an effective amount of a Runt-Related Transcription Factor 1 (RUNX1) inhibitor or a PIM3 Proto-Oncogene, Serine/Threonine Kinase (PIM3) inhibitor.

Embodiment P2

The method of Embodiment P1, wherein said subject comprises proliferative diabetic retinopathy (PDR), macular edema, or non-proliferative diabetic retinopathy.

Embodiment P3

The method of Embodiment P1, wherein said subject comprises a cancer.

Embodiment P4

The method of Embodiment P3, wherein said cancer is other than leukemia.

Embodiment P5

The method of Embodiment P3, wherein said cancer comprises melanoma.

Embodiment P6

The method of Embodiment P3, wherein said cancer comprises a solid tumor.

Embodiment P7

The method of Embodiment P6, wherein said aberrant angiogenesis comprises blood vessel growth toward, into, and/or within said solid tumor.

Embodiment P8

The method of Embodiment P6 or P7, wherein said solid tumor comprises a dimension that is greater than at least about 1, 2, 3, 4, 5, 6, 7, 8, 9, 10 mm or more and/or a volume of at least about 1, 1.5, 2, 3, 4, 5, 6, 7, 8, 9, 10 mm$^3$ or more.

Embodiment P9

The method of any one of Embodiments P1 to P8, wherein said RUNX1 inhibitor or said PIM3 inhibitor is administered as part of a treatment regimen that does not comprise an additional antiangiogenic inhibitor.

Embodiment P10

The method of Embodiment P9, wherein said treatment regimen does not comprise a vascular endothelial growth factor (VEGF) pathway inhibitor.

Embodiment P11

The method of any one of Embodiments P1 to P10, wherein said RUNX1 inhibitor or said PIM3 inhibitor is administered as a monotherapy.

Embodiment P12

The method of any one of Embodiments P1 to P11, wherein said subject is an animal other than a pregnant animal, an infant, a fetus, or an embryo.

Embodiment P13

The method of any one of Embodiments P1 to P12, wherein said subject comprises diabetes.

Embodiment P14

The method of Embodiment P13, wherein said diabetes is type 1 diabetes or type 2 diabetes.

Embodiment P15

The method of any one of Embodiments P1 to P14, wherein said subject comprises retinopathy of prematurity (ROP), diabetic retinopathy (DR), age-related macular degeneration (AMID), a retinal vein occlusion, a vascular malformation, a cerebral cavernous malformation, macular edema, non-proliferative diabetic retinopathy, ocular ischemic syndrome, neovascular glaucoma, a hemangioma, a retinal hemangioma, Coats' Disease, Norrie Disease, or Von Hippel-Lindau disease.

Embodiment P16

The method of any one of Embodiments P1 to P15, wherein said subject is at least about 10, 20, 30, 40, 50, 60, 70, 80, or 90 years old.

Embodiment P17

The method of any one of Embodiments P1 to P16, wherein said RUNX1 or said PIM3 inhibitor comprises an aptamer, an oligonucleotide, a peptide, an antibody or a fragment thereof, or a small molecule.

Embodiment P18

The method of Embodiment P17, wherein said RUNX1 inhibitor binds to RUNX1 and/or CBFβ.

Embodiment P19

The method of Embodiment P17, wherein said RUNX1 inhibitor binds to RUNX1 or said or said PIM3 inhibitor binds to PIM3.

Embodiment P20

The method of Embodiment P17, wherein said RUNX1 inhibitor comprises Ro5-3335.

Embodiment P21

The method of Embodiment P17, wherein said RUNX1 inhibitor or said PIM3 inhibitor comprises an oligonucleotide.

Embodiment P22

The method of Embodiment P21, wherein said oligonucleotide comprises at least about 10, 15, 20, 25, 30, or more nucleotides in a sequence that is complementary to a nucleotide sequence within a gene or mRNA molecule that encodes RUNX1 or PIM3.

Embodiment P23

A method for inhibiting, treating, or preventing aberrant angiogenesis in a subject in need thereof, comprising altering a RUNX1 or PIM3 gene in said subject.

Embodiment P24

The method of Embodiment P23, wherein altering said RUNX1 or PIM3 gene comprises the administration of (i) a Cas protein, a zinc finger nuclease (ZFN), or a transcription activator-like effector-based nuclease (TALEN), or (ii) an expression vector encoding a Cas protein, a ZFN, or a TALEN, to said subject.

Embodiment P25

The method of Embodiment P23 or P24, wherein said gene is altered with via a CRISPR-Cas9 system.

Embodiment P26

A method for inhibiting, treating, or preventing aberrant angiogenesis in a subject in need thereof, comprising administering to said subject a NOTCH inhibitor in an amount that is effective to reduce RUNX1 expression or activity.

Embodiment P27

A composition comprising an effective amount of a RUNX1 inhibitor or a PIM3 inhibitor and an ophthalmically acceptable vehicle.

Embodiment P28

A method for diagnosing aberrant angiogenesis in a subject comprising
  (a) providing a test sample from said subject;
  (b) assaying the level of RUNX1 or PIM3 protein or mRNA in the test sample;
  and
  (c) diagnosing the subject as having aberrant angiogenesis if the level of RUNX1 or PIM3 protein or mRNA is elevated in the test sample compared to a normal control.

Embodiment P29

The method of Embodiment P28, wherein said subject is diagnosed with the aberrant angiogenesis if the level of RUNX1 or PIM3 protein or mRNA is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control.

Embodiment P30

A method for identifying whether a subject is at risk of developing a disease comprising aberrant angiogenesis comprising
  (a) providing a test sample from said subject;
  (b) assaying the level of RUNX1 or PIM3 protein or mRNA in the test sample; and
  (c) identifying the subject as at risk of developing the disease if the level of RUNX1 or PIM3 protein or mRNA is elevated in the test sample compared to a normal control.

Embodiment P31

The method of Embodiment P30, wherein said subject is identified as at risk of developing the disease if the level of RUNX1 or PIM3 protein or mRNA is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control.

Embodiment P32

The method of Embodiment P30 or P31, further comprising directing the subject to obtain (i) additional screening or an additional diagnostic test for the disease if the subject is identified as at risk of developing the disease; or (ii) treatment to reduce, delay, or prevent the onset or progression of the disease.

Embodiment P33

A method for monitoring whether a disease that comprises aberrant angiogenesis is progressing in a subject who has been diagnosed with the disease, comprising periodically determining the level of RUNX1 or PIM3 protein or mRNA in said subject, and (1) identifying the disease as worsening if the level of RUNX1 or PIM3 protein or mRNA increases over time;
(2) identifying the disease as improving if the level of RUNX1 or PIM3 protein or mRNA decreases over time; or
(3) identifying the disease as neither worsening nor improving if the level of RUNX1 or PIM3 protein or mRNA remains the same or about the same over time,
wherein determining the level of RUNX1 or PIM3 protein or mRNA comprises
(a) providing a test sample from said subject; and
(b) assaying the level of RUNX1 or PIM3 protein or mRNA in the test sample.

Embodiment P34

The method of Embodiment P33, wherein the level of RUNX1 or PIM3 protein or mRNA is determined at least about 1, 2, 3, 4, 5, 6, 7, 8, 9, 10 or more times and/or at least once every 1, 2, 3, or 4 weeks; at least once every 1, 2, 3, 4, 5, or 6 weeks; or at least once every 1, 2, 3, 4, or 5 years.

Embodiment P35

A method of prophylaxis for a disease comprising aberrant angiogenesis, comprising identifying whether a subject is at risk of suffering from the disease according to the method of any one of Embodiments P30 to P32, and administering to the subject a treatment for the disease if the subject is identified as at risk of suffering from the disease.

Embodiment P36

A method for adjusting the dose of a compound that is administered to a subject during a treatment regimen for a disease that comprises aberrant angiogenesis, comprising periodically determining the level of RUNX1 or PIM3 protein or mRNA in the subject, and
(1) increasing the dose of the compound if the level of RUNX1 or PIM3 protein or mRNA increases over time;
(2) maintaining or decreasing the dose of the compound if the level of RUNX1 or PIM3 protein or mRNA decreases over time; or
(3) maintaining or increasing the dose of the compound if the level of RUNX1 or PIM3 protein or mRNA remains the same or about the same over time,
wherein determining the level of RUNX1 or PIM3 protein or mRNA comprises
(a) providing a test sample from said subject; and
(b) assaying the level of RUNX1 or PIM3 protein or mRNA in the test sample.

Embodiment P37

A method for identifying whether a therapy has reduced or ameliorated a disease that comprises aberrant angiogenesis in a subject comprising
(a) providing a pre-therapy test sample from said subject;
(b) assaying the pre-therapy level of RUNX1 or PIM3 protein or mRNA in the pre-therapy test sample;
(c) administering the therapy to the subject;
(d) providing a post-therapy test sample from said subject;
(e) assaying the post-therapy level of RUNX1 or PIM3 protein or mRNA in the post-therapy test sample; and
(f) identifying the therapy as having reduced or ameliorated said disease if the level of RUNX1 or PIM3 protein or mRNA in the post-therapy test sample is lower than the level of RUNX1 or PIM3 protein or mRNA in the pre-therapy test sample.

Embodiment P38

The method of any one of Embodiments P28 to P37, wherein said test sample comprises a bodily fluid from said subject.

Embodiment P39

The method of Embodiment P28, wherein said bodily fluid comprises whole blood, a component of whole blood, plasma, or serum.

Embodiment P40

The method of any one of Embodiments P28 to P39, wherein said test sample comprises a tissue biopsy.

Embodiment P41

The method of any one of Embodiments P28 to P40, wherein said subject has diabetes.

Embodiment P42

The method of any one of Embodiments P28 to P41, wherein assaying the level of RUNX1 or PIM3 protein or mRNA comprises contacting said RUNX1 or PIM3 protein or mRNA specific binding agent.

Embodiment P43

The method of Embodiment P42, wherein said binding agent comprises an antibody or a fragment thereof, or a polypeptide or a fragment thereof.

Embodiment P44

The method of Embodiment P43, wherein said binding agent comprises an antibody or a fragment thereof.

Embodiment P45

The method of Embodiment P44, wherein said antibody or fragment thereof is attached to a solid support.

Embodiment P46

The method of any one of Embodiments P28 to P45, wherein said assaying comprises an enzyme immunoassay (EIA) or a reverse transcriptase polymerase chain reaction (RT-PCR).

Embodiment P47

The method of any one of Embodiments P28 to P46, wherein said assaying comprises an enzyme-linked immunosorbent assay (ELISA), a Western blot, a mass spectrometry assay, a radioimmunoassay, or a fluoroimmunoassay.

Embodiment P48

The method of any one of Embodiments P42 or P46, wherein said binding agent comprises an oligonucleotide probe or primer.

Embodiment P49

A kit comprising
(a) (i) an agent for detecting the level of RUNX1; (ii) an agent for detecting the level of PIM3, and
(b) instructions for using the agent for diagnosing or detecting aberrant angiogenesis, for identifying whether a subject is at risk of developing a disease that comprises aberrant angiogenesis, for determining the progression of the disease, for assessing the efficacy of a treatment for the disease, and/or for adjusting the dose of a compound during the treatment of disease.

Embodiment P50

A diagnostic system comprising
(a) an assortment, collection, or compilation of test results data representing the level of RUNX1 or PIM3 in a plurality of test samples;
(b) a means for computing an index value using said level, wherein the index value comprises a diagnostic, prognostic, progression, or treatment score; and
(c) a means for reporting the index value.

Additional embodiments include Embodiments 1 to 55 following.

Embodiment 1

A method for inhibiting, treating, or preventing aberrant angiogenesis in a subject, comprising administering to said subject an effective amount of a Runt-Related Transcription Factor 1 (RUNX1) inhibitor or a PIM3 Proto-Oncogene, Serine/Threonine Kinase (PIM3) inhibitor.

Embodiment 2

The method of Embodiment 1, wherein the aberrant angiogenesis is aberrant ocular angiogenesis.

Embodiment 3

The method of Embodiment 2, wherein said subject comprises proliferative diabetic retinopathy (PDR), macular edema, non-proliferative diabetic retinopathy, age-related macular degeneration, ocular neovascularization, retinopathy of prematurity (ROP), a retinal vein occlusion, ocular ischemic syndrome, neovascular glaucoma, a retinal hemangioma, Coates' disease, FEVR, or Norrie disease.

Embodiment 4

The method of any one of Embodiments 1 to 3, wherein said subject comprises a cancer.

Embodiment 5

The method of Embodiment 3, wherein said cancer is other than leukemia.

Embodiment 6

The method of Embodiment 3, wherein said cancer comprises melanoma.

Embodiment 7

The method of Embodiment 3, wherein said cancer comprises a solid tumor.

Embodiment 8

The method of Embodiment 7, wherein said solid tumor comprises a dimension that is greater than at least about 1, 2, 3, 4, 5, 6, 7, 8, 9, 10 mm or more and/or a volume of at least about 1, 1.5, 2, 3, 4, 5, 6, 7, 8, 9, 10 mm$^3$ or more.

Embodiment 9

The method of any one of Embodiments 1 to 8, wherein said RUNX1 inhibitor or said PIM3 inhibitor is administered as part of a treatment regimen that does not comprise an additional antiangiogenic inhibitor.

Embodiment 10

The method of Embodiment 9, wherein said treatment regimen does not comprise a vascular endothelial growth factor (VEGF) pathway inhibitor.

Embodiment 11

The method of any one of Embodiments 1 to 10, wherein said RUNX1 inhibitor or said PIM3 inhibitor is administered as a monotherapy.

Embodiment 12

The method of any one of Embodiments 1 to 11, wherein said subject is an animal other than a pregnant animal, an infant, a fetus, or an embryo.

Embodiment 13

The method of any one of Embodiments 1 to 12, wherein said subject comprises diabetes.

Embodiment 14

The method of Embodiment 13, wherein said diabetes is type 1 diabetes or type 2 diabetes.

Embodiment 15

The method of any one of Embodiments 1 to 14, wherein said subject comprises retinopathy of prematurity (ROP), diabetic retinopathy (DR), age-related macular degeneration (AMD), a retinal vein occlusion, a vascular malformation, a cerebral cavernous malformation, macular edema, non-proliferative diabetic retinopathy, ocular ischemic syndrome, neovascular glaucoma, a hemangioma, a retinal hemangioma, Coats' Disease, Norrie Disease, FEVR, or Von Hippel-Lindau disease.

Embodiment 16

The method of any one of Embodiments 1 to 15, wherein said subject is at least about 10, 20, 30, 40, 50, 60, 70, 80, or 90 years old.

Embodiment 17

The method of any one of Embodiments 1 to 16, wherein said RUNX1 inhibitor or said PIM3 inhibitor comprises an aptamer, an oligonucleotide, a peptide, an antibody or a fragment thereof, or a small molecule.

Embodiment 18

The method of Embodiment 17, wherein said RUNX1 inhibitor binds to RUNX1 and/or CBFβ.

Embodiment 19

The method of Embodiment 17, wherein said RUNX1 inhibitor binds to RUNX1 or said PIM3 inhibitor binds to PIM3.

Embodiment 20

The method of Embodiment 17, wherein said RUNX1 inhibitor comprises Ro5-3335.

Embodiment 21

The method of Embodiment 17, wherein said RUNX1 inhibitor or said PIM3 inhibitor comprises an oligonucleotide.

Embodiment 22

The method of Embodiment 21, wherein said oligonucleotide comprises at least about 10, 15, 20, 25, 30, or more nucleotides in a sequence that is complementary to a nucleotide sequence within a gene or mRNA molecule that encodes RUNX1 or PIM3.

Embodiment 23

A method for inhibiting, treating, or preventing aberrant angiogenesis in a subject, comprising altering a RUNX1 or PIM3 gene in said subject.

Embodiment 24

The method of Embodiment 23, wherein altering said RUNX1 or PIM3 gene comprises the administration of (i) a Cas protein, a zinc finger nuclease (ZFN), or a transcription activator-like effector-based nuclease (TALEN), or (ii) an expression vector encoding a Cas protein, a ZFN, or a TALEN, to said subject.

Embodiment 25

The method of Embodiment 23, wherein said gene is altered with via a CRISPR-Cas9 system.

Embodiment 26

A method for inhibiting, treating, or preventing aberrant angiogenesis in a subject, comprising administering to said subject a NOTCH inhibitor in an amount that is effective to reduce RUNX1 expression or activity.

Embodiment 27

A composition comprising an effective amount of a RUNX1 inhibitor or a PIM3 inhibitor and an ophthalmically acceptable vehicle.

Embodiment 28

A method for diagnosing aberrant angiogenesis in a subject comprising
  (a) providing a test sample from said subject;
  (b) assaying the level of RUNX1, PIM3, or IGFBP3 protein or mRNA in the test sample; and
  (c) diagnosing the subject as having aberrant angiogenesis if (i) the level of RUNX1 or PIM3 protein or mRNA is elevated in the test sample compared to a normal control; or (ii) the level of IGFBP3 protein or mRNA is lower in the test sample compared to a normal control.

Embodiment 29

The method of Embodiment 28, wherein said subject is diagnosed with the aberrant angiogenesis if (i) the level of RUNX1 or PIM3 protein or mRNA is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control; or (ii) the level of IGFBP3 protein or mRNA in said test sample is less than about 5%, 10%, 15%, 20%, 25%, 30%, 40%, 45%, 50%, 55%, 60%, 65%, 70%, 75%, 80%, or 90% of the level than a normal control.

Embodiment 30

A method for identifying whether a subject is at risk of developing a disease comprising aberrant angiogenesis comprising
  (a) providing a test sample from said subject;
  (b) assaying the level of RUNX1, PIM3, or IGFBP3 protein or mRNA in the test sample; and
  (c) identifying the subject as at risk of developing the disease if the level of RUNX1, PIM3, or IGFBP3 protein or mRNA is elevated in the test sample compared to a normal control.

Embodiment 31

The method of Embodiment 30, wherein said subject is identified as at risk of developing the disease if (i) the level of RUNX1 or PIM3 protein or mRNA is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in said test sample compared to a normal control; or (ii) the level of IGFBP3 protein or mRNA in said test sample is less than about 5%, 10%, 15%, 20%, 25%, 30%, 40%, 45%, 50%, 55%, 60%, 65%, 70%, 75%, 80%, or 90% of the level than a normal control.

Embodiment 32

The method of Embodiment 30, further comprising directing the subject to obtain (i) additional screening or an additional diagnostic test for the disease if the subject is identified as at risk of developing the disease; or (ii) treatment to reduce, delay, or prevent the onset or progression of the disease.

Embodiment 33

A method for monitoring whether a disease that comprises aberrant angiogenesis is progressing in a subject who has been diagnosed with the disease, comprising periodically determining the level of RUNX1, PIM3, or IGFBP3 protein or mRNA in said subject, and
 (1) identifying the disease as worsening if (i) the level of RUNX1 or PIM3 protein or mRNA increases over time, or (ii) the level of IGFBP3 protein or mRNA decreases over time;
 (2) identifying the disease as improving if (i) the level of RUNX1 or PIM3 protein or mRNA decreases over time, or (ii) the level of IGFBP3 protein or mRNA increases over time; or
 (3) identifying the disease as neither worsening nor improving if the level of RUNX1, PIM3, or IGFBP3 protein or mRNA remains the same or about the same over time,
 wherein determining the level of RUNX1, PIM3, or IGFBP3 protein or mRNA comprises
 (a) providing a test sample from said subject; and
 (b) assaying the level of RUNX1, PIM3, or IGFBP3 protein or mRNA in the test sample.

Embodiment 34

The method of Embodiment 33, wherein the level of RUNX1, PIM3, or IGFBP3 protein or mRNA is determined at least about 1, 2, 3, 4, 5, 6, 7, 8, 9, 10 or more times and/or at least once every 1, 2, 3, or 4 weeks; at least once every 1, 2, 3, 4, 5, or 6 weeks; or at least once every 1, 2, 3, 4, or 5 years.

Embodiment 35

A method of prophylaxis for a disease comprising aberrant angiogenesis, comprising identifying whether a subject is at risk of suffering from the disease according to the method of any one of Embodiments 30 to 32, and administering to the subject a treatment for the disease if the subject is identified as at risk of suffering from the disease.

Embodiment 36

A method for adjusting the dose of a compound that is administered to a subject during a treatment regimen for a disease that comprises aberrant angiogenesis, comprising periodically determining the level of RUNX1, PIM3, or IGFBP3 protein or mRNA in the subject, and (1) increasing the dose of the compound if (i) the level of RUNX1 or PIM3 protein or mRNA increases over time, or (ii) the level of IGFBP3 protein or mRNA decreases over time;
 (2) maintaining or decreasing the dose of the compound if (i) the level of RUNX1 or PIM3 protein or mRNA decreases over time, or (ii) the level of IGFBP3 protein or mRNA increases over time; or
 (3) maintaining or increasing the dose of the compound if the level of RUNX1, PIM3, or IGFBP3 protein or mRNA remains the same or about the same over time,
 wherein determining the level of RUNX1, PIM3, or IGFBP3 protein or mRNA comprises
 (a) providing a test sample from said subject; and
 (b) assaying the level of RUNX1, PIM3, or IGFBP3 protein or mRNA in the test sample.

Embodiment 37

A method for identifying whether a therapy has reduced or ameliorated a disease that comprises aberrant angiogenesis in a subject comprising
 (a) providing a pre-therapy test sample from said subject;
 (b) assaying the pre-therapy level of RUNX1, PIM3, or IGFBP3 protein or mRNA in the pre-therapy test sample;
 (c) administering the therapy to the subject;
 (d) providing a post-therapy test sample from said subject;
 (e) assaying the post-therapy level of RUNX1, PIM3, or IGFBP3 protein or mRNA in the post-therapy test sample; and
 (f) identifying the therapy as having reduced or ameliorated said disease if (i) the level of RUNX1 or PIM3 protein or mRNA in the post-therapy test sample is lower than the level of RUNX1 or PIM3 protein or mRNA in the pre-therapy test sample, or (ii) the level of IGFBP3 protein or mRNA in the post-therapy test sample is higher than the level of IGFBP3 protein or mRNA in the pre-therapy test sample.

Embodiment 38

The method of any one of Embodiments 28 to 37, wherein said test sample comprises a bodily fluid from said subject.

Embodiment 39

The method of Embodiment 28, wherein said bodily fluid comprises whole blood, a component of whole blood, plasma, or serum.

Embodiment 40

The method of any one of Embodiments 28 to 39, wherein said test sample comprises a tissue biopsy.

Embodiment 41

The method of any one of Embodiments 28 to 40, wherein said subject has diabetes.

Embodiment 42

The method of any one of Embodiments 28 to 41, wherein assaying the level of RUNX1, PIM3, or IGFBP3 protein or mRNA comprises contacting said RUNX1, PIM3, or IGFBP3 protein or mRNA specific binding agent.

Embodiment 43

The method of Embodiment 28, wherein said binding agent comprises an antibody or a fragment thereof, or a polypeptide or a fragment thereof.

Embodiment 44

The method of Embodiment 43, wherein said binding agent comprises an antibody or a fragment thereof.

Embodiment 45

The method of Embodiment 44, wherein said antibody or fragment thereof is attached to a solid support.

Embodiment 46

The method of any one of Embodiments 28 to 45, wherein said assaying comprises an enzyme immunoassay (EIA) or a reverse transcriptase polymerase chain reaction (RT-PCR).

Embodiment 47

The method of Embodiment 46, wherein said assaying comprises an enzyme-linked immunosorbent assay (ELISA), a Western blot, a mass spectrometry assay, a radioimmunoassay, or a fluoroimmunoassay.

Embodiment 48

The method of any one of Embodiments 42, 46, or 47, wherein said binding agent comprises an oligonucleotide probe or primer.

Embodiment 49

A kit comprising
(a) (i) an agent for detecting the level of RUNX1; (ii) an agent for detecting the level of PIM3; or (iii) an agent or detecting the level of IGFBP3, and
(b) instructions for using the agent for diagnosing or detecting aberrant angiogenesis, for identifying whether a subject is at risk of developing a disease that comprises aberrant angiogenesis, for determining the progression of the disease, for assessing the efficacy of a treatment for the disease, and/or for adjusting the dose of a compound during the treatment of disease.

Embodiment 50

A diagnostic system comprising
(a) an assortment, collection, or compilation of test results data representing the level of RUNX1, PIM3, or IGFBP3 in a plurality of test samples;
(b) a means for computing an index value using said level, wherein the index value comprises a diagnostic, prognostic, progression, or treatment score; and
(c) a means for reporting the index value.

Embodiment 51

A method for inhibiting, treating, or preventing a small vessel disease (SVD) in a subject, comprising administering to said subject an effective amount of a Runt-Related Transcription Factor 1 (RUNX1) inhibitor or a PIM3 Proto-Oncogene, Serine/Threonine Kinase (PIM3) inhibitor.

Embodiment 52

The method of Embodiment 51, wherein the SVD comprises cerebral small vessel disease, cerebral autosomal recessive arteriopathy with subcortical infarcts and leukoencephalopathy (CARASIL), age-related macular degeneration (AMD), cerebral autosomal-dominant arteriopathy with subcortical infarcts and leukoencephalopathy (CADASIL), NOTCH3 loss-of-function-associated SVD, Notch 3 hyper-activation-associated SVD, nephropathy, microangiopathy, heart failure, Alagille syndrome, familial tetralogy of Fallot, patent ductus arteriosus, cerebral cavernous malformation, or diabetic retinopathy.

Embodiment 53

A method for inhibiting, treating, or preventing aberrant angiogenesis in a subject, comprising (i) increasing the expression of IGFBP3 in said subject; or (ii) administering to said subject an effective amount of IGFBP3.

Embodiment 54

A method for reducing NOTCH signaling or function in a cell, comprising contacting the cell with a RUNX1 inhibitor.

Embodiment 55

A method for reducing NOTCH signaling or function in a subject, comprising administering to said subject an effective amount of a RUNX1 inhibitor.

EXAMPLES

Example 1: Identification of RUNX1 as a Mediator of Aberrant Angiogenesis

Aberrant angiogenesis is a hallmark of proliferative diabetic retinopathy (PDR), wet age-related macular degeneration (AMD), retinopathy of prematurity (ROP), cancer, and other conditions. To identify new genes associated with the abnormal growth of vascular endothelial cells (EC), transcriptome analysis was performed on patient-derived CD31+ vascular endothelial cells obtained from surgically removed fibrovascular membranes (FVMs) from patients with PDR. RNA-sequencing identified 200 genes differentially expressed in FVM-derived CD31+ cells compared to postmortem retina-derived CD31+ cells from nondiabetic individuals with enrichment of inflammatory response and vascular development gene ontology categories. RUNX1, a master regulator of the endothelial-hematopoietic transition and vasculogenesis during development, and its targets CD44, PPIB, and PPIF were found to be upregulated in CD31+ cells derived from PDR. Immunohistochemical staining for RUNX1 showed reactivity of nuclei in vessels of FVMs, angiogenic tufts in the retina of mice with oxygen-induced retinopathy (OIR), and in vessels of human melanoma xenografts. High glucose increased RUNX1 expression, independent of osmotic effects, in cultured human microvascular retinal endothelial cells (HRMECs)

and RUNX1 knockdown led to reduced migration and proliferation of these cells. The data herein defines RUNX1 dysregulation as a hallmark of aberrant retinal angiogenesis.

Proliferative diabetic retinopathy is a common cause of blindness in the developed world's working adult population and affects those with both type 1 and type 2 diabetes mellitus. The data herein shows cell population specific profiling of transcriptional changes in CD31+ vascular endothelial cells directly derived from pathologic human samples. It was found that RUNX1 is upregulated in CD31+ cells from proliferative diabetic membranes and functions as a critical regulator of growth and migration of vascular endothelial cells.

A major challenge to understanding neovascularization in PDR is that animal models of diabetes do not develop the proliferative phase of diabetic retinopathy consistently (Jo et al. (2013) J Biomed Sci 20:38; Rakoczy E P, et al. (2010) Am J Pathol 177(5):2659-2670). FVMs in patients are removed to relieve retinal traction with associated retinal detachment and remain largely understudied as they are often discarded after ocular surgery. To establish platforms for discovering the mechanisms underlying aberrant angiogenesis, methods for the isolation and characterization of vascular EC from patient-derived PDR FVMs were developed (Kim L A, et al. (2015) Mol Vis 21:673-687). This cell system was employed to characterize the transcriptomes of freshly isolated ECs using RNA sequencing and identified RUNX1 and other genes as candidates upregulated in neovessels.

Results

RNA-Sequencing of FVM

Figure 1A:
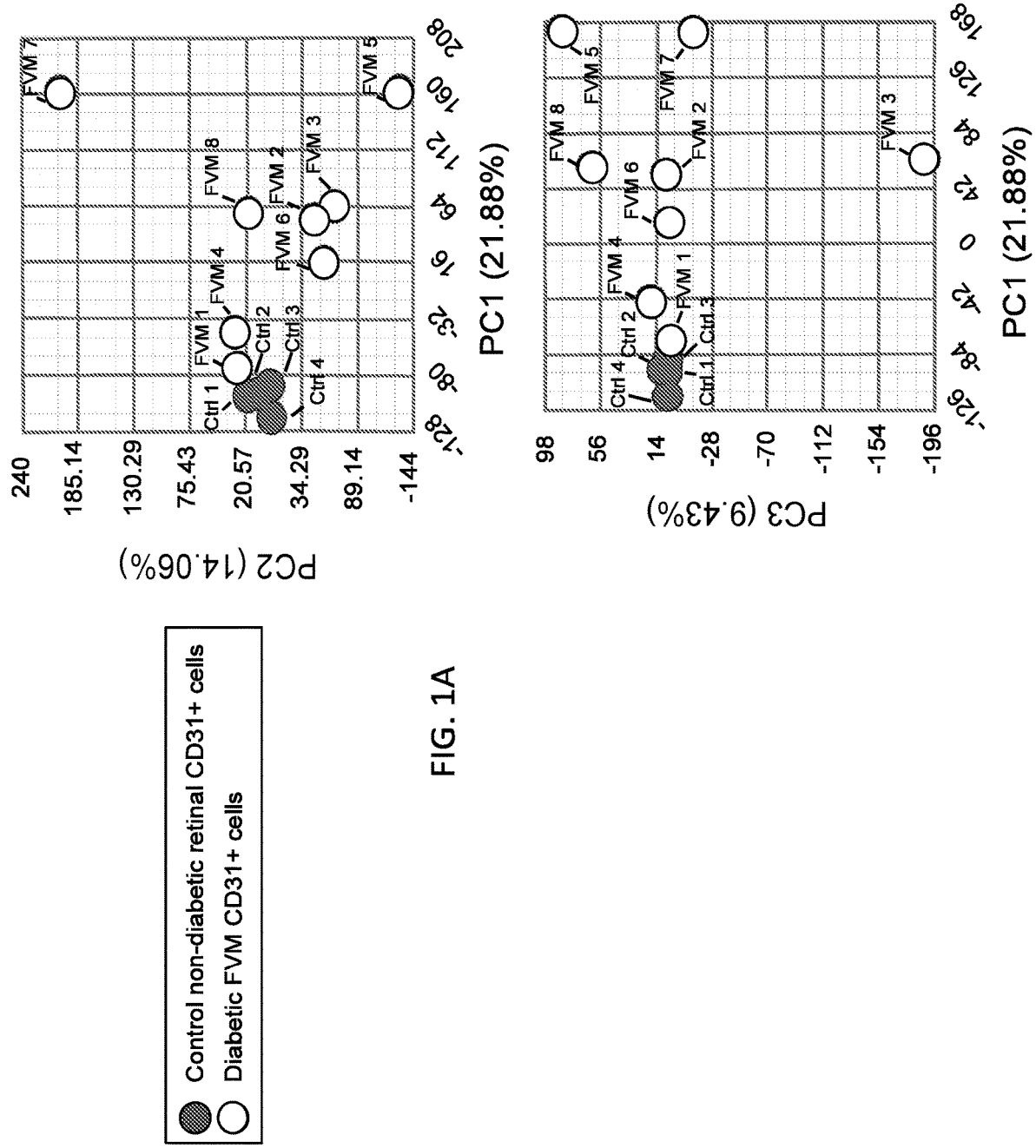
FIG. 1A is a set of graphs showing a Principle Component Analysis of transcriptomes. Two-dimensional representations of the three most significant Principle Components (PC) are provided. PC1, PC2, and PC3 account for 45.37% of the observed sample variance. The wide distribution of transcriptomes from FVM-derived CD31+ cells contrasts the congruity of transcriptomes of cells from normal retinal samples, indicating significant variance in FVM gene expression levels.
Figure 1B:
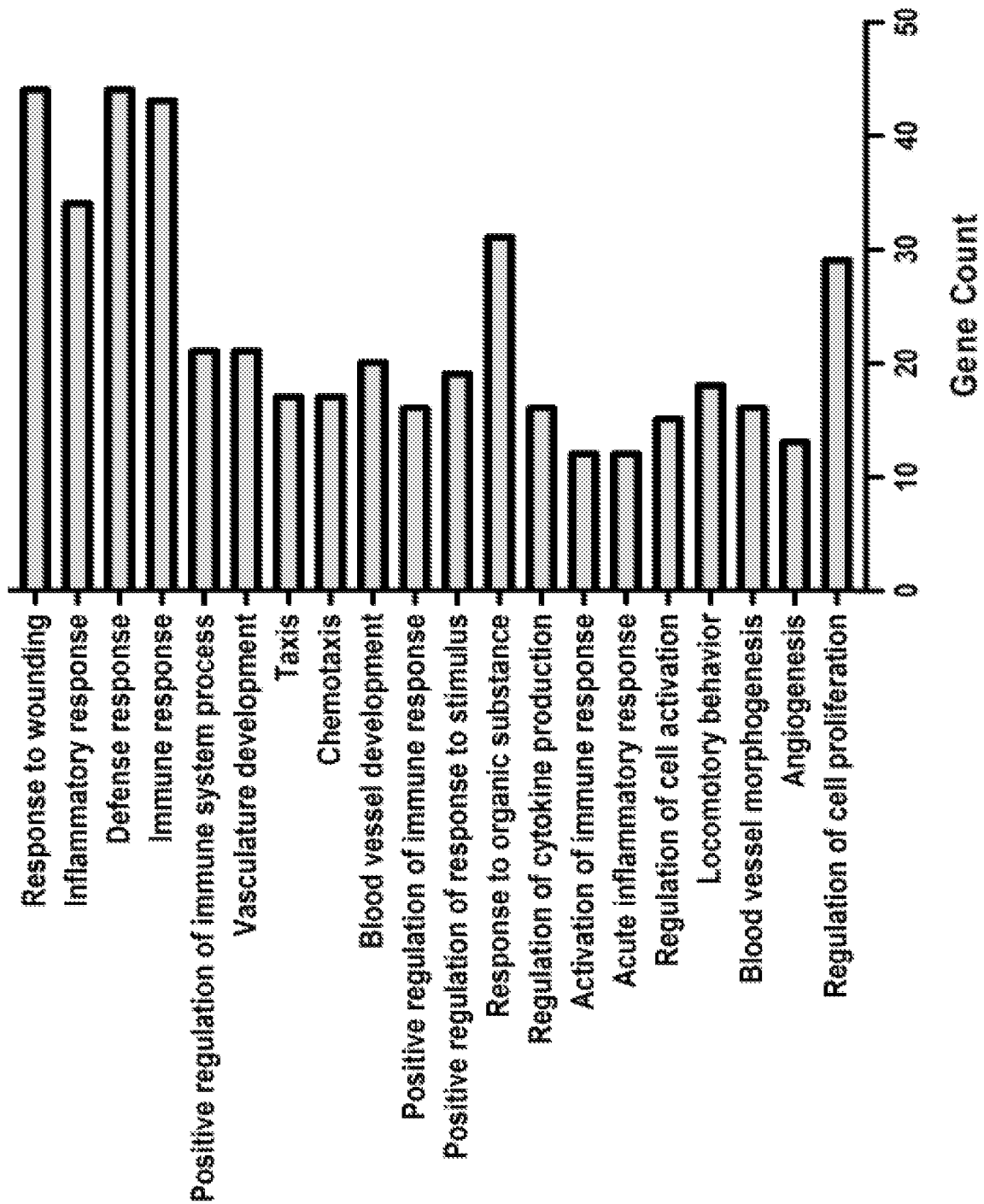
FIG. 1B is a graph showing the top twenty-five pathways presented in order of descending significance with the number of genes from the candidate gene list enriching the pathway.

Whole transcriptomic profiles were constructed for CD31+ cells from FVM and compared to transcriptomes of CD31+ cells from postmortem retinas isolated from non-diabetic individuals (FIG. 9, Table 1) (Lam et al. (2017) Diabetes 66(7):1950-1956; Kim et al. (2015) Mol Vis 21:673-687). The entire content of Lam et al. (2017) Diabetes 66(7):1950-1956, including all supplemental information, is incorporated herein by reference. Postmortem retinas were used to define expression baseline because there is no normal correlate of FVM. CD31+ cells were identified as vascular EC based on their expression of five vascular endothelial markers: CD93, CD31, KLF4, ESAM, and VEGFR1 (Table 2). However, because a single marker, namely CD31, was used for cell isolation, the presence of other cell types cannot be ruled out. Principal component analysis (PCA) of the transcriptomes demonstrated congruent expression profiles for control samples whereas profiles of cells from the FVM samples had more variable gene expression patterns (FIG. 1). The datasets are accessible through the NCBI's Gene Expression Omnibus (GSE94019) (Edgar et al. (2002) Nucleic Acids Res 30(1)207-210).

Figure 2:
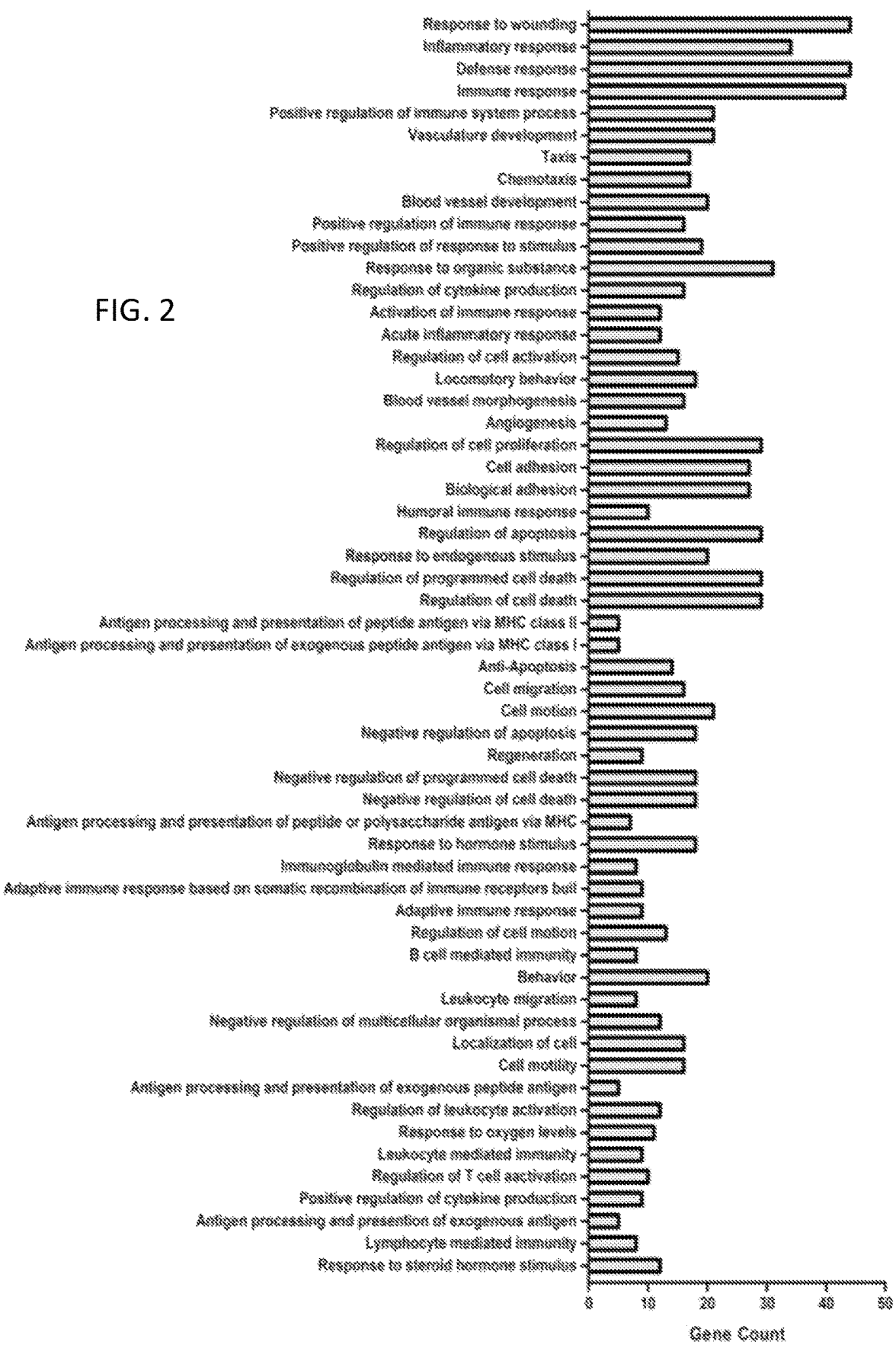
FIG. 2 is a graph showing a Database for Annotation, Visualization and Integrated Discovery (DAVID) Gene Ontology analysis of candidate genes. Pathways are presented in order of descending significance.

Two hundred genes were identified as differentially expressed in CD31+ cells from FVMs vs. controls by cross-referencing analyses from multiple analytical tools (Partek Flow, CuffLinks, EdgeR, and DESeq2) (inclusion criteria: false discovery rate (FDR)<0.05 and fold change ≥±2). Gene set analysis showed enrichment of functional Gene Ontology categories related to related to wound response, vessel development, angiogenesis, and other categories, consistent with the notion that these genes function in aberrant angiogenesis (FIG. 2, Table 3).

TABLE 1

Demographic data for control post-mortem retina and FVM from PDR patients used for RNA-sequencing.

Control Retina Samples

| Age | Sex | Last known HbA1c % (mmol/mol) | Cause of death |
|---|---|---|---|
| 25 | M | Unknown | Metastatic melanoma |
| 54 | M | 5.3 (34) | Colectomy c/b sepsis |
| 77 | M | Unknown | Respiratory failure |
| 87 | F | 5.8 (40) | Right temporoparietal hemorrhage |

Fibrovascular Membrane Samples

| Age | Sex | Type of Diabetes Mellitus | Last known HbA1c % (mmol/mol) | Surgical Indication |
|---|---|---|---|---|
| 29 | F | 1 | Unknown | VH/TRD |
| 51 | F | 2 | 6.5 (48) | VH/TRD/RRD |
| 44 | M | 1 | 7.9 (63) | TRD/RRD |
| 71 | M | 1 | Unknown | TRD/RRD |
| 38 | F | 2 | 6.3 (45) | TRD |
| 40 | F | 2 | 14 (130) | VH/TRD |
| 49 | M | 2 | 8.0 (64) | TRD/RRD |
| 48 | F | 2 | 7.2 (55) | TRD/RRD |

VH: vitreous hemorrhage, TRD: tractional retinal detachment, RRD: rhegmatogenous retinal detachment.

TABLE 2

RNA-sequencing of isolated CD31+ cells. Both control human retinal endothelial cells and CD31+ C-FVM express characteristic vascular endothelial cell markers. Differences in expression levels do not meet criteria for significance.

| | Gene Symbol | | | | |
|---|---|---|---|---|---|
| | CD93 | CD31 | KLF4 | ESAM | VEGFR1 |
| Ctrl 1 | 0.75 | 0.41 | 0.07 | 0.14 | 1.36 |
| Ctrl 2 | 2.17 | 3.26 | 1.09 | 1.41 | 32.83 |
| Ctrl 3 | 59.7 | 47.37 | 2.93 | 20.18 | 257.23 |
| Ctrl 4 | 6.28 | 5.58 | 0.93 | 3.95 | 39.75 |
| FVM 1 | 2.37 | 4.92 | 0.24 | 1.46 | 2.61 |
| FVM 2 | 203.57 | 52.74 | 44.98 | 51.23 | 91 |
| FVM 3 | 78.48 | 15.94 | 30.78 | 0.58 | 88.99 |
| FVM 4 | 103.42 | 156.32 | 31.79 | 36.96 | 38.15 |
| FVM 5 | 304.64 | 93.71 | 73.43 | 59.36 | 189.6 |
| FVM 6 | 164.94 | 50.44 | 33.49 | 19.27 | 63.13 |
| FVM 7 | 423.9 | 116.12 | 57.25 | 101.58 | 298.19 |
| FVM 8 | 313.39 | 76.8 | 27.15 | 55.27 | 136.05 |

TABLE 3

Gene set enrichment analysis of the 200 differentially expressed genes in FVMs.
Pathways that met statistical significance are listed with the relevant genes. Both up- and
downregulated genes were pooled for the analysis and percentages indicate the number of
genes from the list of 200 that were associated with the ontology term.

| Term | % | Genes | Fold Enrichment | PValue | Benjamini | FDR |
|---|---|---|---|---|---|---|
| GO:0009611~response to wounding | 22.11 | C3AR1, TNF, CCL2, AIF1, C3, PDGFA, F13A1, CXCL2, COL3A1, TLR2, NINJ1, ITGB2, C1QC, IL10, CD97, GPX1, CD44, CCL20, CXCR4, HMOX1, IL1B, C2, THBS1, B4GALT1, IRAK2, PTPN6, NFKBIZ, CEBPB, LYN, OLR1, PDPN, IL1RN, LYZ, CCL4L1, PLAUR, CD163, C1QA, C1QB, NUPR1, VCAN, CTSB, VSIG4, PLAU, CD14 | 6.606348502 | 1.66E−23 | 3.26E−20 | 2.85E−20 |
| GO:0006954~inflammatory response | 17.09 | C3AR1, TNF, CCL2, AIF1, C3, CXCL2, TLR2, ITGB2, C1QC, IL10, CD97, CD44, CCL20, CXCR4, HMOX1, IL1B, C2, THBS1, B4GALT1, IRAK2, NFKBIZ, CEBPB, LYN, OLR1, PDPN, IL1RN, LYZ, CCL4L1, CD163, C1QA, C1QB, NUPR1, VSIG4, CD14 | 8.324923077 | 4.76E−21 | 4.67E−18 | 8.17E−18 |
| GO:0006952~defense response | 22.11 | C3AR1, CCL2, TNF, AIF1, C3, CXCL2, TLR2, ITGB2, C1QC, CD74, IL10, CD97, LGALS3BP, CD44, CCL20, CXCR4, HMOX1, IL1B, C2, THBS1, TYROBP, B4GALT1, IRAK2, NFKBIZ, C5AR1, CEBPB, LYN, OLR1, PDPN, IL1RN, LYZ, CST3, CCL4L1, COLEC12, CD163, C1QA, C1QB, LILRB2, CD83, NUPR1, CXCL16, VSIG4, CD14, HLA-DRA | 5.693275945 | 5.57E−21 | 3.64E−18 | 9.55E−18 |
| GO:0006955~immune response | 21.61 | GPR183, CCL2, TNF, HLA-DRB1, C3, CXCL2, TLR2, C1QC, CD74, IL10, CD97, CCL20, CXCR4, FCER1G, IL1B, CD4, C2, HLA-DOA, THBS1, LAIR1, C5AR1, CEBPB, LYN, OLR1, CMKLR1, IL1RN, CCL4L1, COLEC12, GEM, CTSS, HLA-DQA2, | 4.959113384 | 2.94E−18 | 1.44E−15 | 5.05E−15 |

TABLE 3-continued

Gene set enrichment analysis of the 200 differentially expressed genes in FVMs.
Pathways that met statistical significance are listed with the relevant genes. Both up- and
downregulated genes were pooled for the analysis and percentages indicate the number of
genes from the list of 200 that were associated with the ontology term.

| Term | % | Genes | Fold Enrichment | PValue | Benjamini | FDR |
|---|---|---|---|---|---|---|
| GO:0002684~positive regulation of immune system process | 10.55 | C1QA, C1QB, LILRB2, CD83, RGS1, CXCL16, IRF8, CD300LF, VSIG4, LCP1, CD14, HLA-DRA, IRAK2, C3AR1, LYN, C3, TLR2, C1QC, CD74, THY1, C1QA, CD83, C1QB, CD37, IL1B, FCER1G, CD4, C2, THBS1, VSIG4, SASH3, SYK, HLA-DRA | 7.021453287 | 1.64E−11 | 6.44E−09 | 2.82E−08 |
| GO:0001944~vasculature development | 10.55 | B4GALT1, PDPN, PDGFA, COL3A1, MMP19, COL15A1, MMP2, THY1, CITED2, CDH13, GPX1, BGN, CD44, CXCR4, APOE, HMOX1, IL1B, COL1A1, THBS1, TNFAIP2, PLAU | 6.65779236 | 4.32E−11 | 1.41E−08 | 7.41E−08 |
| GO:0006935~chemotaxis | 8.54 | C3AR1, CCL2, C5AR1, CMKLR1, PDGFA, CXCL2, CCL4L1, ITGB2, IL10, PLAUR, CCL20, CXCR4, CXCL16, IL1B, CMTM3, PLAU, SYK | 8.455 | 1.48E−10 | 4.14E−08 | 2.53E−07 |
| GO:0042330~taxis | 8.54 | C3AR1, CCL2, C5AR1, CMKLR1, PDGFA, CXCL2, CCL4L1, ITGB2, IL10, PLAUR, CCL20, CXCR4, CXCL16, IL1B, CMTM3, PLAU, SYK | 8.455 | 1.48E−10 | 4.14E−08 | 2.53E−07 |
| GO:0001568~blood vessel development | 10.05 | B4GALT1, PDGFA, COL3A1, MMP19, COL15A1, MMP2, THY1, CITED2, CDH13, GPX1, BGN, CD44, CXCR4, APOE, HMOX1, IL1B, COL1A1, THBS1, TNFAIP2, PLAU | 6.496038415 | 2.17E−10 | 5.33E−08 | 3.73E−07 |
| GO:0050778~positive regulation of immune response | 8.04 | IRAK2, C3AR1, LYN, C3, TLR2, C1QC, THY1, C1QA, C1QB, IL1B, FCER1G, C2, VSIG4, SASH3, SYK, HLA-DRA | 8.780851927 | 3.52E−10 | 7.67E−08 | 6.04E−07 |
| GO:0048584~positive regulation of response to stimulus | 9.55 | IRAK2, C3AR1, TNF, LYN, C3, TLR2, C1QC, THY1, C1QA, CDH13, C1QB, IL1B, FCER1G, C2, THBS1, VSIG4, SASH3, SYK, HLA-DRA | 6.406580259 | 8.77E−10 | 1.72E−07 | 1.50E−06 |

TABLE 3-continued

Gene set enrichment analysis of the 200 differentially expressed genes in FVMs.
Pathways that met statistical significance are listed with the relevant genes. Both up- and
downregulated genes were pooled for the analysis and percentages indicate the number of
genes from the list of 200 that were associated with the ontology term.

| Term | % | Genes | Fold Enrichment | PValue | Benjamini | FDR |
|---|---|---|---|---|---|---|
| GO: 0010033~response to organic substance | 15.58 | TNF, CCL2, GRB2, PDGFA, COL3A1, TLR2, IL10, ACSL1, CD44, APOE, HMOX1, IL1B, IDH1, CD4, THBS1, IRAK2, IRS2, EGR2, LYN, IL1RN, NR4A2, FBP1, COLEC12, NR4A3, C1QB, CDH13, CD83, CCND1, CXCL16, COL1A1, CD14 | 3.421457127 | 5.06E−09 | 9.02E−07 | 8.68E−06 |
| GO:0001817~regulation of cytokine production | 8.04 | TNF, CEBPB, ATP6AP2, TLR2, IL10, CD83, REL, HMOX1, IL1B, FCER1G, CD4, VSIG4, THBS1, CD14, SASH3, SYK | 7.03438414 | 7.74E−09 | 1.27E−06 | 1.33E−05 |
| GO:0002253~activation of immune response | 6.03 | C1QA, IRAK2, C1QB, C3AR1, LYN, C3, TLR2, C2, VSIG4, C1QC, THY1, SYK | 10.15869837 | 2.35E−08 | 3.55E−06 | 4.04E−05 |
| GO:0002526-acute inflammatory response | 6.03 | C1QA, B4GALT1, C1QB, CEBPB, NUPR1, LYN, C3, IL1B, C2, VSIG4, C1QC, CD163 | 9.744057623 | 3.66E−08 | 5.13E−06 | 6.27E−05 |
| GO:0050865~regulation of cell activation | 7.54 | PDPN, PDGFA, CD74, IL10, THY1, CD83, APOE, HMOX1, IL1B, CD4, VSIG4, HLA-DOA, THBS1, SASH3, SYK | 6.820840336 | 3.91E−08 | 5.12E−06 | 6.71E−05 |
| GO:0007626~locomotory behavior | 9.05 | C3AR1, CCL2, C5AR1, CMKLR1, PDGFA, CXCL2, NR4A2, CCL4L1, ITGB2, IL10, PLAUR, CCL20, CXCR4, CXCL16, IL1B, CMTM3, PLAU, SYK | 5.227651353 | 5.75E−08 | 7.05E−06 | 9.86E−05 |
| GO:0048514~blood vessel morphogenesis | 8.04 | B4GALT1, PDGFA, MMP19, COL15A1, THY1, CITED2, CDH13, GPX1, BGN, CXCR4, APOE, HMOX1, IL1B, THBS1, TNFAIP2, PLAU | 6.034234737 | 6.10E−08 | 7.04E−06 | 1.05E−04 |
| GO: 0001525~angiogenesis | 6.53 | B4GALT1, GPX1, CDH13, CXCR4, PDGFA, HMOX1, MMP19, COL15A1, IL1B, THBS1, TNFAIP2, PLAU, THY1 | 6.989825119 | 3.28E−07 | 3.57E−05 | 5.62E−04 |
| GO:0042127~regulation of cell proliferation | 14.57 | TNF, CCL2, AIF1, PDGFA, IFI30, IL10, GPX1, APOE, HMOX1, CHST11, IL1B, THBS1, GPNMB, RHOG, SYK, B4GALT1, ODC1, PTPN6, IRS2, LYN, | 2.932296883 | 4.64E−07 | 4.80E−05 | 7.97E−04 |

TABLE 3-continued

Gene set enrichment analysis of the 200 differentially expressed genes in FVMs.
Pathways that met statistical significance are listed with the relevant genes. Both up- and
downregulated genes were pooled for the analysis and percentages indicate the number of
genes from the list of 200 that were associated with the ontology term.

| Term | % | Genes | Fold Enrichment | PValue | Benjamini | FDR |
|---|---|---|---|---|---|---|
| | | SPARC, CDH13, CCND1, NUPR1, GRN, VSIG4, PMP22, SASH3, PLAU | | | | |
| GO:0007155~cell adhesion | 13.57 | B4GALT1, CCL2, TNF, OLR1, PDPN, COL3A1, COL15A1, CCL4L1, NINJ1, POSTN, ITGB2, SIRPA, THY1, CD97, CDH13, LGALS3BP, EZR, CD44, ITGAX, FAT1, TGFBI, CD4, VCAN, GPNMB, MFAP4, THBS1, SYK | 3.069378151 | 5.61E−07 | 5.50E−05 | 9.62E−04 |
| GO:0022610~biological adhesion | 13.57 | B4GALT1, CCL2, TNF, OLR1, PDPN, COL3A1, COL15A1, CCL4L1, NINJ1, POSTN, ITGB2, SIRPA, THY1, CD97, CDH13, LGALS3BP, EZR, CD44, ITGAX, FAT1, TGFBI, CD4, VCAN, GPNMB, MFAP4, THBS1, SYK | 3.06499958 | 5.76E−07 | 5.38E−05 | 9.89E−04 |
| GO:0006959~humoral immune response | 5.03 | C1QA, CD83, C1QB, GPR183, TNF, CCL2, C3, C2, VSIG4, C1QC | 10.07297096 | 5.83E−07 | 5.20E−05 | 9.99E−04 |
| GO:0042981~regulation of apoptosis | 14.57 | BID, TNF, CCL2, TLR2, AKAP13, IL10, CD74, CITED2, GPX1, CD44, APOE, HMOX1, CHST11, IL1B, THBS1, BMF, PHLDA1, B4GALT1, CEBPB, LGALS1, BCL2A1, NR4A2, PIM3, PPIF, CDH13, NUPR1, CTSB, TNFAIP3, PRNP | 2.870295581 | 7.13E−07 | 6.08E−05 | 0.001223367 |
| GO:0009719~response to endogenous stimulus | 10.05 | IRS2, TNF, EGR2, CCL2, LYN, PDGFA, GRB2, IL1RN, NR4A2, FBP1, NR4A3, IL10, CDH13, C1QB, CCND1, HMOX1, IDH1, IL1B, COL1A1, THBS1 | 3.929702251 | 7.32E−07 | 5.98E−05 | 0.001255444 |
| GO:0043067~regulation of programmed cell death | 14.57 | BID, TNF, CCL2, TLR2, AKAP13, IL10, CD74, CITED2, GPX1, CD44, APOE, HMOX1, CHST11, IL1B, THBS1, BMF, PHLDA1, B4GALT1, CEBPB, LGALS1, BCL2A1, NR4A2, PIM3, | 2.842016807 | 8.69E−07 | 6.82E−05 | 0.001490175 |

TABLE 3-continued

Gene set enrichment analysis of the 200 differentially expressed genes in FVMs. Pathways that met statistical significance are listed with the relevant genes. Both up- and downregulated genes were pooled for the analysis and percentages indicate the number of genes from the list of 200 that were associated with the ontology term.

| Term | % | Genes | Fold Enrichment | PValue | Benjamini | FDR |
|---|---|---|---|---|---|---|
| GO:0010941~regulation of cell death | 14.57 | PPIF, CDH13, NUPR1, CTSB, TNFAIP3, PRNP BID, TNF, CCL2, TLR2, AKAP13, IL10, CD74, CITED2, GPX1, CD44, APOE, HMOX1, CHST11, IL1B, THBS1, BMF, PHLDA1, B4GALT1, CEBPB, LGALS1, BCL2A1, NR4A2, PIM3, PPIF, CDH13, NUPR1, CTSB, TNFAIP3, PRNP | 2.831555395 | 9.35E−07 | 7.05E−05 | 0.001603421 |
| GO:0019886~antigen processing and presentation of exogenous peptide antigen via MHC class II | 2.51 | IFI30, FCER1G, HLA-DOA, CD74, HLA-DRA | 49.73529412 | 1.58E−06 | 1.15E−04 | 0.002714716 |
| GO:0002495~antigen processing and presentation of peptide antigen via MHC class II | 2.51 | IFI30, FCER1G, HLA-DOA, CD74, HLA-DRA | 49.73529412 | 1.58E−06 | 1.15E−04 | 0.002714716 |
| GO:0006916~anti-apoptosis | 7.04 | CCL2, CEBPB, TNF, BCL2A1, IL10, CITED2, CDH13, GPX1, APOE, HMOX1, IL1B, TNFAIP3, THBS1, PRNP | 5.408109652 | 1.86E−06 | 1.31E−04 | 0.00319842 |
| GO:0016477~cell migration | 8.04 | B4GALT1, GPX1, CDH13, TNF, CCL2, CD44, CXCR4, CXCL16, NR4A2, IL1B, ITGB2, VCAN, THBS1, IL10, PLAU, SYK | 4.61312873 | 1.92E−06 | 1.30E−04 | 0.003292614 |
| GO:0006928~cell motion | 10.55 | B4GALT1, DNAH9, TNF, EGR2, CCL2, NR4A2, CCL4L1, ITGB2, IL10, PLAUR, CD97, CDH13, GPX1, CD44, CXCR4, CXCL16, IL1B, VCAN, THBS1, PLAU, SYK | 3.518117647 | 1.97E−06 | 1.29E−04 | 0.003387397 |
| GO:0043066~negative regulation of apoptosis | 9.05 | TNF, CCL2, CEBPB, BCL2A1, NR4A2, PIM3, IL10, CD74, CITED2, CDH13, GPX1, APOE, HMOX1, CHST11, IL1B, TNFAIP3, THBS1, PRNP | 4.046261216 | 2.12E−06 | 1.34E−04 | 0.003639777 |
| GO:0031099~regeneration | 4.52 | GPX1, CCND1, CCL2, AXL, NINJ1, VCAN, NR4A3, PLAU, PLAUR | 10.37953964 | 2.20E−06 | 1.35E−04 | 0.00377086 |
| GO:0043069~negative regulation of programmed cell death | 9.05 | TNF, CCL2, CEBPB, BCL2A1, NR4A2, PIM3, IL10, CD74, | 3.989906603 | 2.57E−06 | 1.53E−04 | 0.004401468 |

TABLE 3-continued

Gene set enrichment analysis of the 200 differentially expressed genes in FVMs. Pathways that met statistical significance are listed with the relevant genes. Both up- and downregulated genes were pooled for the analysis and percentages indicate the number of genes from the list of 200 that were associated with the ontology term.

| Term | % | Genes | Fold Enrichment | PValue | Benjamini | FDR |
|---|---|---|---|---|---|---|
| GO:0060548~negative regulation of cell death | 9.05 | CITED2, CDH13, GPX1, APOE, HMOX1, CHST11, IL1B, TNFAIP3, THBS1, PRNP, TNF, CCL2, CEBPB, BCL2A1, NR4A2, PIM3, IL10, CD74, CITED2, CDH13, GPX1, APOE, HMOX1, CHST11, IL1B, TNFAIP3, THBS1, PRNP | 3.978823529 | 2.66E−06 | 1.54E−04 | 0.004570045 |
| GO:0002504~antigen processing and presentation of peptide or polysaccharide antigen via MHC class II | 3.52 | HLA-DRB1, IFI30, FCER1G, HLA-DOA, HLA-DQA2, CD74, HLA-DRA | 16.8798574 | 2.91E−06 | 1.63E−04 | 0.004996137 |
| GO:0009725~response to hormone stimulus | 9.05 | IRS2, TNF, EGR2, CCL2, LYN, PDGFA, GRB2, IL1RN, FBP1, NR4A3, IL10, C1QB, CCND1, HMOX1, IDH1, IL1B, COL1A1, THBS1 | 3.902933162 | 3.45E−06 | 1.88E−04 | 0.005922811 |
| GO:0016064~immunoglobulin mediated immune response | 4.02 | C1QA, C1QB, C3, FCER1G, C2, C1QC, CD74, HLA-DRA | 11.78910675 | 4.53E−06 | 2.40E−04 | 0.007772813 |
| GO:0002250~adaptive immune response | 4.52 | C1QA, C1QB, C3, FCER1G, C2, C1QC, CD74, IL10, HLA-DRA | 9.301145913 | 5.08E−06 | 2.62E−04 | 0.008718605 |
| GO:0002460~adaptive immune response based on somatic recombination of immune receptors built from immunoglobulin superfamily domains | 4.52 | C1QA, C1QB, C3, FCER1G, C2, C1QC, CD74, IL10, HLA-DRA | 9.301145913 | 5.08E−06 | 2.62E−04 | 0.008718605 |
| GO:0051270~regulation of cell motion | 6.53 | B4GALT1, IRS2, LYN, PDGFA, PDPN, THY1, CITED2, CDH13, APOE, CXCR4, HMOX1, CXCL16, THBS1 | 5.360073148 | 5.44E−06 | 2.74E−04 | 0.009339329 |
| GO:0019724~B cell mediated immunity | 4.02 | C1QA, C1QB, C3, FCER1G, C2, C1QC, CD74, HLA-DRA | 11.36806723 | 5.81E−06 | 2.85E−04 | 0.009967394 |
| GO:0007610~behavior | 10.05 | C3AR1, EGR2, CCL2, C5AR1, CMKLR1, PDGFA, CXCL2, NR4A2, CCL4L1, ITGB2, NR4A3, IL10, PLAUR, CCL20, CXCR4, CXCL16, IL1B, CMTM3, PLAU, SYK | 3.393452904 | 6.33E−06 | 3.03E−04 | 0.010861559 |

TABLE 3-continued

Gene set enrichment analysis of the 200 differentially expressed genes in FVMs.
Pathways that met statistical significance are listed with the relevant genes. Both up- and
downregulated genes were pooled for the analysis and percentages indicate the number of
genes from the list of 200 that were associated with the ontology term.

| Term | % | Genes | Fold Enrichment | PValue | Benjamini | FDR |
|---|---|---|---|---|---|---|
| GO:0050900~leukocyte migration | 4.02 | B4GALT1, TNF, CCL2, CXCL16, IL1B, ITGB2, IL10, SYK | 11.16862745 | 6.55E−06 | 3.06E−04 | 0.011244287 |
| GO:0051241~negative regulation of multicellular organismal process | 6.03 | CD83, TNF, PDGFA, APOE, HMOX1, LGMN, CST3, APOC1, VSIG4, THBS1, IL10, PLAU | 5.82266858 | 6.59E−06 | 3.01E−04 | 0.011303048 |
| GO:0048870~cell motility | 8.04 | B4GALT1, GPX1, CDH13, TNF, CCL2, CD44, CXCR4, CXCL16, NR4A2, IL1B, ITGB2, VCAN, THBS1, IL10, PLAU, SYK | 4.147307913 | 7.06E−06 | 3.15E−04 | 0.01210256 |
| GO:0051674~localization of cell | 8.04 | B4GALT1, GPX1, CDH13, TNF, CCL2, CD44, CXCR4, CXCL16, NR4A2, IL1B, ITGB2, VCAN, THBS1, IL10, PLAU, SYK | 4.147307913 | 7.06E−06 | 3.15E−04 | 0.01210256 |
| GO:0002478~antigen processing and presentation of exogenous peptide antigen | 2.51 | IFI30, FCER1G, HLA-DOA, CD74, HLA-DRA | 36.17112299 | 7.24E−06 | 3.16E−04 | 0.01242693 |
| GO:0002694~regulation of leukocyte activation | 6.03 | CD83, HMOX1, IL1B, CD4, HLA-DOA, VSIG4, THBS1, CD74, SASH3, IL10, THY1, SYK | 5.752515946 | 7.40E−06 | 3.16E−04 | 0.012696405 |
| GO:0070482~response to oxygen levels | 5.53 | CCL2, PDPN, CXCR4, PDGFA, HMOX1, NR4A2, HIF3A, THBS1, MMP2, PLAU, CITED2 | 6.20809345 | 1.07E−05 | 4.47E−04 | 0.018391701 |
| GO:0002443~leukocyte mediated immunity | 4.52 | C1QA, C1QB, LYN, C3, FCER1G, C2, C1QC, CD74, HLA-DRA | 8.327770178 | 1.17E−05 | 4.76E−04 | 0.019987007 |
| GO:0050863~regulation of T cell activation | 5.03 | CD83, IL1B, CD4, HLA-DOA, VSIG4, CD74, SASH3, IL10, THY1, SYK | 6.801407743 | 1.56E−05 | 6.24E−04 | 0.026744069 |
| GO:0001819~positive regulation of cytokine production | 4.52 | CD83, TNF, ATP6AP2, TLR2, FCER1G, IL1B, THBS1, SASH3, CD14 | 7.957647059 | 1.63E−05 | 6.40E−04 | 0.027988484 |
| GO:0019884~antigen processing and presentation of exogenous antigen | 2.51 | IFI30, FCER1G, HLA-DOA, CD74, HLA-DRA | 28.42016807 | 2.13E−05 | 8.21E−04 | 0.036600887 |
| GO:0002449~lymphocyte mediated immunity | 4.02 | C1QA, C1QB, C3, FCER1G, C2, C1QC, CD74, HLA-DRA | 9.094453782 | 2.59E−05 | 9.78E−04 | 0.044487655 |
| GO:0048545~response to steroid hormone stimulus | 6.03 | C1QB, CCND1, TNF, CCL2, PDGFA, HMOX1, IL1RN, IL1B, IDH1, COL1A1, THBS1, IL10 | 4.973529412 | 2.91E−05 | 0.00107648 | 0.049898956 |

RUNX1 is Upregulated in Cultured EC Exposed to High Glucose

Figure 3A:
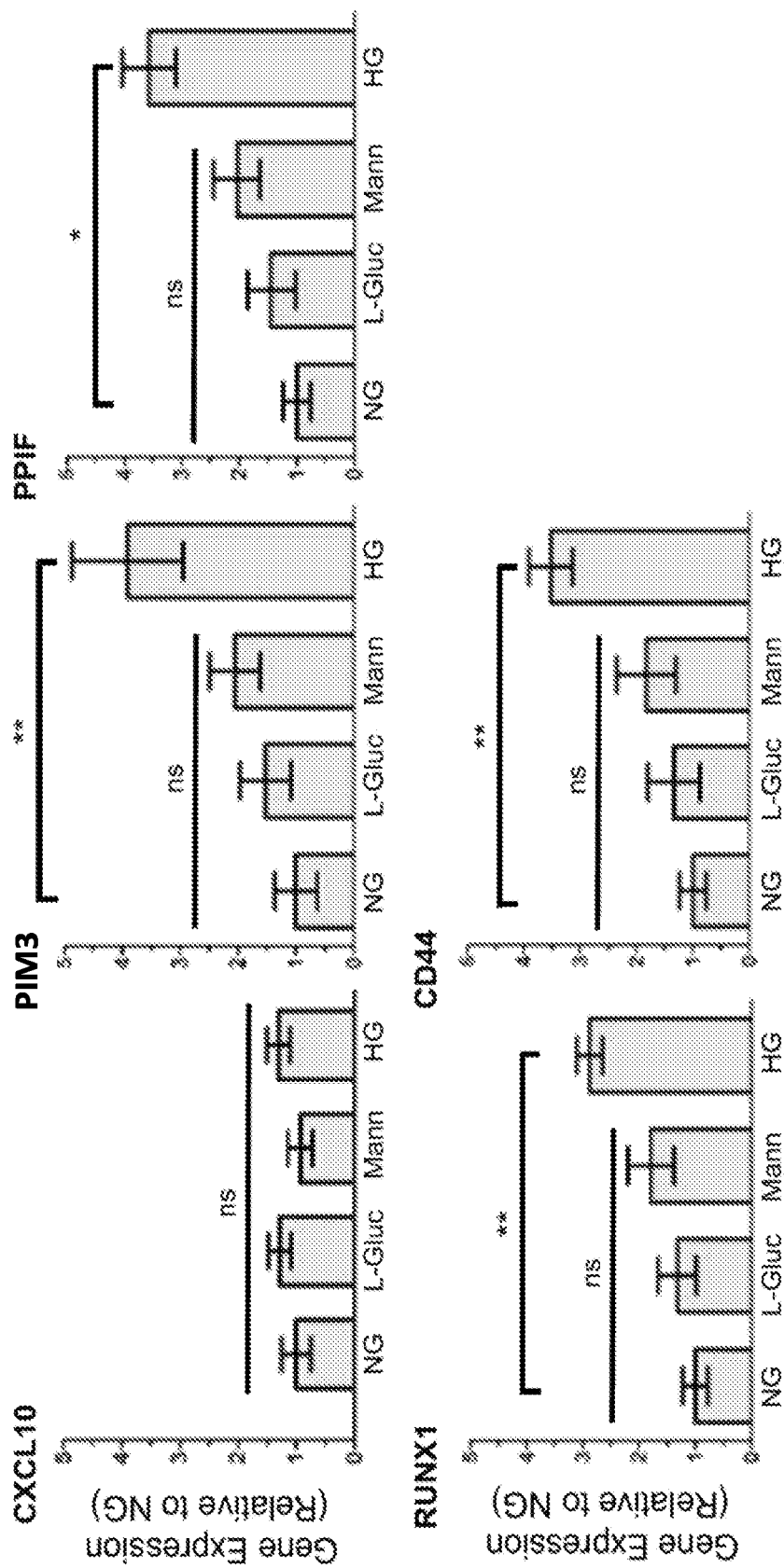
FIGS. 3A and B are graphs showing the effect of elevated glucose on human retinal microvascular endothelial cells (HRMEC) gene expression.
Figure 3B:
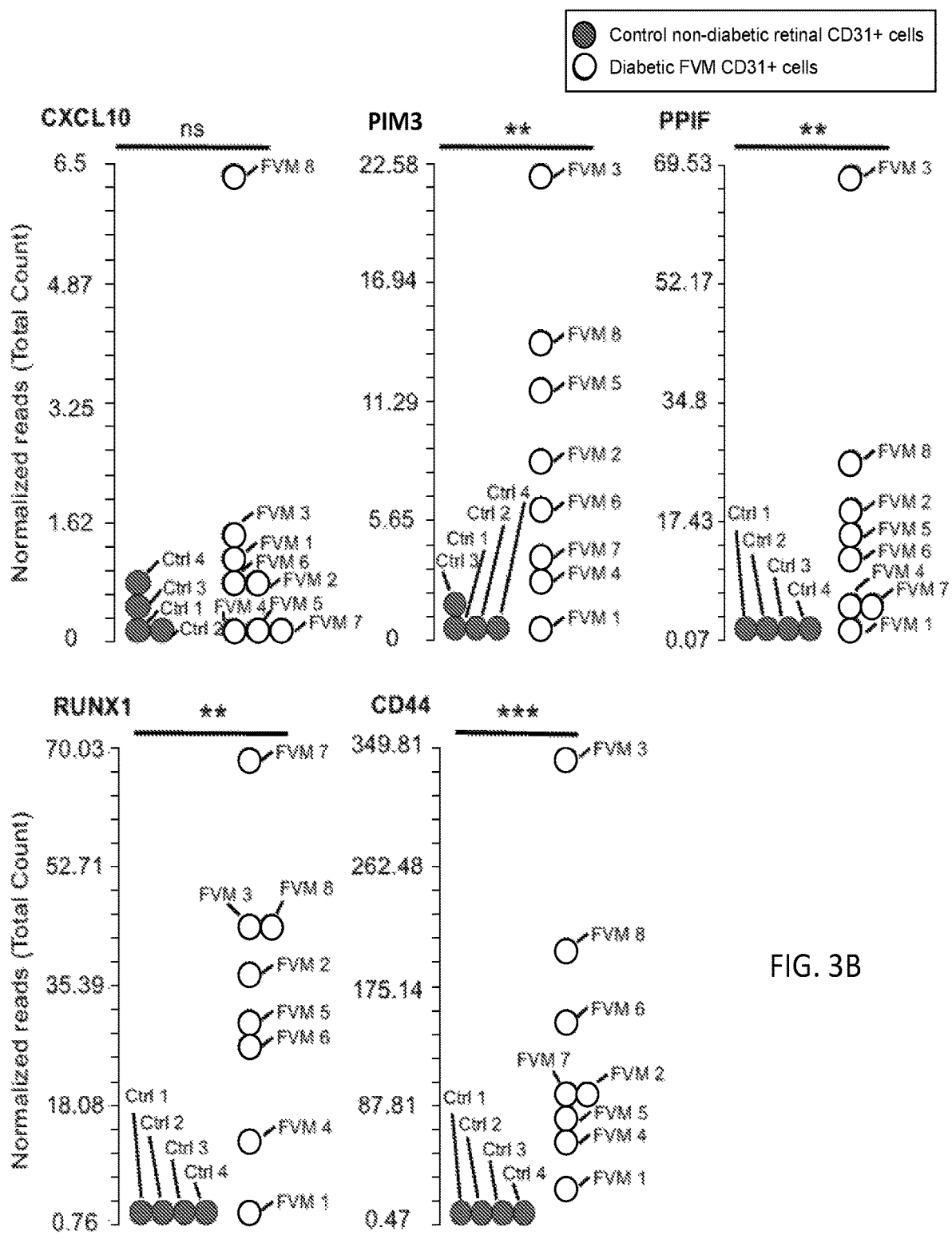
FIG. 3B: Results of FVM ribonucleic acid (RNA)-sequencing (reads per kilobase of transcript per million mapped reads, RPKM) show increased expression of PIM3, PPIF, RUNX1, and CD44 in ECs from patients with PDR compared to non-diabetic patients. CXCL10 did not exhibit increased expression in FVMs ($n_{controls}=4$; $n_{PDR-FVM}=8$). ns: not significant, * $p<0.05$,  $p<0.01$, * $p<0.001$.
Figure 4A:
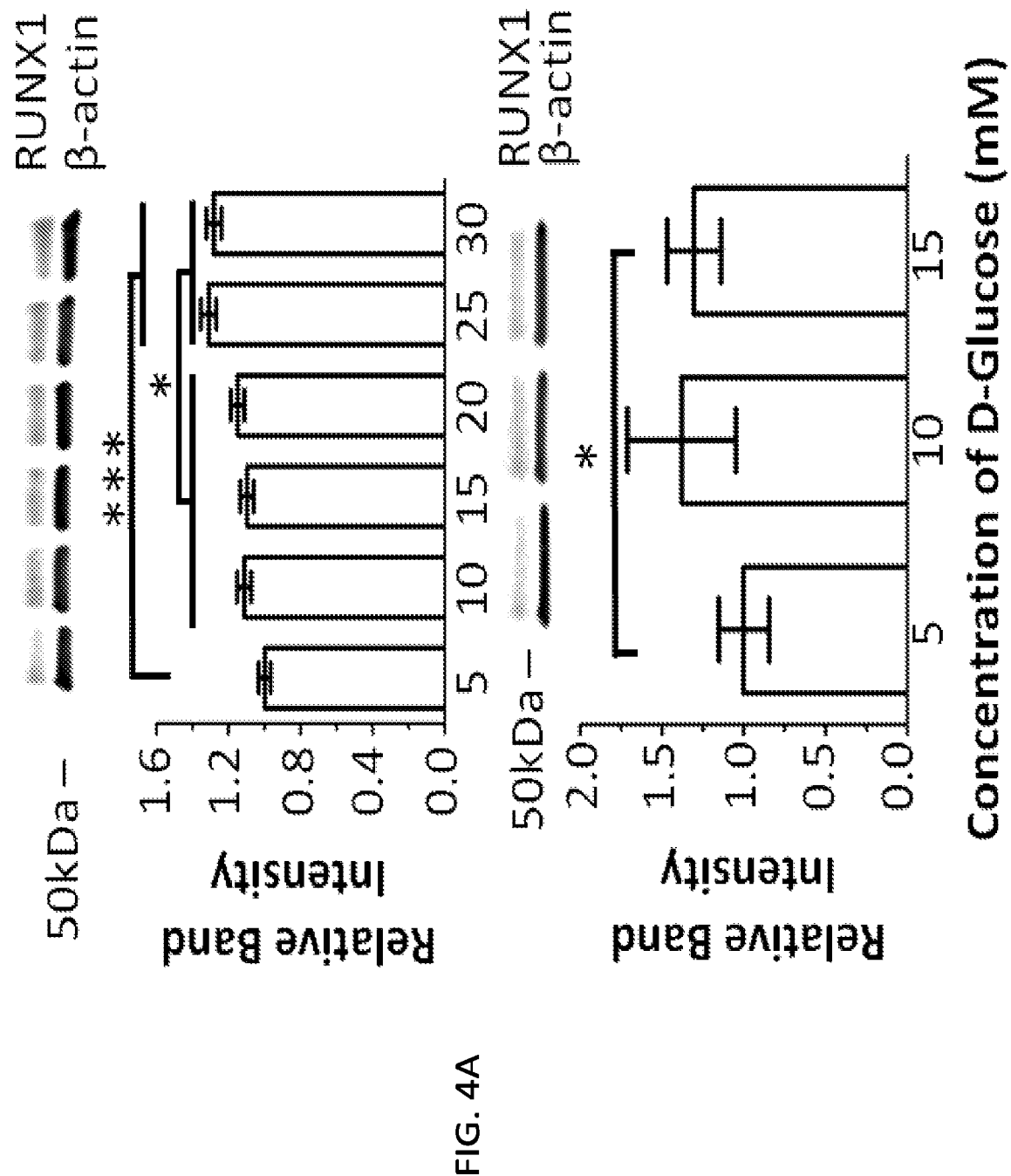
FIGS. 4A and B are images and graphs showing the effect of elevated glucose on expression of RUNX1 protein.
Figure 4B:
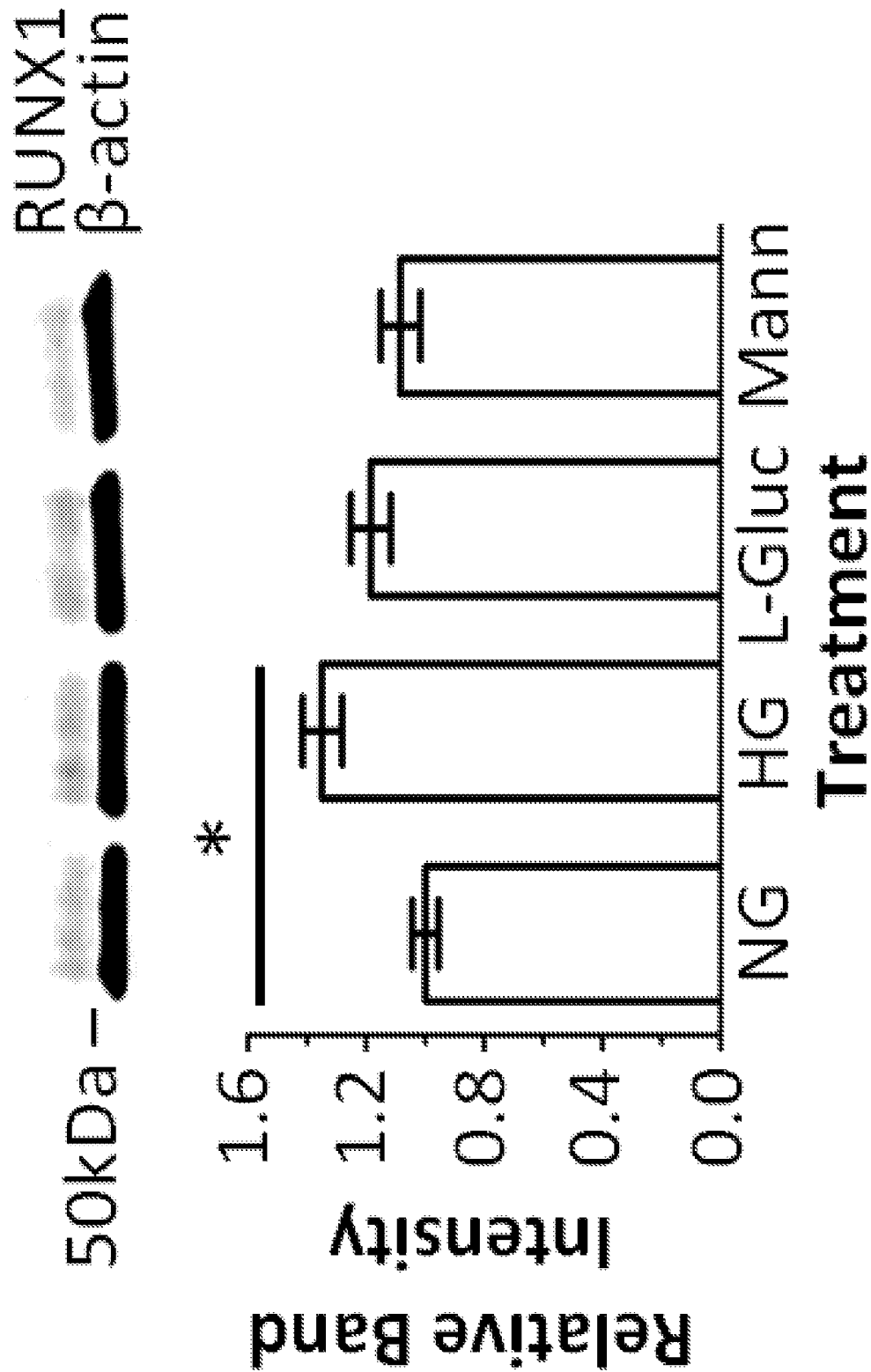
FIG. 4B: The increase in RUNX1 protein induced by 30 mM D-glucose was independent of osmotic forces (n=3; experiment performed in triplicate). * $p<0.05$,  $p<0.01$, * $p<0.001$.

Hyperglycemia is a major risk factor for progression to PDR in diabetic patients (The Diabetes Control and Complications Trial Research Group, Diabetes, 1995, 44(8):968-983). qRT-PCR was used to screen the candidate gene list for genes regulated by high glucose in primary cultures of HRMECs. Four out of one hundred and one genes were glucose responsive consistent with transcriptomic data (fold change ±SEM): RUNX1 (2.9 fold change), peptidyl-prolyl cis-trans isomerase F (PPIF; 3.6 fold change), serine/threonine-protein kinase PIM3 (Pim3; 3.9 fold change), and CD44 (3.5 fold change) (FIG. 3A). These changes were consistent with results from RNA-sequencing (FIG. 3B). RUNX1 is involved in endothelial cell biology and may have a role upstream of PPIF and CD44. Consistent with the transcriptomic and qPCR analyses, exposure of HRMEC cultures to high glucose induced a 30% increase in RUNX1 protein while osmotic controls had no significant effect (FIG. 4).

Figure 5E:
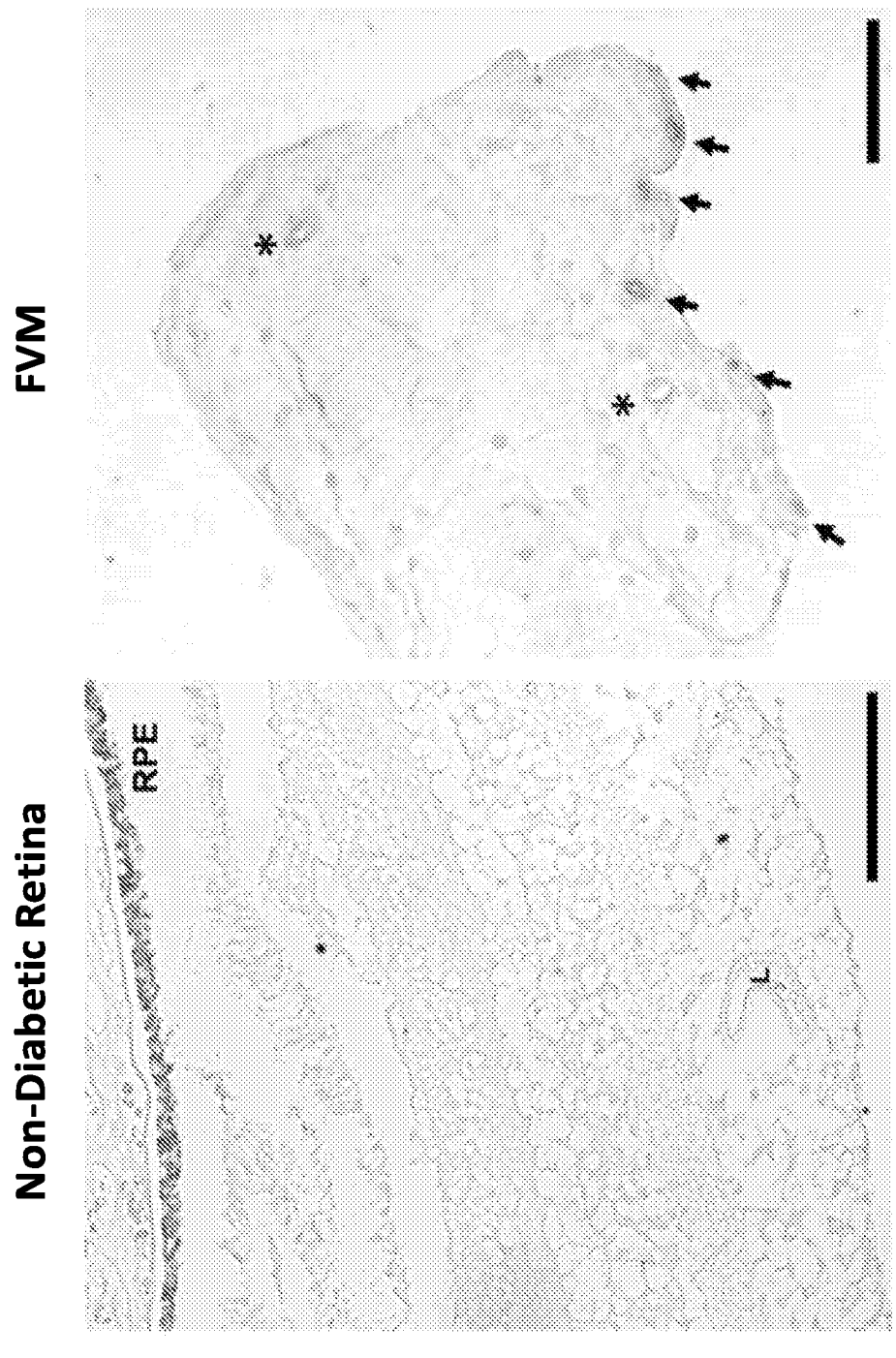

RUNX1 was focused on for further studies because of its documented roles in EC biology (The Diabetes Control and Complications Trial Research Group (1995) Diabetes 44(8): 968-983; McLeod et al. (2012) Invest Ophthalmol Vis Sci 53(13):7912-7927; Iwatsuki et al. (2005) Oncogene 24(7): 1129-1137). Exposure of HRMEC and HUVEC cultures to high glucose induced a 30% increase in RUNX1 protein while osmotic controls had no significant effect in HRMEC and HUVECs (FIGS. 4A and B). Lastly, we confirmed increased RUNX1 protein expression in vessels from FVM compared to retina from non-diabetic control using immunohistochemical staining (FIG. 5E).

TABLE 4

Primer sequences used for qRT-PCR and transcriptomic analysis. siRNA sequences are listed at the bottom of the table. Previously published sequences are denoted by an asterisk (*). The underlined primers are those used for analyses displayed in figures.

| Gene/ Symbol | Array | Alias (Genecards.org) | Forward Primer Sequence | Reverse primer Sequence |
|---|---|---|---|---|
| AIF1* | Wound, Inflammation Proliferation, Phosphoprotein | Allograft Inflammatory Factor 1 | GATGATGCTGGGCA AGAGAT (SEQ ID NO: 37) | CCTTCAAATCAGG GCAACTC (SEQ ID NO: 38) |
| AMPD3 | Phosphoprotein | Adenosine Monophosphate Deaminase 3 | AAAAGGAAGCCAAG GAGAGG (SEQ ID NO: 39) | GGGACCGAATCAT CTTGAAA (SEQ ID NO: 40) |
| APOE* | Signal, Apoptosis, Proliferation, Phosphoprotein | Apolipoprotein E | TTCTGTGGGCTGCGT TGCTG (SEQ ID NO: 41) | TACACTGCCAGGC GCTTCTG (SEQ ID NO: 42) |
| ARL4C | Metabolism | ADP-Ribosylation Factor-Like 4C | CCAGTCCCTGCATAT CGTCAT (SEQ ID NO: 43) | TTCACGAACTCGTT GAACTTGA (SEQ ID NO: 44) |
| ATP6AP2* | Signal, Phosphoprotein | ATPase, H+ Transporting, Lysosomal Accessory Protein 2 | AGGGAGTGAACAAA CTGGCTCTA (SEQ ID NO: 45) | TACCATATACACTC TATTCTCCAAAGGG TA (SEQ ID NO: 46) |
| AXL | Signal, Phosphoprotein | AXL Receptor Tyrosine Kinase | CCGTGGACCTACTCT GGCT (SEQ ID NO: 47) | CCTTGGCGTTATGG GCTTC (SEQ ID NO: 48) |
| B2M | Signal | Beta-2-Microglobulin | <u>ACTGAATTCACCCCC ACTGA</u> (SEQ ID NO: 49) | <u>CCTCCATGATGCTG CTTACA</u> (SEQ ID NO: 50) |
| BASP1* | Phosphoprotein | Brain Abundant, Membrane Attached Signal Protein 1 | CGGAGCCCACTTAG CTTGTC (SEQ ID NO: 51) | GAGAGAATGTTTG TCACTCCCAAA (SEQ ID NO: 52) |
| BGN* | Signal | Biglycan | CTGGCATCCCCAAA GACCTC (SEQ ID NO: 53) | GCTCCCGTTCTCGA TCATCC (SEQ ID NO: 54) |
| BMF* | Apoptosis | Bcl2 Modifying Factor | GACCCAACCCGGGA GCTTGC (SEQ ID NO: 55) | GAAGGCCAGGGCC ACAGCAG (SEQ ID NO: 56) |
| C10orf10 | Signal | Chromosome 10 Open Reading Frame 10 | TGCCCACAATTCGG GAGAC (SEQ ID NO: 57) | AGACCTCACGTAG TCATCCAG (SEQ ID NO: 58) |
| CCL2 | Signal, Wound, Apoptosis, Inflammation | Chemokine (C-C Motif) Ligand 2 | GCCTCCAGCATGAA AGTCTC (SEQ ID NO: 59) | AGGTGACTGGGGC ATTGAT (SEQ ID NO: 60) |

TABLE 4-continued

Primer sequences used for qRT-PCR and transcriptomic analysis. siRNA sequences are listed at the bottom of the table. Previously published sequences are denoted by an asterisk (*). The underlined primers are those used for analyses displayed in figures.

| Gene/Symbol | Array | Alias (Genecards.org) | Forward Primer Sequence | Reverse primer Sequence |
|---|---|---|---|---|
| CCL20 | Signal, Wound, Inflammation | Chemokine (C-C Motif) Ligand 20 | GTGCTGCTACTCCACCTCTG (SEQ ID NO: 61) | CGTGTGAAGCCCACAATAAA (SEQ ID NO: 62) |
| CCND1 | Proliferation, Phosphoprotein | Cyclin D1 | GCTGCGAAGTGGAAACCATC (SEQ ID NO: 63) | CCTCCTTCTGCACACATTTGAA (SEQ ID NO: 64) |
| CD14 | Signal, Wound, Inflammation | CD14 Molecule | ACGCCAGAACCTTGTGAGC (SEQ ID NO: 65) | GCATGGATCTCCACCTCTACTG (SEQ ID NO: 66) |
| CD300LF | Signal, Phosphoprotein | CD300 Molecule-Like Family Member F | GGAACCGACCTACTGCAACAT (SEQ ID NO: 67) | CTGATGGTGCTGTATTCCGTG (SEQ ID NO: 68) |
| CD44* | Signal, Wound, Apoptosis, Inflammation, Phosphoprotein | CD44 Molecule (Indian Blood Group) | <u>CGGACACCATGGACAAGTTT</u> (SEQ ID NO: 69) | <u>GAAAGCCTTGCAGAGGTCAG</u> (SEQ ID NO: 70) |
| CD83 | Signal | CD83 Molecule | CTCCGAAGATGTGGACTTGC (SEQ ID NO: 71) | TCCATCCTCTCTTCACCACC (SEQ ID NO: 72) |
| CDCP1 | Signal, Phosphoprotein | CUB Domain Containing Protein 1 | CTGAACTGCGGGGTCTCTAT (SEQ ID NO: 73) | GGCAGAGCAATCTCAAAAGC (SEQ ID NO: 74) |
| CDH13 | Signal, Apoptosis, Angiogenesis, Proliferation, Phosphoprotein | Cadherin 13 | AGTGTTCCATATCAATCAGCCAG (SEQ ID NO: 75) | CGAGACCTCATAGCGTAGCTT (SEQ ID NO: 76) |
| CECR1 | Signal | Cat Eye Syndrome Chromosome Region, Candidate 1 | CAGAGAGCATCTGGCTTCAA (SEQ ID NO: 77) | TCATGGTGCTCTCCACTGAG (SEQ ID NO: 78) |
| CHMP1B | Cell Cycle | Charged Multivesicular Body Protein 1B | AAAGAACTGAGTAGGAGTGCCA (SEQ ID NO: 79) | TGTATCCTCGCAACTTCCATGT (SEQ ID NO: 80) |
| CHST11 | Apoptosis, Proliferation | Carbohydrate (Chondroitin 4) Sulfotransferase 11 | TCCCTTTGGTGTGGACATCT (SEQ ID NO: 81) | GCAGGACAGCAGTGTTTGAG (SEQ ID NO: 82) |
| COLEC12 | Phosphoprotein | Collectin Sub-Family Member 12 | AGAGGAGGAGGAGGTGCAAT (SEQ ID NO: 83) | TGATAGAAAACTTCAGTGCCCA (SEQ ID NO: 84) |
| CREG1 | Cell Cycle | Cellular Repressor Of E1A-Stimulated Genes 1 | GGCGTGCCCTATTTCTACCTG (SEQ ID NO: 85) | CAAAGTCATGGTCAGTGTAGCAT (SEQ ID NO: 86) |
| CST3 | Signal | Cystatin C | CCAGCAACGACATGTACCAC (SEQ ID NO: 87) | CAGCTCCACGTCCAAGAAGT (SEQ ID NO: 88) |
| CTSB | Signal, Wound, Apoptosis | Cathepsin B | ACAACGTGGACATGAGCTACT (SEQ ID NO: 89) | TCGGTAAACATAACTCTCTGGGG (SEQ ID NO: 90) |
| CTSD | Signal | Cathepsin D | AGCCCTCCAGCCTTCTG (SEQ ID NO: 91) | CGGATGGACGTGAACTTGT (SEQ ID NO: 92) |
| CTSL | Metabolism | Cathepsin L | GCGCGTGACTGGTTGAG (SEQ ID NO: 93) | AAAGGCAGCAAGGATGAGTG (SEQ ID NO: 94) |

TABLE 4-continued

Primer sequences used for qRT-PCR and transcriptomic analysis. siRNA sequences are listed at the bottom of the table. Previously published sequences are denoted by an asterisk (*). The underlined primers are those used for analyses displayed in figures.

| Gene/Symbol | Array | Alias (Genecards.org) | Forward Primer Sequence | Reverse primer Sequence |
|---|---|---|---|---|
| CTSS | Signal | Cathepsin S | CTTGTGGTTGGCTATGGTGAT (SEQ ID NO: 95) | CCTTTATTTCTTGCCATCCG (SEQ ID NO: 96) |
| CXCL16 | Signal | Chemokine (C-X-C Motif) Ligand 16 | GTGTGTGGAGGCAACAAGG (SEQ ID NO: 97) | CACAATCCCCGAGTAAGCAT (SEQ ID NO: 98) |
| CXCL2 | Signal, Wound, Inflammation | Chemokine (C-X-C Motif) Ligand 2 | GGGCAGAAAGCTTGTCTCAA (SEQ ID NO: 99) | GCTTCCTCCTTCCTTCTGGT (SEQ ID NO: 100) |
| CXCR4* | Wound, Angiogenesis, Inflammation, Phosphoprotein | Chemokine (C-X-C Motif) Receptor 4 | CCAGTAGCCACCGCATCT (SEQ ID NO: 101) | ATAGTCCCCTGAGCCCATTT (SEQ ID NO: 102) |
| DBI | Phosphoprotein | Diazepam Binding Inhibitor (GABA Receptor Modulator, Acyl-CoA Binding Protein) | TGGCCACTACAAACAAGCAA (SEQ ID NO: 103) | TCCCTTTCAGCTCATTCCAG (SEQ ID NO: 104) |
| DHRS3 | Stress response | Dehydrogenase/Reductase (SDR Family) Member 3 | TTCCTGCCACGTATGCTGG (SEQ ID NO: 105) | TTTGGATGTGCAGTAGTCGATG (SEQ ID NO: 106) |
| EGR2 | Phosphoprotein | Early Growth Response 2 | TTGACCAGATGAACGGAGTG (SEQ ID NO: 107) | AGCAAAGCTGCTGGGATATG (SEQ ID NO: 108) |
| EPB41L3 | Cell Structure | Erythrocyte Membrane Protein Band 4.1-Like 3 | GAGCCTAGTCCCCACGC (SEQ ID NO: 109) | GCTTGGATTCCGAGTCTGAT (SEQ ID NO: 110) |
| EZR | Phosphoprotein | Ezrin | ACCAATCAATGTCCGAGTTACC (SEQ ID NO: 111) | GCCGATAGTCTTTACCACCTGA (SEQ ID NO: 112) |
| FAM49A | Signal | Family With Sequence Similarity 49, Member A | AGCTAAGCTGGTTCATCCCA (SEQ ID NO: 113) | GACTTTGAGCAGGTTTCCCA (SEQ ID NO: 114) |
| FAT1 | Signal, Phosphoprotein | FAT Atypical Cadherin 1 | CATCCTGTCAAGATGGGTGTTT (SEQ ID NO: 115) | TCCGAGAATGTACTCTTCAGCTT (SEQ ID NO: 116) |
| FSCN1 | Phosphoprotein | Fascin Actin-Bundling Protein 1 | CAAGGACGAGCTCTTTGCTC (SEQ ID NO: 117) | TGATTGGCAGACAGGTCCAT (SEQ ID NO: 118) |
| G0S2 | Phosphoprotein | G0/G1 Switch 2 | CTGACCGCTGCCAACTG (SEQ ID NO: 119) | CTCCTGGACCGTTTCCATCT (SEQ ID NO: 120) |
| GAL3ST4 | Signal | Galactose-3-O-Sulfotransferase 4 | TCCACATCCTCTGTCACCAC (SEQ ID NO: 121) | GGTCTCGGACAATGGAAAAA (SEQ ID NO: 122) |
| GPR183 | Phosphoprotein | G Protein-Coupled Receptor 183 | ACTGGAGAATCGGAGATGCCT (SEQ ID NO: 123) | AATGAAGCGGTCAATACTCAGG (SEQ ID NO: 124) |
| GPX1* | Wound, Apoptosis, Angiogenesis, Proliferation | Glutathione Peroxidase 1 | CAACCAGTTTGGGCATCAGR (SEQ ID NO: 125) | GTTCACCTCGCACTTCTCG (SEQ ID NO: 126) |

TABLE 4-continued

Primer sequences used for qRT-PCR and transcriptomic analysis. siRNA sequences are listed at the bottom of the table. Previously published sequences are denoted by an asterisk (*). The underlined primers are those used for analyses displayed in figures.

| Gene/Symbol | Array | Alias (Genecards.org) | Forward Primer Sequence | Reverse primer Sequence |
|---|---|---|---|---|
| GRN | Signal, Proliferation | Granulin | AGGAGAACGCTACCACGGA (SEQ ID NO: 127) | GGCAGCAGGTATAGCCATCTG (SEQ ID NO: 128) |
| GTF2B | Phosphoprotein | General Transcription Factor IIB | GCCGGTGATATGATCTGTCC (SEQ ID NO: 129) | GTCATTGCTGAAAGTTCGCC (SEQ ID NO: 130) |
| HES1 | Signal | Hes Family BHLH Transcription Factor 1 | <u>ACGTGCGAGGGCGTTAATAC</u> (SEQ ID NO: 131) | <u>GGGGTAGGTCATGGCATTGA</u> (SEQ ID NO: 132) |
| HIF3A | Stress response | Hypoxia Inducible Factor 3, Alpha Subunit | CCCAGTCGGAGAGTATCGTC (SEQ ID NO: 133) | GAATGGGTCTGCGAGAGTGT (SEQ ID NO: 134) |
| HPRT1 | Metabolism | Hypoxanthine Phosphoribosyltransferase 1 | <u>CCTGGCGTCGTGATTAGTGAT</u> (SEQ ID NO: 135) | <u>AGACGTTCAGTCCTGTCCATAA</u> (SEQ ID NO: 136) |
| HTRA1* | Signal | HtrA Serine Peptidase 1 | TGGAATCTCCTTTGCAATCC (SEQ ID NO: 137) | TTCTTGGTGATGGCTTTTCC (SEQ ID NO: 138) |
| IDH1 | Metabolism | Isocitrate Dehydrogenase 1 (NADP+), Soluble | GTCGTCATGCTTATGGGGAT (SEQ ID NO: 139) | CTTTTGGGTTCCGTCACTTG (SEQ ID NO: 140) |
| IFI30 | Signal, Proliferation, Phosphoprotein | Interferon, Gamma-Inducible Protein 30 | GCTAGCCTTCCTGACCATTG (SEQ ID NO: 141) | CCATGATAGTGTCTGGCGAC (SEQ ID NO: 142) |
| IGFBP3 | Signal, Angiogenesis | Insulin-like growth factor-binding protein 3 | CTC TGC GTC AAC GCT AGT GC (SEQ ID NO: 143) | CGG TCT TCC TCC GAC TCA CT (SEQ ID NO: 144) |
| IRAK2 | Wound, Inflammation | Interleukin-1 Receptor-Associated Kinase 2 | CTGCCACCCCAATGTCTTACC (SEQ ID NO: 145) | AGGGAACCATTTGCCATGTAG (SEQ ID NO: 146) |
| IRS2 | Proliferation, Phosphoprotein | Insulin Receptor Substrate 2 | ACCTACGCCAGCATTGACTT (SEQ ID NO: 147) | CATCCTGGTGATAAAGCCAGA (SEQ ID NO: 148) |
| LAPTM5 | Hematopoiesis | Lysosomal Protein Transmembrane 5 | AGACCTGCTGCTGCTTCAAT (SEQ ID NO: 149) | CATGGGCCACCTCTACTGAG (SEQ ID NO: 150) |
| LGALS1 | Signal | Lectin, Galactoside-Binding, Soluble, 1 | TCGCCAGCAACCTGAATCTC (SEQ ID NO: 151) | GCACGAAGCTCTTAGCGTCA (SEQ ID NO: 152) |
| LGALS3BP | Signal, Apoptosis, Phosphoprotein | Lectin, Galactoside-Binding, Soluble, 3 Binding Protein | GAGGAGGCTCCACACGG (SEQ ID NO: 153) | AGCAGCCACACCCAGAAG (SEQ ID NO: 154) |
| LGMN | Signal | Legumain | CTGAAGATGGAGGCAAGCAC (SEQ ID NO: 155) | TTGCGGTGAATGATCTGGTA (SEQ ID NO: 156) |
| LHFPL2 | Signal | Lipoma HMGIC Fusion Partner-Like 2 | TCTTCAATGTCTGTGGGCTG (SEQ ID NO: 157) | GTCTATGGCCTTCTGGCAAC (SEQ ID NO: 158) |
| LST1 | Proliferation, Phosphoprotein | Leukocyte Specific Transcript 1 | CTGGCCAGTTTGGAGTCGT (SEQ ID NO: 159) | TCCTTGCTCTTTTAGGCGAA (SEQ ID NO: 160) |

TABLE 4-continued

Primer sequences used for qRT-PCR and transcriptomic analysis. siRNA sequences are listed at the bottom of the table. Previously published sequences are denoted by an asterisk (*). The underlined primers are those used for analyses displayed in figures.

| Gene/Symbol | Array | Alias (Genecards.org) | Forward Primer Sequence | Reverse primer Sequence |
|---|---|---|---|---|
| LTBP2 | Signal, Phosphoprotein | Latent Transforming Growth Factor Beta Binding Protein 2 | ACCTTGGCCAGAGC ACAG (SEQ ID NO: 161) | TGGGAAGGGTGGG TCTG (SEQ ID NO: 162) |
| LYN | Wound, Inflammation, Proliferation, Phosphoprotein | LYN Proto-Oncogene, Src Family Tyrosine Kinase | CTGAACTCAAGTCA CCGTGG (SEQ ID NO: 163) | TCCATCGTCACTCA AGCTGT (SEQ ID NO: 164) |
| MAFB | Hematopoiesis | V-Maf Avian Musculoaponeurotic Fibrosarcoma Oncogene Homolog B | CATAGAGAACGTGG CAGCAA (SEQ ID NO: 165) | ATGCCCGGAACTTT TTCTTT (SEQ ID NO: 166) |
| MMP19 | Signal, Angiogenesis | Matrix Metallopeptidase 19 | GCCTCGTTGTGGCCT AGAG (SEQ ID NO: 167) | ATGCGGAAAGTCA GGTGCTTC (SEQ ID NO: 168) |
| MMP2* | Signal, Phosphoprotein | Matrix Metallopeptidase 2 | CAGATGCCTGGAAT GCCATC (SEQ ID NO: 169) | GCAGCCTAGCCAG TCGGATT (SEQ ID NO: 170) |
| NEK6 | Phosphoprotein | NIMA-Related Kinase 6 | CAGGACTGTGTCAA GGAGATCG (SEQ ID NO: 171) | ATGTTCAGCTCGTT GTCTTCG (SEQ ID NO: 172) |
| NFKBIZ | Wound, Inflammation | Nuclear Factor Of Kappa Light Polypeptide Gene Enhancer In B-Cells Inhibitor, Zeta | ACACCCACAAACCA ACTCTGG (SEQ ID NO: 173) | GGCAAAACTGTGA TTCTGGACC (SEQ ID NO: 174) |
| NINJ1 | Wound | Ninjurin 1 | ACCGAGGAGTACGA GCTCAA (SEQ ID NO: 175) | GCTCTTCTTGCTGG CGTAAT (SEQ ID NO: 176) |
| NPC2 | Signal | Niemann-Pick Disease, Type C2 | AGCTACATTCCTGCT CCTGG (SEQ ID NO: 177) | TGGGCTCACATTCA CTTCCT (SEQ ID NO: 178) |
| NR4A2* | Apoptosis, Phosphoprotein | Nuclear Receptor Subfamily 4, Group A, Member 2 | CGACATTTCTGCCTT CTCC (SEQ ID NO: 179) | GGTAAAGTGTCCA GGAAAAG (SEQ ID NO: 180) |
| ODC1 | Proliferation, Phosphoprotein | Ornithine Decarboxylase 1 | GGCTGCGACTCAGG CTC (SEQ ID NO: 181) | CCCTTGGAACAGC AGTGAC (SEQ ID NO: 182) |
| OLFML2B | Signal | Olfactomedin-Like 2B | CCCCGAAGAAGAAG ATGACA (SEQ ID NO: 183) | CCATATGTGTTCTG GGTGGTC (SEQ ID NO: 184) |
| PDGFA* | Signal, Wound, Angiogenesis, Proliferation | Platelet-Derived Growth Factor Alpha Polypeptide | TCCACGCCACTAAG CATGTG (SEQ ID NO: 185) | CGTAAATGACCGT CCTGGTCTT (SEQ ID NO: 186) |
| PHLDA1 | Apoptosis | Pleckstrin Homology-Like Domain, Family A, Member 1 | CTCCAACTCTGCCTG AAAGG (SEQ ID NO: 187) | TGTTTTGCTTTTGA TCCAAGTG (SEQ ID NO: 188) |
| PIM3 | Apoptosis, Phosphoprotein | PIM3 Proto-Oncogene, Serine/Threonine Kinase | <u>AAGGACGAAAATCT GCTTGTGG</u> (SEQ ID NO: 189) | <u>CGAAGTCGGTGTA GACCGTG</u> (SEQ ID NO: 190) |
| PLAU | Signal, Wound, Angiogenesis, | Plasminogen Activator, | GGGAATGGTCACTT TTACCGAG | GGGCATGGTACGT TTGCTG |

TABLE 4-continued

Primer sequences used for qRT-PCR and transcriptomic analysis. siRNA sequences are listed at the bottom of the table. Previously published sequences are denoted by an asterisk (*). The underlined primers are those used for analyses displayed in figures.

| Gene/ Symbol | Array | Alias (Genecards.org) | Forward Primer Sequence | Reverse primer Sequence |
|---|---|---|---|---|
| | Proliferation, Phosphoprotein | Urokinase | (SEQ ID NO: 191) | (SEQ ID NO: 192) |
| PLAUR | Signal, Wound | Plasminogen Activator, Urokinase Receptor | AGCCTTACCGAGGT TGTGTG (SEQ ID NO: 193) | AAATGCATTCGAG GTAACGG (SEQ ID NO: 194) |
| PLD3 | Signal | Phospholipase D Family, Member 3 | GGAGATCTGCCTCA ATGGAA (SEQ ID NO: 195) | CCACGTTGAGTAG AGCCTTCA (SEQ ID NO: 196) |
| PMP22 | Proliferation | Peripheral Myelin Protein 22 | TCAGGAAATGTCCA CCACTG (SEQ ID NO: 197) | GCTGAAGATGATC GACAGGA (SEQ ID NO: 198) |
| PPIB | Signal | Peptidylprolyl Isomerase B (Cyclophilin B) | AAGGACTTCATGAT CCAGGG (SEQ ID NO: 199) | TGAAGTTCTCATCG GGGAAG (SEQ ID NO: 200) |
| PPIF | Apoptosis | Peptidylprolyl Isomerase F | <u>ACAGGGTGATCCCT TCCTTC</u> (SEQ ID NO: 201) | <u>AAGTTCTCGTCAG GAAAGCG</u> (SEQ ID NO: 202) |
| PRNP | Signal, Apoptosis, Phosphoprotein | Prion Protein | CACGACTGCGTCAA TATCACA (SEQ ID NO: 203) | CTCCATCATCTTAA CGTCGGTC (SEQ ID NO: 204) |
| RCC2 | Phosphoprotein | Regulator of Chromosome Condensation 2 | AAGGAGCGCGTCAA ACTTGAA (SEQ ID NO: 205) | GCTTGCTGTTTAGG CACTTCTT (SEQ ID NO: 206) |
| REL | Phosphoprotein | V-Rel Avian Reticuloendotheliosis Viral Oncogene Homolog | GCAGAGGGGAATGC GTTTTAG (SEQ ID NO: 207) | AGAAGGGTATGTT CGGTTGTTG (SEQ ID NO: 208) |
| RGS1 | Signal | Regulator of G-Protein Signaling 1 | GGAAAAACTTCTTG CCAACC (SEQ ID NO: 209) | TAGTCTTCACAAGC CAGCCA (SEQ ID NO: 210) |
| RHOG | Proliferation | Ras Homolog Family Member G | ACGATGCAGAGCAT CAAGTG (SEQ ID NO: 211) | TTTGGGGAAAGCG TTAGTTG (SEQ ID NO: 212) |
| RILPL2 | Signal | Rab Interacting Lysosomal Protein-Like 2 | ACGTGTATGACATCT CCTACCTG (SEQ ID NO: 213) | ACGCGGACGACTT TGAACTG (SEQ ID NO: 214) |
| RUNX1* | Phosphoprotein | Runt-Related Transcription Factor 1 | <u>TCCACAAACCCACC GCAAGT</u> (SEQ ID NO: 215) | <u>CGCTCGGAAAAGG ACAAGC</u> (SEQ ID NO: 216) |
| RUNX2 | Phosphoprotein | Runt-Related Transcription Factor 2 | ACCATGGTGGAGAT CATCGCCG (SEQ ID NO: 217) | TCCCATCTGGTACC TCTCCGAGGG (SEQ ID NO: 218) |
| Runx3 | Phosphoprotein | Runt-Related Transcription Factor 3 | AGG CAA TGA CGA GAA CTA CTC C (SEQ ID NO: 219) | GTG GGG TTG GTG AAC ACA GT (SEQ ID NO: 220) |
| SAMSN1 | Phosphoprotein | SAM Domain, SH3 Domain And Nuclear Localization Signals 1 | TGCTCAAGAGAAAG CCATCC (SEQ ID NO: 221) | TTATTCCGAAAAC GATCGAAA (SEQ ID NO: 222) |
| SCD | Phosphoprotein | Stearoyl-CoA Desaturase (Delta-9-Desaturase) | TTCCTACCTGCAAGT TCTACACC (SEQ ID NO: 223) | CCGAGCTTTGTAA GAGCGGT (SEQ ID NO: 224) |

TABLE 4-continued

Primer sequences used for qRT-PCR and transcriptomic analysis. siRNA sequences are listed at the bottom of the table. Previously published sequences are denoted by an asterisk (*). The underlined primers are those used for analyses displayed in figures.

| Gene/Symbol | Array | Alias (Genecards.org) | Forward Primer Sequence | Reverse primer Sequence |
|---|---|---|---|---|
| SDC4 | Signal, Phosphoprotein | Syndecan 4 | TCCCCACCGAACCCAAGAA (SEQ ID NO: 225) | CCTTGTTGGACACATCCTCAC (SEQ ID NO: 226) |
| SH2B3 | Phosphoprotein | SH2B Adaptor Protein 3 | CTGGAGCTCTTCGACCCA (SEQ ID NO: 227) | GTTGTCAGGCATCTCAAGCC (SEQ ID NO: 228) |
| SMS | Phosphoprotein | Spermine Synthase | CCTCACTATGGCAGCAGCAC (SEQ ID NO: 229) | TCCTGGAAAATGGACTGGAG (SEQ ID NO: 230) |
| THBS1 | Signal, Wound, Apoptosis, Angiogenesis, Inflammation, Proliferation | Thrombospondin 1 | CAATGCCACAGTTCCTGATG (SEQ ID NO: 231) | CACAGCTCGTAGAACAGGAGG (SEQ ID NO: 232) |
| THY1* | Signal, Angiogenesis | Thy-1 Cell Surface Antigen | TCAGGAAATGGCTTTTCCCA (SEQ ID NO: 233) | TCCTCAATGAGATGCCATAAGCT (SEQ ID NO: 234) |
| TNFAIP2 | Angiogenesis, Phosphoprotein | Tumor Necrosis Factor, Alpha-Induced Protein 2 | CACCTACATGCTGCTGCTCT (SEQ ID NO: 235) | CCCATACCCTGCAGCTCAC (SEQ ID NO: 236) |
| TNFAIP3 | Apoptosis | Tumor Necrosis Factor, Alpha-Induced Protein 3 | TTGTCCTCAGTTTCGGGAGAT (SEQ ID NO: 237) | ACTTCTCGACACCAGTTGAGTT (SEQ ID NO: 238) |
| TTYH2 | Phosphoprotein | Tweety Family Member 2 | CCCCTGTCTCCGAGTACATGA (SEQ ID NO: 239) | CTCCCGATTAGTGGCACGTTC (SEQ ID NO: 240) |
| UNC93B1 | Phosphoprotein | Unc-93 Homolog B1 (C. Elegans) | TTTTGGAACGAAGTGGATGATGT (SEQ ID NO: 241) | GGCACAAGCGTGTAGTAGC (SEQ ID NO: 242) |
| VAMP8 | Phosphoprotein | Vesicle-Associated Membrane Protein 8 | ACTTGGAACATCTCCGCAAC (SEQ ID NO: 243) | CTTCCACCAGAATTTCCGAG (SEQ ID NO: 244) |
| ZSWIM6 | Signal | Zinc Finger, SWIM-Type Containing 6 | AAGCGGCTGCGTAGACAAC (SEQ ID NO: 245) | GGCTCCGATTGTATTGCAGGT (SEQ ID NO: 246) |
| RUNX1 siRNA1 | small interfering RNA | hs.Ri.RUNX1.13.3 | CCUUUCAUGUUAAUCAAACAAGUG A (SEQ ID NO: 247) | UCACUUGUUUGAUUAACAUGAAAGG A (SEQ ID NO: 248) |
| RUNX1 siRNA2 | small interfering RNA | HSC.RNAI.N001001890.12.1 | ACUAGAUGAUCAGACCAAGCCCGGG (SEQ ID NO: 249) | CCCGGGCUUGGUCUGAUCAUCUAGUUU (SEQ ID NO: 250) |
| Control siRNA | small interfering RNA | Negative Control 1:DS NC1 | | | siRNA sequences:
Human RUNX1
Duplex name: hs.Ri.RUNX1.13.3
Duplex sequences (SEQ ID NO: 247)
5'-rCrCrUrUrUrCrArUrGrUrUrArArUrCrArArArCrArArGrUGA-3'

(SEQ ID NO: 248)
5'-rUrCrArCrUrUrGrUrUrUrGrArUrUrArArCrArUrGrArArArGrGrGrA-3'

(SEQ ID NO: 247)
5'-CCUUUCAUGUUAAUCAAACAAGUGA-3'

(SEQ ID NO: 248)
3'-AGGGAAAGUACAAUUAGUUUGUUCACU-5'

Human RUNX1
Duplex name: HSC.RNAI.N001001890.12.1_10 nm
Duplex sequences (SEQ ID NO: 249)
5'-rArCrUrArGrArUrGrArUrCrArGrArCrCrArArGrCrCrCrGGG-3'

(SEQ ID NO: 250)
5'-rCrCrCrGrGrGrCrUrUrGrGrUrCrUrGrArUrCrArUrCrUrArGrUrUrU-3'

(SEQ ID NO: 249)
5'-ACUAGAUGAUCAGACCAAGCCCGGG-3'

(SEQ ID NO: 250)
3'-UUUGAUCUACUAGUCUGGUUCGGGCCC-5'

Human PIM3
Duplex name: hsRi.PIM3.13.1
Duplex sequences (SEQ ID NO: 251)
5'-rGrCrCrUrGrArGrCrGrUrUrUrArArUrUrUrArUrUrCrArGTA-3'

(SEQ ID NO: 252)
5'-rUrArCrUrGrArArUrArArArUrUrArArArCrGrCrUrCrArGrGrUrC-3'

(SEQ ID NO: 251)
5'-CCUGAGCGUUUAAUUUAUUCAGTA-3'

(SEQ ID NO: 252)
3'-CUCGGACUCGCAAAUUAAAUAAGUCAU-5'

Human PIM3
Duplex name: hsRi.PIM3.13.2
Duplex sequences (SEQ ID NO: 253)
5'-rGrGrCrGrUrGrCrUrUrCrUrCrUrArCrGrArUrArUrGrGrUGT-3'

(SEQ ID NO: 254)
5-rArCrCrCrGrCrArCrGrArArGrArGrArUrGrCrUrArUrArCrCrArCrA-3'

(SEQ ID NO: 253)
5'-GGCGUGCUUCUCUACGAUAUGGUGT-3'

(SEQ ID NO: 254)
3'-ACCCGCACGAAGAGAUGCUAUACCACA-5'

In the siRNA sequences shown above, each T may optionally be a U.

RUNX1 is Upregulated in Human FVMs, Retinas of Mice with OIR, and Melanoma Tumor Vessels To further investigate the relevance of these findings, sections of diabetic patient-derived FVMs and control retinas from non-diabetics were stained for the presence of RUNX1. There was strong RUNX1 staining in blood vessels of FVMs localized to the nuclei (FIG. 5B, D), in contrast to blood vessels in retinas from non-diabetics where RUNX1 immunostaining was undetectable (FIG. 5A, C). To test the hypothesis that elevated RUNX1 is associated with aberrant angiogenesis broadly, retinas from C57BL/6J mice with OIR were stained for RUNX1 expression (Smith L E, et al. (1994) Invest Ophthalmol Vis Sci 35(1):101-111). Immunostaining for isolectin B4 was used to visualize both normal retinal vessels and neovascular tufts. Neovascular tufts in these retina were strongly immuno-positive for RUNX1 whereas the underlying normal retinal vasculature was unstained (FIGS. 6A-C). Paraffin-embedded sections of human melanoma inoculated in nude mice also demonstrated positive immunostaining for Runx1 in nuclei of peritumoral vessels compared to normal capillaries of the hypodermis (Kozlowski et al. (1984) J Natl Cancer Inst 72(4):913-917). Control sections exposed to secondary antibody alone showed no specific staining (FIG. 6D). RUNX1 expression was mainly found in capillaries, consistent with RUNX1's role in angiogenesis (FIG. 6E-F).

Figure 8A:
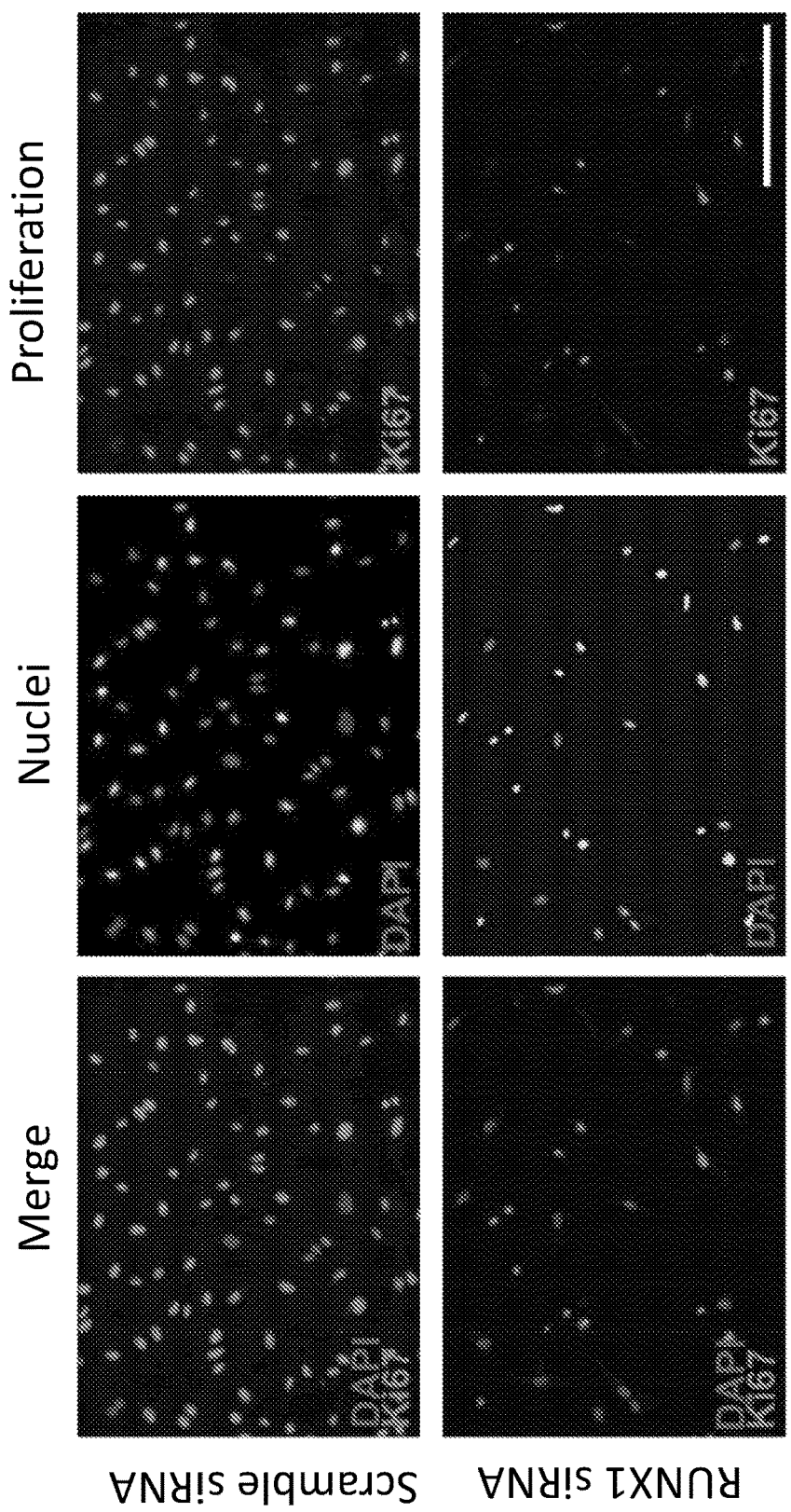
FIGS. 8A and B are a set of images and a graph, respectively, showing the role of RUNX1 in HRMEC proliferation.
Figure 8B:
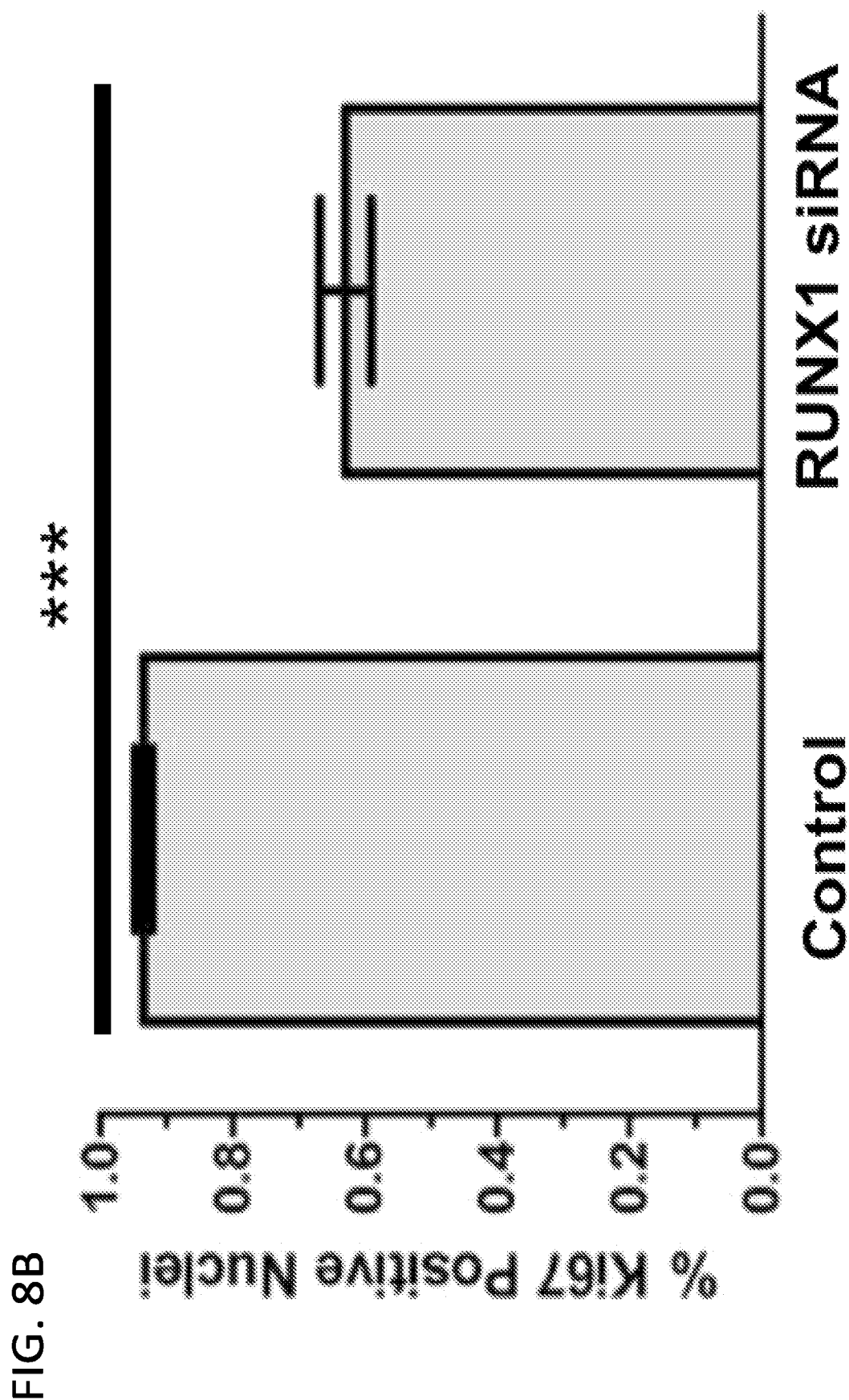
FIG. 8B: Quantification of percentage of 4',6-diamidino-2-phenylindole (DAPI) positive nuclei colocalized with Ki67 stain (n=6, experiment performed in duplicate).
Figure 10A:
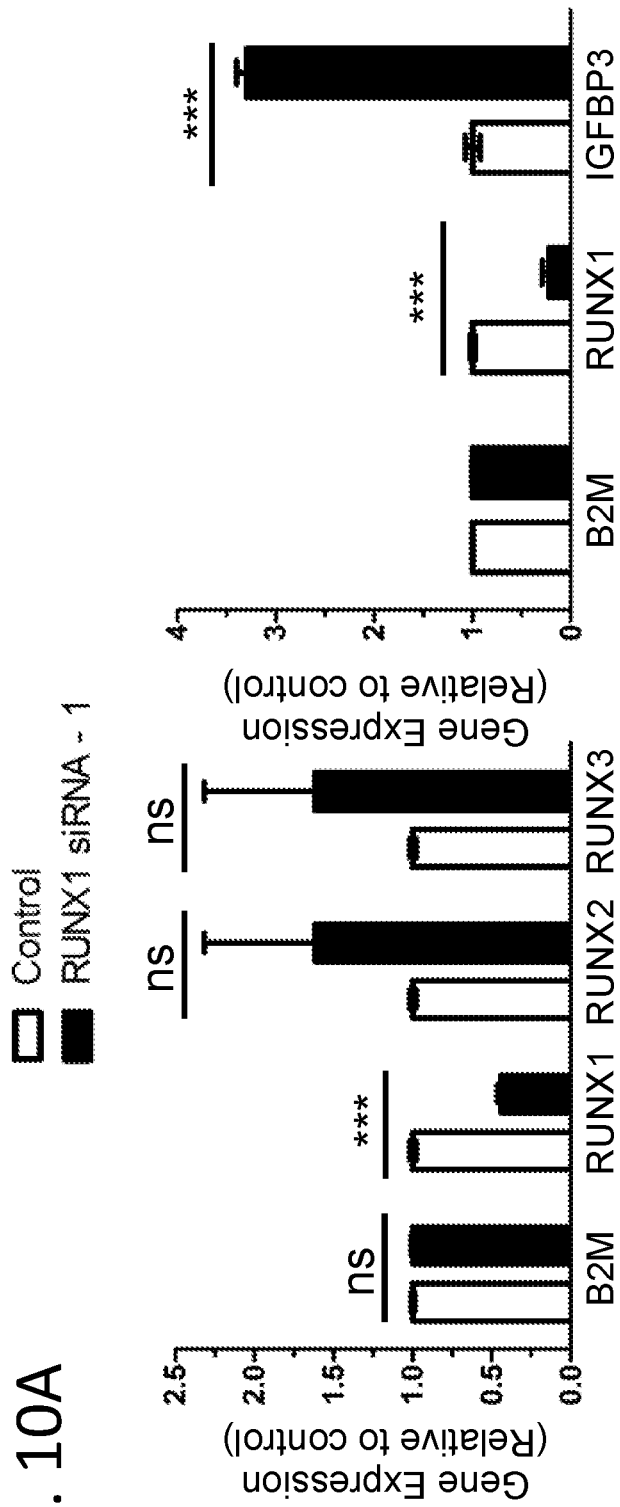
FIG. 10A is a set of graphs.
Figure 10B:
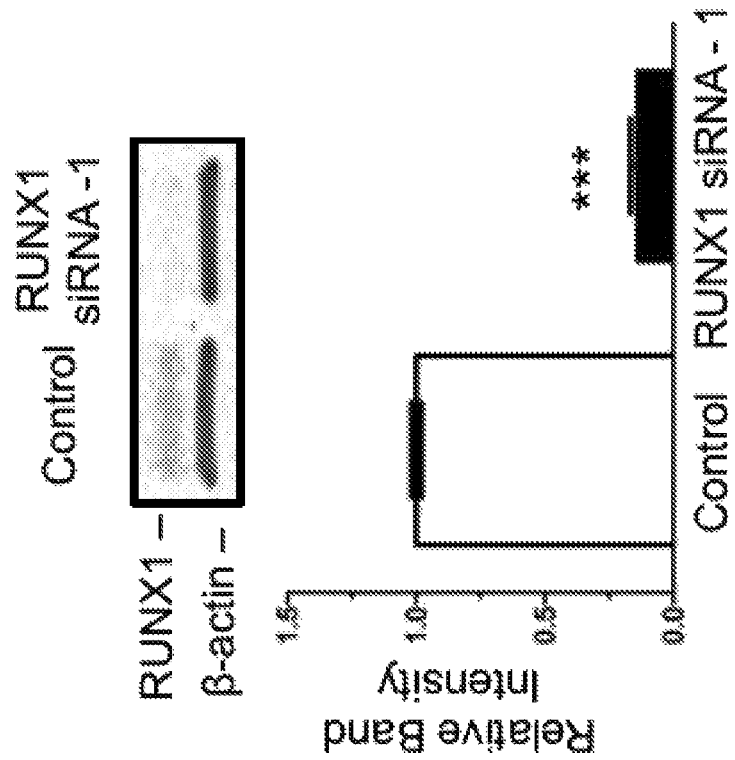
FIG. 10B is a graph and an image.
Figure 10C:
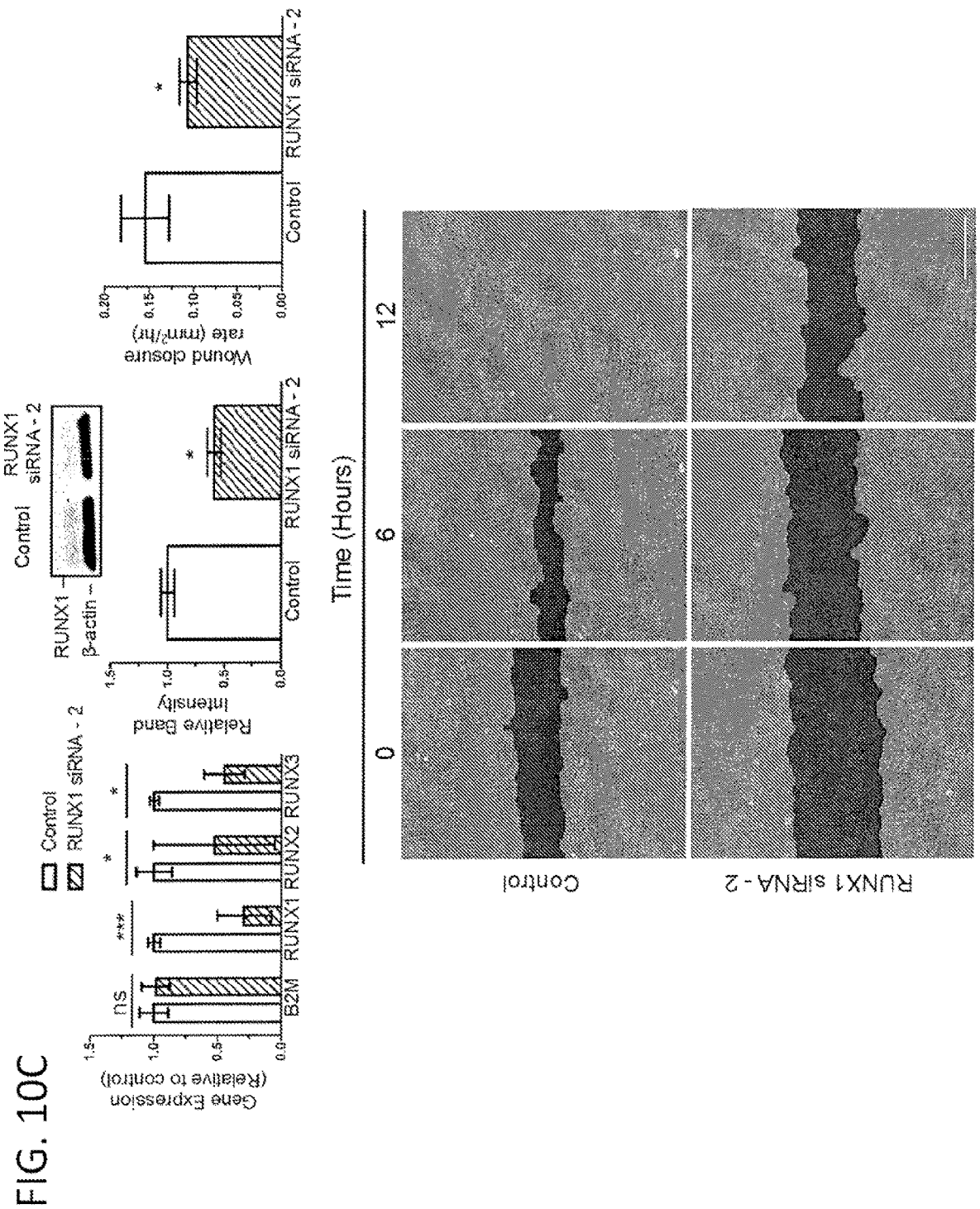
FIG. 10C is a set of images and graphs that collectively show efficient siRNA knockdown of RUNX1 expression and function demonstrated by qRT-PCR, Western Blot, and scratch assay.
Figure 11:
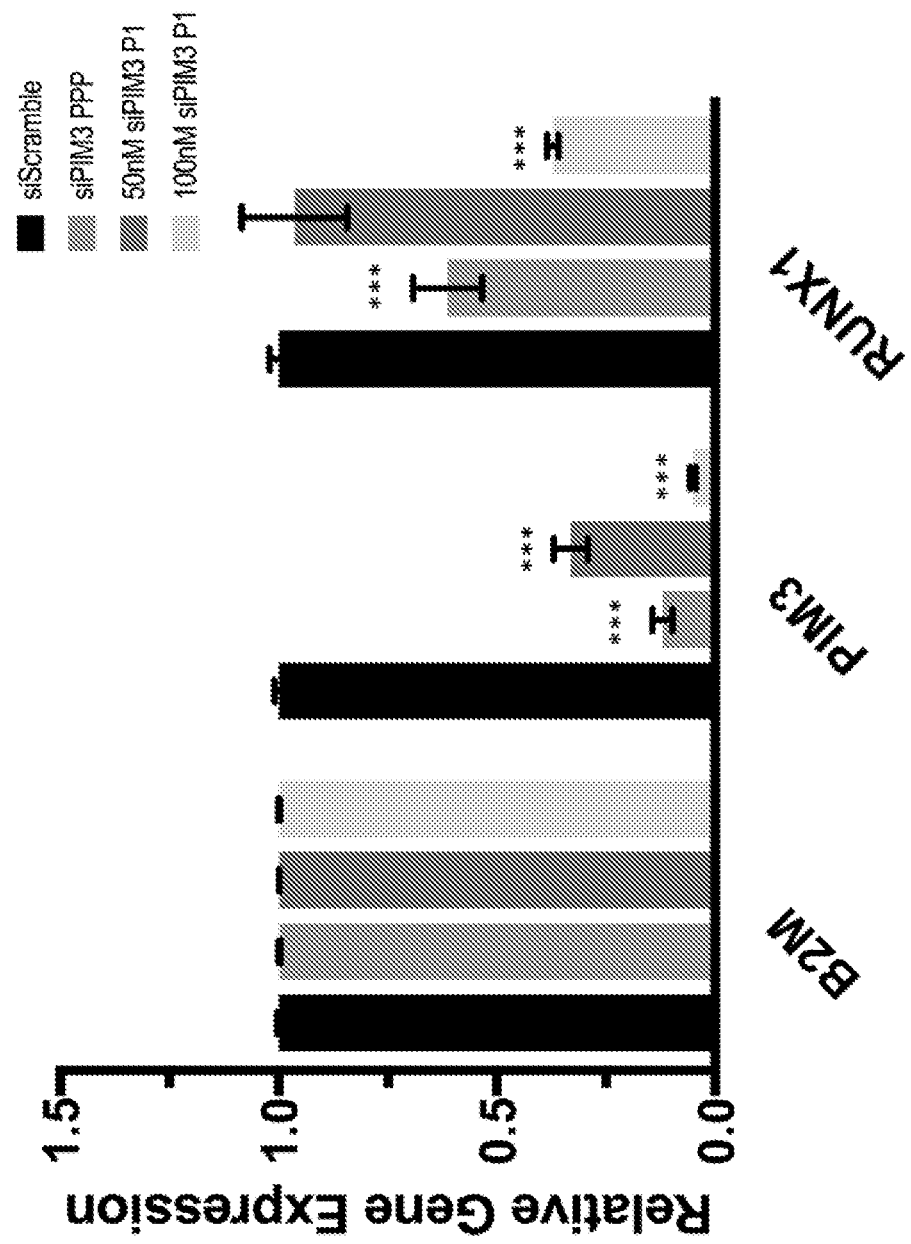
FIG. 11 is a graph showing PIM3 knockdown with siRNA. PIM3 siRNA knockdown leads to the downregulation of RUNX1. Transfection of human retinal microvascular endothelial cells with siRNA targeting PIM3 significantly reduced PIM3 and RUNX1 mRNA expression. Human primary cultured vascular endothelial cells were transfected with siRNA specific for PIM3 (HSC.R-NAI.N001001852.12-TriFECTA RNAi Kit: PIM3 from Integrated DNA Technologies) using Dharmafect 1 and harvested 48 hours later. RNA was extracted prior to cDNA synthesis and qPCR with primers specific for beta-2-microglobulin as calibrator, PIM3, and RUNX1. siScramble is control. siPIM3PPP corresponds to the condition in which three oligos from the siRNA kit specific for PIM3 knockdown were mixed at equimolar amounts to obtain 100 nM dose. siPIM P1 corresponds to condition in which 50 nM or 100 nM of one oligo from the siRNA kit specific for PIM3 was used for knockdown. * $p<0.001$
Figure 12:
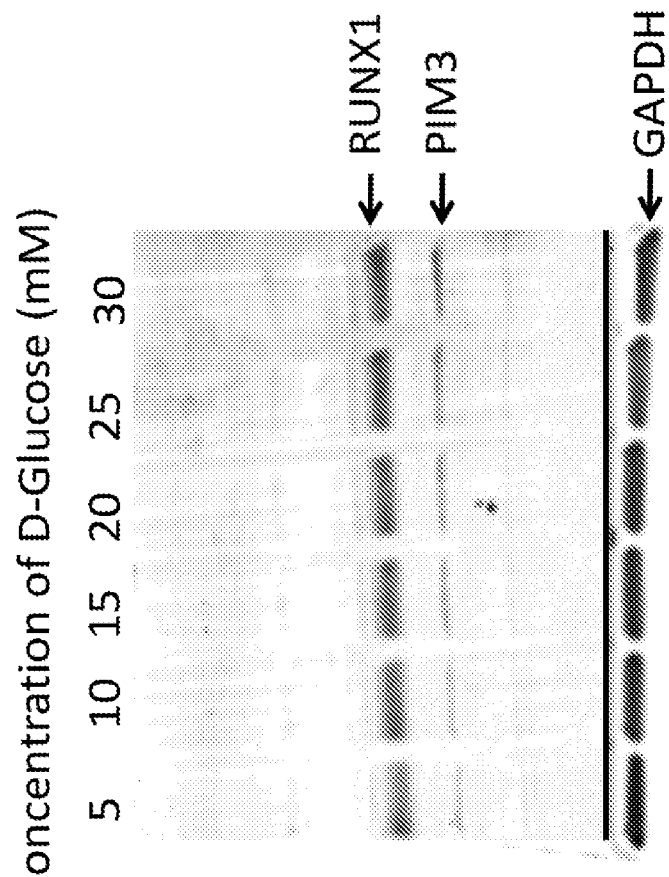
FIG. 12** is an image showing glucose-dependent PIM3 protein expression. Human microvascular retinal endothelial cells exhibited increased PIM3 protein expression in response to glucose in a dose dependent fashion. The same response was observed for RUNX1. Human microvascular retinal endothelial cells were cultured in EGM-2 supplemented with different concentrations of D-glucose for 96 hrs. After harvest, proteins were extracted using RIPA buffer and analyzed by western blot. The following commercially available antibodies were used for detection of specific proteins: RUNX1 antibody from Santacruz (sc-365644), PIM3 antibody from Abcam (ab71321). GAPDH protein was detected as loading control.
Figure 13:
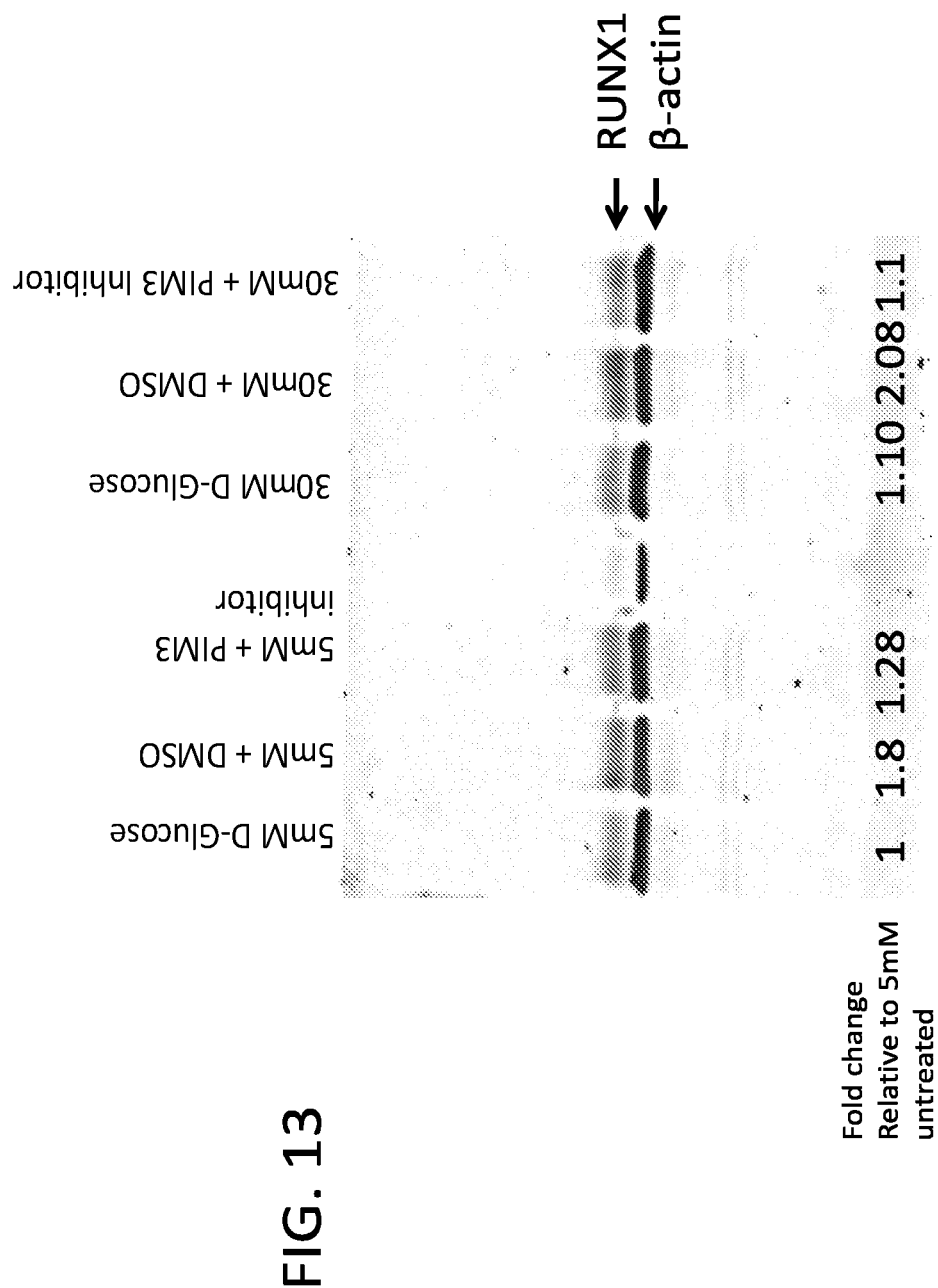
FIG. 13 is an image showing that a commercially available small molecule PIM3 inhibitor (PIM3 kinase inhibitor VII from EMD Millipore) reduced total RUNX1 protein levels in primary culture retinal endothelial cells in normal and high glucose conditions. Human microvascular retinal endothelial cells were cultured in EGM-2 supplemented with different concentrations of D-glucose for 72 hours in the presence of PIM3 inhibitor (PIM3 kinase inhibitor VII from EMD Millipore, Cat No. 526526, 0.05 µM) or vehicle (DMSO). After harvest, proteins were extracted using RIPA buffer and analyzed by western blot. RUNX1 was detected using antibodies from Santacruz (sc-365644). β-actin was used as a loading control.
Figure 14:
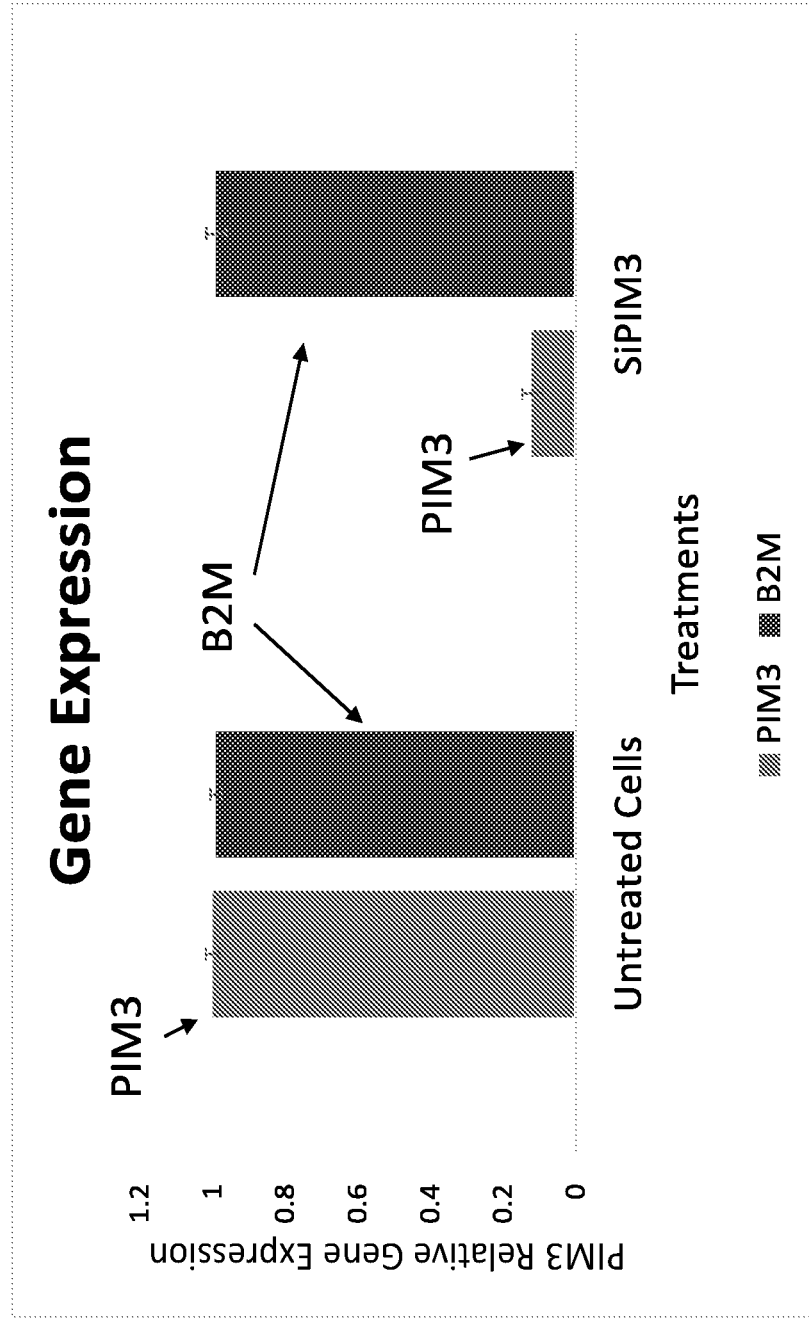
FIG. 14 is a graph showing PIM3 gene expression. PIM3 expression was 88% downregulated in the treated cells with siPIM3 compared with the control (Untreated Cells). qRT-RNA took place 48 hours after transfection. RNA was extracted using Rneasy Mini Kits (Qiagen). The primers were purchased from Integrated DNA technologies. cDNA was obtained using iScript cDNA synthesis kit (Bio-Rad Laboratories) and probed using FastStart Universal SYBR Green Master (Hoffmann-La Roche). B2M was used as a calibrator gene control.
Figure 15A:
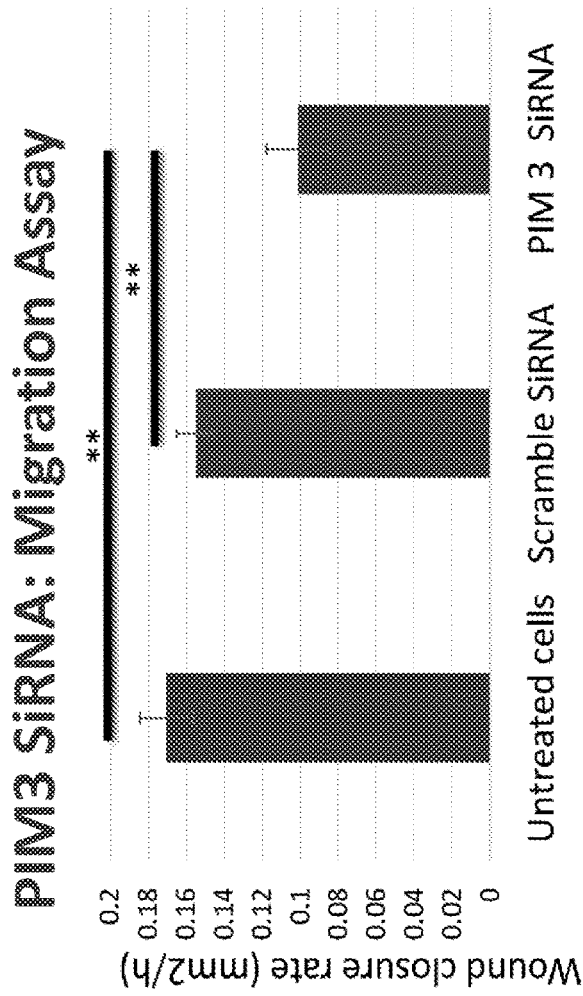
FIG. 15A is a graph and FIG. 15B is a series of images showing a 35% reduction in cell migration in Human Retinal Microvascular Endothelial Cells (HRMECs) transfected with PIM3 SiRNA compared with Scramble SiRNA. Migration was assessed with the wound scratch assay. This experiment was executed 24 hours after transfection. One scratch was done per well. The cells were imaged on an EVOS® system every three hours for 12 h. Tscratch Matlab Modules were used for image analysis.
Figure 15B:
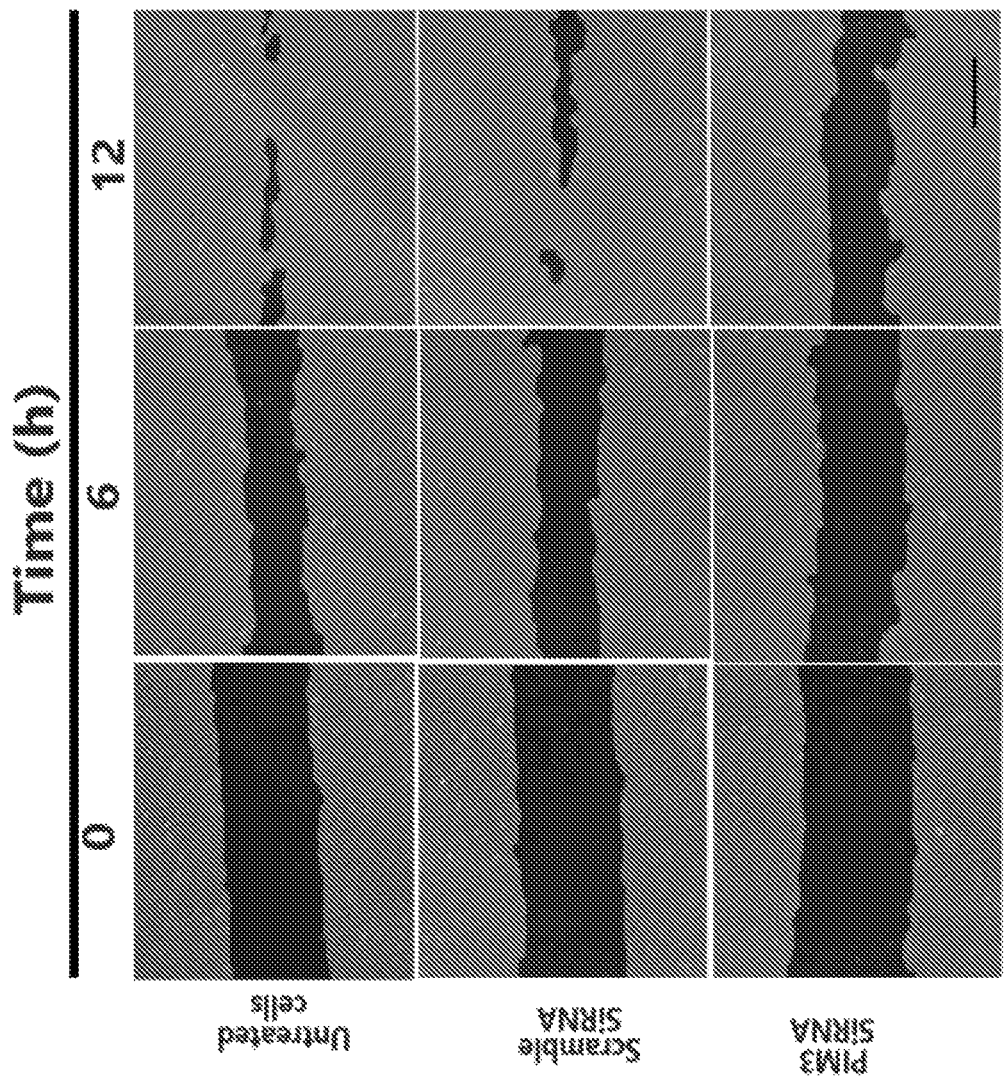
Figure 16A:
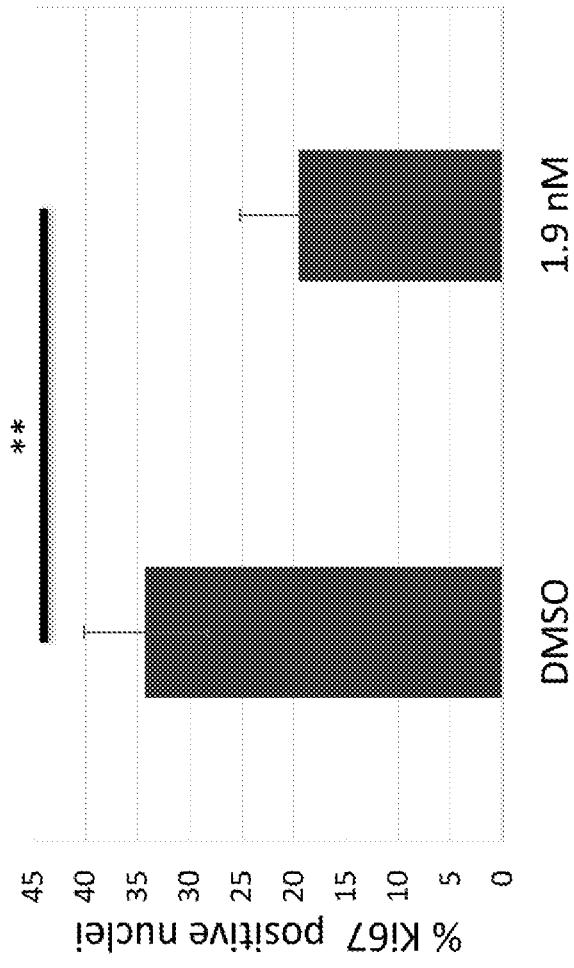
FIG. 16A is a graph and FIG. 16B is a series of fluorescent images showing a 43% reduction in cell migration in HRMECs treated with the PIM kinases inhibitor AZD1208 (from Selleckchem catalogue #S7104) inhibitor compared with the DMSO control. AZD1208 is a pan-PIM inhibitor that inhibits PIM1, PIM2, and PIM3. The AZD1208 was used as a PIM3 kinase inhibitor and Dimethyl Sulfoxide (DMSO) as a control. HRMECs were treated for DMSO and PIM3 inhibitor for 48 hours before proliferation assay. The antibody Ki67 was used as a proliferation marker. The cells were imaged on an EVOS® system. Image J were used for image analysis.
Figure 16B:
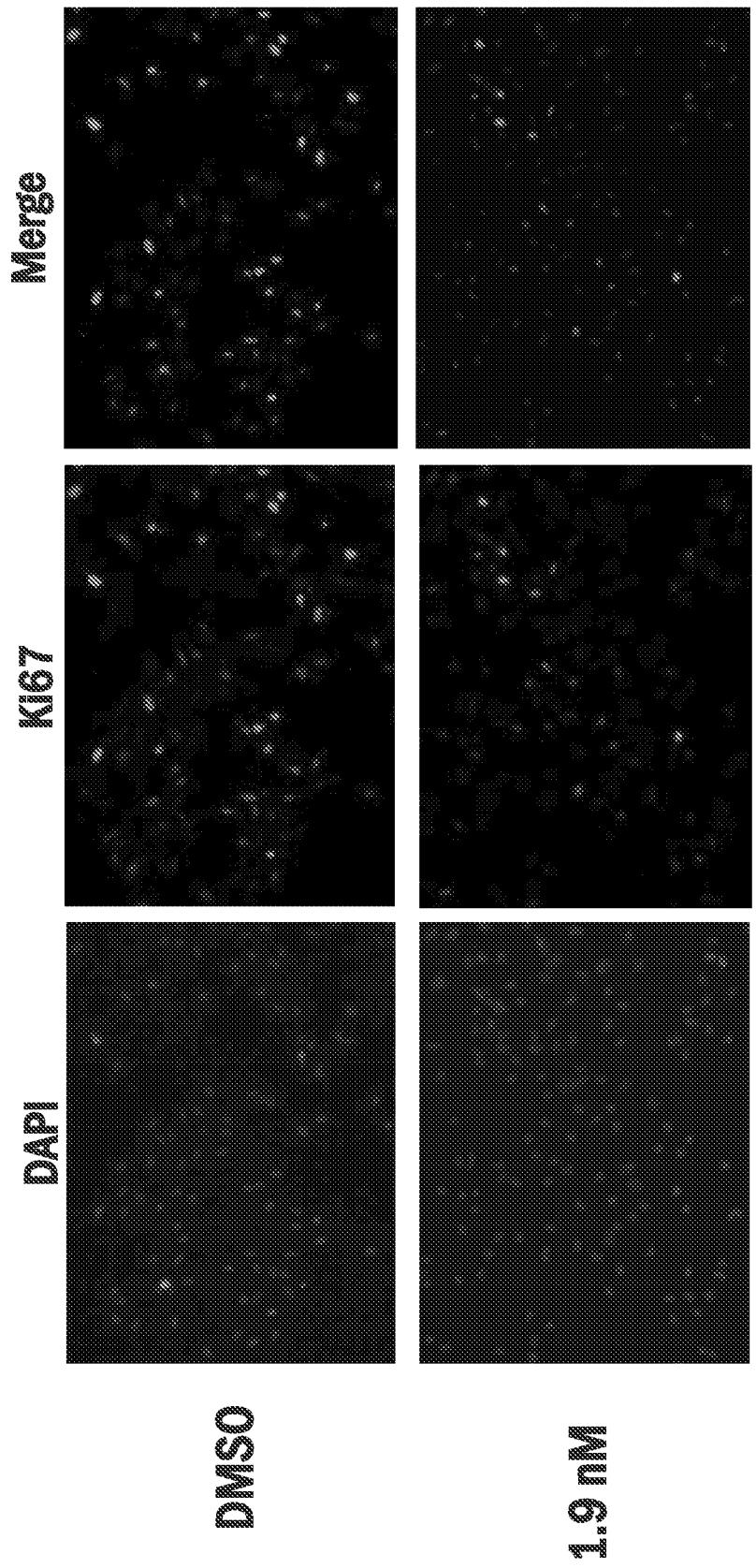
Figure 17A:
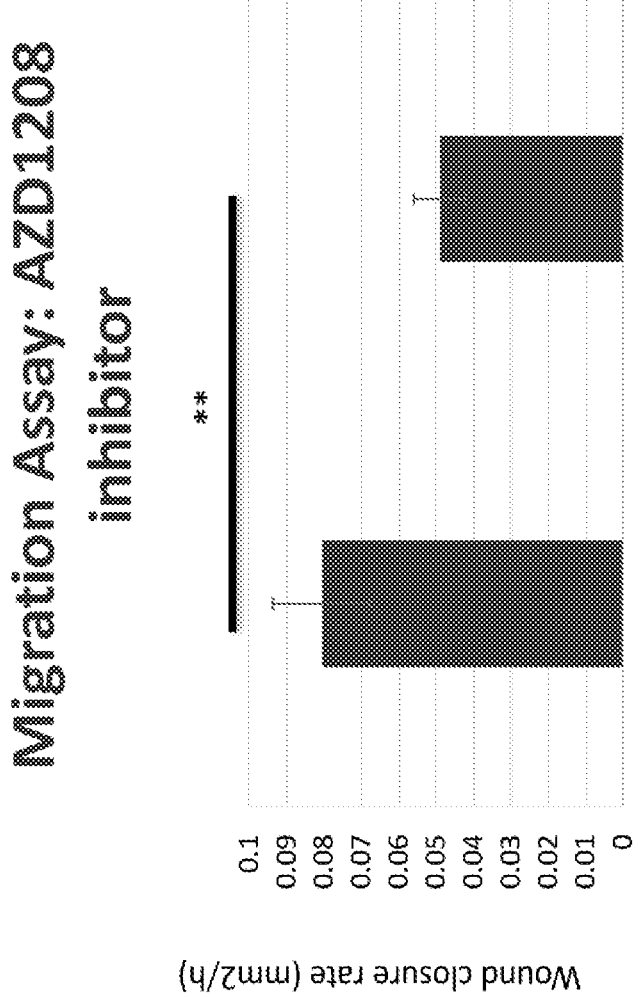
FIG. 17A is a graph and FIG. 17B is a series of images showing a 39% reduction in cell migration in HRMECs treated with the AZD1208 inhibitor at 1.9 nM compared with DMSO vehicle control. Migration was assessed with the wound scratch assay. The AZD1208 was used as a PIM3 kinase inhibitor (Selleck Chemicals). A concentration of 1.9 nM (IC50) was tested. HRMECs were treated for DMSO and PIM3 inhibitor for 16 hours before wound assay. One scratch was done per well. The cells were imaged on an EVOS® system every three hours for 12 h. Tscratch Matlab Module were used for image analysis.
Figure 17B:
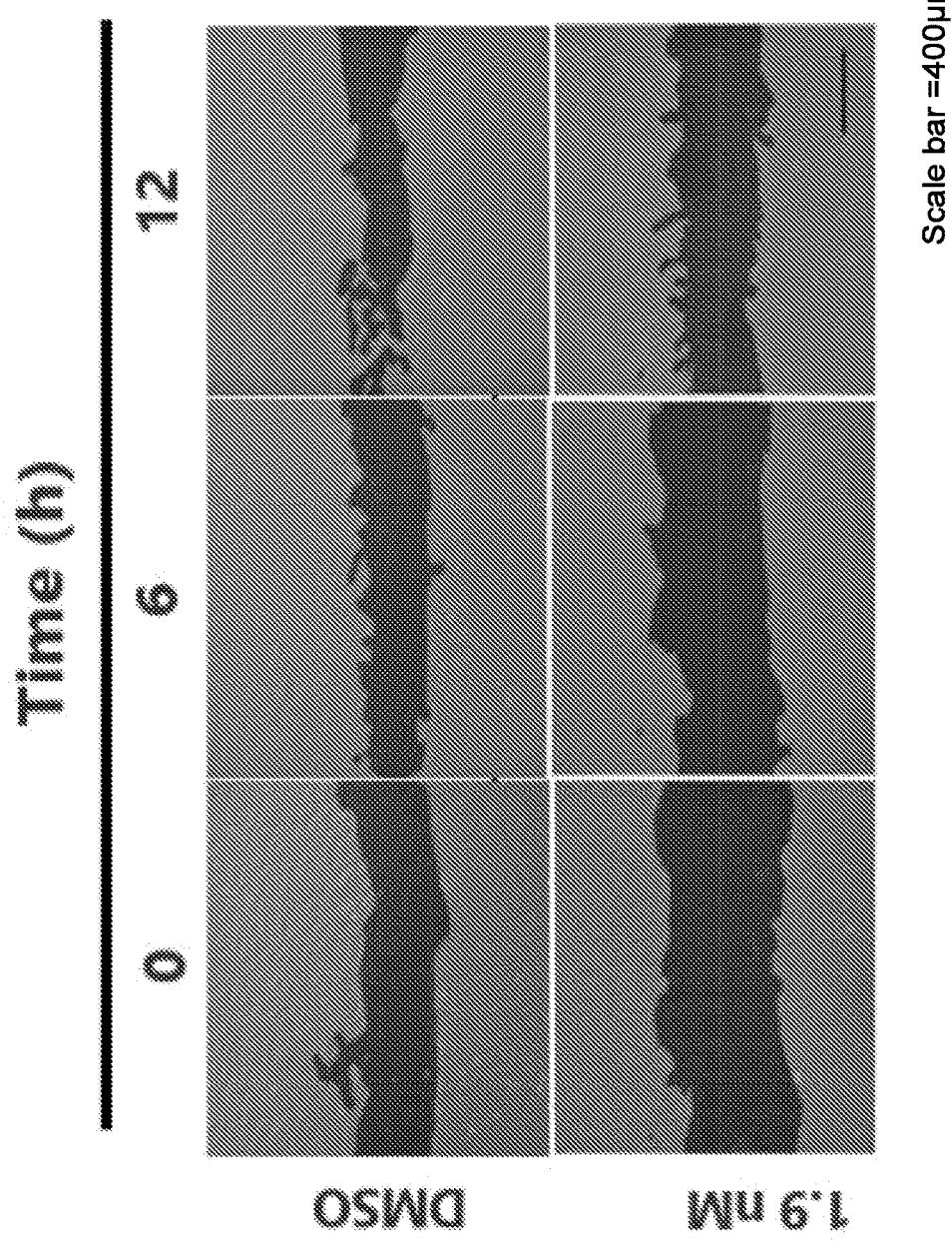
Figure 18:
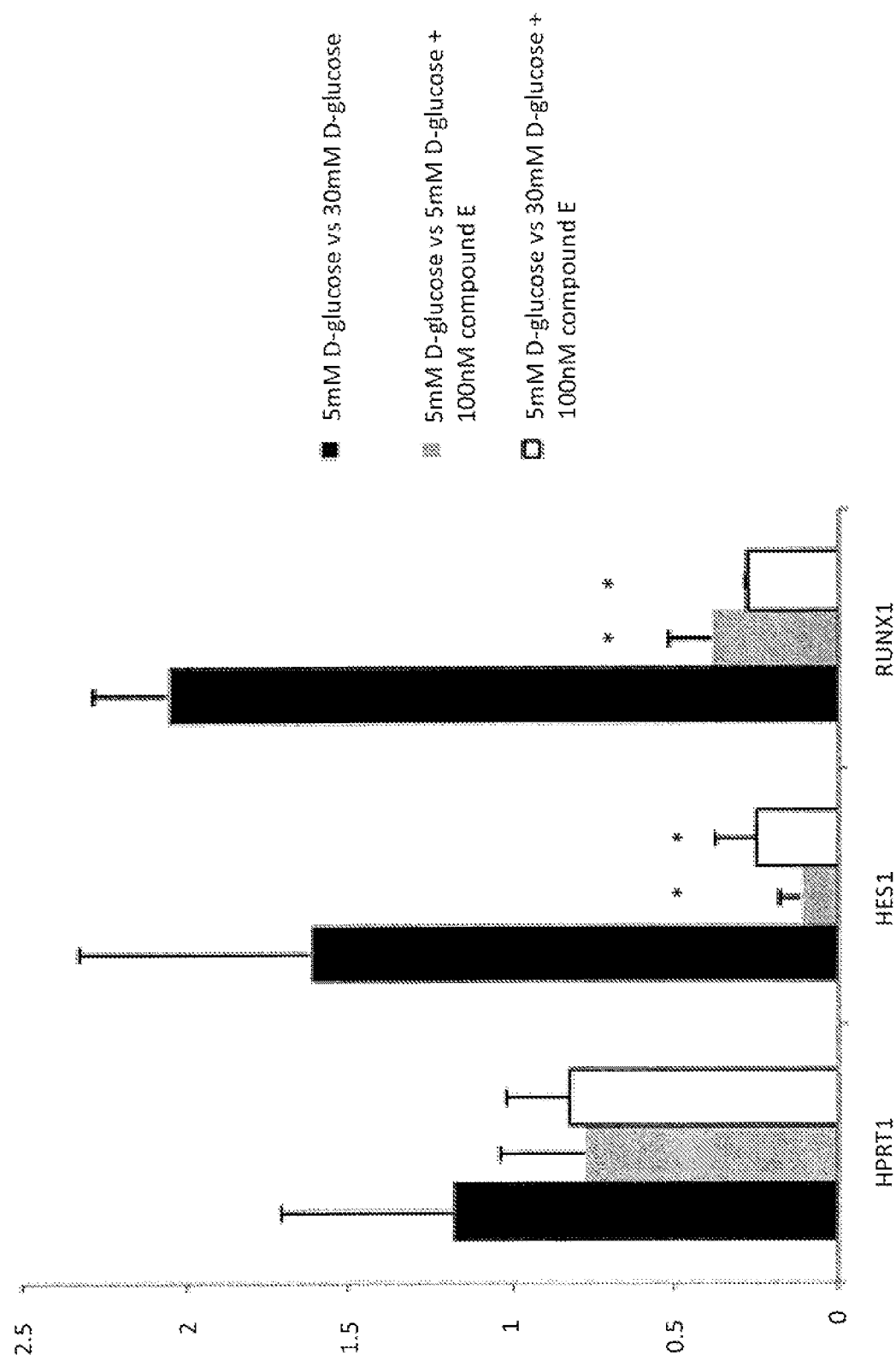
FIG. 18 is a graph showing that gamma-secretase inhibition using Compound E small molecule (100 nM) reduced the expression of HES1, a canonical downstream target for Notch activity and RUNX1 in primary culture human microvascular endothelial cells. Reduction of HES1 and RUNX1 expression was effective under normal glucose (5 mM D-glucose and high glucose 30 mM D-glucose). Cells were incubated with Compound E or DMSO vehicle control in different glucose concentrations for 72 hours before harvest followed by qRT-PCR for each gene. HPRT1 expression was used as control.
Figure 19:
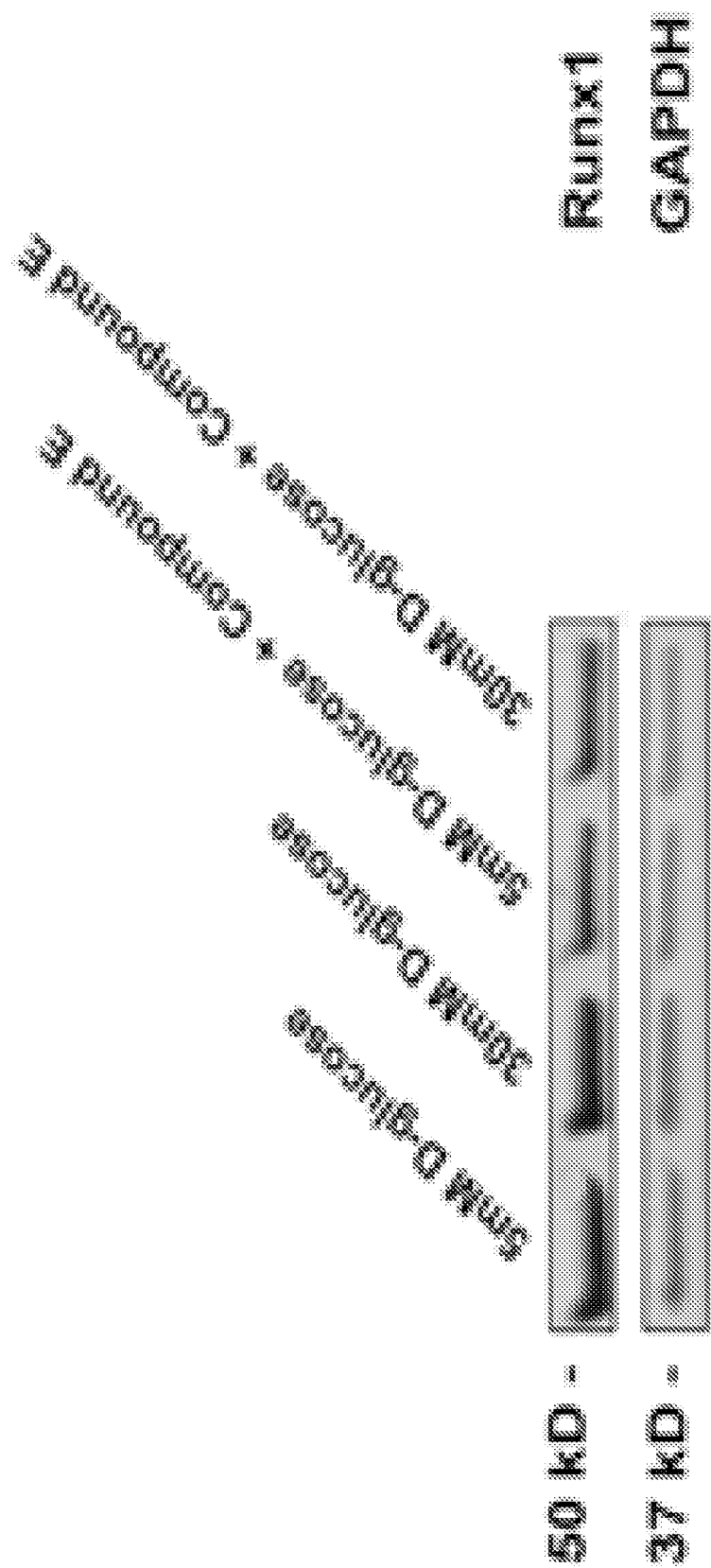
FIG. 19 is set of images showing that gamma-secretase inhibition using Compound E small molecule (100 nM) reduces the expression of RUNX1 in primary culture human microvascular endothelial cells. Reduction of RUNX1 expression was effective under normal glucose (5 mM D-glucose and high glucose (30 mM D-glucose). Cells were incubated with Compound E in different glucose concentrations for 72 hours before harvest followed by western blot with RUNX1 and GAPDH specific antibodies.

RUNX1 Regulates Migration and Proliferation of Endothelial Cells In Vitro siRNA knockdown was validated for specificity and efficacy and used to test RUNX1's angiogenic functions (FIGS. 10A and B). siRNA knockdown resulted in a 60% decrease in RUNX1 RNA expression and did not significantly affect RUNX2 or RUNX3 RNA expression. In addition, a canonical downstream target of RUNX1 activity was increased significantly for IGFBP3 (330% increase). The contribution of RUNX1 to EC migration was assayed by the scratch-wound assay and its role in proliferation was assayed using labeling of Ki67, a marker of cell proliferation. Knockdown of RUNX1 resulted in a 60% decrease in wound closure rate, suggesting a major role of RUNX1 in endothelial cell migration (FIG. 7). As a quality check, the coefficient of determination (r2 value) for the simple linear regression was calculated comparing wound closure (dependent variable) to time (independent variable) (control r2=0.99, scramble siRNA r2=0.97, and RUNX1 siRNA r2=0.97). EC transfected with RUNX1 siRNA had 60% fewer Ki67 positive cells compared to controls, indicating RUNX1 plays a significant role in retinal endothelial cell proliferation (FIG. 8).

Figure 8C:
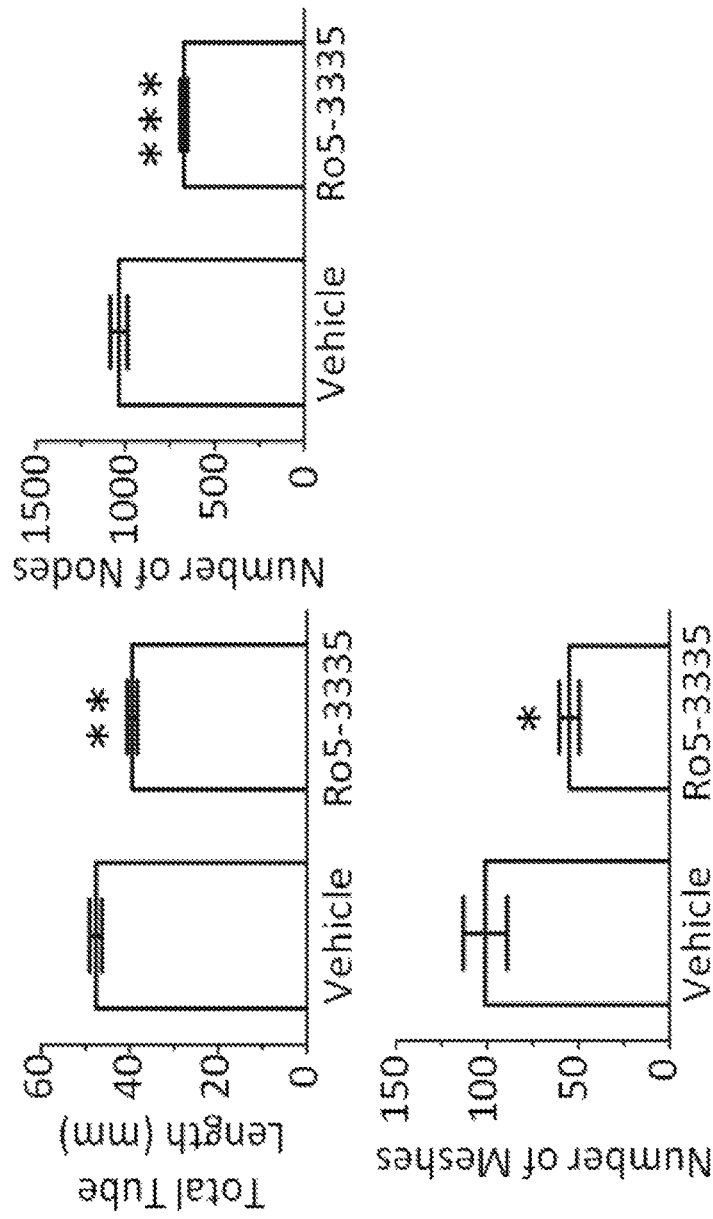
FIG. 8C: HRMEC treated with Ro-3335 RUNX1 inhibitor overnight exhibited reduced tube forming capacity compared to vehicle treated cells at 6 h after plating. There was statistically significant reduction in tube length, meshes, and nodes. (scale bar=500 µm. n=4, experiment performed in duplicate). * $p<0.05$,  $p<0.01$, * $p<0.001$ *** $p<0.001$.

Ro5-3335 RUNX1-CBFβ Inhibitor Blocks EC Tube Formation In Vitro and Aberrant Angiogenesis In Vivo To investigate the potential therapeutic relevance of RUNX1, the small molecule Ro5-3335 RUNX1-CBFβ Inhibitor II was tested in vitro and in vivo (Namba et al. (2000) Oncogene 19(1):106-114). Treatment with RUNX1 inhibitor reduced total tube length (18% reduction), nodes (35% reduction) and meshes (46% reduction), supporting RUNX1's role in vascular morphogenesis (FIG. 8C).

Neovascular tufts of P17 C57BL/6J mice with OIR identified by isolectin B4 and CD31 staining showed increased expression of RUNX1, whereas RUNX1 staining was absent from the underlying normal retinal vasculature, indicating a role for RUNX1 in active angiogenesis (FIG. 6E). In vivo testing of the effects on aberrant angiogenesis of RUNX1 inhibition was conducted by injecting Ro5-3335 intravitreally in mice with OIR. There was no significant change in the extent of vaso-obliteration and no effect was observed in the contralateral eye (data not shown). Eyes treated with inhibitor exhibited a 50% reduction in neovascularization compared to vehicle treated eyes (FIG. 6E).

Gene Profiling Analysis of Patient Derived Endothelial Cells Reveals Co-Expression of 16 Genes Involved in Angiogenesis, 12 of these Genes have Putative RUNX1 TFBSs.

In order to initially identify increased expression of RUNX1, RNA-Seq was performed on patient-derived ECs from patients with PDR, which led to the discovery of 200 differentially expressed genes (DEGs), these transcriptomes were deposited in the Gene Expression Omnibus (GSE94019). (Lam J D, Oh D J, Wong L L, et al. Identification of RUNX1 as a Mediator of Aberrant Retinal Angiogenesis. Diabetes. 2017.) Gene ontology analysis of this data set using Database for Annotation, Visualization, and Integrated Discovery (DAVID) (Huang da W, Sherman B T, Lempicki R A. Bioinformatics enrichment tools: paths toward the comprehensive functional analysis of large gene lists. Nucleic Acids Res. 2009; 37:1-13) revealed enrichment of several ontological processes directly associated with blood vessel development and differential expression of 16 key proteins involved in angiogenesis: COL4A1, CCL2, MMP19, MMP2, SYK, THBS1, GPX1, TGFBI, PDGFA, THY1, HMOX1, TNFAIP2, HIF3A, COL15A1, B4GALT1, CDH13. Based on the assumption that these co-expressed genes are co-regulated by RUNX1, used oPOSSUM was used, which integrates a database of predicted, conserved TFBSs and statistical methods for identifying overrepresented gene sets. (Ho Sui S J, Mortimer J R, Arenillas D J, et al. oPOSSUM: identification of over-represented transcription factor binding sites in co-expressed genes. Nucleic Acids Res. 2005; 33:3154-3164) Identification of predicted RUNX1 TFBSs using oPOSSUM revealed that 12 of these transcripts had putative RUNX1 binding sites: B4GALT1, CCL2, CDH13, COL15A1, COL4A1, GPX1, HIF3A, PDGFA, SYK, TGFBI, THBS1, THY1. Thus, 12 out of 16 genes (75%) involved in angiogenesis have putative RUNX1 binding sites, whereas only 75 out of 200 (37.5%) DEGs have RUNX1 binding sites. This enrichment of angiogenic genes with RUNX1 TFBSs was found to be statistically significant with a p-value=0.0015 using a hypergeometric probability function. These data support our rationale that RUNX1 is a potential regulator of critical genes necessary for angiogenesis.

Identification of RUNX1 as a Mediator of Aberrant Angiogenesis

RUNX1 was identified as a gene dysregulated in patient-derived CD31+ vascular endothelial cells obtained from human PDR fibrovascular membranes (FVM) via transcriptomic analysis. In vitro studies using human retinal microvascular endothelial cells (HRMECs) showed increased RUNX1 RNA and protein expression in response to high glucose whereas RUNX1 inhibition reduced HRMEC migration, proliferation, and tube formation. Immunohistochemical staining for RUNX1 showed reactivity in vessels of patient-derived FVM and angiogenic tufts in the retina of mice with oxygen-induced retinopathy (OIR) and human melanoma xenografts, suggesting that RUNX1 upregulation is a hallmark of aberrant retinal angiogenesis. Inhibition of RUNX1 activity with the Ro5-3335 small molecule resulted in a significant reduction of neovascular tufts in OIR, supporting the feasibility of targeting RUNX1 in aberrant retinal angiogenesis.

To identify novel genes underlying aberrant retinal angiogenesis, whole transcriptomes of CD31+ cells from FVMs of PDR patients were analyzed. Gene ontology analysis of differentially regulated genes in ECs from FVMs showed enrichment of genes involved in immune response, wound healing, and vascular development functional categories. Four genes exhibited significant changes in expression in response to high glucose. Analyses of RUNX1 expression in FVMs, OIR samples, and melanoma samples along with in vitro functional studies suggest a role for RUNX1 in the regulation of proliferation, migration, and morphogenesis of EC in aberrant angiogenesis.

RUNX proteins have pleiotropic functions in vascular development, hematopoiesis, and cancer through direct transcriptional regulation of target genes and complex interactions with fundamental signaling mechanisms including Notch and Transforming growth factor beta (TGF-β) pathways [Burns et al. (2005) Genes Dev 19(19):2331-2342; Ito Y & Miyazono K (2003) Curr Opin Genet Dev 13(1):43-47]. Mammals express three genes (RUNX1, RUNX2, and RUNX3) encoding the DNA binding α subunit of the core binding factor (CBF) transcriptional complex. Another gene encodes for the β subunit (CBFβ), which stabilizes the RUNX-DNA complex and prevents RUNX degradation [Lichtinger et al. (2010) Blood Cells Mol Dis 44(4):287-290; Michaud J, et al. (2008) BMC Genomics 9:363]. In early development, RUNX1 is a master regulator of the endothelial-hematopoietic transition through which blood cells are generated from endothelium, and though less studied, it is also implicated in angiogenesis and vasculogenesis [Burns et al. (2005) Genes Dev 19(19):2331-2342; Chen et al. (2009) Nature 457(7231):887-891; Iwatsuki K, et al. (2005) Oncogene 24(7):1129-1137; McLeod D S, et al. (2012) Invest Ophthalmol Vis Sci 53(13):7912-7927; Kalev-Zylinska M L, et al. (2002) Development 129(8):2015-2030; Namba K, et al. (2000) Oncogene 19(1):106-114; Lie A L M, et al. (2014) Blood 124(11):e11-20].

Studies in model organisms have shown that glucose levels regulate hematopoietic stem cell production by endothelial-to-hematopoietic transition (EHT) in a RUNX1-dependent manner [Harris J M, et al. (2013) Blood 121(13):2483-2493]. High glucose triggers RUNX1 expression via reactive-oxygen species-mediated upregulation of hypoxia-inducible factor 1 [Harris J M, et al. (2013) Blood 121(13):2483-2493; Imanirad P, et al. (2014) Stem Cell Res 12(1):24-35]. CD44, PPIB, and PPIF, known targets of RUNX1, are also upregulated in CD31+ cells from PDR (Michaud J, et al. (2008) BMC Genomics 9:363). Without wishing to be bound by any scientific theory, the results herein demonstrate that high glucose can regulate RUNX1 and indicate that RUNX1 is a therapeutic target in conditions with aberrant retinal angiogenesis.

Previous studies of PDR have mainly focused on gene expression in FVMs or biomarkers in the vitreous [Ishikawa K, et al. (2015) Invest Ophthalmol Vis Sci 56(2):932-946; Yoshida S, et al. (2010) Br J Ophthalmol 94(6):795-801; McAuley A K, et al. (2014) J Diabetes Complications 28(3):419-425]. FVMs from PDR may be highly informative pathological tissues but are largely unstudied. The window for processing samples post-surgery is narrow and intraoperative confounders such as FVM size, location, and involvement of sensory retina further complicate successful sample acquisition and limit sample size. Employing multiple sequencing analysis algorithms improved confidence in the results and reduced the dataset to a manageable size but reducing the pool of candidate genes invariably also excluded some genes of potential interest. Further characterization of candidate genes using different screening conditions may reveal involvement in other processes related to the pathobiology of PDR such as inflammation and oxidative stress.

The data herein shows elevated RUNX1 expression in ECs of patient-derived FVMs from patients with PDR. Also, the data herein demonstrate a role for RUNX1 in EC migration, proliferation, and vascular morphogenesis. Furthermore, selectively enhanced expression of RUNX1 in neovascular tufts is shown in an experimental model of OIR and that inhibition of RUNX1 function reduced retinal neovascularization. These findings, including the high glucose-dependent expression of RUNX1, indicate that PIM3 and RUNX1 are useful targets for treating aberrant angiogenesis in multiple conditions.

Profiling purified ECs unmasks changes that would otherwise be obscured by analysis of mixed cell populations. These findings, including the glucose activation of RUNX1, identify a novel pathway of for therapeutic targeting, and show that RUNX1 is involved in pathologic retinal angiogenesis. Therefore, inhibition of expression or activity in the eye leads to a clinical benefit to patents afflicted with the pathologies described herein, including retinal neovascular disorders such as PDR, ROP, AMD, retinal vein occlusions, ocular ischemic syndrome, neovascular glaucoma, retinal hemangiomas, and other conditions characterized by aberrant angiogenesis.

Methods

FVMs were collected and CD31+ cells were isolated as previously described [Kim L A, et al. (2015) Mol Vis 21:673-687]. RNA-sequencing was performed using an Illumina HiSeq 2000 (Illumina Inc.), aligned with TopHat (Trapnell et al. (2009) Bioinformatics 25(9):1105-1111], and analyzed using Partek Flow, CuffLinks, EdgeR, and DESeq2. A mixed model ANOVA was used with a threshold false discovery rate (FDR) of <0.05 and fold change >±2 for significance. Gene Ontology was determined using the Database for Annotation, Visualization, and Integrated Discovery (DAVID). Gene Ontology was determined using the DAVID [Huang et al. (2009) Nucleic Acids Res 37(1):1-13]. FVMs and cells were immunostained with standard protocols for paraffin embedded samples. HRMECs were exposed to treatment media for 72 h before the following assays were conducted: qRT-PCR followed manufacturer's instructions (Qiagen); gene knockdown was achieved with 100 nM siRNA using DharmaFECT 1; standard western blot protocols were used with fluorescent visualization; scratch assays followed standard protocols, monitored for 12 h, and quantified with the TScratch Matlab module [Liang et al. Nature protocols 2(2):329-333; Geback et al. (2009) Biotechniques 46(4):265-274].

Control retinal samples were obtained from cadaver eyes of subject without a diagnosis of diabetes mellitus.

Human Study Approval and Design:

Research protocols adhered to the Association for Research in Vision and Ophthamology (ARVO) Statement on Human Subjects and the tenets of the Declaration of Helsinki.

Inclusion criteria were: aged 18-70, diagnosis of PDR as determined by Early Treatment Diabetic Retinopathy Study (ETDRS) criteria, active fibrovascular proliferation diagnosed by a study ophthalmologist, and evidence of retinal detachment (tractional or rhegmatogenous) or non-clearing vitreous hemorrhage requiring pars plana vitrectomy. Exclusion criteria were: age less than 18 years old, pregnancy, history of prior penetrating eye trauma, not medically cleared for surgery, history of adverse reactions to fluorescein dye, chronic use of systemic or ocular medications for diseases other than diabetes, or PDR with concomitant radiation retinopathy.

Pre- and post-operation assessments were performed in compliance with standards of care; this includes visual acuity assessment, complete ocular examination, fundus photography with wide field imaging (Optos), and fluorescein angiography where indicated and possible. All patients underwent standard 23-gauge three-port pars plana vitrectomy with membrane peeling, endolaser panretinal photocoagulation, and retinal tamponade with either non-expansile perfluoropropane gas (C3F8) or silicone oil.

A total of sixteen surgically removed FVM samples were included in this study. Eight samples (3 male, 5 female), in part or in whole, were used for cell isolation and RNA-sequencing analysis. Of these patients, three patients had type 1 diabetes mellitus and five patients had type 2 diabetes. The mean age of patients was 46.25 (range: 29-71 years). All patients were medically cleared for surgery and all operations were completed without complication. In addition, four post-mortem retinas (3 males, 1 female) were included in this study with a mean age of 60.8 (Table 1).

Processing of FVMs:

FVM samples collected perioperatively were dissected into pieces for immunohistochemistry and/or cell isolation. Isolation of CD31+ cells for RNA-sequencing was performed as previously described (Kim L A, et al. (2015) Mol Vis 21:673-687). Briefly, FVM samples were digested with collagenase II (Worthington Biochemical Corporation) for 1 h before incubation with 20 μL of CD31 Dynabeads® (Invitrogen) in phosphate buffered saline (PBS) containing 2% fetal bovine serum (FBS) for 15 min. Cells attached to beads were pulled from solution using a magnetic rack, washed, and lysed directly into RNA extraction buffer (RLT, Qiagen) supplemented with beta-mercaptoethanol.

Whole Transcriptome Sequencing:

CD31+ cells were isolated from FVM as previously described (Kim L A 2015 Mol Vis 21:673-687). RNA-sequencing was performed using an Illumina HiSeq 2000 (Illumina), aligned to reference genome UCSC hg19/GRCh37 with TopHat, and analyzed using Partek® Flow® (Partek), CuffLinks, EdgeR, and DESeq2 (Trapnell et al. (2009) Bioinformatics 25(9):1105-1111). A mixed model ANOVA was used with a threshold false discovery rate (FDR) of <0.05 and fold change ≥±2 for significance. Gene Ontology was determined using the Database for Annotation, Visualization, and Integrated Discovery (DAVID) (Huang da W et al. (2009) Nucleic Acids Res 37(1):1-13.

Transcriptome Analysis:

Raw sequencing data were processed as follows: data sets were filtered to exclude adaptor sequences and sequences containing 5% or more low quality base calls, trimmed using the Quality Score method, and aligned to the *Homo Sapiens* reference genome (UCSC hg19/GRCh37) using TopHat version 2.0.5 (Trapnell et al. (2009) Bioinformatics 25(9): 1105-1111.). Absolute gene expression was measured by the standard reads per mapping to the genome per kilobase of transcript per million reads sequenced (RPKM) using the built-in Partek E/M method. Differential gene expression analysis was performed using a mixed-model ANOVA comparing normal retinal CD31+ cells to FVM CD31+ cells. A threshold of FDR <0.05 was applied to identify significant genetic changes. Principle mixed model analysis of variance was performed using Partek® Flow® software, version 3.0 Copyright ©; 2015 (Partek Inc.). Comparing alternative differential gene expression analysis methods (CuffLinks, EdgeR, and DESeq2) further refined the dataset.

DAVID Gene Set Enrichment Analysis:

Gene set enrichment analysis was performed using DAVID version 6.7 (Huang et al. (2009) Nucleic Acids Res 37(1):1-13). The list of 200 genes meeting the above inclusion criteria was uploaded to DAVID to identify involved pathways focusing on the 'GOTERM_BP_FAT' gene ontology category.

OIR Mouse Model:

OIR was induced in wild-type C57BL/6J mice as previously described (Smith L E et al., (1994) Invest Ophthalmol Vis Sci 35(1):101-111). Intravitreal injections with 1 μL of 75 μM Ro5-3335 RUNX1 inhibitor or DMSO were performed on left eyes only at P13 and P15 under ketamine/xylazine anesthesia. Pups were euthanized at P17 and eyes were collected, fixed in 4% paraformaldehyde, and used for retinal flat mounts ($n_{vehicle}$=7; $n_{Ro5-3335}$=9). Avascular and neovascular areas were quantified using Photoshop as previously described (Connor H M et al., (2009) Nature Protocols 4(11):1565-1573).

Human Melanoma Mice:

Male, pathogen-free nude mice were purchased from Charles River (Wilmington, Mass.) and used when they were 8 weeks of age. The mice were maintained under specific pathogen-free conditions. Tumor cell inoculation: Human melanoma cells (A375SM) were provided by Isaiah J. Fidler (MD Anderson Cancer Center, Houston, Tex.) (Kozlowski et al. (1984) J Natl Cancer Inst 72(4):913-917). A375SM cells were free of *mycoplasma*, reovirus type 3, pneumonia virus of mice, mouse adenovirus, murine hepatitis virus, lymphocytic choriomeningitis virus, ectromelia virus, and lactate dehydrogenase virus (Microbiological Associates). Tumor cells [$10^6$ cells per 100 μl of Hanks' Balanced Salt Soln (HBSS)] were injected subdermally into the right dorsolateral flank of nude mice. Mice were euthanized 4 weeks after tumor cell injection. Mice were necropsied and tumors were fixed in 10% buffered formalin and embedded in paraffin.

Immunohistological Staining:

FVMs and cells were incubated with mouse anti-RUNX1 (Santa Cruz) followed by biotinylated secondary antibody (Vector Laboratories), horseradish peroxidase (HRP)-labeled avidin (PerkinElmer), tyramide signal amplification (TSA, PerkinElmer), Vector Red chromogenic substrate (Vector Laboratories) and Gill no. 3 hematoxylin counterstain (Sigma-Aldrich). Immunofluorescent staining for CD31 (mouse anti-CD31; Dako) and Ki67 (rabbit anti-Ki67; Novus Biologicals) was performed as previously described (Kim L A, et al. (2015) Mol Vis 21:673-687). The number of Ki67 positive nuclei was averaged for three fields of view per sample at 20× magnification.

Mouse retinal whole mounts were blocked with 1% BSA, 0.1% Triton X-100, and 3% serum in PBlec buffer, incubated with primary (isolectin D34 Alexa Fluor 488 Conjugate; Life Technologies, rat anti-CD31; BD Pharmingen and rabbit anti-RUNX1; LifeSpan BioSciences) and secondary (donkey anti-rat Alexa Fluor 594 and donkey anti-rabbit Alexa Fluor 647 or goat anti-rabbit Alexa Fluor 594; Life Technologies). Samples were imaged with an Axioskop 2 MOT Plus microscope (Carl Zeiss) or TCS-SP5 confocal microscope (Leica).

Cell Culture:

HRMEC (Cell Systems) and human umbilical vein endothelial cells (HUVEC; Lonza) were grown at 37° C. with 5% $CO_2$ using endothelial growth media plus antibiotics (Lonza) and 2% FBS (Atlanta Biologicals). For the qRT-PCR gene candidate screen in high glucose, cells were treated for 48 h with endothelial basal media-2 with 2% platelet-poor plasma derived serum (Alfa Aesar) and D-glucose (Sigma-Aldrich) or osmotic control (Mannitol and L-glucose; Sigma-Aldrich).

Immunofluorescent Staining of C-FVM and HRMEC:

HRMEC were probed for CD31 as previously described (Kim L A, et al. (2015) Mol Vis 21:673-687). Briefly, following fixation, permeabilization, and blocking, cells were incubated with primary antibody for 1 h at room temperature (mouse anti-CD31 1:50; Dako) followed by secondary antibody (goat anti-mouse Alexa Fluor 647 1:200; Life Technologies Corp.). Prolong Gold anti-fade mounting medium with 4',6-diamidino-2-phenylindole (DAPI; Life Technologies Corp.) was used for mounting and nuclear counterstain. Samples were washed with PBS three times for 10 min at room temperature between steps. Samples were imaged using a Zeiss Axioskop 2 MOT Plus microscope (Carl Zeiss Inc.).

HRMEC were probed for proliferation with the Ki67 marker as follows: cells were permeabilized with 0.5% Triton X-100 in PBS for 5 min, blocked with 5% goat serum in PBS for 2 h at room temperature, incubated with primary antibody overnight at 4° C. (rabbit anti-Ki67 1:50; Novus Biologicals), and incubated with secondary for 2 h at room temperature (goat anti-rabbit Alexa Fluor 594 1:250; Life Technologies Corp.). Samples were imaged using an EVOS® imaging system. The number of Ki67 positive nuclei was averaged for three fields of view per sample at 20× magnification.

siRNA Gene Knockdown:

siRNA (75 nm) (Integrated DNA Technologies; sequences in Table 4) was transfected for 6-8 h using DharmaFECT 1 (GE Life Sciences—Dharmacon) in Opti-MEM (Life Technologies).

Qrt-PCR Analysis:

RNA was extracted using RNeasy Mini Kits (Qiagen). Primers were purchased from Integrated DNA Technologies for 200 candidate genes (Table 4). Genes were excluded from further analysis if there was no amplification or amplification was outside the linear range. This resulted in a final list of 101 genes analyzed by qRT-PCR. cDNA was prepared using the iScript cDNA synthesis kit (Bio-Rad Laboratories) and probed using FastStart Universal SYBR Green Master (Hoffmann-La Roche). Fluorescent intensities were normalized to spike-in controls (ERCC RNA Spike-In Mix; Life Technologies), HPRT1, and B2M.

Western Blot Analysis: Cells were lysed using RIPA buffer (Cell Signaling Technology (CST)). Samples were separated on a 4-15% SDS-PAGE, transferred to polyvinylidene difluoride membranes, blocked with Odyssey Blocking Buffer (LI-COR Biosciences, Lincoln, Nebr.), and probed with mouse anti-RUNX1 (Santa Cruz Biotechnology Inc.), rabbit anti-β-actin (CST), IRDye 680RD donkey anti-rabbit, and IRDye 800CW donkey anti-mouse (LI-COR) antibodies. Immunoreactive bands were visualized using the Odyssey Infrared Imaging System and band intensities normalized to β-actin were quantified using Image Studio version 2.1 (LI-COR).

Scratch-Wound Migration Assay:

Migration was assessed with the scratch-wound assay (Liang C C et al. (2007) Nature Protocols 2(2):329-333). One scratch was generated per well and imaged on an EVOS® imaging system every three hours for 12 h. Images were analyzed with the TScratch Matlab module (Geback et al. (2009) Biotechniques 46(4):265-274).

Tube Forming Assay:

HRMEC were treated overnight with 75 µM Ro5-3335 or DMSO before plating 20000 cells onto wells pre-coated with basement membrane extract (Trevigen). Cells were imaged six h after plating and tube formation was quantified using the Angiogenesis Analyzer plugin for ImageJ.

Statistical Analysis:

All results are presented as means±SEM. Student's t-test was performed for statistical comparisons between two groups and one-way ANOVA (Kruskal-Wallis test) was used for comparisons between multiple groups. A P value <0.05 was considered a significant result.

Figure 20:
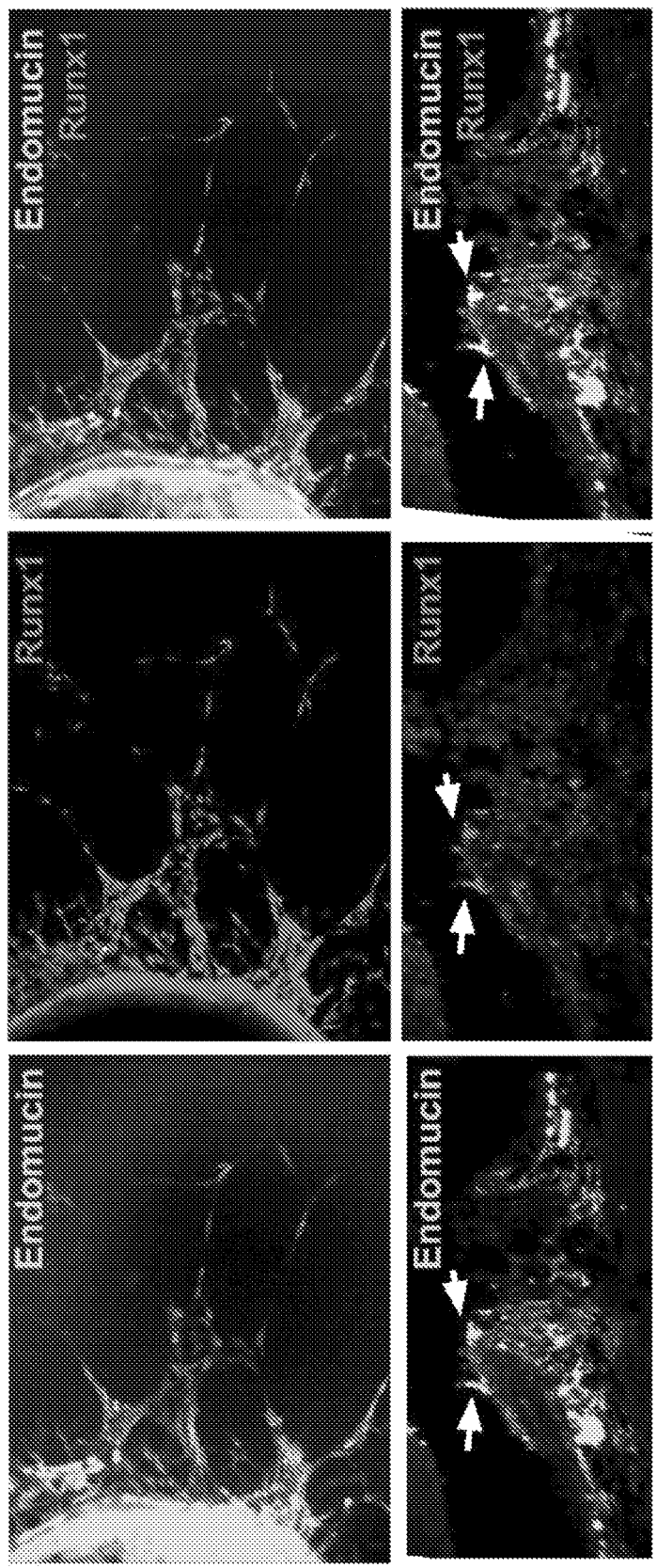
FIG. 20 is a set of fluorescent images showing that choroidal explant and laser-induced CNV demonstrates RUNX1 expression. Choroidal endothelial cells are endomucin+(green). Angiogenic choroidal sprouts/vessels are RUNX1+(red). Merged image reveals co-staining of endomucin and RUNX1 within the choroidal sprouts (top panels), and within new choroidal vessels (white arrows) in laser-induced choroidal neovascularization (CNV) (bottom panels).

Example 2. Choroidal Explants and Laser-Induced Choroidal Neovascularization Reveal Specific Runx1 Expression in Sprouts/Neovessels Robust expression of RUNX1 was found in angiogenic sprouts from ex-vivo mouse choroidal explant assays (Shao Z, Friedlander M, Hurst C G, et al. Choroid sprouting assay: an ex vivo model of microvascularangiogenesis. PLoS One. 2013; 8:e69552) and in neovessels from a laser-induced CNV mouse model (FIG. 20). (Giani A, Thanos A, Roh M I, et al. In vivo evaluation of laser-induced choroidal neovascularization using spectral-domain optical coherence tomography. Invest Ophthalmol Vis Sci. 2011; 52:3880-3887) Choroidal explants were obtained from 1 mm punch biopsy from P21 mice embedded in Matrigel and cultured for 48 h. For laser-induced CNV, a 532-nm laser (Oculight GLx Laser System; IRIDEX) attached to a slit lamp was used for photocoagulation (100-mW power, 100-µm spot size, and 0.1-s pulse duration) at four sites around the optic nerve in a clockwise manner.

Figure 21:
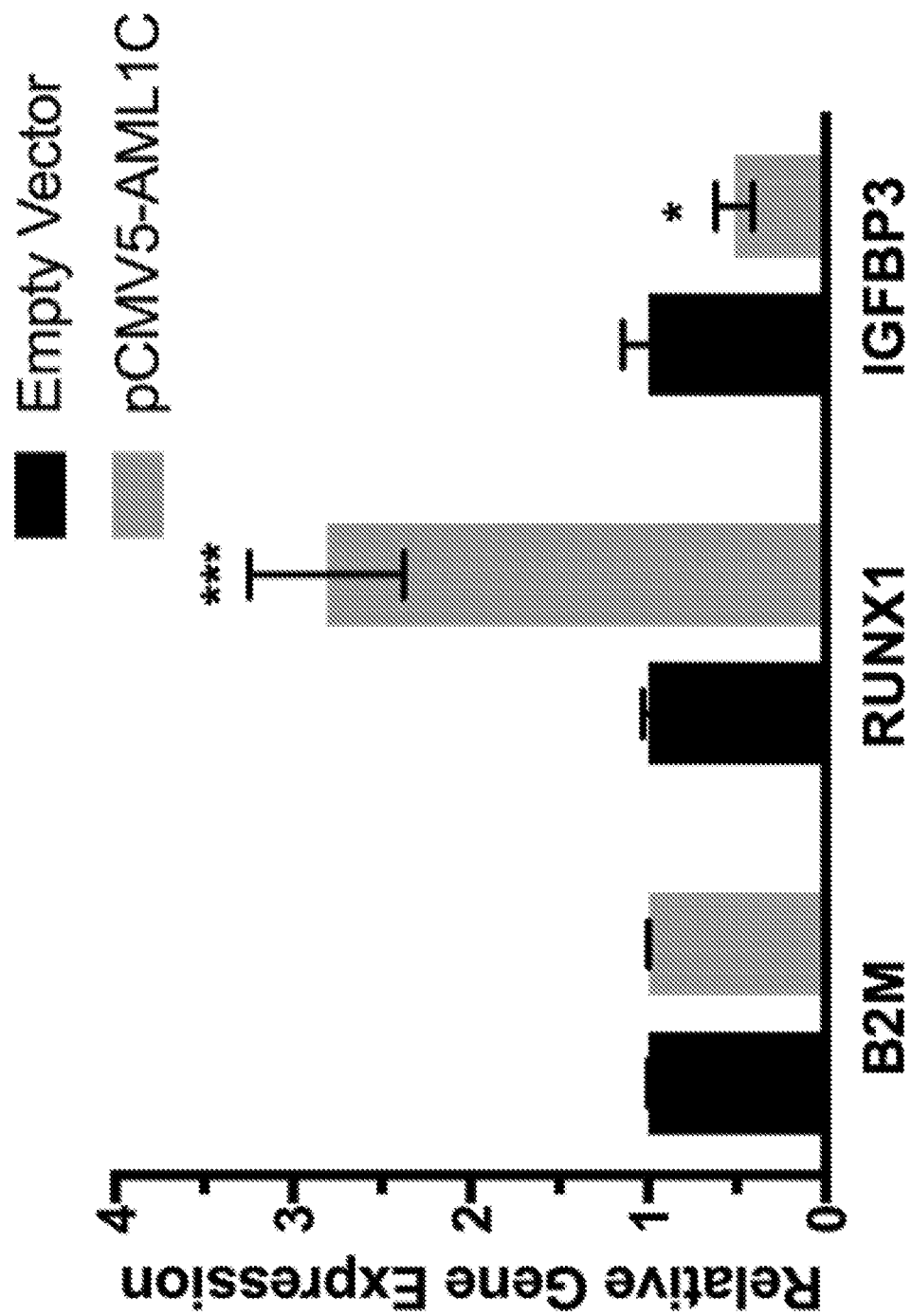
FIG. 21 is a graph showing RUNX1 overexpression and effect on IGFBP3 expression. Nucleofection of RUNX1 leads to a ~2.8 fold increase in RUNX 1 expression and ~2 fold decrease in IGFBP3 expression.
Figure 22:
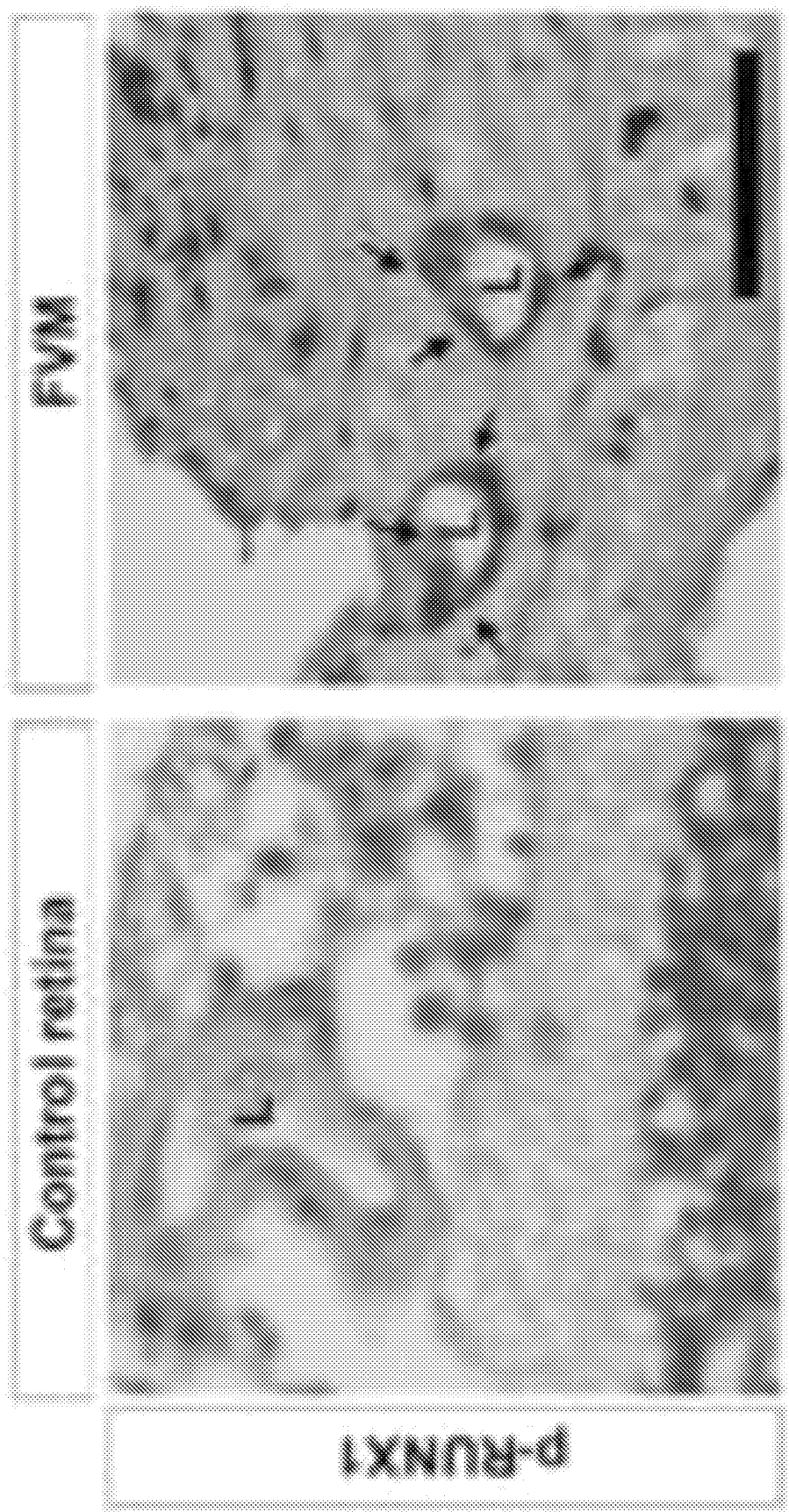
FIG. 22 is a set of images showing that immunohistology of control retina and FVM identifies specific staining of phosphorylated RUNX1 (pRUNX1) within blood vessels in FVM but not in control retina. Scale bar=50 μm. S249 phosphorylated RUNX1 staining was largely absent from vessels in control retina but prominent in vessels from FVM (Santa Cruz Biotechnology, sc-293146).

Example 3: Overexpression of RUNX1 by Nucleofection Suppresses IGFBP3 Expression HRMEC were transfected with pCMV5-AML1c (Addgene Plasmid #12426) (the plasmid contains the sequence of RUNX1 encoding 480 amino acids; in the sequences listed herein this corresponds to RUNX1g) or pCMV5 empty vector using the HCAEC Nucleofector kit (VPB-1001; Program S-005) following manufacturer's optimized protocol. Transfection media was removed after 4 hours. qRT-PCR performed 48 hr following transfection demonstrated ~2.8 fold (p<0.001) increased expression of RUNX1 relative to cells transfected with empty vector and associated ~2 fold (p<0.05) decrease in IGFBP3 expression (FIG. 21).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for inhibiting, treating, or preventing aberrant angiogenesis or small vessel diseases (SVDs) in a subject, comprising:
administering to said subject an effective amount of a Runt-Related Transcription Factor 1 (RUNX1) inhibitor,
wherein the subject has proliferative diabetic retinopathy (PDR), macular edema, non-proliferative diabetic retinopathy, age-related macular degeneration (AMD), ocular neovascularization, ocular ischemic syndrome, retinopathy of prematurity (ROP), a retinal vein occlusion, ocular ischemic syndrome, neovascular glaucoma, a retinal hemangioma, Coates' disease, familial exudative vitreoretinopathy (FEVR), type 1 diabetes, type 2 diabetes, diabetic retinopathy (DR), a hemangioma, neovascular glaucoma, a vascular malformation, a cerebral cavernous malformation, Von Hippel-Lindau disease, Norrie disease, a melanoma, a solid tumor, or a cancer other than leukemia; and
wherein said RUNX1 inhibitor binds to RUNX1 and/or CBFβ.

2. The method of claim 1, wherein the aberrant angiogenesis is aberrant ocular angiogenesis.

3. The method of claim 1, wherein said subject has proliferative diabetic retinopathy (PDR), macular edema, non-proliferative diabetic retinopathy, age-related macular degeneration (AMD), ocular neovascularization, ocular ischemic syndrome, retinopathy of prematurity (ROP), a retinal vein occlusion, ocular ischemic syndrome, neovascular glaucoma, a retinal hemangioma, Coates' disease, familial exudative vitreoretinopathy (FEVR), type 1 diabetes, type 2 diabetes, diabetic retinopathy (DR), a hemangioma, neovascular glaucoma, a vascular malformation, a cerebral cavernous malformation, Von Hippel-Lindau disease or Norrie disease.

4. The method of claim 1, wherein said subject has a melanoma, a solid tumor or a cancer other than leukemia.

5. The method of claim 4, wherein said solid tumor comprises a dimension that is greater than at least about 1, 2, 3, 4, 5, 6, 7, 8, 9, 10 mm or more and/or a volume of at least about 1, 1.5, 2, 3, 4, 5, 6, 7, 8, 9, 10 mm$^3$ or more.

6. The method of claim 1, wherein said RUNX1 inhibitor is administered as part of a treatment regimen that does not comprise an additional antiangiogenic inhibitor.

7. The method of claim 6, wherein said treatment regimen does not comprise a vascular endothelial growth factor (VEGF) pathway inhibitor.

8. The method of claim 1, wherein said RUNX1 inhibitor is administered as a monotherapy.

9. The method of claim 1, wherein said RUNX1 inhibitor comprises an aptamer, an oligonucleotide, a peptide, an antibody or a fragment thereof, or a small molecule.

10. The method of claim 9, wherein said RUNX1 inhibitor binds to CBFβ.

11. The method of claim 9, wherein said RUNX1 inhibitor binds to RUNX1.

12. The method of claim 9, wherein said RUNX1 inhibitor comprises Ro5-3335.

13. The method of claim 9, wherein said oligonucleotide comprises at least about 10, 15, 20, 25, 30, or more nucleotides in a sequence that is complementary to a nucleotide sequence within a gene or mRNA molecule that encodes RUNX1.

14. The method of claim 1, wherein the SVD comprises cerebral small vessel disease, cerebral autosomal recessive arteriopathy with subcortical infarcts and leukoencephalopathy (CARASIL), age-related macular degeneration (AMD), cerebral autosomal-dominant arteriopathy with subcortical infarcts and leukoencephalopathy (CADASIL), NOTCH3 loss-of-function-associated SVD, Notch 3 hyperactivation-associated SVD, nephropathy, microangiopathy, heart failure, Alagille syndrome, familial tetralogy of Fallot, patent ductus arteriosus, cerebral cavernous malformation, or diabetic retinopathy.

15. The method of claim 1, wherein the ocular neovascularization is corneal neovascularization.

* * * * *